US 11,715,549 B2

(12) United States Patent
Rigoutsos et al.

(10) Patent No.: US 11,715,549 B2
(45) Date of Patent: Aug. 1, 2023

(54) SYSTEMS-LEVEL ANALYSIS OF 32 TCGA CANCERS REVEALS DISEASE-DEPENDENT TRNA FRAGMENTATION PATTERNS AND VERY SELECTIVE ASSOCIATIONS WITH MESSENGER RNAS AND REPEAT ELEMENTS

(71) Applicant: Thomas Jefferson University, Philadelphia, PA (US)

(72) Inventors: Isidore Rigoutsos, Astoria, NY (US); Aristeidis G. Telonis, Philadelphia, PA (US)

(73) Assignee: THOMAS JEFFERSON UNIVERSITY, Philadelphia, PA (US)

(*) Notice: Subject to any disclaimer, the term of this patent is extended or adjusted under 35 U.S.C. 154(b) by 561 days.

(21) Appl. No.: 16/609,880

(22) PCT Filed: May 1, 2018

(86) PCT No.: PCT/US2018/030525
§ 371 (c)(1),
(2) Date: Oct. 31, 2019

(87) PCT Pub. No.: WO2018/204412
PCT Pub. Date: Nov. 8, 2018

(65) Prior Publication Data
US 2020/0202976 A1    Jun. 25, 2020

Related U.S. Application Data

(60) Provisional application No. 62/492,662, filed on May 1, 2017.

(51) Int. Cl.
*G16B 30/00* (2019.01)
*G16B 20/00* (2019.01)

(52) U.S. Cl.
CPC ............ *G16B 30/00* (2019.02); *G16B 20/00* (2019.02)

(58) Field of Classification Search
CPC .. G16B 30/00; G16B 20/00; C12Q 2600/112; C12Q 2600/158; C12Q 2600/178; C12Q 1/6886; C12N 15/11
See application file for complete search history.

(56) References Cited

U.S. PATENT DOCUMENTS

| 8,465,918 B2 * | 6/2013 | Croce | C12Q 1/6886 |
| | | | 435/6.1 |
| 9,687,466 B2 * | 6/2017 | Bacha | A61K 31/047 |

(Continued)

FOREIGN PATENT DOCUMENTS

| WO | 2012078209 A1 | 6/2012 |
| WO | 2015120022 A1 | 8/2015 |
| WO | 2016069641 A1 | 5/2016 |

OTHER PUBLICATIONS

European Partial Supplementary Search Report dated Feb. 11, 2021 in corresponding European Patent Application No. 18794729.6 filed May 1, 2018.

(Continued)

*Primary Examiner* — Gregory M Desire
(74) *Attorney, Agent, or Firm* — Cozen O'Connor

(57) ABSTRACT

Methods of treating a disease by leveraging positive and negative correlations between tRNA-derived fragments (tRF) and messenger RNA (mRNA) wherein said correlations can be used to establish a level of granularity that is specific to a disease of interest wherein said disease-specific positive and negative correlations can allow a level of therapeutic intervention that will be unprecedented because it will have been informed by three dimensions: at least one mRNA of interest; at least one tRF that are positively/

(Continued)

negatively correlated with it; and, the identity of the disease in which one wishes to modulate the abundance of the at least one mRNA of interest.

19 Claims, 128 Drawing Sheets

Specification includes a Sequence Listing.

(56) References Cited

U.S. PATENT DOCUMENTS

| | | | |
|---|---|---|---|
| 9,689,041 B2* | 6/2017 | Ye | C12Q 1/6886 |
| 10,351,865 B2* | 7/2019 | Kragler | C12N 15/102 |
| 2015/0119350 A1 | 4/2015 | Kebebew et al. | |
| 2015/0203920 A1 | 7/2015 | Dutta et al. | |
| 2016/0046997 A1* | 2/2016 | Lyng | G01N 33/57411 514/19.3 |
| 2016/0376592 A1* | 12/2016 | Bergstein | A61K 31/713 514/44 A |
| 2017/0166972 A1* | 6/2017 | Perera | C12N 15/113 |
| 2019/0015379 A1* | 1/2019 | Bacha | A61P 37/04 |
| 2020/0370122 A1* | 11/2020 | Zhou | G01N 33/57415 |

OTHER PUBLICATIONS

Green, D., et al., "Transfer RNA-derived small RNAs in the cancer transcriptome", Pflugers Arch, European Journal of Physiology, vol. 468, pp. 1041-1047, 2016.
Raina, M., et al., "tRNAs as regulators of biological regulators", Frontiers in Genetics, vol. 5, Article 171, 14 pages, 2014.
Rigoutsos, I., et al., "Abstract A29: Gender-specific and race-specific regulatory non-coding RNAs are prevalent in healthy and in cancerous tissues", Cancer Research, Tumor Heterogeneity and/or Genetics/Genome, vol. 76, Issue 3 Supplement, 4 pages, 2016.
Magee, R., et al., "Threshold-seq: a tool for determining the threshold in short RNA-seq datasets", Bioinformatics, vol. 33, No. 13, pp. 2034-2036, 2017.
Martinez, G., et al., "tRNA-derived small RNAs target transposable element transcripts", Nucleic Acids Research, vol. 45, No. 9, pp. 5142-5152, 2017.
Maute, R.L., et al., "tRNA-derived microRNA modulates proliferation and the DNA damage response and is down-regulated in B cell lymphoma", Proc Natl Acad Sci USA, vol. 110, No. 4, pp. 1404-1409, 2013.
Meza, R., et al., "Lung Cancer Incidence Trends by Gender, Race and Histology in the United States, 1973-2010", PLOS One, vol. 10, No. 3, Article No. e0121323, 14 pages, 2015.
Mustoe, A.M., et al., "Hierarchy of RNA Functional Dynamics", Annual Review of Biochemistry, vol. 83, pp. 441-466, 2014.
Olvedy, M., et al., "A comprehensive repertoire of tRNA-derived fragments in prostate cancer", Oncotarget, vol. 7, No. 17, pp. 24766-24777, 2016.
Paggi, M.G., et al., "Gender-related disparities in non-small cell lung cancer", Cancer Letters, vol. 298, No. 1, pp. 1-8 2010.
Paik, S., et al., "A multigene assay to predict recurrence of tamoxifen-treated, node-negative breast cancer", The New England Journal of Medicine, vol. 351, pp. 2817-2826, 2004.
Perou, C.M., "Molecular stratification of triple-negative breast cancer", The Oncologist, vol. 16, Supplement 1, pp. 61-70, 2011.
Pliatsika, V., et al., "MINTbase: a framework for the interactive exploration of mitochondrial and nuclear tRNA fragments", Bioinformatics, vol. 32, No. 16, pp. 2481-2489, 2016.
Rigoutsos, I., et al, "Short blocks from the noncoding parts of the human genome have instances within nearly all known genes and relate to biological processes", Proc Natl Acad Sci USA, vol. 103, No. 17, pp. 6605-6610, 2006.
Rigoutsos, I., "Short RNAs: how big is this iceberg?", Current Biology, vol. 20, No. 3, pp. R110-R113, 2010.

Selitsky, S.R., et al., "Small tRNA-derived RNAs are increased and more abundant than microRNAs in chronic hepatitis B and C", Scientific Reports, vol. 5, Article No. 7675, 2015.
Sharma, U. et al., "Biogenesis and function of tRNA fragments during sperm maturation and fertilization in mammals", Science, vol. 351, No. 6271, pp. 391-396, 2016.
Shigematsu, M., et al., "tRNA-Derived Short Non-coding RNA as Interacting Partners of Argonaute Proteins", Gene Regulation and Systems Biology, vol. 9, pp. 27-33, 2015.
Shigematsu, M., et al., "5'-Terminal nucleotide variations in human cytoplasmic tRNAHisGUG and its 5'-halves", RNA, vol. 23, pp. 161-168, 2017.
Siegel, R.L., et al., "Cancer statistics, 2015", CA: A Cancer Journal for Clinicians, vol. 65, No. 1, pp. 5-29, 2015.
Slamon, D.J., et al., "Human breast cancer: correlation of relapse and survival with amplification of the HER-2/neu oncogene", Science, vol. 235, No. 4785, pp. 177-182, 1987.
Sobala, A., et al., "Small RNAs derived from the 5' end of tRNA can inhibit protein translation in human cells", RNA Biology, vol. 10, No. 4, pp. 553-563, 2013.
Spratt, D.E., et al., "Racial/Ethnic Disparities in Genomic Sequencing", JAMA Oncology, vol. 2, No. 8, pp. 1070-1074, 2016.
Sra, S., et al., "Generalized nonnegative matrix approximations with Bregman divergences", Advances in neural information . . . , 2005.
Suzuki, T., et al., "Human Mitochondrial tRNAs: Biogenesis, Function, Structural Aspects, and Diseases", Annual Review of Genetics, vol. 45, pp. 299-329, 2011.
Suzuki, T., et al., "A complete landscape of post-transcriptional modifications in mammalian mitochondrial tRNAs", Nucleic Acids Research, vol. 42, No. 11, pp. 7346-7357, 2014.
Telonis, A.G., et al., "Nuclear and mitochondrial tRNA-lookalikes in the human genome", Frontiers in Genetics, vol. 5, Article No. 344, 11 pages, 2014.
Telonis, A.G., et al., "Beyond the one-locus-one-miRNA paradigm: microRNA isoforms enable deeper insights into breast cancer heterogeneity", Nucleic Acids Research, vol. 43, No. 19, pp. 9158-9175, 2015.
Telonis, A.G., et al., "Dissecting tRNA-derived fragment complexities using personalized transcriptomes reveals novel fragment classes and unexpected dependencies", Oncotarget, vol. 6, No. 28, pp. 24797-24822, 2015.
Telonis, A.G., et al., "Consequential considerations when mapping tRNA fragments", BMC Bioinformatics, vol. 17, Article No. 123, 4 pages, 2016.
Telonis, A.G., et al., "Knowledge about the presence or absence of miRNA isoforms (isomiRs) can successfully discriminate amongst 32 TCGA cancer types", Nucleic Acids Research, vol. 45, No. 6, pp. 2973-2985, 2017.
Thompson, D.M., et al., "The RNase Rny1p cleaves tRNAs and promotes cell death during oxidative stress in *Saccharomyces cerevisiae*", J Cell Biol., vol. 185, No. 1, pp. 43-50, 2009.
Torres, A.G., et al., "Role of tRNA modifications in human diseases", Trends in Molecular Medicine, vol. 20, No. 6, pp. 306-314, 2014.
Tsirigos, A., et al.,"Human and mouse introns are linked to the same processes and functions through each genome's most frequent non-conserved motifs", Nucleic Acids Research, vol. 36, No. 10, pp. 3484-3493, 2008.
Tsirigos, A., et al.,"Alu and b1 repeats have been selectively retained in the upstream and intronic regions of genes of specific functional classes", PLOS Computational Biology, vol. 5, No. 12, Article No. e1000610, 10 pages, 2009.
Underwood, W., 3rd, et al., "Gender and geographic influence on the racial disparity in bladder cancer mortality in the US", Journal of the American College of Surgeons, vol. 202, No. 2, pp. 284-290, 2006.
UniProt Consortium, "UniProt: a hub for protein information", Nucleic Acids Research, vol. 43, No. D1, pp. D204-D212, 2015.
Van't Veer, L.J., et al., "Gene expression profiling predicts clinical outcome of breast cancer", Nature, vol. 415, pp. 530-536, 2002.
Yamasaki, S., et al., "Angiogenin cleaves tRNA and promotes stress-induced translational repression", Journal of Cell Biology, vol. 185, No. 1, pp. 35-42, 2009.

(56) References Cited

OTHER PUBLICATIONS

Yeung, M.L., et al., "Pyrosequencing of small non-coding RNAs in HIV-1 infected cells: evidence for the processing of a viral-cellular double-stranded RNA hybrid", Nucleic Acids Research, vol. 37, No. 19, pp. 6575-6586, 2009.

Zhang, Y., "Understanding the gender disparity in bladder cancer risk: the impact of sex hormones and liver on bladder susceptibility to carcinogens", J Environ Sci Health C Environ Carcinog Ecotoxicol Rev, vol. 31, No. 4, pp. 287-304, 2013.

Zheng, G., et al., "Efficient and quantitative high-throughput tRNA sequencing", Nature Methods, vol. 12, No. 9, pp. 835-837, 2015.

Zheng, L.-L., et al., "tRF2Cancer: A web server to detect tRNA-derived small RNA fragments (tRFs) and their expression in multiple cancers", Nucleic Acids Research, vol. 44, No. W1, pp. W185-W193, 2016.

Abbott, J.A., et al., "Transfer RNA and human disease", Frontiers in Genetics, vol. 5, Article 158, 18 pages, 2014.

Alberg, A.J., et al., "Epidemiology of lung cancer: Diagnosis and management of lung cancer", 3rd ed: American College of Chest Physicians evidence-based clinical practice guidelines, Chest, vol. 143, No. 5, Supplement, pp. e1S-e29S, 2013.

American Lung Association, "A.L. Lung Cancer Fact Sheet, 4", http://www.lung.org/lung-disease/lungcancer/resources/facts-figures/lung-cancer-fact-sheet, html.

Anderson, P., et al., "tRNA fragments in human health and disease", FEBS Letters, vol. 588, pp. 4297-4304, 2014.

Bao, W., et al., "Repbase Update, a database of repetitive elements in eukaryotic genomes", Mobile DNA, vol. 6, No. 11, 6 pages, 2015.

Belancio, V.P., et al., "All y'all need to know 'bout retroelements in cancer", Semin Cancer Biol, vol. 20, No. 4, pp. 200-210, 2010.

Brunet, J.-P., et al, "Metagenes and molecular pattern discovery using matrix factorization", Proceedings of the National Academy of Sciences of the United States of America, vol. 101, No. 12, pp. 4164-4169, 2004.

Burge, F., et al., "Closing the Gender Gap: Can We Improve Bladder Cancer Survival in Women?—A Systematic Review of Diagnosis, Treatment and Outcomes", Urologia Internationalis, vol. 97, pp. 373-379, 2016.

Carey, L.A., et al., "Race, breast cancer subtypes, and survival in the Carolina Breast Cancer Study", JAMA, vol. 295, No. 21, pp. 2492-2502, 2006.

Chen, Q., et al., "Sperm tsRNAs contribute to intergenerational inheritance of an acquired metabolic disorder", Science (New York, NY), vol. 351, No. 6271, pp. 397-400, 2016.

Chu, A., et al., "Large-scale profiling of microRNAs for the cancer genome atlas", Nucleic Acids Research, vol. 44, No. 1, Article No. e3, 2015.

Cognat, V., et al., "The nuclear and organellar tRNA-derived RNA fragment population in *Arabidopsis thaliana* is highly dynamic", Nucleic Acids Research, vol. 45, No. 6, pp. 3460-3472, 2016.

Cohn, J.A., et al., "Sex disparities in diagnosis of bladder cancer after initial presentation with hematuria: a nationwide clams-based investigation", Cancer, vol. 120, No. 4, pp. 555-561, 2014.

Cozen, A.E., et al., "ARM-seq: AlkB-facilitated RNA methylation sequencing reveals a complex landscape of modified tRNA fragments", Nature Methods, vol. 12, No. 9, pp. 879-884, 2015.

Dawson, S.J., et al., "Triple negative breast cancers: clinicaland prognostic implications", European Journal of Cancer, vol. 45, Supplement 1, pp. 27-40, 2009.

Dela Cruz, C.S., et al., "Lung Cancer: Epidemiology, Etiology, and Prevention", Clin Chest Med., vol. 32, No. 4, pp. 605-644, 2011.

Deng, J., et al., "Respiratory Syncytial Virus Utilizes a tRNA Fragment to Suppress Antiviral Responses through a Novel Targeting Mechanism", Molecular Therapy, vol. 23, No. 10, pp. 1622-1629, 2015.

Dobruch, J., et al., "Gender and Bladder Cancer: A Collaborative Review of Etiology, Biology, and Outcomes", European Urology, vol. 69, No. 2, pp. 300-310, 2016.

Durdevic, Z., et al., "tRNA modifications: Necessary for correct tRNA-derived fragments during the recovery from stress?", BioEssays, vol. 35, No. 4, pp. 323-327, 2013.

Fajkovic, H., et al., "Impact of gender on bladder cancer incidence, staging, and prognosis", World Journal of Urology, vol. 29, pp. 457-463, 2011.

Fu, H., et al., "Stress induces tRNA cleavage by angiogenin in mammalian cells", FEBS Letters, vol. 583, No. 2, pp. 437-442, 2009.

Gapp, K., et al., "Implication of sperm RNAs in transgenerational inheritance of the effects of early trauma in mice", Nature Neuroscience, vol. 17, No. 5, pp. 667-669, 2014.

Gebetsberger, J., et al., "A tRNA-derived fragment competes with mRNA for ribosome binding and regulates translation during stress", RNA Biology, vol. 14, No. 10, pp. 1364-1373, 2016.

Goodarzi, H., et al., "Endogenous tRNA-Derived Fragments Suppress Breast Cancer Progression via YBX1 Displacement", Cell, vol. 161, pp. 790-802, 2015.

Grewal, S.S., "Why should cancer biologists care about tRNAs? tRNA synthesis, mRNA translation and the control of growth", Biochimica et Biophysica Acta (BBA), vol. 1849, No. 7, pp. 898-907, 2015.

Gu, C., et al., "tRNA modifications regulate translation during cellular stress", FEBS Letters, vol. 588, pp. 4287-4296, 2014.

Gu, W., et al., tRNAHis maturation: an essential yeast protein catalyzes addition of a guanine nucleotide to the 5' end of tRNAHis, Genes & Development, vol. 17, pp. 2889-2901, 2003.

Hasler, D., et al., "The Lupus Autoantigen La Prevents Mischanneling of tRNA Fragments into the Human MicroRNA Pathway", Molecular Cell, vol. 63, No. 1, pp. 110-124, 2016.

Heinemann, I.U., et al., "tRNAHis-guanylyltransferase establishes tRNAHis identity", Nucleic Acids Research, vol. 40, No. 1, pp. 333-344, 2012.

Hollenbeck, B.K., et al., "Racial differences in treatment and outcomes among patients with early stage bladder cancer", Cancer, vol. 116, No. 1, pp. 50-56, 2010.

Honda, S., et al., "Sex hormone-dependent tRNA halves enhance cell proliferation in breast and prostate cancers", Proc Natl Acad Sci USA, vol. 112, pp. E3816-E3825, 2015.

Huang, D.W., et al., "Systematic and integrative analysis of large gene lists using DAVID bioinfomnatics resources", Nature Protocols, vol. 4, pp. 44-57, 2009.

Ivanov, P., et al., "Angiogenin-induced tRNA fragments inhibit translation initiation", Molecular Cell, vol. 43, No. 4, pp. 613-623, 2011.

Jackman, J.E., et al., "tRNAHis guanylyltransferase adds G-1 to the 5' end of tRNAHis by recognition of the anticodon, one of several features unexpectedly shared with tRNA synthetases", RNA, vol. 12, pp. 1007-1014, 2006.

Jacobs, B.L., et al., "Disparities in bladder cancer", Urologic Oncology: Seminars and Original Investigations, vol. 30, No. 1, pp. 81-88, 2012.

Jemal, A., et al., "Global Cancer Statistics", CA: A Cancer Journal for Clinicians, vol. 61, No. 2, pp. 69-90, 2011.

Kawaji, H., et al., "Hidden layers of human small RNAs", BMC Genomics, vol. 9, Article No. 157, 21 pages, 2008.

Keam, S.P., et al., "tRNA-Derived Fragments (tRFs): Emerging New Roles for an Ancient RNA in the Regulation of Gene Expression", Life (Basel) 5, No. 4, pp. 1638-1651, 2015.

Keam, S.P., et al., "tRNA-Derived RNA Fragments Associate with Human Multisynthetase Complex (MSC) and Modulate Ribosomal Protein Translation", Journal of Proteome Research, vol. 16, No. 2, pp. 413-420, acs.proteome.6b00267, 2016.

Kirchner, S., et al., "Emerging roles of tRNA in adaptive translation, signalling dynamics and disease", Nature Reviews Genetics, vol. 16, pp. 98-112, 2015.

Koboldt, D.C., et al., "Comprehensive molecular portraits of human breast tumours", Nature, vol. 490, pp. 61-70, 2012.

Kumar, P., et al., "Meta-analysis of tRNA derived RNA fragments reveals that they are evolutionarily conserved and associate with AGO proteins to recognize specific RNA targets", BMC Biology, vol. 12, No. 78, 14 pages, 2014.

(56) References Cited

OTHER PUBLICATIONS

Lathan, C.S., "Lung Cancer Disparities in the Era of Personalized Medicine", The American Journal of Hematology/Oncology®, vol. 11, No. 2, 8 pages, 2015.

Laurent, L., et al., "Dynamic changes in the human methylome during differentiation", Genome Research, vol. 20, pp. 320-331, 2010.

Lee, C.T., et al., "Racial disparity in bladder cancer: trends in tumor presentation at diagnosis", The Journal of Urology, vol. 176, No. 3, pp. 927-934, 2006.

Lee, Y.S., et al., "A novel class of small RNAs: tRNA-derived RNA fragments (tRFs)", Genes & Development, vol. 23, pp. 2639-2649, 2009.

Loher, P., et al., "IsomiR expression profiles in human lymphoblastoid cell lines exhibit population and gender dependencies", Oncotarget, vol. 5, No. 18, pp. 8790-8802, 2014.

Loher, P., et al., "MINTmap: fast and exhaustive profiling of nuclear and mitochondrial tRNA fragments from short RNA-seq data", Sci Rep, vol. 7, Article No. 41184, 2017.

Machnicka, M.A., et al., "MODOMICS: a database of RNA modification pathways—2013 update", Nucleic Acids Research, vol. 41, No. D1, pp. D262-D267, 2013.

Magee, R., et al., "Comments on: A comprehensive repertoire of tRNA-derived fragments in prostate cancer", bioRxv, 18 pages, 2016.

Genbank Accession No. SHPTRHGUG, Sheet His-tRNA-GUG, Apr. 18, 1994, retrieved from internet www.ncbi.nlm.nih.gov/nuccore/175940.

International Search Report and Written Opinion in International Application No. PCT/US18/30525 dated Sep. 21, 2018, International Searching Authority/United States.

Supplementary European Search Report dated May 12, 2021 in corresponding European Patent Application No. 18794729.6 filed May 1, 2018.

Dutta, A., et al., "Transfer RNA Fragments (tRFs), MicroRNA-like Short RNAs Generated Independent of Dicer, Associate with Target mRNAs in Ago complexes and are De-Regulated in Many Cancers", Biochemistry and Molecular Biology, The FASEB Journal, vol. 29, Issue 51, 4 pages, 2015.

\* cited by examiner

5'-tRFs

3'-tRFs

All i-tRF starting positions

All i-tRF ending positions

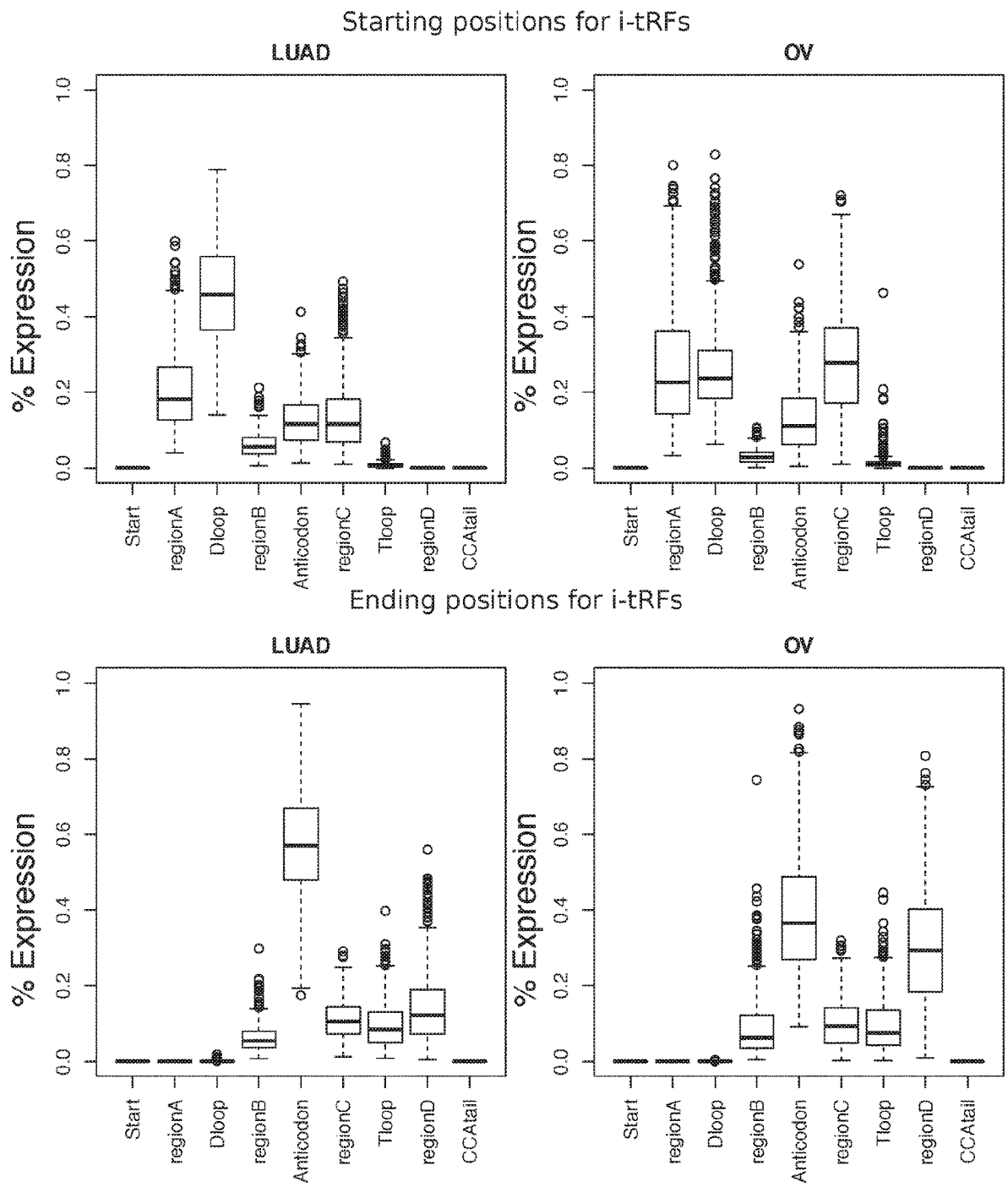

Exons

Exclusive to Males

Isoacceptor source

Structural type

Length

Genomic origin

Exclusive to Females

Isoacceptor source

Structural type

Length

Genomic origin (F) COAD (G) DLBC (H) ESCA (I) HNSC (J) KICH (K) KIRC

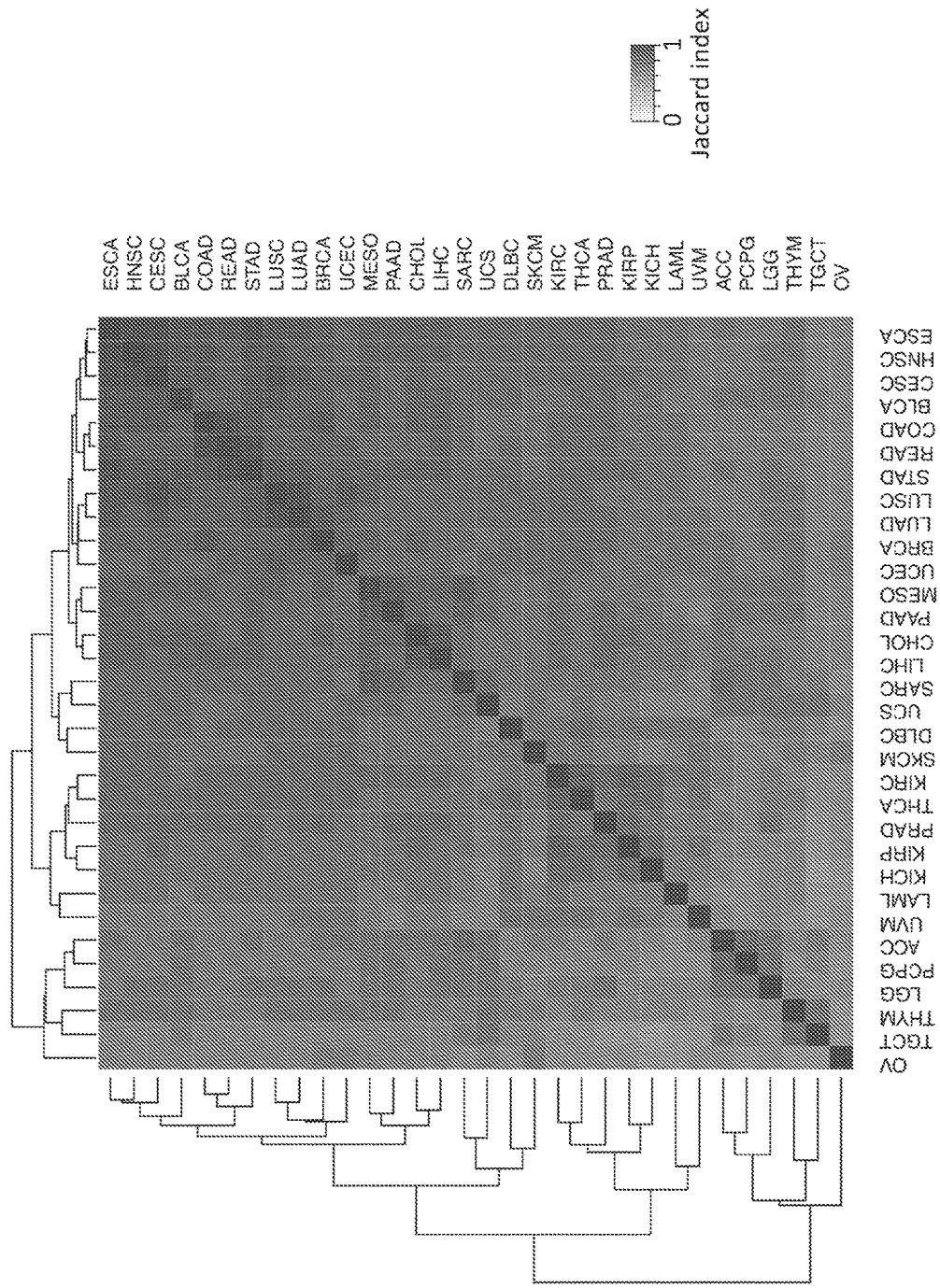

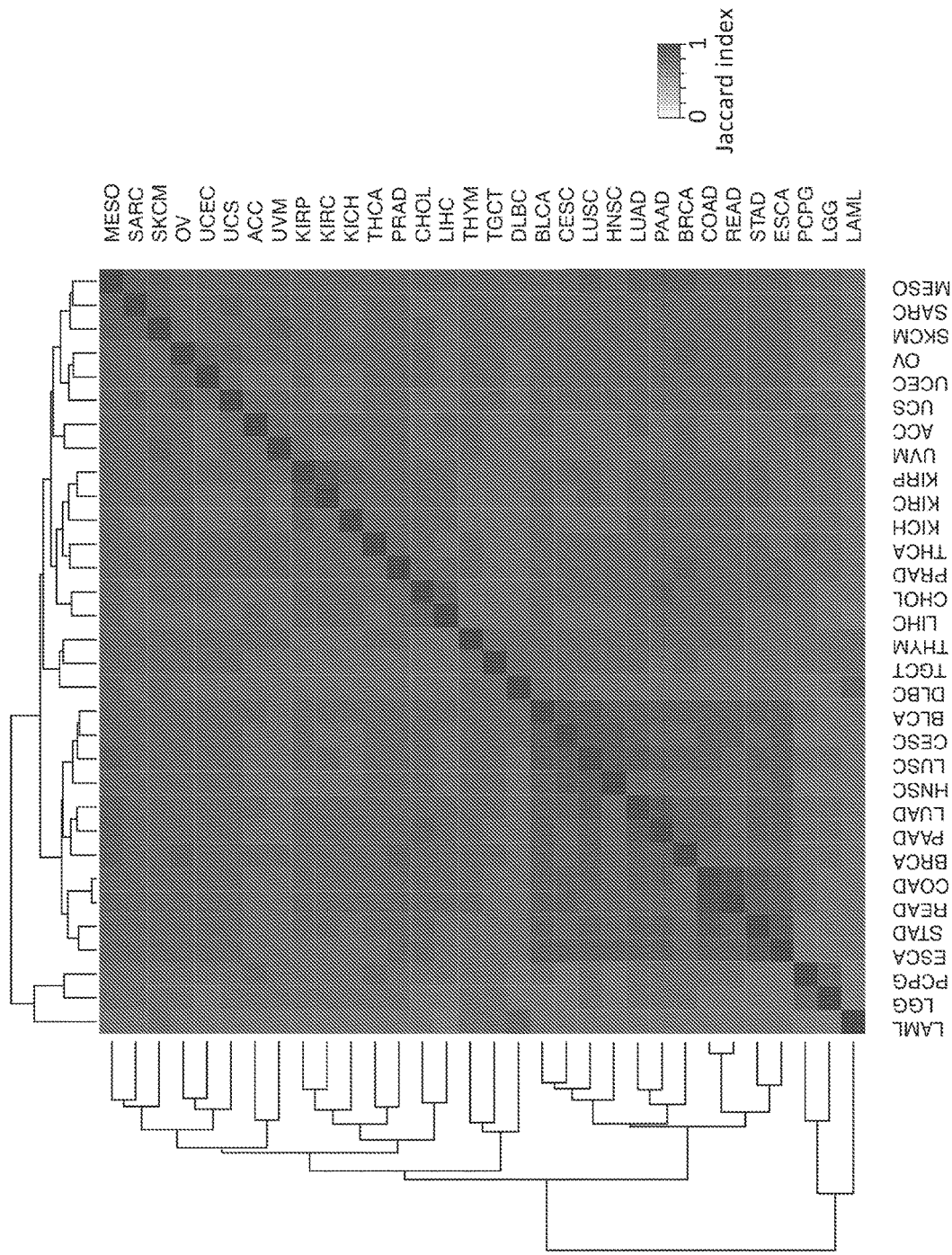

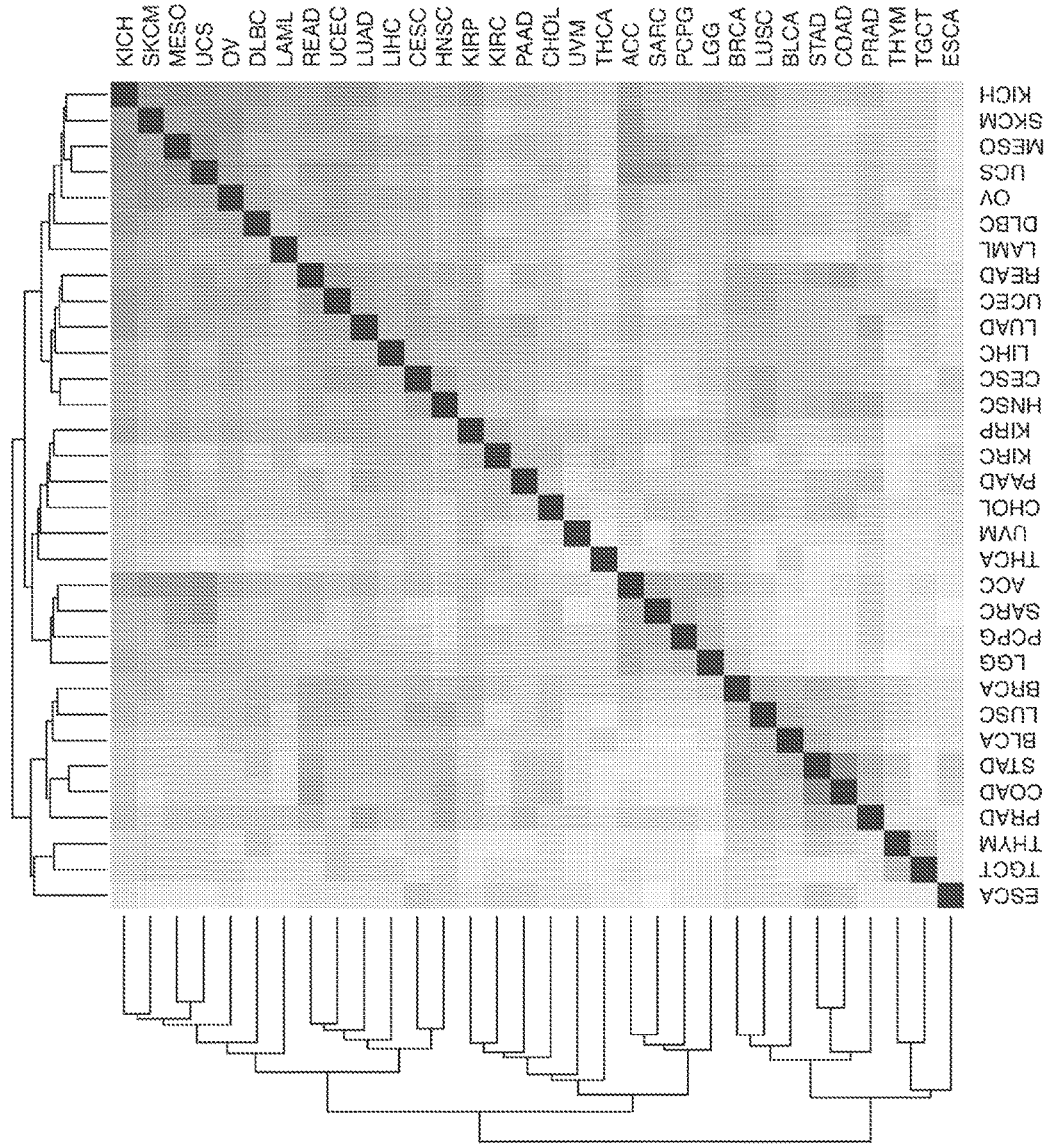

In either White or Black/African-American isoaceptor source structural type tRF length (nt)

genome of origin

Exclusive to White isoaceptor source structural type tRF length (nt)

genome of origin

Exclusive to Black/African-American isoaceptor source structural type tRF length (nt)

genome of origin

In both White and Black/African-American isoaceptor source structural type tRF length (nt)

genome of origin

FIG. 19 (cont.)

Legend isoaceptor source

- Ala (nu)
- His (nu)
- Val (mt)
- Arg (nu)
- Leu (nu)
- Ala (mt)
- Gln (nu)
- Met (nu)
- Glu (mt)
- Glu (nu)
- Tyr (nu)
- Pro (mt)
- Gly (nu)
- Val (nu)
- Other structural type

- 5'-half
- 5'-tRF
- i-tRF
- 3'-half
- 3'-tRF tRF length (nt)

- $\leq 19$
- $>19$ and $\leq 21$
- $>21$ and $\leq 23$
- $>23$ and $\leq 25$
- $>25$ genome of origin

- nuclear tRNA
- mitochondrial tRNA

FIG. 20B

| Cancer | Correlation | mRNA Gene | tRF | Orientation (with respect to gene) |
|---|---|---|---|---|
| BLCA | Negative | CYP4B1 | chr17.trna16-GlnTTG@12.30.19_2_13\|Out | Sense |
| DLBC | Positive | DNAJC8 | chr17.trna16-GlnTTG@13.30.18_2_13\|Out | Antisense |
| KIRC | Positive | PARK7 | chr17.trna4-ArgTCT@1.19.19_1_4\|Out | Sense |
| LAML | Negative | C1orf63 | chr16.trna17-LeuCAG@69.86CCA.18_2_7\|Out | Sense |
| LGG | Positive | PAFAH2 | chr17.trna16-GlnTTG@19.40.22_1_5\|Out | Sense |
| LGG | Positive | UBXN11 | chr17.trna16-GlnTTG@19.40.22_1_5\|Out | Sense |
| LGG | Positive | UBXN11 | chr17.trna16-GlnTTG@19.41.23_1_5\|Out | Sense |
| LGG | Positive | UBXN11 | chr17.trna16-GlnTTG@20.40.21_1_5\|Out | Sense |
| LGG | Positive | WASF2 | chr17.trna16-GlnTTG@19.40.22_1_5\|Out | Sense |
| LGG | Positive | WASF2 | chr17.trna16-GlnTTG@19.41.23_1_5\|Out | Sense |
| LUAD | Negative | CROCC | chr1.trna111-HisGTG@13.30.18_1_10\|Out | Sense |
| LUAD | Negative | CROCC | chr1.trna111-HisGTG@15.30.16_1_10\|Out | Sense |
| LUSC | Negative | UBR4 | chrMT.trnaMT-LeuTAA@1.18.18_1_5\|Out | Antisense |
| PCPG | Positive | FCN3 | chr1.trna85-ValCAC@1.20.20_2_17\|Out | Sense |
| PRAD | Negative | C1orf63 | chr16.trna17-LeuCAG@69.86CCA.18_2_7\|Out | Sense |
| PRAD | Positive | PRDM2 | chr16.trna17-LeuCAG@69.86CCA.18_2_7\|Out | Antisense |
| PRAD | Positive | PRDM2 | chr16.trna17-LeuCAG@69.86CCA.18_2_7\|Out | Sense |
| PRAD | Positive | UBE4B | chr16.trna17-LeuCAG@69.86CCA.18_2_7\|Out | Sense |
| PRAD | Positive | WASF2 | chr17.trna16-GlnTTG@16.31.16_2_12\|Out | Sense |
| SKCM | Positive | PARK7 | chr17.trna4-ArgTCT@1.19.19_1_4\|Out | Sense |
| TGCT | Positive | STIL | chr6.trna67-AlaAGC@58.75CCA.18_2_3\|Out | Sense |
| THYM | Negative | FNBP1L | chr1.trna34-LeuCAG@71.86CCA.16_1_7\|Out | Sense |
| THYM | Negative | FNBP1L | chr16.trna17-LeuCAG@71.86CCA.16_2_7\|Out | Antisense |
| THYM | Negative | KIAA1522 | chr16.trna17-LeuCAG@69.86CCA.18_2_7\|Out | Sense |
| THYM | Negative | KIAA1522 | chr16.trna17-LeuCAG@71.86CCA.16_2_7\|Out | Sense |
| THYM | Negative | NFIA | chr16.trna17-LeuCAG@71.86CCA.16_2_7\|Out | Sense |
| THYM | Negative | ZFYVE9 | chr16.trna17-LeuCAG@71.86CCA.16_2_7\|Out | Antisense |
| THYM | Negative | ZFYVE9 | chr16.trna17-LeuCAG@71.86CCA.16_2_7\|Out | Sense |

```
                            SEQUENCE LISTING

<160> NUMBER OF SEQ ID NOS: 372

<210> SEQ ID NO 1
<211> LENGTH: 24
<212> TYPE: DNA
<213> ORGANISM: Homo sapiens

<400> SEQUENCE: 1
tatagtggtt agtactctgc gttg                                          24

<210> SEQ ID NO 2
<211> LENGTH: 30
<212> TYPE: DNA
<213> ORGANISM: Homo sapiens

<400> SEQUENCE: 2
ggctcgttgg tctaggggta tgattctcgc                                    30

<210> SEQ ID NO 3
<211> LENGTH: 21
<212> TYPE: DNA
<213> ORGANISM: Homo sapiens

<400> SEQUENCE: 3
cgtatagtgg ttagtactct g                                             21

<210> SEQ ID NO 4
<211> LENGTH: 24
<212> TYPE: DNA
<213> ORGANISM: Homo sapiens

<400> SEQUENCE: 4
tcgtatagtg gttagtactc tgcg                                          24

<210> SEQ ID NO 5
<211> LENGTH: 21
<212> TYPE: DNA
<213> ORGANISM: Homo sapiens

<400> SEQUENCE: 5
taggatgggg tgtgataggt g                                             21

<210> SEQ ID NO 6
<211> LENGTH: 24
<212> TYPE: DNA
<213> ORGANISM: Homo sapiens

<400> SEQUENCE: 6
gctcagtggt agagcatttg actg                                          24
```

```
<210> SEQ ID NO 7
<211> LENGTH: 29
<212> TYPE: DNA
<213> ORGANISM: Homo sapiens

<400> SEQUENCE: 7
gcattggtgg ttcagtggta gaattctcg                                    29

<210> SEQ ID NO 8
<211> LENGTH: 30
<212> TYPE: DNA
<213> ORGANISM: Homo sapiens

<400> SEQUENCE: 8
agtaaggtca gctaaataag ctatcgggcc                                   30

<210> SEQ ID NO 9
<211> LENGTH: 25
<212> TYPE: DNA
<213> ORGANISM: Homo sapiens

<400> SEQUENCE: 9
ggtaaaatgg ctgagtgaag cattg                                        25

<210> SEQ ID NO 10
<211> LENGTH: 24
<212> TYPE: DNA
<213> ORGANISM: Homo sapiens

<400> SEQUENCE: 10
ggtaaaatgg ctgagtgaag catt                                         24

<210> SEQ ID NO 11
<211> LENGTH: 29
<212> TYPE: DNA
<213> ORGANISM: Homo sapiens

<400> SEQUENCE: 11
taaaatggct gagtgaagca ttggactgt                                    29

<210> SEQ ID NO 12
<211> LENGTH: 23
<212> TYPE: DNA
<213> ORGANISM: Homo sapiens

<400> SEQUENCE: 12
gttcttgtag ttgaaataca acg                                          23

<210> SEQ ID NO 13
<211> LENGTH: 25
<212> TYPE: DNA
<213> ORGANISM: Homo sapiens

<400> SEQUENCE: 13
aaaacatcag attgtgaatc tgaca                                        25

<210> SEQ ID NO 14
<211> LENGTH: 19
<212> TYPE: DNA
<213> ORGANISM: Homo sapiens

<400> SEQUENCE: 14
gggggtgtag ctcagtggt                                               19
```

```
<210> SEQ ID NO 15
<211> LENGTH: 24
<212> TYPE: DNA
<213> ORGANISM: Homo sapiens

<400> SEQUENCE: 15
tgtaatggtt agcactctgg actc                                          24

<210> SEQ ID NO 16
<211> LENGTH: 29
<212> TYPE: DNA
<213> ORGANISM: Homo sapiens

<400> SEQUENCE: 16
tccctggtgg tctagtggtt aggattcgg                                     29

<210> SEQ ID NO 17
<211> LENGTH: 23
<212> TYPE: DNA
<213> ORGANISM: Homo sapiens

<400> SEQUENCE: 17
ggggatgtag ctcagtggta gag                                           23

<210> SEQ ID NO 18
<211> LENGTH: 30
<212> TYPE: DNA
<213> ORGANISM: Homo sapiens

<400> SEQUENCE: 18
agaaatatgt ctgataaaag agttactttg                                    30

<210> SEQ ID NO 19
<211> LENGTH: 26
<212> TYPE: DNA
<213> ORGANISM: Homo sapiens

<400> SEQUENCE: 19
caaaacatca gattgtgaat ctgaca                                        26

<210> SEQ ID NO 20
<211> LENGTH: 22
<212> TYPE: DNA
<213> ORGANISM: Homo sapiens

<400> SEQUENCE: 20
tcgtatagtg gttagtactc tg                                            22

<210> SEQ ID NO 21
<211> LENGTH: 19
<212> TYPE: DNA
<213> ORGANISM: Homo sapiens

<400> SEQUENCE: 21
tgtttagacg ggctcacat                                                19

<210> SEQ ID NO 22
<211> LENGTH: 28
<212> TYPE: DNA
<213> ORGANISM: Homo sapiens

<400> SEQUENCE: 22
tccctggtgg tctagtggtt aggattcg                                      28
```

```
<210> SEQ ID NO 23
<211> LENGTH: 22
<212> TYPE: DNA
<213> ORGANISM: Homo sapiens

<400> SEQUENCE: 23
aatccagcga tccgagttca aa                                                  22

<210> SEQ ID NO 24
<211> LENGTH: 20
<212> TYPE: DNA
<213> ORGANISM: Homo sapiens

<400> SEQUENCE: 24
ggtagcgtgg ccgagcggtc                                                     20

<210> SEQ ID NO 25
<211> LENGTH: 23
<212> TYPE: DNA
<213> ORGANISM: Homo sapiens

<400> SEQUENCE: 25
cttacgaccc cttatttacc cca                                                 23

<210> SEQ ID NO 26
<211> LENGTH: 26
<212> TYPE: DNA
<213> ORGANISM: Homo sapiens

<400> SEQUENCE: 26
ctgccttcca agcagttgac ccgggt                                              26

<210> SEQ ID NO 27
<211> LENGTH: 23
<212> TYPE: DNA
<213> ORGANISM: Homo sapiens

<400> SEQUENCE: 27
cgtatagtgg ttagtactct gcg                                                 23

<210> SEQ ID NO 28
<211> LENGTH: 19
<212> TYPE: DNA
<213> ORGANISM: Homo sapiens

<400> SEQUENCE: 28
gtctctgtgg cgcaatgga                                                      19

<210> SEQ ID NO 29
<211> LENGTH: 30
<212> TYPE: DNA
<213> ORGANISM: Homo sapiens

<400> SEQUENCE: 29
gcccggctag ctcagtcggt agagcatggg                                          30

<210> SEQ ID NO 30
<211> LENGTH: 23
<212> TYPE: DNA
<213> ORGANISM: Homo sapiens

<400> SEQUENCE: 30
tgtaatggtt agcactctgg act                                                 23
```

```
<210> SEQ ID NO 31
<211> LENGTH: 26
<212> TYPE: DNA
<213> ORGANISM: Homo sapiens

<400> SEQUENCE: 31
tgatcgtata gtggttagta ctctgc                                        26

<210> SEQ ID NO 32
<211> LENGTH: 20
<212> TYPE: DNA
<213> ORGANISM: Homo sapiens

<400> SEQUENCE: 32
gtggtagaat tctcgcctgc                                               20

<210> SEQ ID NO 33
<211> LENGTH: 19
<212> TYPE: DNA
<213> ORGANISM: Homo sapiens

<400> SEQUENCE: 33
tggtagaatt ctcgcctgc                                                19

<210> SEQ ID NO 34
<211> LENGTH: 21
<212> TYPE: DNA
<213> ORGANISM: Homo sapiens

<400> SEQUENCE: 34
agtggtagaa ttctcgcctg c                                             21

<210> SEQ ID NO 35
<211> LENGTH: 22
<212> TYPE: DNA
<213> ORGANISM: Homo sapiens

<400> SEQUENCE: 35
gttcgattcc ccgacgggga gc                                            22

<210> SEQ ID NO 36
<211> LENGTH: 21
<212> TYPE: DNA
<213> ORGANISM: Homo sapiens

<400> SEQUENCE: 36
gagtgaagca ttggactgta a                                             21

<210> SEQ ID NO 37
<211> LENGTH: 22
<212> TYPE: DNA
<213> ORGANISM: Homo sapiens

<400> SEQUENCE: 37
cagtggtaga attctcgcct gc                                            22

<210> SEQ ID NO 38
<211> LENGTH: 20
<212> TYPE: DNA
<213> ORGANISM: Homo sapiens

<400> SEQUENCE: 38
tggtagaatt ctcgcctgcc                                               20
```

```
<210> SEQ ID NO 39
<211> LENGTH: 20
<212> TYPE: DNA
<213> ORGANISM: Homo sapiens

<400> SEQUENCE: 39
tggttagtac tctgcgttgt                                              20

<210> SEQ ID NO 40
<211> LENGTH: 23
<212> TYPE: DNA
<213> ORGANISM: Homo sapiens

<400> SEQUENCE: 40
gttcgattcc ccgacgggga gcc                                          23

<210> SEQ ID NO 41
<211> LENGTH: 23
<212> TYPE: DNA
<213> ORGANISM: Homo sapiens

<400> SEQUENCE: 41
ggttccatag tgtagtggtt atc                                          23

<210> SEQ ID NO 42
<211> LENGTH: 22
<212> TYPE: DNA
<213> ORGANISM: Homo sapiens

<400> SEQUENCE: 42
ggtagcgtgg ccgagtggtc ta                                           22

<210> SEQ ID NO 43
<211> LENGTH: 24
<212> TYPE: DNA
<213> ORGANISM: Homo sapiens

<400> SEQUENCE: 43
ggagatttca acttaacttg accg                                         24

<210> SEQ ID NO 44
<211> LENGTH: 21
<212> TYPE: DNA
<213> ORGANISM: Homo sapiens

<400> SEQUENCE: 44
ggggttttgc agtccttacc a                                            21

<210> SEQ ID NO 45
<211> LENGTH: 23
<212> TYPE: DNA
<213> ORGANISM: Homo sapiens

<400> SEQUENCE: 45
gtagtcgtgg ccgagtggtt aag                                          23

<210> SEQ ID NO 46
<211> LENGTH: 22
<212> TYPE: DNA
<213> ORGANISM: Homo sapiens

<400> SEQUENCE: 46
cactctggac tctgaatcca gc                                           22
```

```
<210> SEQ ID NO 47
<211> LENGTH: 23
<212> TYPE: DNA
<213> ORGANISM: Homo sapiens

<400> SEQUENCE: 47
ggagatttca acttaacttg acc                                              23

<210> SEQ ID NO 48
<211> LENGTH: 22
<212> TYPE: DNA
<213> ORGANISM: Homo sapiens

<400> SEQUENCE: 48
ggttcagtgg tagaattctc gc                                               22

<210> SEQ ID NO 49
<211> LENGTH: 22
<212> TYPE: DNA
<213> ORGANISM: Homo sapiens

<400> SEQUENCE: 49
tcgaaaccgg gcggaaacac ca                                               22

<210> SEQ ID NO 50
<211> LENGTH: 23
<212> TYPE: DNA
<213> ORGANISM: Homo sapiens

<400> SEQUENCE: 50
ggttccatgg tgtaatggtt agc                                              23

<210> SEQ ID NO 51
<211> LENGTH: 22
<212> TYPE: DNA
<213> ORGANISM: Homo sapiens

<400> SEQUENCE: 51
ggcgcggtgg ccaagtggta ag                                               22

<210> SEQ ID NO 52
<211> LENGTH: 23
<212> TYPE: DNA
<213> ORGANISM: Homo sapiens

<400> SEQUENCE: 52
ggttcagtgg tagaattctc gcc                                              23

<210> SEQ ID NO 53
<211> LENGTH: 22
<212> TYPE: DNA
<213> ORGANISM: Homo sapiens

<400> SEQUENCE: 53
tcgaatccca ccgctgccac ca                                               22

<210> SEQ ID NO 54
<211> LENGTH: 22
<212> TYPE: DNA
<213> ORGANISM: Homo sapiens

<400> SEQUENCE: 54
taatggttag cactctggac tc                                               22
```

<210> SEQ ID NO 55
<211> LENGTH: 23
<212> TYPE: DNA
<213> ORGANISM: Homo sapiens

<400> SEQUENCE: 55
gaaaaagtca tggaggccat ggg                                    23

<210> SEQ ID NO 56
<211> LENGTH: 20
<212> TYPE: DNA
<213> ORGANISM: Homo sapiens

<400> SEQUENCE: 56
gatttcaact taacttgacc                                        20

<210> SEQ ID NO 57
<211> LENGTH: 23
<212> TYPE: DNA
<213> ORGANISM: Homo sapiens

<400> SEQUENCE: 57
ggtcccatgg tgtaatggtt agc                                    23

<210> SEQ ID NO 58
<211> LENGTH: 21
<212> TYPE: DNA
<213> ORGANISM: Homo sapiens

<400> SEQUENCE: 58
cagtggtaga attctcgcct g                                      21

<210> SEQ ID NO 59
<211> LENGTH: 21
<212> TYPE: DNA
<213> ORGANISM: Homo sapiens

<400> SEQUENCE: 59
ctaagccagg gattgtgggt t                                      21

<210> SEQ ID NO 60
<211> LENGTH: 24
<212> TYPE: DNA
<213> ORGANISM: Homo sapiens

<400> SEQUENCE: 60
gggggtgtag ctcagtggta gagc                                   24

<210> SEQ ID NO 61
<211> LENGTH: 22
<212> TYPE: DNA
<213> ORGANISM: Homo sapiens

<400> SEQUENCE: 61
ctgtcacgcg ggagaccggg gt                                     22

<210> SEQ ID NO 62
<211> LENGTH: 20
<212> TYPE: DNA
<213> ORGANISM: Homo sapiens

<400> SEQUENCE: 62
cattggtcgt ggttgtagtc                                        20

```
<210> SEQ ID NO 63
<211> LENGTH: 17
<212> TYPE: DNA
<213> ORGANISM: Homo sapiens

<400> SEQUENCE: 63
aacttgaccg ctctgac                                                    17

<210> SEQ ID NO 64
<211> LENGTH: 19
<212> TYPE: DNA
<213> ORGANISM: Homo sapiens

<400> SEQUENCE: 64
ttggtcgtgg ttgtagtcc                                                  19

<210> SEQ ID NO 65
<211> LENGTH: 19
<212> TYPE: DNA
<213> ORGANISM: Homo sapiens

<400> SEQUENCE: 65
attggtcgtg gttgtagtc                                                  19

<210> SEQ ID NO 66
<211> LENGTH: 21
<212> TYPE: DNA
<213> ORGANISM: Homo sapiens

<400> SEQUENCE: 66
aacacctctt tacagtgacc a                                               21

<210> SEQ ID NO 67
<211> LENGTH: 20
<212> TYPE: DNA
<213> ORGANISM: Homo sapiens

<400> SEQUENCE: 67
attggtcgtg gttgtagtcc                                                 20

<210> SEQ ID NO 68
<211> LENGTH: 24
<212> TYPE: DNA
<213> ORGANISM: Homo sapiens

<400> SEQUENCE: 68
gtcgtggttg tagtccgtgc gaga                                            24

<210> SEQ ID NO 69
<211> LENGTH: 21
<212> TYPE: DNA
<213> ORGANISM: Homo sapiens

<400> SEQUENCE: 69
cattggtcgt ggttgtagtc c                                               21

<210> SEQ ID NO 70
<211> LENGTH: 21
<212> TYPE: DNA
<213> ORGANISM: Homo sapiens

<400> SEQUENCE: 70
actctggact ctgaatccag c                                               21
```

```
<210> SEQ ID NO 71
<211> LENGTH: 18
<212> TYPE: DNA
<213> ORGANISM: Homo sapiens

<400> SEQUENCE: 71
ttggtcgtgg ttgtagtc                                                 18

<210> SEQ ID NO 72
<211> LENGTH: 17
<212> TYPE: DNA
<213> ORGANISM: Homo sapiens

<400> SEQUENCE: 72 aagactttttt ctctgac                                                 17

<210> SEQ ID NO 73
<211> LENGTH: 18
<212> TYPE: DNA
<213> ORGANISM: Homo sapiens

<400> SEQUENCE: 73
agactttttc tctgacca                                                 18

<210> SEQ ID NO 74
<211> LENGTH: 17
<212> TYPE: DNA
<213> ORGANISM: Homo sapiens

<400> SEQUENCE: 74
ttgtgaatct gacaaca                                                  17

<210> SEQ ID NO 75
<211> LENGTH: 19
<212> TYPE: DNA
<213> ORGANISM: Homo sapiens

<400> SEQUENCE: 75
gtttatgtag cttacctcc                                                19

<210> SEQ ID NO 76
<211> LENGTH: 22
<212> TYPE: DNA
<213> ORGANISM: Homo sapiens

<400> SEQUENCE: 76
gagaaagctc acaagaactg ct                                            22

<210> SEQ ID NO 77
<211> LENGTH: 19
<212> TYPE: DNA
<213> ORGANISM: Homo sapiens

<400> SEQUENCE: 77
gagaaagctc acaagaact                                                19

<210> SEQ ID NO 78
<211> LENGTH: 16
<212> TYPE: DNA
<213> ORGANISM: Homo sapiens

<400> SEQUENCE: 78
caccccataa acacca                                                   16
```

```
<210> SEQ ID NO 79
<211> LENGTH: 18
<212> TYPE: DNA
<213> ORGANISM: Homo sapiens

<400> SEQUENCE: 79
atcccatcct cgtcgcca                                              18

<210> SEQ ID NO 80
<211> LENGTH: 17
<212> TYPE: DNA
<213> ORGANISM: Homo sapiens

<400> SEQUENCE: 80
tcccaccgct gccacca                                               17

<210> SEQ ID NO 81
<211> LENGTH: 18
<212> TYPE: DNA
<213> ORGANISM: Homo sapiens

<400> SEQUENCE: 81
ttcaggtcgc agtctccc                                              18

<210> SEQ ID NO 82
<211> LENGTH: 16
<212> TYPE: DNA
<213> ORGANISM: Homo sapiens

<400> SEQUENCE: 82
ctctttacag tgacca                                                16

<210> SEQ ID NO 83
<211> LENGTH: 19
<212> TYPE: DNA
<213> ORGANISM: Homo sapiens

<400> SEQUENCE: 83
ataacccaga ggtcgatgg                                             19

<210> SEQ ID NO 84
<211> LENGTH: 19
<212> TYPE: DNA
<213> ORGANISM: Homo sapiens

<400> SEQUENCE: 84
aacttgaccg ctctgacca                                             19

<210> SEQ ID NO 85
<211> LENGTH: 17
<212> TYPE: DNA
<213> ORGANISM: Homo sapiens

<400> SEQUENCE: 85
tccccggcac ctccacc                                               17

<210> SEQ ID NO 86
<211> LENGTH: 16
<212> TYPE: DNA
<213> ORGANISM: Homo sapiens

<400> SEQUENCE: 86
cccacttctg acacca                                                16
```

```
<210> SEQ ID NO 87
<211> LENGTH: 18
<212> TYPE: DNA
<213> ORGANISM: Homo sapiens

<400> SEQUENCE: 87
accctgctcg ctgcgcca                                                 18

<210> SEQ ID NO 88
<211> LENGTH: 20
<212> TYPE: DNA
<213> ORGANISM: Homo sapiens

<400> SEQUENCE: 88
agtggtagag catttgactg                                               20

<210> SEQ ID NO 89
<211> LENGTH: 22
<212> TYPE: DNA
<213> ORGANISM: Homo sapiens

<400> SEQUENCE: 89
gggggtgtag ctcagtggta ga                                            22

<210> SEQ ID NO 90
<211> LENGTH: 19
<212> TYPE: DNA
<213> ORGANISM: Homo sapiens

<400> SEQUENCE: 90
tggttagtac tctgcgttg                                                19

<210> SEQ ID NO 91
<211> LENGTH: 20
<212> TYPE: DNA
<213> ORGANISM: Homo sapiens

<400> SEQUENCE: 91
ctaagccagg gattgtgggt                                               20

<210> SEQ ID NO 92
<211> LENGTH: 21
<212> TYPE: DNA
<213> ORGANISM: Homo sapiens

<400> SEQUENCE: 92
tagtggttag tactctgcgt t                                             21

<210> SEQ ID NO 93
<211> LENGTH: 21
<212> TYPE: DNA
<213> ORGANISM: Homo sapiens

<400> SEQUENCE: 93
tagaattctc gcctgccacg c                                             21

<210> SEQ ID NO 94
<211> LENGTH: 19
<212> TYPE: DNA
<213> ORGANISM: Homo sapiens

<400> SEQUENCE: 94
gtggttagta ctctgcgtt                                                19
```

-continued

<210> SEQ ID NO 95
<211> LENGTH: 17
<212> TYPE: DNA
<213> ORGANISM: Homo sapiens

<400> SEQUENCE: 95
tcccaccaga gtcgcca                                                17

<210> SEQ ID NO 96
<211> LENGTH: 17
<212> TYPE: DNA
<213> ORGANISM: Homo sapiens

<400> SEQUENCE: 96
ttccggctcg aaggacc                                                17

<210> SEQ ID NO 97
<211> LENGTH: 18
<212> TYPE: DNA
<213> ORGANISM: Homo sapiens

<400> SEQUENCE: 97
gtagtcgtgg ccgagtgg                                               18

<210> SEQ ID NO 98
<211> LENGTH: 17
<212> TYPE: DNA
<213> ORGANISM: Homo sapiens

<400> SEQUENCE: 98
tccggctcgg aggacca                                                17

<210> SEQ ID NO 99
<211> LENGTH: 16
<212> TYPE: DNA
<213> ORGANISM: Homo sapiens

<400> SEQUENCE: 99
cccaccagag tcgcca                                                 16

<210> SEQ ID NO 100
<211> LENGTH: 17
<212> TYPE: DNA
<213> ORGANISM: Homo sapiens

<400> SEQUENCE: 100
tcctgccgac tacgcca                                                17

<210> SEQ ID NO 101
<211> LENGTH: 16
<212> TYPE: DNA
<213> ORGANISM: Homo sapiens

<400> SEQUENCE: 101
cccagcggtg cctcca                                                 16

<210> SEQ ID NO 102
<211> LENGTH: 17
<212> TYPE: DNA
<213> ORGANISM: Homo sapiens

<400> SEQUENCE: 102
tctcggtggg acctcca                                                17

```
<210> SEQ ID NO 103
<211> LENGTH: 18
<212> TYPE: DNA
<213> ORGANISM: Homo sapiens

<400> SEQUENCE: 103
gtcccaccag agtcgcca                                                   18

<210> SEQ ID NO 104
<211> LENGTH: 18
<212> TYPE: DNA
<213> ORGANISM: Homo sapiens

<400> SEQUENCE: 104
atcccggacg agccccca                                                   18

<210> SEQ ID NO 105
<211> LENGTH: 18
<212> TYPE: DNA
<213> ORGANISM: Homo sapiens

<400> SEQUENCE: 105
atcacgtcgg ggtcacca                                                   18

<210> SEQ ID NO 106
<211> LENGTH: 18
<212> TYPE: DNA
<213> ORGANISM: Homo sapiens

<400> SEQUENCE: 106
atcccaccag agtcgcca                                                   18

<210> SEQ ID NO 107
<211> LENGTH: 16
<212> TYPE: DNA
<213> ORGANISM: Homo sapiens

<400> SEQUENCE: 107
ccggctcgaa ggacca                                                     16

<210> SEQ ID NO 108
<211> LENGTH: 18
<212> TYPE: DNA
<213> ORGANISM: Homo sapiens

<400> SEQUENCE: 108
gacccagtgg cctaatgg                                                   18

<210> SEQ ID NO 109
<211> LENGTH: 21
<212> TYPE: DNA
<213> ORGANISM: Homo sapiens

<400> SEQUENCE: 109 gggggatgtag ctcagtggta g                                              21

<210> SEQ ID NO 110
<211> LENGTH: 18
<212> TYPE: DNA
<213> ORGANISM: Homo sapiens

<400> SEQUENCE: 110
gggggtgtag ctcagtgg                                                   18
```

-continued

<210> SEQ ID NO 111
<211> LENGTH: 18
<212> TYPE: DNA
<213> ORGANISM: Homo sapiens

<400> SEQUENCE: 111
gacctcgtgg cgcaacgg                                                 18

<210> SEQ ID NO 112
<211> LENGTH: 19
<212> TYPE: DNA
<213> ORGANISM: Homo sapiens

<400> SEQUENCE: 112
tgaatctgac aacagaggc                                                19

<210> SEQ ID NO 113
<211> LENGTH: 18
<212> TYPE: DNA
<213> ORGANISM: Homo sapiens

<400> SEQUENCE: 113
ggctccgtgg cgcaatgg                                                 18

<210> SEQ ID NO 114
<211> LENGTH: 17
<212> TYPE: DNA
<213> ORGANISM: Homo sapiens

<400> SEQUENCE: 114
ctctgtggcg caatcgg                                                  17

<210> SEQ ID NO 115
<211> LENGTH: 18
<212> TYPE: DNA
<213> ORGANISM: Homo sapiens

<400> SEQUENCE: 115
ggccgcgtgg cctaatgg                                                 18

<210> SEQ ID NO 116
<211> LENGTH: 19
<212> TYPE: DNA
<213> ORGANISM: Homo sapiens

<400> SEQUENCE: 116
ggttccatag tgtagtggt                                                19

<210> SEQ ID NO 117
<211> LENGTH: 24
<212> TYPE: DNA
<213> ORGANISM: Homo sapiens

<400> SEQUENCE: 117
gacgaggtgg ccgagtggtt aagg                                          24

<210> SEQ ID NO 118
<211> LENGTH: 24
<212> TYPE: DNA
<213> ORGANISM: Homo sapiens

<400> SEQUENCE: 118
tggttagtac tctgcgttgt ggcc                                          24

```
<210> SEQ ID NO 119
<211> LENGTH: 18
<212> TYPE: DNA
<213> ORGANISM: Homo sapiens

<400> SEQUENCE: 119
gggggtatag ctcagtgg                                                 18

<210> SEQ ID NO 120
<211> LENGTH: 19
<212> TYPE: DNA
<213> ORGANISM: Homo sapiens

<400> SEQUENCE: 120
gcctcgttag cgcagtagg                                                19

<210> SEQ ID NO 121
<211> LENGTH: 22
<212> TYPE: DNA
<213> ORGANISM: Homo sapiens

<400> SEQUENCE: 121
tcgaatccca ctcctgacac ca                                            22

<210> SEQ ID NO 122
<211> LENGTH: 23
<212> TYPE: DNA
<213> ORGANISM: Homo sapiens

<400> SEQUENCE: 122
ctgtagatcc ttaggtcgct ggt                                           23

<210> SEQ ID NO 123
<211> LENGTH: 22
<212> TYPE: DNA
<213> ORGANISM: Homo sapiens

<400> SEQUENCE: 123
tcgaatccca cttctgacac ca                                            22

<210> SEQ ID NO 124
<211> LENGTH: 27
<212> TYPE: DNA
<213> ORGANISM: Homo sapiens

<400> SEQUENCE: 124
tggtgtaatg gttagcactc tggactc                                       27

<210> SEQ ID NO 125
<211> LENGTH: 23
<212> TYPE: DNA
<213> ORGANISM: Homo sapiens

<400> SEQUENCE: 125
tggtgtaatg gttagcactc tgg                                           23

<210> SEQ ID NO 126
<211> LENGTH: 22
<212> TYPE: DNA
<213> ORGANISM: Homo sapiens

<400> SEQUENCE: 126
ctttgaatcc agcgatccga gt                                            22
```

```
<210> SEQ ID NO 127
<211> LENGTH: 22
<212> TYPE: DNA
<213> ORGANISM: Homo sapiens

<400> SEQUENCE: 127
tcaatccccg gcacctccac ca                                        22

<210> SEQ ID NO 128
<211> LENGTH: 22
<212> TYPE: DNA
<213> ORGANISM: Homo sapiens

<400> SEQUENCE: 128
tcgatccccg gcatctccac ca                                        22

<210> SEQ ID NO 129
<211> LENGTH: 21
<212> TYPE: DNA
<213> ORGANISM: Homo sapiens

<400> SEQUENCE: 129
cactgtaaag ctaacttagc a                                         21

<210> SEQ ID NO 130
<211> LENGTH: 19
<212> TYPE: DNA
<213> ORGANISM: Homo sapiens

<400> SEQUENCE: 130
atggttagca ctctggact                                            19

<210> SEQ ID NO 131
<211> LENGTH: 29
<212> TYPE: DNA
<213> ORGANISM: Homo sapiens

<400> SEQUENCE: 131
atttcaactt aacttgaccg ctctgacca                                 29

<210> SEQ ID NO 132
<211> LENGTH: 19
<212> TYPE: DNA
<213> ORGANISM: Homo sapiens

<400> SEQUENCE: 132
ggtagcgtgg ccgagcggt                                            19

<210> SEQ ID NO 133
<211> LENGTH: 16
<212> TYPE: DNA
<213> ORGANISM: Homo sapiens

<400> SEQUENCE: 133
ggggtatgat tctcgc                                               16

<210> SEQ ID NO 134
<211> LENGTH: 18
<212> TYPE: DNA
<213> ORGANISM: Homo sapiens

<400> SEQUENCE: 134
atcctgccga ctacgcca                                             18
```

```
<210> SEQ ID NO 135
<211> LENGTH: 19
<212> TYPE: DNA
<213> ORGANISM: Homo sapiens

<400> SEQUENCE: 135
cactctggac tctgaatcc                                                   19

<210> SEQ ID NO 136
<211> LENGTH: 17
<212> TYPE: DNA
<213> ORGANISM: Homo sapiens

<400> SEQUENCE: 136
cccacccagg gacgcca                                                     17

<210> SEQ ID NO 137
<211> LENGTH: 18
<212> TYPE: DNA
<213> ORGANISM: Homo sapiens

<400> SEQUENCE: 137
ggctcgttgg tctagggg                                                    18

<210> SEQ ID NO 138
<211> LENGTH: 18
<212> TYPE: DNA
<213> ORGANISM: Homo sapiens

<400> SEQUENCE: 138
agtggttagt actctgcg                                                    18

<210> SEQ ID NO 139
<211> LENGTH: 16
<212> TYPE: DNA
<213> ORGANISM: Homo sapiens

<400> SEQUENCE: 139
cggttaggat tcctgg                                                      16

<210> SEQ ID NO 140
<211> LENGTH: 18
<212> TYPE: DNA
<213> ORGANISM: Homo sapiens

<400> SEQUENCE: 140
aatggttagc actctgga                                                    18

<210> SEQ ID NO 141
<211> LENGTH: 17
<212> TYPE: DNA
<213> ORGANISM: Homo sapiens

<400> SEQUENCE: 141
gaattctcgc ctgccac                                                     17

<210> SEQ ID NO 142
<211> LENGTH: 19
<212> TYPE: DNA
<213> ORGANISM: Homo sapiens

<400> SEQUENCE: 142
gtggtagagc atttgactg                                                   19
```

```
<210> SEQ ID NO 143
<211> LENGTH: 17
<212> TYPE: DNA
<213> ORGANISM: Homo sapiens

<400> SEQUENCE: 143
tccgggtgcc ccctcca                                                  17

<210> SEQ ID NO 144
<211> LENGTH: 18
<212> TYPE: DNA
<213> ORGANISM: Homo sapiens

<400> SEQUENCE: 144
tggttagtac tctgcgtt                                                 18

<210> SEQ ID NO 145
<211> LENGTH: 18
<212> TYPE: DNA
<213> ORGANISM: Homo sapiens

<400> SEQUENCE: 145 tagggtatg attctcgg                                                  18

<210> SEQ ID NO 146
<211> LENGTH: 19
<212> TYPE: DNA
<213> ORGANISM: Homo sapiens

<400> SEQUENCE: 146
ctgtagatcc ttaggtcgc                                                19

<210> SEQ ID NO 147
<211> LENGTH: 17
<212> TYPE: DNA
<213> ORGANISM: Homo sapiens

<400> SEQUENCE: 147
ggctcgttgg tctaggg                                                  17

<210> SEQ ID NO 148
<211> LENGTH: 20
<212> TYPE: DNA
<213> ORGANISM: Homo sapiens

<400> SEQUENCE: 148
ccggagctgg ggattgtggg                                               20

<210> SEQ ID NO 149
<211> LENGTH: 19
<212> TYPE: DNA
<213> ORGANISM: Homo sapiens

<400> SEQUENCE: 149
ggagctgggg attgtgggt                                                19

<210> SEQ ID NO 150
<211> LENGTH: 18
<212> TYPE: DNA
<213> ORGANISM: Homo sapiens

<400> SEQUENCE: 150
tagtggttag tactctgc                                                 18
```

```
<210> SEQ ID NO 151
<211> LENGTH: 17
<212> TYPE: DNA
<213> ORGANISM: Homo sapiens

<400> SEQUENCE: 151
gtggttagta ctctgcg                                                    17

<210> SEQ ID NO 152
<211> LENGTH: 17
<212> TYPE: DNA
<213> ORGANISM: Homo sapiens

<400> SEQUENCE: 152
tctcgctggg gcctcca                                                    17

<210> SEQ ID NO 153
<211> LENGTH: 19
<212> TYPE: DNA
<213> ORGANISM: Homo sapiens

<400> SEQUENCE: 153
cggagctggg gattgtggg                                                  19

<210> SEQ ID NO 154
<211> LENGTH: 18
<212> TYPE: DNA
<213> ORGANISM: Homo sapiens

<400> SEQUENCE: 154
cactctggac tttgaatc                                                   18

<210> SEQ ID NO 155
<211> LENGTH: 16
<212> TYPE: DNA
<213> ORGANISM: Homo sapiens

<400> SEQUENCE: 155
tggttagtac tctgcg                                                     16

<210> SEQ ID NO 156
<211> LENGTH: 18
<212> TYPE: DNA
<213> ORGANISM: Homo sapiens

<400> SEQUENCE: 156
atcctgctca cagcgcca                                                   18

<210> SEQ ID NO 157
<211> LENGTH: 17
<212> TYPE: DNA
<213> ORGANISM: Homo sapiens

<400> SEQUENCE: 157
tggttagtac tctgcgt                                                    17

<210> SEQ ID NO 158
<211> LENGTH: 18
<212> TYPE: DNA
<213> ORGANISM: Homo sapiens

<400> SEQUENCE: 158
cggagctggg gattgtgg                                                   18
```

```
<210> SEQ ID NO 159
<211> LENGTH: 19
<212> TYPE: DNA
<213> ORGANISM: Homo sapiens

<400> SEQUENCE: 159
tagtggttag tactctgcg                                               19

<210> SEQ ID NO 160
<211> LENGTH: 18
<212> TYPE: DNA
<213> ORGANISM: Homo sapiens

<400> SEQUENCE: 160
accccactcc tggtacca                                                18

<210> SEQ ID NO 161
<211> LENGTH: 19
<212> TYPE: DNA
<213> ORGANISM: Homo sapiens

<400> SEQUENCE: 161
gctctcaccg ccgcggccc                                               19

<210> SEQ ID NO 162
<211> LENGTH: 18
<212> TYPE: DNA
<213> ORGANISM: Homo sapiens

<400> SEQUENCE: 162
gtccctgttc gggcgcca                                                18

<210> SEQ ID NO 163
<211> LENGTH: 19
<212> TYPE: DNA
<213> ORGANISM: Homo sapiens

<400> SEQUENCE: 163
agatcaagag gtccccggt                                               19

<210> SEQ ID NO 164
<211> LENGTH: 18
<212> TYPE: DNA
<213> ORGANISM: Homo sapiens

<400> SEQUENCE: 164
cagtggtaga gcatttga                                                18

<210> SEQ ID NO 165
<211> LENGTH: 18
<212> TYPE: DNA
<213> ORGANISM: Homo sapiens

<400> SEQUENCE: 165
gtcctgccgc ggtcgcca                                                18

<210> SEQ ID NO 166
<211> LENGTH: 22
<212> TYPE: DNA
<213> ORGANISM: Homo sapiens

<400> SEQUENCE: 166
ttagcactct ggactctgaa tc                                           22
```

```
<210> SEQ ID NO 167
<211> LENGTH: 24
<212> TYPE: DNA
<213> ORGANISM: Homo sapiens

<400> SEQUENCE: 167
cataacccag aggtcgatgg atcg                                          24

<210> SEQ ID NO 168
<211> LENGTH: 23
<212> TYPE: DNA
<213> ORGANISM: Homo sapiens

<400> SEQUENCE: 168
ttagcactct ggactctgaa tcc                                           23

<210> SEQ ID NO 169
<211> LENGTH: 22
<212> TYPE: DNA
<213> ORGANISM: Homo sapiens

<400> SEQUENCE: 169
tagcactctg gactctgaat cc                                            22

<210> SEQ ID NO 170
<211> LENGTH: 22
<212> TYPE: DNA
<213> ORGANISM: Homo sapiens

<400> SEQUENCE: 170
tccctgtggt ctagtggtta gg                                            22

<210> SEQ ID NO 171
<211> LENGTH: 17
<212> TYPE: DNA
<213> ORGANISM: Homo sapiens

<400> SEQUENCE: 171
tcccacttct gacacca                                                  17

<210> SEQ ID NO 172
<211> LENGTH: 21
<212> TYPE: DNA
<213> ORGANISM: Homo sapiens

<400> SEQUENCE: 172
tcgattccgg ctcgaaggac c                                             21

<210> SEQ ID NO 173
<211> LENGTH: 22
<212> TYPE: DNA
<213> ORGANISM: Homo sapiens

<400> SEQUENCE: 173
ttagcactct ggactttgaa tc                                            22

<210> SEQ ID NO 174
<211> LENGTH: 23
<212> TYPE: DNA
<213> ORGANISM: Homo sapiens

<400> SEQUENCE: 174
ttagcactct ggactttgaa tcc                                           23
```

```
<210> SEQ ID NO 175
<211> LENGTH: 23
<212> TYPE: DNA
<213> ORGANISM: Homo sapiens

<400> SEQUENCE: 175
tagcactctg gactctgaat cca                                          23

<210> SEQ ID NO 176
<211> LENGTH: 24
<212> TYPE: DNA
<213> ORGANISM: Homo sapiens

<400> SEQUENCE: 176
agcactctgg actctgaatc cagc                                         24

<210> SEQ ID NO 177
<211> LENGTH: 21
<212> TYPE: DNA
<213> ORGANISM: Homo sapiens

<400> SEQUENCE: 177
tagcactctg gactctgaat c                                            21

<210> SEQ ID NO 178
<211> LENGTH: 22
<212> TYPE: DNA
<213> ORGANISM: Homo sapiens

<400> SEQUENCE: 178
tccctggtgg tctagtggtt ag                                           22

<210> SEQ ID NO 179
<211> LENGTH: 22
<212> TYPE: DNA
<213> ORGANISM: Homo sapiens

<400> SEQUENCE: 179
agcactctgg actctgaatc ca                                           22

<210> SEQ ID NO 180
<211> LENGTH: 23
<212> TYPE: DNA
<213> ORGANISM: Homo sapiens

<400> SEQUENCE: 180
gcactctgga ctctgaatcc agc                                          23

<210> SEQ ID NO 181
<211> LENGTH: 24
<212> TYPE: DNA
<213> ORGANISM: Homo sapiens

<400> SEQUENCE: 181
gctcacatca ccccataaac acca                                         24

<210> SEQ ID NO 182
<211> LENGTH: 23
<212> TYPE: DNA
<213> ORGANISM: Homo sapiens

<400> SEQUENCE: 182
aacatcagat tgtgaatctg aca                                          23
```

```
<210> SEQ ID NO 183
<211> LENGTH: 22
<212> TYPE: DNA
<213> ORGANISM: Homo sapiens

<400> SEQUENCE: 183
tcacatcacc ccataaacac ca                                              22

<210> SEQ ID NO 184
<211> LENGTH: 23
<212> TYPE: DNA
<213> ORGANISM: Homo sapiens

<400> SEQUENCE: 184
cactgtaaag ctaacttagc att                                             23

<210> SEQ ID NO 185
<211> LENGTH: 19
<212> TYPE: DNA
<213> ORGANISM: Homo sapiens

<400> SEQUENCE: 185
catcacccca taaacacca                                                  19

<210> SEQ ID NO 186
<211> LENGTH: 23
<212> TYPE: DNA
<213> ORGANISM: Homo sapiens

<400> SEQUENCE: 186
ctcacatcac cccataaaca cca                                             23

<210> SEQ ID NO 187
<211> LENGTH: 17
<212> TYPE: DNA
<213> ORGANISM: Homo sapiens

<400> SEQUENCE: 187
agtggtagaa ttctcgc                                                    17

<210> SEQ ID NO 188
<211> LENGTH: 20
<212> TYPE: DNA
<213> ORGANISM: Homo sapiens

<400> SEQUENCE: 188
tgccgtgatc gtatagtggt                                                 20

<210> SEQ ID NO 189
<211> LENGTH: 20
<212> TYPE: DNA
<213> ORGANISM: Homo sapiens

<400> SEQUENCE: 189
ctctggactc tgaatccagc                                                 20

<210> SEQ ID NO 190
<211> LENGTH: 17
<212> TYPE: DNA
<213> ORGANISM: Homo sapiens

<400> SEQUENCE: 190
atcccaccgc tgccacc                                                    17
```

```
<210> SEQ ID NO 191
<211> LENGTH: 18
<212> TYPE: DNA
<213> ORGANISM: Homo sapiens

<400> SEQUENCE: 191
atccgggtgc ccctcca                                                   18

<210> SEQ ID NO 192
<211> LENGTH: 18
<212> TYPE: DNA
<213> ORGANISM: Homo sapiens

<400> SEQUENCE: 192
atccggctcg gaggacca                                                  18

<210> SEQ ID NO 193
<211> LENGTH: 18
<212> TYPE: DNA
<213> ORGANISM: Homo sapiens

<400> SEQUENCE: 193
atctcggtgg gacctcca                                                  18

<210> SEQ ID NO 194
<211> LENGTH: 20
<212> TYPE: DNA
<213> ORGANISM: Homo sapiens

<400> SEQUENCE: 194
ggggatgtag ctcagtggta                                                20

<210> SEQ ID NO 195
<211> LENGTH: 20
<212> TYPE: DNA
<213> ORGANISM: Homo sapiens

<400> SEQUENCE: 195
gcattggtgg ttcagtggta                                                20

<210> SEQ ID NO 196
<211> LENGTH: 26
<212> TYPE: DNA
<213> ORGANISM: Homo sapiens

<400> SEQUENCE: 196
ggagatttca acttaacttg accgct                                         26

<210> SEQ ID NO 197
<211> LENGTH: 19
<212> TYPE: DNA
<213> ORGANISM: Homo sapiens

<400> SEQUENCE: 197
aatctcggtg gaacctcca                                                 19

<210> SEQ ID NO 198
<211> LENGTH: 18
<212> TYPE: DNA
<213> ORGANISM: Homo sapiens

<400> SEQUENCE: 198
cagtggtaga attctcgc                                                  18
```

```
<210> SEQ ID NO 199
<211> LENGTH: 20
<212> TYPE: DNA
<213> ORGANISM: Homo sapiens

<400> SEQUENCE: 199
gcatgggtgg ttcagtggta                                              20

<210> SEQ ID NO 200
<211> LENGTH: 18
<212> TYPE: DNA
<213> ORGANISM: Homo sapiens

<400> SEQUENCE: 200
ctggactctg aatccagc                                                18

<210> SEQ ID NO 201
<211> LENGTH: 18
<212> TYPE: DNA
<213> ORGANISM: Homo sapiens

<400> SEQUENCE: 201
gcgttggtgg tatagtgg                                                18

<210> SEQ ID NO 202
<211> LENGTH: 16
<212> TYPE: DNA
<213> ORGANISM: Homo sapiens

<400> SEQUENCE: 202
tcccacatgg tctagc                                                  16

<210> SEQ ID NO 203
<211> LENGTH: 18
<212> TYPE: DNA
<213> ORGANISM: Homo sapiens

<400> SEQUENCE: 203
gtttccgtag tgtagtgg                                                18

<210> SEQ ID NO 204
<211> LENGTH: 16
<212> TYPE: DNA
<213> ORGANISM: Homo sapiens

<400> SEQUENCE: 204
gcgttggtgg tatagt                                                  16

<210> SEQ ID NO 205
<211> LENGTH: 16
<212> TYPE: DNA
<213> ORGANISM: Homo sapiens

<400> SEQUENCE: 205
ggctcgttgg tctagg                                                  16

<210> SEQ ID NO 206
<211> LENGTH: 19
<212> TYPE: DNA
<213> ORGANISM: Homo sapiens

<400> SEQUENCE: 206
tggttagcac tctggactc                                               19
```

<210> SEQ ID NO 207
<211> LENGTH: 18
<212> TYPE: DNA
<213> ORGANISM: Homo sapiens

<400> SEQUENCE: 207
attggtcgtg gttgtagt                                                 18

<210> SEQ ID NO 208
<211> LENGTH: 16
<212> TYPE: DNA
<213> ORGANISM: Homo sapiens

<400> SEQUENCE: 208
cccaccgctg ccacca                                                   16

<210> SEQ ID NO 209
<211> LENGTH: 18
<212> TYPE: DNA
<213> ORGANISM: Homo sapiens

<400> SEQUENCE: 209
actctggact ctgaatcc                                                 18

<210> SEQ ID NO 210
<211> LENGTH: 16
<212> TYPE: DNA
<213> ORGANISM: Homo sapiens

<400> SEQUENCE: 210
caacttaact tgaccg                                                   16

<210> SEQ ID NO 211
<211> LENGTH: 17
<212> TYPE: DNA
<213> ORGANISM: Homo sapiens

<400> SEQUENCE: 211
ctctggactc tgaatcc                                                  17

<210> SEQ ID NO 212
<211> LENGTH: 16
<212> TYPE: DNA
<213> ORGANISM: Homo sapiens

<400> SEQUENCE: 212
cccagtggaa ccacca                                                   16

<210> SEQ ID NO 213
<211> LENGTH: 20
<212> TYPE: DNA
<213> ORGANISM: Homo sapiens

<400> SEQUENCE: 213
atggttagca ctctggactc                                               20

<210> SEQ ID NO 214
<211> LENGTH: 19
<212> TYPE: DNA
<213> ORGANISM: Homo sapiens

<400> SEQUENCE: 214
gcattggtgg ttcagtggt                                                19

```
<210> SEQ ID NO 215
<211> LENGTH: 16
<212> TYPE: DNA
<213> ORGANISM: Homo sapiens

<400> SEQUENCE: 215
tctggactct gaatcc                                                     16

<210> SEQ ID NO 216
<211> LENGTH: 21
<212> TYPE: DNA
<213> ORGANISM: Homo sapiens

<400> SEQUENCE: 216
gtgtaatggt tagcactctg g                                               21

<210> SEQ ID NO 217
<211> LENGTH: 18
<212> TYPE: DNA
<213> ORGANISM: Homo sapiens

<400> SEQUENCE: 217
gcattggtgg ttcagtgg                                                   18

<210> SEQ ID NO 218
<211> LENGTH: 27
<212> TYPE: DNA
<213> ORGANISM: Homo sapiens

<400> SEQUENCE: 218
tccctggtgg tctagtggtt aggattc                                         27

<210> SEQ ID NO 219
<211> LENGTH: 29
<212> TYPE: DNA
<213> ORGANISM: Homo sapiens

<400> SEQUENCE: 219
gggggtatag ctcaggggta gagcatttg                                       29

<210> SEQ ID NO 220
<211> LENGTH: 24
<212> TYPE: DNA
<213> ORGANISM: Homo sapiens

<400> SEQUENCE: 220
gacccagtgg cctaatggat aagg                                            24

<210> SEQ ID NO 221
<211> LENGTH: 25
<212> TYPE: DNA
<213> ORGANISM: Homo sapiens

<400> SEQUENCE: 221
ggtagcgtgg ccgagcggtc taagg                                           25

<210> SEQ ID NO 222
<211> LENGTH: 30
<212> TYPE: DNA
<213> ORGANISM: Homo sapiens

<400> SEQUENCE: 222
gcatgggtgg ttcagtggta gaattctcgc                                      30
```

```
<210> SEQ ID NO 223
<211> LENGTH: 24
<212> TYPE: DNA
<213> ORGANISM: Homo sapiens

<400> SEQUENCE: 223
ggggatgtag ctcagtggta gagc                                          24

<210> SEQ ID NO 224
<211> LENGTH: 22
<212> TYPE: DNA
<213> ORGANISM: Homo sapiens

<400> SEQUENCE: 224
taacccagag gtcgatggat cg                                            22

<210> SEQ ID NO 225
<211> LENGTH: 29
<212> TYPE: DNA
<213> ORGANISM: Homo sapiens

<400> SEQUENCE: 225
gcactggtgg ttcagtggta gaattctcg                                     29

<210> SEQ ID NO 226
<211> LENGTH: 26
<212> TYPE: DNA
<213> ORGANISM: Homo sapiens

<400> SEQUENCE: 226
tcccacatgg tctagcggtt aggatt                                        26

<210> SEQ ID NO 227
<211> LENGTH: 22
<212> TYPE: DNA
<213> ORGANISM: Homo sapiens

<400> SEQUENCE: 227
tcccacatgg tctagcggtt ag                                            22

<210> SEQ ID NO 228
<211> LENGTH: 26
<212> TYPE: DNA
<213> ORGANISM: Homo sapiens

<400> SEQUENCE: 228
tccctggtgg tctagtggtt aggatt                                        26

<210> SEQ ID NO 229
<211> LENGTH: 30
<212> TYPE: DNA
<213> ORGANISM: Homo sapiens

<400> SEQUENCE: 229
gcactggtgg ttcagtggta gaattctcgc                                    30

<210> SEQ ID NO 230
<211> LENGTH: 25
<212> TYPE: DNA
<213> ORGANISM: Homo sapiens

<400> SEQUENCE: 230
ggctcgttgg tctaggggta tgatt                                         25
```

```
<210> SEQ ID NO 231
<211> LENGTH: 28
<212> TYPE: DNA
<213> ORGANISM: Homo sapiens

<400> SEQUENCE: 231
gcatgggtgg ttcagtggta gaattctc                                    28

<210> SEQ ID NO 232
<211> LENGTH: 27
<212> TYPE: DNA
<213> ORGANISM: Homo sapiens

<400> SEQUENCE: 232
gcatgggtgg ttcagtggta gaattct                                     27

<210> SEQ ID NO 233
<211> LENGTH: 24
<212> TYPE: DNA
<213> ORGANISM: Homo sapiens

<400> SEQUENCE: 233
tcccacatgg tctagcggtt agga                                        24

<210> SEQ ID NO 234
<211> LENGTH: 24
<212> TYPE: DNA
<213> ORGANISM: Homo sapiens

<400> SEQUENCE: 234
gtagtcgtgg ccgagtggtt aagg                                        24

<210> SEQ ID NO 235
<211> LENGTH: 30
<212> TYPE: DNA
<213> ORGANISM: Homo sapiens

<400> SEQUENCE: 235
tccctggtgg tctagtggct aggattcggc                                  30

<210> SEQ ID NO 236
<211> LENGTH: 22
<212> TYPE: DNA
<213> ORGANISM: Homo sapiens

<400> SEQUENCE: 236
tggccgcagc aacctcggtt cg                                          22

<210> SEQ ID NO 237
<211> LENGTH: 30
<212> TYPE: DNA
<213> ORGANISM: Homo sapiens

<400> SEQUENCE: 237
gtcaggatgg ccgagcggtc taaggcgctg                                  30

<210> SEQ ID NO 238
<211> LENGTH: 24
<212> TYPE: DNA
<213> ORGANISM: Homo sapiens

<400> SEQUENCE: 238
gtgtaatggt tagcactctg gact                                        24
```

```
<210> SEQ ID NO 239
<211> LENGTH: 23
<212> TYPE: DNA
<213> ORGANISM: Homo sapiens

<400> SEQUENCE: 239
gtttccgtag tgtagtggtc atc                                              23

<210> SEQ ID NO 240
<211> LENGTH: 23
<212> TYPE: DNA
<213> ORGANISM: Homo sapiens

<400> SEQUENCE: 240
gttcagtggt agaattctcg cct                                              23

<210> SEQ ID NO 241
<211> LENGTH: 30
<212> TYPE: DNA
<213> ORGANISM: Homo sapiens

<400> SEQUENCE: 241
gtttccgtag tgtagtggtt atcacgttcg                                       30

<210> SEQ ID NO 242
<211> LENGTH: 24
<212> TYPE: DNA
<213> ORGANISM: Homo sapiens

<400> SEQUENCE: 242
ggcgcggtgg ccaagtggta aggc                                             24

<210> SEQ ID NO 243
<211> LENGTH: 29
<212> TYPE: DNA
<213> ORGANISM: Homo sapiens

<400> SEQUENCE: 243
tcgtggttgt agtccgtgcg agaatacca                                        29

<210> SEQ ID NO 244
<211> LENGTH: 26
<212> TYPE: DNA
<213> ORGANISM: Homo sapiens

<400> SEQUENCE: 244
tggttgtagt ccgtgcgaga atacca                                           26

<210> SEQ ID NO 245
<211> LENGTH: 22
<212> TYPE: DNA
<213> ORGANISM: Homo sapiens

<400> SEQUENCE: 245
tcccatatgg tctagcggtt ag                                               22

<210> SEQ ID NO 246
<211> LENGTH: 26
<212> TYPE: DNA
<213> ORGANISM: Homo sapiens

<400> SEQUENCE: 246
tttcaactta acttgaccgc tctgac                                           26
```

```
<210> SEQ ID NO 247
<211> LENGTH: 23
<212> TYPE: DNA
<213> ORGANISM: Homo sapiens

<400> SEQUENCE: 247
tcccatatgg tctagcggtt agg                                        23

<210> SEQ ID NO 248
<211> LENGTH: 24
<212> TYPE: DNA
<213> ORGANISM: Homo sapiens

<400> SEQUENCE: 248
tcaacttaac ttgaccgctc tgac                                       24

<210> SEQ ID NO 249
<211> LENGTH: 25
<212> TYPE: DNA
<213> ORGANISM: Homo sapiens

<400> SEQUENCE: 249
gagaaagctc acaagaactg ctaac                                      25

<210> SEQ ID NO 250
<211> LENGTH: 23
<212> TYPE: DNA
<213> ORGANISM: Homo sapiens

<400> SEQUENCE: 250
gcccccatgt ctaacaacat ggc                                        23

<210> SEQ ID NO 251
<211> LENGTH: 26
<212> TYPE: DNA
<213> ORGANISM: Homo sapiens

<400> SEQUENCE: 251
tggagttaaa gactttttct ctgacc                                     26

<210> SEQ ID NO 252
<211> LENGTH: 30
<212> TYPE: DNA
<213> ORGANISM: Homo sapiens

<400> SEQUENCE: 252
tggtcgtggt tgtagtccgt gcgagaatac                                 30

<210> SEQ ID NO 253
<211> LENGTH: 25
<212> TYPE: DNA
<213> ORGANISM: Homo sapiens

<400> SEQUENCE: 253
gtagtcgtgg ccgagtggtt aaggc                                      25

<210> SEQ ID NO 254
<211> LENGTH: 30
<212> TYPE: DNA
<213> ORGANISM: Homo sapiens

<400> SEQUENCE: 254
ggtcgtggtt gtagtccgtg cgagaatacc                                 30
```

```
<210> SEQ ID NO 255
<211> LENGTH: 30
<212> TYPE: DNA
<213> ORGANISM: Homo sapiens

<400> SEQUENCE: 255
tgccgtgatc gtatagtggt tagtactctg                                    30

<210> SEQ ID NO 256
<211> LENGTH: 30
<212> TYPE: DNA
<213> ORGANISM: Homo sapiens

<400> SEQUENCE: 256
ggccccatgg tgtaatggtt agcactctgg                                    30

<210> SEQ ID NO 257
<211> LENGTH: 27
<212> TYPE: DNA
<213> ORGANISM: Homo sapiens

<400> SEQUENCE: 257
ttcaacttaa cttgaccgct ctgacca                                       27

<210> SEQ ID NO 258
<211> LENGTH: 30
<212> TYPE: DNA
<213> ORGANISM: Homo sapiens

<400> SEQUENCE: 258
ggttccatag tgtagtggtt atcacgtctg                                    30

<210> SEQ ID NO 259
<211> LENGTH: 29
<212> TYPE: DNA
<213> ORGANISM: Homo sapiens

<400> SEQUENCE: 259
cattggtcgt ggttgtagtc cgtgcgaga                                     29

<210> SEQ ID NO 260
<211> LENGTH: 27
<212> TYPE: DNA
<213> ORGANISM: Homo sapiens

<400> SEQUENCE: 260
gcattggtgg ttcagtggta gaattct                                       27

<210> SEQ ID NO 261
<211> LENGTH: 29
<212> TYPE: DNA
<213> ORGANISM: Homo sapiens

<400> SEQUENCE: 261
ggagatttca acttaacttg accgctctg                                     29

<210> SEQ ID NO 262
<211> LENGTH: 20
<212> TYPE: DNA
<213> ORGANISM: Homo sapiens

<400> SEQUENCE: 262
tgtaatggtt agcactctgg                                               20
```

```
<210> SEQ ID NO 263
<211> LENGTH: 25
<212> TYPE: DNA
<213> ORGANISM: Homo sapiens

<400> SEQUENCE: 263
ttcaacttaa cttgaccgct ctgac                                              25

<210> SEQ ID NO 264
<211> LENGTH: 21
<212> TYPE: DNA
<213> ORGANISM: Homo sapiens

<400> SEQUENCE: 264
tgtaatggtt agcactctgg a                                                  21

<210> SEQ ID NO 265
<211> LENGTH: 20
<212> TYPE: DNA
<213> ORGANISM: Homo sapiens

<400> SEQUENCE: 265
ggttccatag tgtagcggtt                                                    20

<210> SEQ ID NO 266
<211> LENGTH: 18
<212> TYPE: DNA
<213> ORGANISM: Homo sapiens

<400> SEQUENCE: 266
aaagactttt tctctgac                                                      18

<210> SEQ ID NO 267
<211> LENGTH: 20
<212> TYPE: DNA
<213> ORGANISM: Homo sapiens

<400> SEQUENCE: 267
aatggttagc actctggact                                                    20

<210> SEQ ID NO 268
<211> LENGTH: 20
<212> TYPE: DNA
<213> ORGANISM: Homo sapiens

<400> SEQUENCE: 268
ggttccatag tgtagtggtt                                                    20

<210> SEQ ID NO 269
<211> LENGTH: 28
<212> TYPE: DNA
<213> ORGANISM: Homo sapiens

<400> SEQUENCE: 269
atttcaactt aacttgaccg ctctgacc                                           28

<210> SEQ ID NO 270
<211> LENGTH: 19
<212> TYPE: DNA
<213> ORGANISM: Homo sapiens

<400> SEQUENCE: 270
acttaacttg accgctctg                                                     19
```

<210> SEQ ID NO 271
<211> LENGTH: 19
<212> TYPE: DNA
<213> ORGANISM: Homo sapiens

<400> SEQUENCE: 271
ggggatgtag ctcagtggt                                               19

<210> SEQ ID NO 272
<211> LENGTH: 19
<212> TYPE: DNA
<213> ORGANISM: Homo sapiens

<400> SEQUENCE: 272
gtttccgtag tgtagtggt                                               19

<210> SEQ ID NO 273
<211> LENGTH: 28
<212> TYPE: DNA
<213> ORGANISM: Homo sapiens

<400> SEQUENCE: 273
gcattggtgg ttcagtggta gaattctc                                     28

<210> SEQ ID NO 274
<211> LENGTH: 19
<212> TYPE: DNA
<213> ORGANISM: Homo sapiens

<400> SEQUENCE: 274
gtctctgtgg cgcaatcgg                                               19

<210> SEQ ID NO 275
<211> LENGTH: 20
<212> TYPE: DNA
<213> ORGANISM: Homo sapiens

<400> SEQUENCE: 275
gtctctgtgg cgcaatcggt                                              20

<210> SEQ ID NO 276
<211> LENGTH: 16
<212> TYPE: DNA
<213> ORGANISM: Homo sapiens

<400> SEQUENCE: 276
cccagcatct ccacca                                                  16

<210> SEQ ID NO 277
<211> LENGTH: 17
<212> TYPE: DNA
<213> ORGANISM: Homo sapiens

<400> SEQUENCE: 277
tgaagcattg gactgta                                                 17

<210> SEQ ID NO 278
<211> LENGTH: 22
<212> TYPE: DNA
<213> ORGANISM: Homo sapiens

<400> SEQUENCE: 278
gagtgaagca ttggactgta aa                                           22

```
<210> SEQ ID NO 279
<211> LENGTH: 21
<212> TYPE: DNA
<213> ORGANISM: Homo sapiens

<400> SEQUENCE: 279
aatggttagc actctggact c                                              21

<210> SEQ ID NO 280
<211> LENGTH: 20
<212> TYPE: DNA
<213> ORGANISM: Homo sapiens

<400> SEQUENCE: 280
gtggttagta ctctgcgttg                                                20

<210> SEQ ID NO 281
<211> LENGTH: 23
<212> TYPE: DNA
<213> ORGANISM: Homo sapiens

<400> SEQUENCE: 281
ggcggcccgg gttcgactcc cgg                                            23

<210> SEQ ID NO 282
<211> LENGTH: 21
<212> TYPE: DNA
<213> ORGANISM: Homo sapiens

<400> SEQUENCE: 282
ggtagcgtgg ccgagcggtc t                                              21

<210> SEQ ID NO 283
<211> LENGTH: 23
<212> TYPE: DNA
<213> ORGANISM: Homo sapiens

<400> SEQUENCE: 283
ccgcctgtca cgcgggagac cgg                                            23

<210> SEQ ID NO 284
<211> LENGTH: 26
<212> TYPE: DNA
<213> ORGANISM: Homo sapiens

<400> SEQUENCE: 284
cgtatagtgg ttagtactct gcgttg                                         26

<210> SEQ ID NO 285
<211> LENGTH: 23
<212> TYPE: DNA
<213> ORGANISM: Homo sapiens

<400> SEQUENCE: 285
tcgtatagtg gttagtactc tgc                                            23

<210> SEQ ID NO 286
<211> LENGTH: 22
<212> TYPE: DNA
<213> ORGANISM: Homo sapiens

<400> SEQUENCE: 286
tagtggttag tactctgcgt tg                                             22
```

```
<210> SEQ ID NO 287
<211> LENGTH: 17
<212> TYPE: DNA
<213> ORGANISM: Homo sapiens

<400> SEQUENCE: 287
ggttagcact ctggact                                                   17

<210> SEQ ID NO 288
<211> LENGTH: 21
<212> TYPE: DNA
<213> ORGANISM: Homo sapiens

<400> SEQUENCE: 288
ataacccaga ggtcgatgga t                                              21

<210> SEQ ID NO 289
<211> LENGTH: 24
<212> TYPE: DNA
<213> ORGANISM: Homo sapiens

<400> SEQUENCE: 289
ttggtcgtgg ttgtagtccg tgcg                                           24

<210> SEQ ID NO 290
<211> LENGTH: 29
<212> TYPE: DNA
<213> ORGANISM: Homo sapiens

<400> SEQUENCE: 290
ggttccatgg tgtaatggtt agcactctg                                      29

<210> SEQ ID NO 291
<211> LENGTH: 29
<212> TYPE: DNA
<213> ORGANISM: Homo sapiens

<400> SEQUENCE: 291
gggggtatag ctcagtggta gagcatttg                                      29

<210> SEQ ID NO 292
<211> LENGTH: 20
<212> TYPE: DNA
<213> ORGANISM: Homo sapiens

<400> SEQUENCE: 292
ttggtcgtgg ttgtagtccg                                                20

<210> SEQ ID NO 293
<211> LENGTH: 26
<212> TYPE: DNA
<213> ORGANISM: Homo sapiens

<400> SEQUENCE: 293
gggttcgatt ccccgacggg gagcca                                         26

<210> SEQ ID NO 294
<211> LENGTH: 21
<212> TYPE: DNA
<213> ORGANISM: Homo sapiens

<400> SEQUENCE: 294
ggctccagtc tcttcggggg c                                              21
```

```
<210> SEQ ID NO 295
<211> LENGTH: 28
<212> TYPE: DNA
<213> ORGANISM: Homo sapiens

<400> SEQUENCE: 295
ccctggtggt ctagtggtta ggattcgg                                        28

<210> SEQ ID NO 296
<211> LENGTH: 30
<212> TYPE: DNA
<213> ORGANISM: Homo sapiens

<400> SEQUENCE: 296
cccacatggt ctagcggtta ggattcctgg                                      30

<210> SEQ ID NO 297
<211> LENGTH: 24
<212> TYPE: DNA
<213> ORGANISM: Homo sapiens

<400> SEQUENCE: 297
gacctcgtgg cgcaacggta gcgc                                            24

<210> SEQ ID NO 298
<211> LENGTH: 23
<212> TYPE: DNA
<213> ORGANISM: Homo sapiens

<400> SEQUENCE: 298
ttggtcgtgg ttgtagtccg tgc                                             23

<210> SEQ ID NO 299
<211> LENGTH: 19
<212> TYPE: DNA
<213> ORGANISM: Homo sapiens

<400> SEQUENCE: 299
agtcggtaga gcatcagac                                                  19

<210> SEQ ID NO 300
<211> LENGTH: 25
<212> TYPE: DNA
<213> ORGANISM: Homo sapiens

<400> SEQUENCE: 300
gttaagatgg cagagcccgg taatc                                           25

<210> SEQ ID NO 301
<211> LENGTH: 25
<212> TYPE: DNA
<213> ORGANISM: Homo sapiens

<400> SEQUENCE: 301
attggtcgtg gttgtagtcc gtgcg                                           25

<210> SEQ ID NO 302
<211> LENGTH: 23
<212> TYPE: DNA
<213> ORGANISM: Homo sapiens

<400> SEQUENCE: 302
gttaaagact ttttctctga cca                                             23
```

```
<210> SEQ ID NO 303
<211> LENGTH: 24
<212> TYPE: DNA
<213> ORGANISM: Homo sapiens

<400> SEQUENCE: 303
gttgtagtcc gtgcgagaat acca                                          24

<210> SEQ ID NO 304
<211> LENGTH: 21
<212> TYPE: DNA
<213> ORGANISM: Homo sapiens

<400> SEQUENCE: 304
tggtagagcg gaggactgta g                                             21

<210> SEQ ID NO 305
<211> LENGTH: 22
<212> TYPE: DNA
<213> ORGANISM: Homo sapiens

<400> SEQUENCE: 305
ttgtgaatct gacaacagag gc                                            22

<210> SEQ ID NO 306
<211> LENGTH: 20
<212> TYPE: DNA
<213> ORGANISM: Homo sapiens

<400> SEQUENCE: 306
atggtgagca ctctggactc                                               20

<210> SEQ ID NO 307
<211> LENGTH: 28
<212> TYPE: DNA
<213> ORGANISM: Homo sapiens

<400> SEQUENCE: 307
cgtgatcgta tagtggttag tactctgc                                      28

<210> SEQ ID NO 308
<211> LENGTH: 24
<212> TYPE: DNA
<213> ORGANISM: Homo sapiens

<400> SEQUENCE: 308
attggtcgtg gttgtagtcc gtgc                                          24

<210> SEQ ID NO 309
<211> LENGTH: 18
<212> TYPE: DNA
<213> ORGANISM: Homo sapiens

<400> SEQUENCE: 309
ttaacttgac cgctctga                                                 18

<210> SEQ ID NO 310
<211> LENGTH: 29
<212> TYPE: DNA
<213> ORGANISM: Homo sapiens

<400> SEQUENCE: 310
gagatttcaa cttaacttga ccgctctga                                     29
```

```
<210> SEQ ID NO 311
<211> LENGTH: 18
<212> TYPE: DNA
<213> ORGANISM: Homo sapiens

<400> SEQUENCE: 311
atcaccccat aaacacca                                              18

<210> SEQ ID NO 312
<211> LENGTH: 18
<212> TYPE: DNA
<213> ORGANISM: Homo sapiens

<400> SEQUENCE: 312
gtttagacgg gctcacat                                              18

<210> SEQ ID NO 313
<211> LENGTH: 20
<212> TYPE: DNA
<213> ORGANISM: Homo sapiens

<400> SEQUENCE: 313
cggagctggg gattgtgggt                                            20

<210> SEQ ID NO 314
<211> LENGTH: 19
<212> TYPE: DNA
<213> ORGANISM: Homo sapiens

<400> SEQUENCE: 314
cttaacttga ccgctctga                                             19

<210> SEQ ID NO 315
<211> LENGTH: 30
<212> TYPE: DNA
<213> ORGANISM: Homo sapiens

<400> SEQUENCE: 315
agatttcaac ttaacttgac cgctctgacc                                 30

<210> SEQ ID NO 316
<211> LENGTH: 16
<212> TYPE: DNA
<213> ORGANISM: Homo sapiens

<400> SEQUENCE: 316
gtttagacgg gctcac                                                16

<210> SEQ ID NO 317
<211> LENGTH: 16
<212> TYPE: DNA
<213> ORGANISM: Homo sapiens

<400> SEQUENCE: 317
acttgaccgc tctgac                                                16

<210> SEQ ID NO 318
<211> LENGTH: 18
<212> TYPE: DNA
<213> ORGANISM: Homo sapiens

<400> SEQUENCE: 318
atgtttagac gggctcac                                              18
```

```
<210> SEQ ID NO 319
<211> LENGTH: 20
<212> TYPE: DNA
<213> ORGANISM: Homo sapiens

<400> SEQUENCE: 319
ggttcgattc cccgacgggg                                              20

<210> SEQ ID NO 320
<211> LENGTH: 21
<212> TYPE: DNA
<213> ORGANISM: Homo sapiens

<400> SEQUENCE: 320
aacttaactt gaccgctctg a                                            21

<210> SEQ ID NO 321
<211> LENGTH: 30
<212> TYPE: DNA
<213> ORGANISM: Homo sapiens

<400> SEQUENCE: 321
gagatttcaa cttaacttga ccgctctgac                                   30

<210> SEQ ID NO 322
<211> LENGTH: 22
<212> TYPE: DNA
<213> ORGANISM: Homo sapiens

<400> SEQUENCE: 322
caacttaact tgaccgctct ga                                           22

<210> SEQ ID NO 323
<211> LENGTH: 17
<212> TYPE: DNA
<213> ORGANISM: Homo sapiens

<400> SEQUENCE: 323
tgtttagacg ggctcac                                                 17

<210> SEQ ID NO 324
<211> LENGTH: 20
<212> TYPE: DNA
<213> ORGANISM: Homo sapiens

<400> SEQUENCE: 324
cttaacttga ccgctctgac                                              20

<210> SEQ ID NO 325
<211> LENGTH: 23
<212> TYPE: DNA
<213> ORGANISM: Homo sapiens

<400> SEQUENCE: 325
gcccggatag ctcagtcggt aga                                          23

<210> SEQ ID NO 326
<211> LENGTH: 19
<212> TYPE: DNA
<213> ORGANISM: Homo sapiens

<400> SEQUENCE: 326
tagaattctc gcctgccac                                               19
```

```
<210> SEQ ID NO 327
<211> LENGTH: 23
<212> TYPE: DNA
<213> ORGANISM: Homo sapiens

<400> SEQUENCE: 327
taacccagag gtcgatggat cga                                              23

<210> SEQ ID NO 328
<211> LENGTH: 25
<212> TYPE: DNA
<213> ORGANISM: Homo sapiens

<400> SEQUENCE: 328
gcccggctag ctcagtcggt agagc                                            25

<210> SEQ ID NO 329
<211> LENGTH: 20
<212> TYPE: DNA
<213> ORGANISM: Homo sapiens

<400> SEQUENCE: 329
tagaattctc gcctgccacg                                                  20

<210> SEQ ID NO 330
<211> LENGTH: 20
<212> TYPE: DNA
<213> ORGANISM: Homo sapiens

<400> SEQUENCE: 330
gtctctgtgg cgcaatggac                                                  20

<210> SEQ ID NO 331
<211> LENGTH: 21
<212> TYPE: DNA
<213> ORGANISM: Homo sapiens

<400> SEQUENCE: 331
tgctaatcca ttgtgctttg c                                                21

<210> SEQ ID NO 332
<211> LENGTH: 18
<212> TYPE: DNA
<213> ORGANISM: Homo sapiens

<400> SEQUENCE: 332
gggccagtgg cgcaatgg                                                    18

<210> SEQ ID NO 333
<211> LENGTH: 25
<212> TYPE: DNA
<213> ORGANISM: Homo sapiens

<400> SEQUENCE: 333
tttcaactta acttgaccgc tctga                                            25

<210> SEQ ID NO 334
<211> LENGTH: 22
<212> TYPE: DNA
<213> ORGANISM: Homo sapiens

<400> SEQUENCE: 334
tgtagtccgt gcgagaatac ca                                               22
```

-continued

```
<210> SEQ ID NO 335
<211> LENGTH: 19
<212> TYPE: DNA
<213> ORGANISM: Homo sapiens

<400> SEQUENCE: 335
gccccggtgg cctaatgga                                                19

<210> SEQ ID NO 336
<211> LENGTH: 19
<212> TYPE: DNA
<213> ORGANISM: Homo sapiens

<400> SEQUENCE: 336
ccttttccca aggacacca                                                19

<210> SEQ ID NO 337
<211> LENGTH: 19
<212> TYPE: DNA
<213> ORGANISM: Homo sapiens

<400> SEQUENCE: 337
gggggtatag ctcagtggg                                                19

<210> SEQ ID NO 338
<211> LENGTH: 18
<212> TYPE: DNA
<213> ORGANISM: Homo sapiens

<400> SEQUENCE: 338
gccccagtgg cctaatgg                                                 18

<210> SEQ ID NO 339
<211> LENGTH: 18
<212> TYPE: DNA
<213> ORGANISM: Homo sapiens

<400> SEQUENCE: 339
gagaaagctc acaagaac                                                 18

<210> SEQ ID NO 340
<211> LENGTH: 20
<212> TYPE: DNA
<213> ORGANISM: Homo sapiens

<400> SEQUENCE: 340
ggccgcgtgg cctaatggat                                               20

<210> SEQ ID NO 341
<211> LENGTH: 16
<212> TYPE: DNA
<213> ORGANISM: Homo sapiens

<400> SEQUENCE: 341
acttttctct tgacca                                                   16

<210> SEQ ID NO 342
<211> LENGTH: 17
<212> TYPE: DNA
<213> ORGANISM: Homo sapiens

<400> SEQUENCE: 342
gttaagatgg cagagcc                                                  17
```

-continued

```
<210> SEQ ID NO 343
<211> LENGTH: 18
<212> TYPE: DNA
<213> ORGANISM: Homo sapiens

<400> SEQUENCE: 343
gttaagatgg cagagccc                                                     18

<210> SEQ ID NO 344
<211> LENGTH: 24
<212> TYPE: DNA
<213> ORGANISM: Homo sapiens

<400> SEQUENCE: 344
gttaagatgg cagagcccgg taat                                              24

<210> SEQ ID NO 345
<211> LENGTH: 23
<212> TYPE: DNA
<213> ORGANISM: Homo sapiens

<400> SEQUENCE: 345
aatccagcga tccgagttca aat                                               23

<210> SEQ ID NO 346
<211> LENGTH: 28
<212> TYPE: DNA
<213> ORGANISM: Homo sapiens

<400> SEQUENCE: 346
aaatggctga gtgaagcatt ggactgta                                          28

<210> SEQ ID NO 347
<211> LENGTH: 23
<212> TYPE: DNA
<213> ORGANISM: Homo sapiens

<400> SEQUENCE: 347
tcctcgttag tatagtggtg agt                                               23

<210> SEQ ID NO 348
<211> LENGTH: 19
<212> TYPE: DNA
<213> ORGANISM: Homo sapiens

<400> SEQUENCE: 348
gagtgaagca ttggactgt                                                    19

<210> SEQ ID NO 349
<211> LENGTH: 24
<212> TYPE: DNA
<213> ORGANISM: Homo sapiens

<400> SEQUENCE: 349
ggctgagtga agcattggac tgta                                              24

<210> SEQ ID NO 350
<211> LENGTH: 19
<212> TYPE: DNA
<213> ORGANISM: Homo sapiens

<400> SEQUENCE: 350
agtgaagcat tggactgta                                                    19
```

```
<210> SEQ ID NO 351
<211> LENGTH: 23
<212> TYPE: DNA
<213> ORGANISM: Homo sapiens

<400> SEQUENCE: 351
tggtctaggg gtatgattct cgc                                              23

<210> SEQ ID NO 352
<211> LENGTH: 24
<212> TYPE: DNA
<213> ORGANISM: Homo sapiens

<400> SEQUENCE: 352
agccgtgatc gtatagtggt tagt                                             24

<210> SEQ ID NO 353
<211> LENGTH: 18
<212> TYPE: DNA
<213> ORGANISM: Homo sapiens

<400> SEQUENCE: 353
gtgaagcatt ggactgta                                                    18

<210> SEQ ID NO 354
<211> LENGTH: 25
<212> TYPE: DNA
<213> ORGANISM: Homo sapiens

<400> SEQUENCE: 354
atggctgagt gaagcattgg actgt                                            25

<210> SEQ ID NO 355
<211> LENGTH: 25
<212> TYPE: DNA
<213> ORGANISM: Homo sapiens

<400> SEQUENCE: 355
ggtagtgtgg ccgagcggtc taagg                                            25

<210> SEQ ID NO 356
<211> LENGTH: 22
<212> TYPE: DNA
<213> ORGANISM: Homo sapiens

<400> SEQUENCE: 356
tgagtgaagc attggactgt aa                                               22

<210> SEQ ID NO 357
<211> LENGTH: 22
<212> TYPE: DNA
<213> ORGANISM: Homo sapiens

<400> SEQUENCE: 357
ctgagtgaag cattggactg ta                                               22

<210> SEQ ID NO 358
<211> LENGTH: 26
<212> TYPE: DNA
<213> ORGANISM: Homo sapiens

<400> SEQUENCE: 358
atggctgagt gaagcattgg actgta                                           26
```

```
<210> SEQ ID NO 359
<211> LENGTH: 28
<212> TYPE: DNA
<213> ORGANISM: Homo sapiens

<400> SEQUENCE: 359
agatttcaac ttaacttgac cgctctga                                          28

<210> SEQ ID NO 360
<211> LENGTH: 20
<212> TYPE: DNA
<213> ORGANISM: Homo sapiens

<400> SEQUENCE: 360
tgagtgaagc attggactgt                                                   20

<210> SEQ ID NO 361
<211> LENGTH: 20
<212> TYPE: DNA
<213> ORGANISM: Homo sapiens

<400> SEQUENCE: 361
ctcacaagaa ctgctaactc                                                   20

<210> SEQ ID NO 362
<211> LENGTH: 23
<212> TYPE: DNA
<213> ORGANISM: Homo sapiens

<400> SEQUENCE: 362
agccgtgatc gtatagtggt tag                                               23

<210> SEQ ID NO 363
<211> LENGTH: 23
<212> TYPE: DNA
<213> ORGANISM: Homo sapiens

<400> SEQUENCE: 363
gctgagtgaa gcattggact gta                                               23

<210> SEQ ID NO 364
<211> LENGTH: 21
<212> TYPE: DNA
<213> ORGANISM: Homo sapiens

<400> SEQUENCE: 364
tcagaaggct gcgtgttcga a                                                 21

<210> SEQ ID NO 365
<211> LENGTH: 23
<212> TYPE: DNA
<213> ORGANISM: Homo sapiens

<400> SEQUENCE: 365
ggccgtgatc gtatagtggt tag                                               23

<210> SEQ ID NO 366
<211> LENGTH: 24
<212> TYPE: DNA
<213> ORGANISM: Homo sapiens

<400> SEQUENCE: 366
ggccgtgatc gtatagtggt tagt                                              24
```

```
<210> SEQ ID NO 367
<211> LENGTH: 24
<212> TYPE: DNA
<213> ORGANISM: Homo sapiens

<400> SEQUENCE: 367
tgccgtgatc gtatagtggt tagt                                          24

<210> SEQ ID NO 368
<211> LENGTH: 27
<212> TYPE: DNA
<213> ORGANISM: Homo sapiens

<400> SEQUENCE: 368
aatggctgag tgaagcattg gactgta                                       27

<210> SEQ ID NO 369
<211> LENGTH: 24
<212> TYPE: DNA
<213> ORGANISM: Homo sapiens

<400> SEQUENCE: 369
tggctgagtg aagcattgga ctgt                                          24

<210> SEQ ID NO 370
<211> LENGTH: 22
<212> TYPE: DNA
<213> ORGANISM: Homo sapiens

<400> SEQUENCE: 370
tcgaatccga gtcacggcac ca                                            22

<210> SEQ ID NO 371
<211> LENGTH: 20
<212> TYPE: DNA
<213> ORGANISM: Homo sapiens

<400> SEQUENCE: 371
gagtgaagca ttggactgta                                               20

<210> SEQ ID NO 372
<211> LENGTH: 23
<212> TYPE: DNA
<213> ORGANISM: Homo sapiens

<400> SEQUENCE: 372
tcccacatgg tctagcggtt agg                                           23
```

SYSTEMS-LEVEL ANALYSIS OF 32 TCGA CANCERS REVEALS DISEASE-DEPENDENT TRNA FRAGMENTATION PATTERNS AND VERY SELECTIVE ASSOCIATIONS WITH MESSENGER RNAS AND REPEAT ELEMENTS

CROSS REFERENCE TO RELATED APPLICATIONS

This application is a National Phase of International Application No. PCT/US2018/30525, filed May 1, 2018, which claims priority to U.S. Provisional Patent Application No. 62/492,662, filed May, 2017, which are incorporated herein by reference in their entirety.

SEQUENCE LISTING

The instant application contains a Sequence Listing which has been filed electronically in ASCII format and is hereby incorporated by reference in its entirety. Said ASCII copy, created on May 1, 2018, is named 6107_178PCT_403809_SEQ_ID.txt and is 54,138 bytes in size.

FIELD OF INVENTION

This application is generally related to the use of tRNA fragments as novel therapeutics that can target specific messenger RNAs in cancers and other diseases.

BACKGROUND OF INVENTION

Activity in recent years has been drawing increasing attention to a new group of molecules that appear to be produced at the same time as transfer RNAs (tRNAs). These molecules are referred to as "tRNA-derived fragments" or tRFs and are believed to arise from both the precursor and the mature tRNAs (1-3). For those tRFs that overlap the span of the mature tRNA, four structural categories were reported originally: 5'-tRFs, 3'-tRFs, 5'-halves (5'-tRHs), and 3'-halves (3'-tRHs). In a recent analysis of hundreds of human tissues, we reported a fifth structural category, the "internal tRFs" or i-tRFs that comprises numerous members expressed in high abundance (4). In the same analysis, we also demonstrated that the identity and abundance of tRFs depends on previously unrecognized variables such as a person's sex, population origin, and race as well as on tissue, tissue state, and disease subtype (4). Despite these dependencies, samples from the same tissue obtained from individuals with the same sex, race and disease subtype were found to express the same tRFs and with the same relative abundances, which indicates that these molecules are constitutive (4). More recent work showed that tRNA "halves" can be produced under stress conditions (5,6) as well as constitutively (7-9) and to exist in variants that are not visible by standard RNA-seq (7).

In terms of function, tRFs have been shown to associate with Argonaute (10) in a cell-type specific manner (4). This indicates that at least a subset of tRFs enter the RNA interference (RNAi) pathway. In addition, tRFs have been shown to be produced differentially in response to infections (11,12), in cancer tissues compared to normal (4,13,14), to be affected by diet (15), by trauma (16), to be involved in trans-generational inheritance (17), and to regulate translation (18).

In summary, there is very strong evidence that tRFs: 1) represent a novel category of regulatory molecules in their own right; 2) are important in homeostasis and in disease; and, 3) warrant in-depth studies (19,20). In this presentation, we extend our earlier work (4) to the entirety of the TCGA collection. Specifically, we processed 11,198 cancer samples representing 32 cancer types with an emphasis on identifying intra- and inter-cancer features involving tRFs. The 32 cancer types included: ACC (Adrenocortical carcinoma), BLCA (Bladder Urothelial Carcinoma), BRCA (Breast invasive carcinoma), CESC (Cervical squamous cell carcinoma and endocervical adenocarcinoma), CHOL (Cholangiocarcinoma), COAD (Colon adenocarcinoma), DLBC (Lymphoid Neoplasm Diffuse Large B-cell Lymphoma), ESCA (Esophageal carcinoma), HNSC (Head and Neck squamous cell carcinoma), KICH (Kidney Chromophobe), KIRC (Kidney renal clear cell carcinoma), KIRP (Kidney renal papillary cell carcinoma), LAML (Acute Myeloid Leukemia), LGG (Brain Lower Grade Glioma), LIHC (Liver hepatocellular carcinoma), LUAD (Lung adenocarcinoma), LUSC (Lung squamous cell carcinoma), MESO (Mesothelioma), OV (Ovarian serous cystadenocarcinoma), PAAD (Pancreatic adenocarcinoma), PCPG (Pheochromocytoma and Paraganglioma), PRAD (Prostate adenocarcinoma), READ (Rectum adenocarcinoma), SARC (Sarcoma), SKCM (Skin Cutaneous Melanoma), STAD (Stomach adenocarcinoma), TGCT (Testicular Germ Cell Tumors), THCA (Thyroid carcinoma), THYM (Thymoma), UCEC (Uterine Corpus Endometrial Carcinoma), UCS (Uterine Carcinosarcoma), and UVM (Uveal Melanoma). Lastly, where relevant, we use the NIH/TCGA designations to refer to race groups (see Methods).

SUMMARY OF INVENTION

We have identified many tRNA fragments (tRFs) that form positively- and negatively-correlated pairs with messenger RNAs (mRNAs). When we compare the tRFs that are expressed in any two of the 32 cancers, we see that they largely agree. I.e., for the purposes of this analysis, largely the same tRFs are expressed in each of the 32 cancers. When we compare the miRNAs that are expressed in any two of the 32 cancers, we see that they largely agree. I.e., for the purposes of this analysis, largely the same miRNAs are expressed in each of the 32 cancers. When we compare the mRNAs that are expressed in any two of the 32 cancers, we see that they largely agree. I.e., for the purposes of this analysis, largely the same mRNAs are expressed in each of the 32 cancers.

However, things change when we focus only on the subset of tRFs, miRNAs, or mRNAs that participate in tRF:mRNA or miRNA:mRNA pairs and are either negatively-correlated or positively-correlated. In particular, when we focus on tRFs that participate in either positively-correlated or negatively-correlated tRF:mRNA pairs, and compare them across cancers, we see that they are largely cancer-specific. When we focus on miRNAs that participate in either positively-correlated or negatively-correlated miRNA:mRNA pairs, and compare them across cancers, we see that they are largely cancer-specific. When we focus on the mRNAs that are either positively-correlated or negatively-correlated with either tRFs or miRNAs, and compare them across cancers, we see that they are largely cancer-specific.

In other words, the mRNAs that are either positively-correlated or negatively correlated with either tRFs or miRNAs in cancer X have little overlap with the mRNAs that are either positively-correlated or negatively correlated with either tRFs or miRNAs in cancer Y. However, the pathways to which these mRNAs belong are conserved across cancers.

This last statement captures a very important finding. Essentially, it states that even though the tRFs in cancer X and in cancer Y are disrupting the same pathway they do so by disrupting different gene-members of the pathway.

FIG. 8 provides a tangible example of this observation with the help of two cancers: colon adenocarcinoma (COAD) and pancreatic adenocarcinoma (PAAD). The shown pathway is a signal transduction pathway known as "the PI3K-AKT pathway." This pathway is activated by extracellular stimuli, promotes cell survival and growth, and is very often deregulated in the cancer context. In the solid-line-contour rectangle we indicate how many tRFs are produced from isodecoders of the shown nuclear and mitochondrial tRNAs and are correlated (either negatively or positively) with PI3K-AKT pathway mRNAs in COAD but not in PAAD. In the dashed-line-contour rectangle we indicate the analogous information for PAAD. Finally, in the compound-contour (triple-line) rectangle we indicate how many tRFs are produced from isodecoders of the shown nuclear and mitochondrial tRNAs and are correlated with PI3K-AKT pathway mRNAs in both COAD and in PAAD. Note, however, that the tRFs that are common in COAD and PAAD may be correlated with the same or with different mRNAs in these two cancers. Or, these tRFs could be correlated with the same mRNA in the two cancers but the correlation could have a different sign in each cancer, e.g. the correlation could be positive in COAD and negative in PAAD. As can be seen, comparatively fewer tRFs that are common to both cancer types participate in correlated pairs. Among the PI3K-AKT genes, the mRNAs of those genes shown with the solid contour are correlated with tRFs only in COAD. Analogously, the mRNAs of the pathway's genes with the dashed contour are correlated with tRFs only in PAAD. Finally, the mRNAs of the pathway's genes with the compound-line contour are correlated with tRFs in COAD and in PAAD (but not necessarily with the same tRF in the two cancers).

mRNAs from the PI3K-AKT pathway are correlated with 54 tRFs in COAD and 48 tRFs in PAAD. In terms of origin, these tRFs differ radically: in COAD, 48 of the 54 tRFs are produced by mitochondrial tRNAs; in PAAD, 32 of the 45 tRFs are produced by nuclear tRNAs. The tRFs that are correlated with mRNAs from the PI3K-AKT pathway are largely unique to each cancer: 44 of the 54 tRFs are specific to COAD (and, thus, absent from PAAD); 35 of the 45 tRFs are specific to PAAD. Here, it is also important to stress that the differences in tRFs do not arise from endpoint variations of the same precursor molecule; instead the tRFs that participate in correlated pairs with mRNAs originate from completely distinct tRNA templates in each cancer.

Equally striking is the relatively small overlap of the affected mRNAs in each cancer. In PAAD, the tRFs are correlated with many mRNAs that are unique to PAAD and are located "deep" (i.e. further downstream) inside the pathway (nodes with a dashed contour). On the other hand, in COAD, the tRFs that are correlated with mRNAs that are unique to COAD are characteristically at the input layer to the pathway (nodes with a solid contour).

The pathway's members that are correlated with tRFs in both COAD and PAAD (nodes with a compound-line contour) deserve special mention. As we indicated above, the fact that these genes' mRNAs are correlated with tRFs in both cancers does not necessarily mean that they are partnered with the same tRF in both cancers, or that the sign of the correlation is the same in both cancers. Let us take the integrin alpha subunits (ITGA box/compound-line contour). In COAD, the subunits ITGA1, ITGA4, ITGA5, ITGAV, and ITGAX are correlated with many mitochondrial tRFs that are present only in COAD (but not in PAAD). IN PAAD, the subunit ITGA7 is correlated with a mitochondrial tRF that is present only in PAAD (but not in COAD). Lastly, two mitochondrial tRFs are correlated with the subunits ITGA1, ITGA4, and ITGAV in both COAD and PAAD.

Note that, in this example and accompanying Figure, we focused on positively- and negatively-correlated tRF:mRNA pairs. It is reasonable to assume that at least some of the negative correlations are indicative of direct molecular interactions between tRFs and mRNAs. As a matter of fact, we and others have provided evidence that tRFs can be loaded on Argonaute (i.e. can act like miRNAs), thereby entering the RNA interference pathway and having functional downstream effects. An increase in the abundance of an Argonaute-loaded tRF would result in a decrease in the abundance of its natural targets.

A tRF can also lead to a down-regulation of another transcript through a method that is known as "decoying." Recent publications provided experimental evidence that a tRF can act as a molecular decoy to an RNA binding protein (RBP) that would otherwise stabilize its target. By decoying the (stabilizing) RBP, the tRF would induce an apparent decrease in the abundance of the protein's natural target(s).

Our analyses also included positively-correlated tRF:mRNA pairs. Again, it is reasonable to assume that at least some of these positive correlations are indicative of direct molecular interactions, presumably through "decoying" of a miRNA or of a destabilizing RBP. The decoying transcript can be non-coding or protein coding. In this discussion, without loss of generality, we focus on decoying transcripts that are tRFs. In the case of a miRNA or of a destabilizing RBP, the decoying transcript would sponge away the miRNA or the RBP, leading to an apparent increase in the abundance of the miRNA's or RBP's natural target(s).

Both positively- and negatively-correlated tRF:mRNA pairs suggest many and terrific opportunities for therapeutic intervention. As FIG. 8 shows, these elaborate relationships highlight a level of granularity that is specific to each cancer type and which is now known to us. If harnessed correctly, the cancer-specific positive and negative correlations that we have uncovered have the potential to permit a level of therapeutic intervention on an mRNA that will be unprecedented because it will have been informed by three dimensions:

the mRNA of interest;
the tRFs that are positively/negatively correlated with it; and,
the cancer type in which one wishes to target this mRNA.

For example, let us assume that one wishes to "target" the same gene e.g. ITGAV (CD51), in multiple cancers, e.g. COAD and PAAD. ITGAV is a gene whose increased levels have been linked with tumorigenicity in both COAD and PAAD. In the case of COAD, there are 18 different tRFs that are correlated with ITGAV's mRNA and could be modulated in order to affect its levels. On the other hand, our analysis shows that in the case of PAAD there is only one such tRF (from the mitochondrial Phe tRNA) that can be used for this purpose.

It is important to know the cancer type as the cancer type frames the context that defines which tRF will interact with which mRNA, and whether a tRF and an mRNA are positively- or negatively-correlated. The therapeutic intervention will aim to counterbalance the mRNA deregulation. But because the mRNAs can participate in different positive or negative correlations in different cancers, it means that the therapeutic intervention may need to have opposing goals in different cancer types for the same mRNA.

Preferred embodiments are directed towards a method of treating a disease in a patient comprising: selecting at least one gene that is transcribed in the ailing tissue of the said patient; selecting at least one tRF that is correlated with the at least one gene that is transcribed in the ailing tissue of the said patient; and administering a therapeutic composition sufficient to modify the abundance of the at least one tRF or of the at least one gene. Ailing tissue meaning a tissue that is diseased, most preferably, that disease is a cancer.

In preferred embodiments, the cancer can be one of: ACC (Adrenocortical carcinoma), BLCA (Bladder Urothelial Carcinoma), BRCA (Breast invasive carcinoma), CESC (Cervical squamous cell carcinoma and endocervical adenocarcinoma), CHOL (Cholangiocarcinoma), COAD (Colon adenocarcinoma), DLBC (Lymphoid Neoplasm Diffuse Large B-cell Lymphoma), ESCA (Esophageal carcinoma), HNSC (Head and Neck squamous cell carcinoma), KICH (Kidney Chromophobe), KIRC (Kidney renal clear cell carcinoma), KIRP (Kidney renal papillary cell carcinoma), LAML (Acute Myeloid Leukemia), LGG (Brain Lower Grade Glioma), LIHC (Liver hepatocellular carcinoma), LUAD (Lung adenocarcinoma), LUSC (Lung squamous cell carcinoma), MESO (Mesothelioma), OV (Ovarian serous cystadenocarcinoma), PAAD (Pancreatic adenocarcinoma), PCPG (Pheochromocytoma and Paraganglioma), PRAD (Prostate adenocarcinoma), READ (Rectum adenocarcinoma), SARC (Sarcoma), SKCM (Skin Cutaneous Melanoma), STAD (Stomach adenocarcinoma), TGCT (Testicular Germ Cell Tumors), THCA (Thyroid carcinoma), THYM (Thymoma), UCEC (Uterine Corpus Endometrial Carcinoma), UCS (Uterine Carcinosarcoma), or UVM (Uveal Melanoma). These are referred to as the 32 cancer subtypes throughout.

In preferred embodiments, the method comprises at least one gene, wherein the genes are those as enumerated herein. The method of claim 1 where the at least one gene is selected among the list of genes of claims 66-96 to be dysregulated in the disease at hand.

In preferred embodiments, the tRF is selected among the 1,700 tRFs found to be statistically significantly correlated with genes. In preferred embodiments, the gene is selected among the 12,509 genes found to be statistically significantly correlated with tRFs.

In preferred embodiments, selection among the tRF's, where the tRF and the gene are positively correlated. In certain embodiments, we administer a therapeutic to raise the tRF's abundance. In other embodiments, we wish to lower the tRF's abundance. Accordingly, we administer a preparation comprising a therapeutic agent that lowers the tRF's abundance.

Alternatively, in some embodiments, where the tRF and the gene are negatively correlated. Therefore, we may wish to lower the tRF's abundance. Accordingly, we administer a preparation comprising a therapeutic agent that lowers the tRF's abundance. In other embodiments, we wish to raise the tRF's abundance and accordingly, we administer a preparation comprising a therapeutic agent that raises the tRF's abundance.

In aspects where the tRF and gene are positively or negatively correlated, we may wish to do either lower the gene's abundance, accordingly, we administer a preparation comprising a therapeutic agent that lowers the gene's abundance. Alternatively, we can raise the gene's abundance, though a therapeutic. The method of claim 8 where we wish to lower the gene's abundance. Embodiments therefore raise or lower the gene abundance or raise or lower the tRF abundance.

In certain embodiments, the tRFs are considered in order of decreasing desirability. For example, we can evaluate where a tRF's desirability is decided by the number of tRF-gene correlations in which it participates. And methods can be applied where the genes are considered in order of decreasing desirability; for example, where a gene's desirability is decided by the number of tRF-gene correlations in which it participates.

In certain embodiments, the gene abundance is lowered or raised by proxy.

In certain embodiments, the gene abundance of the gene in a correlated or anticorrelated pair is directly lowered or directly raised.

In further embodiments, a method of treating a patient for a cancer through by focusing on disease-specific tRFs among those that are correlated with genes or by focusing on disease-specific genes among those that are correlated with tRFs corresponding to the disease in said patient comprising: selecting at least one of these disease-specific tRFs; selecting at least one of these disease-specific genes; and administering a therapeutic composition sufficient to modify the abundance of the at least one disease-specific tRF or of the at least one disease-specific gene.

The method wherein the disease type is ACC (Adrenocortical carcinoma) and the tRF and the tRF is selected from the group of sequences consisting of SEQ 1 through SEQ 31.

The method wherein the disease is BLCA (Bladder Urothelial Carcinoma) and the tRF is selected from the group of sequences consisting of SEQ 32 through SEQ 40.

The method wherein the disease is BRCA (Breast invasive carcinoma) and the tRF is selected from the group of sequences consisting of SEQ 41 through SEQ 58.

The method wherein the disease is CESC (Cervical squamous cell carcinoma and endocervical adenocarcinoma) and the tRF is selected from the group of sequences consisting of SEQ 59 through SEQ 71.

The method wherein the disease is COAD (Colon adenocarcinoma) and the tRF is selected from the group of sequences consisting of SEQ 72 through SEQ 77.

The method wherein the disease is DLBC (Lymphoid Neoplasm Diffuse Large B-cell Lymphoma) and the tRF is selected from the group of sequences consisting of SEQ 78 through SEQ 88.

The method wherein the disease is ESCA (Esophageal carcinoma) and the tRF is selected from the group of sequences consisting of SEQ 89 through SEQ 94.

The method wherein the disease is HNSC (Head and Neck squamous cell carcinoma) and the tRF is selected from the group of sequences consisting of SEQ 95 through SEQ 109.

The method wherein the disease is KICH (Kidney Chromophobe) and the tRF is selected from the group of sequences consisting of SEQ 110 through SEQ 120.

The method wherein the disease is KIRC (Kidney renal clear cell carcinoma) and the tRF is selected from the group of sequences consisting of SEQ 121 through SEQ 128.

The method wherein the disease is KIRP (Kidney renal papillary cell carcinoma) and the tRF is selected from the group of sequences consisting of SEQ 129 through SEQ 132.

The method wherein the disease is LAML (Acute Myeloid Leukemia) and the tRF is selected from the group of sequences consisting of SEQ 133 through SEQ 165.

The method wherein the disease is LGG (Brain Lower Grade Glioma) and the tRF is selected from the group of sequences consisting of SEQ 166 through SEQ 180.

The method wherein the disease is LIHC (Liver hepatocellular carcinoma) and the tRF is selected from the group of sequences consisting of SEQ 181 through SEQ 186.

The method wherein the disease is LUAD (Lung adenocarcinoma) and the tRF is selected from the group of sequences consisting of SEQ 187 through SEQ 194.

The method wherein the disease is LUSC (Lung squamous cell carcinoma) and the tRF is selected from the group of sequences consisting of SEQ 195 through SEQ 217.

The method wherein the disease is MESO (Mesothelioma) and the tRF is selected from the group of sequences consisting of SEQ 218 through SEQ 235.

The method, wherein the disease is OV (Ovarian serous cystadenocarcinoma), and the tRF is sequence SEQ 236.

The method wherein the disease is PAAD (Pancreatic adenocarcinoma) and the tRF is selected from the group of sequences consisting of SEQ 237 through SEQ 242.

The method wherein the disease is PCPG (Pheochromocytoma and Paraganglioma) and the tRF is selected from the group of sequences consisting of SEQ 243 through SEQ 251.

The method wherein the disease is PRAD (Prostate adenocarcinoma) and the tRF is selected from the group of sequences consisting of SEQ 252 through SEQ 261.

The method wherein the disease is READ (Rectum adenocarcinoma) and the tRF is selected from the group of sequences consisting of SEQ 262 through SEQ 270.

The method wherein the disease is SARC (Sarcoma) and the tRF is selected from the group of sequences consisting of SEQ 271 through SEQ 275.

The method wherein the disease is SKCM (Skin Cutaneous Melanoma) and the tRF is selected from the group of sequences consisting of SEQ 276 through SEQ 283.

The method wherein the disease is STAD (Stomach adenocarcinoma) and the tRF is selected from the group of sequences consisting of SEQ 284 through SEQ 291.

The method wherein the disease is TGCT (Testicular Germ Cell Tumors) and the tRF is selected from the group of sequences consisting of SEQ 292 through SEQ 308.

The method wherein the disease is THCA (Thyroid carcinoma) and the tRF is selected from the group of sequences consisting of SEQ 309 through SEQ 324.

The method wherein the disease is THYM (Thymoma) and the tRF is selected from the group of sequences consisting of SEQ 325 through SEQ 331.

The method wherein the disease is UCEC (Uterine Corpus Endometrial Carcinoma) and the tRF is selected from the group of sequences consisting of SEQ 332 through SEQ 344.

The method wherein the disease is UVM (Uveal Melanoma) and the tRF is selected from the group of sequences consisting of SEQ 345 through SEQ 372.

The method wherein the disease type is ACC (Adrenocortical carcinoma), and the gene is selected from the group consisting of: CSDC2, CSGALNACT1, RERG, PCMTD1, PLCB3, YEATS2, BIRC2, MVP, MYST3, ARL6IP5, TRANK1, TMEM45A, ACVR1, PGCP, VCL, MSRA, C10orf54, DCUN1D3, CTDSPL2, SIK2, TMCO6, SRCAP, TMEM159, PLEKHO2, HLA-E, TAX1BP3, C11orf75, RCE1, NDRG4, MR1, MARK2, FAM21B, HLA-B, RBL2, CABC1.

The method wherein the disease type is BLCA (Bladder Urothelial Carcinoma), and the gene is selected from the group consisting of: ACTG2, TGFBR3, PRELP, RERE, OSR1, TCEAL1, NNAT, GCOM1, MMP2, MYST4, SYNPO2, C16orf45, FYCO1, MYH11, CSRP1, MEIS2, ACTA2, CLU, LOXL1, IGFBP4, TXNIP, SLIT3, CHRDL2, MYL9.

The method wherein the disease type is BRCA (Breast invasive carcinoma), and the gene is selected from the group consisting of: CRTC1, CALCOCO1, SLC27A1, CROCC, PGPEP1, PSD4, TBC1D17, PHF15, ARAP1, TNFRSF14, NISCH, MED16, RGS12, MYO15B, AGXT2L2, RFX1, C21orf2, NEURL4, TPCN1, HOOK2, LTBP3, SPHK2, ABTB1, ABCD4, ZBTB48, CIRBP, CYTH2, ZNF446, PHF1, RPS9, MZF1, FAM160A2, KIF13B, GLTSCR2, WDR81, SH2B1, RHOBTB2, CRY2, LTBP4, HDAC7, ZNF219, MUM1, RBM5, RAPGEF3, CCDC9.

The method wherein the disease type is CESC (Cervical squamous cell carcinoma and endocervical adenocarcinoma), and the gene is selected from the group consisting of: NBPF10, JRK, SMG5, ALDH1A2, MFAP4, ZFYVE1, CDC42BPB, ENTPD4, IGF1, ZFYVE26, APOLD1, LOC200030, KIAA0430, UBN1, VASH1, RANBP10, WDR37, MGP, MON1B, CNN1, MAT2A, PGR, KIAA0100, C14orf21, HCFC1, LRP10, DIDO1, FBXL18, ATP6V0A1, RGS2, MLXIP, TRIM56, CTGF, KIAA0284, DES, SFRP4, PDPK1, TAOK2, SMCR8, CLN8, UNC119B, TRIM25, CYB561D1, TBC1D2B, DNAJC5, CRAMP1L, ZNF646, ZC3HAV1, KHNYN, PSKH1, RGS1.

The method wherein the disease type is COAD (Colon adenocarcinoma), and the gene is selected from the group consisting of: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL1RA, HEG1, HIPK3, NEXN, TMEM140, AMOTL1, A2M, TIE1, AKT3, CD163, LPHN2, OSMR, CSF1R, DAAM2, IL1R1, GPC6, SLC8A1, FBN1, GNB4, GPNMB, DOCK2, KIAA1462, CSF2RB, MYO5A, S1PR1, ARHGEF6.

The method wherein the disease type is DLBC (Lymphoid Neoplasm Diffuse Large B-cell Lymphoma), we found that the mRNAs of the following genes satisfy these criteria: GOLGA2, DCHS1, CLDND1, CSRNP2, FRMD8, SLCO2A1, ARHGAP23, NID1, DUSP7, TBC1D20, YAP1, WDR82, TMEM43, TJP1, CARD8, ZNF213, KIAA0232, EPAS1, VPS11, PHC1, SKI, DAG1, ANKRD40, FAT1, PHF12.

The method wherein the disease type is ESCA (Esophageal carcinoma), and the gene is selected from the group consisting of: SSC5D, PDLIM3, CELF2, TIMP3, ABCC9, CALD1, COL8A1, GREM1, THBS4, PRUNE2, TMEM47, PBXIP1, PLN, CCDC80, C7, PODN, DDR2, PPP1R12B, MRVI1, LMOD1, C7orf58, HSPB7, TAGLN, PPP1R16B, GFRA1, LOC728264, SGCD, PGM5.

The method wherein the disease type is HNSC (Head and Neck squamous cell carcinoma), and the gene is selected from the group consisting of: GABBR1, C14orf179, METT11D1, C6orf125, ZNF692, FKBP2, FAM113A, LOC388789, TAZ, WASH3P, CDK5RAP3, PLBD2, SDR39U1, CPT1B, UBL5, C14orf2, LOC146880, THAP3, ANKRD13D, C12orf47, ATP5E, ATPIF1, SYF2, C8orf59, WASH7P, NPIPL3, CDK10, C1orf151, MRPS21, C19orf60, C7orf47, CENPT, GAS5, KIFC2, NFIC, RPL39, UQCRB, COX6C, LUC7L, CCS, COMMD6, ZNF133, SNHG12, C11orf31, NPEPL1.

The method wherein the disease type is KICH (Kidney Chromophobe), and the gene is selected from the group consisting of: BMPR1A, EXT1, TFAM, PDCD11, MTIF2, POLR3A, MAPK8, PRDX3, COQ5.

The method wherein the disease type is KIRC (Kidney renal clear cell carcinoma), and the gene is selected from the group consisting of: ARHGAP19, KIAA1671, KIAA0754, KIAA1147, ZNF45, KLF13, MYO9A, FUT11, ASH1L, KIF13A, TUBGCP3, MTF1, FAM168A.

The method wherein the disease type is KIRP (Kidney renal papillary cell carcinoma), and the gene is selected from the group consisting of: GLCCI1, CDK13, POGZ, UBN2, CREBZF, NPHP3, VEZF1, CHD1, YPEL2, LRRC37B2, GPATCH8, ENC1, TTC18, C11orf61, RSBN1L, EFNB2, PHIP, RBAK, SPEN, RBM9, SMURF2, ZNF264, ZNF587, PTPN12, TPBG, RBM33, DMTF1, CCNT2, ARID4B, ARGLU1, CREB1, KIAA0753, BTAF1, C17orf85, RLF, MLL5, ZFC3H1, ZNF160, PRPF38B, SETD5, ARRDC4, HOOK3, RC3H1, MLL3, RNF207, MAP3K1, PLEKHH2, CCDC57, DAPK1, LUC7L3.

The method wherein the disease type is LAML (Acute Myeloid Leukemia), and the gene is selected from the group consisting of: SUPT5H, SKIV2L, IKBKG, HGS, MIB2, MED15, STK25, ANAPC2, RHOT2, SFI1, CUL9, ARHGEF1, GTPBP2, KIAA0892, MBD1, UCKL1, DHX16, ZFYVE27, APBA3, PI4 KB, C19orf6, SPSB3, CAPN10, FLYWCH1, ATG4B, CDC37, LZTR1, MAN2C1, C1orf63, DVL1, EDC4, DHX34, PCNXL3, EXOC3, FUK, FBXL6, LMF2, HDAC10, E4F1, TSC2, ZDHHC8, CPSF3L, FAM160B2, CLCN7, LRRC14, D2HGDH, ZNF335, FHOD1, SOLH, ZBTB17, POLRMT, SLC26A1, KIAA0415, SELO, SAPS2, NME3, KLHL36, SCYL1, USP19, DGKZ, CYHR1, ATG2A, VPS16, XAB2, ACTR5, ZNF76, ATP13A1, RNF31, GPN2, MUS81, FAM73B, TTC15, CXXC1, TRMT2A, WDR8, PTGES2, TELO2, RFNG, SLC39A13.

The method wherein the disease type is LGG (Brain Lower Grade Glioma), and the gene is: EXD3.

The method wherein the disease type is LIHC (Liver hepatocellular carcinoma), we found that the mRNA of the following gene satisfies these criteria: DYRK2.

The method wherein the disease type is LUAD (Lung adenocarcinoma), and the gene is selected from the group consisting of: CROCCL1, RHPN1, ABCA7, RGL3, PDXDC2, ENGASE, ATG16L2, CSAD, TTLL3, ARHGEF12, ANKS3, LOC100132287, SGSM2, HEXDC, LPIN3, ACCS, PLEKHMIP, ANO9, ELMOD3, KIAA0895L, AP1G2, ACAP3, ECHDC2, NXF1, JMJD7-PLA2G4B, TMEM175, CCDC64B, ANKMY1.

The method wherein the disease type is LUSC (Lung squamous cell carcinoma), and the gene is selected from the group consisting of: PKD1, CHKB-CPT1B, WDR90, MACF1, RBM6, LENG8, TAF1C, COL16A1, CAPN12, RBM39, ACIN1, FNBP4, PILRB, DMPK, SFRS5, AHSA2, RBM25, PLCG1, SNRNP70, NCRNA00201, GIGYF1, SRRM2, GOLGA8B, ZGPAT, RTEL1, COL27A1, MAPK8IP3, PABPC1L, HSPG2, AKAP13, LRP1, NKTR, ATAD3B, TUBGCP6, ZNF276, MICALL2, CLCN6, NSUN5P2, NEAT1, LAMA5, CHD2, PPP1R12C, FAM193B, NPIP, CDK11A, STX16, LTBP2, LOC91316, NBEAL2, FLJ45340, LRDD, CCDC88B, GOLGA8A.

The method wherein the disease type is MESO (Mesothelioma), and the gene is selected from the group consisting of: C15orf40, SNUPN, CHTF8, CLNS1A, CSNK1D, DPF2, PCIF1, DNAJC4, SECISBP2, C5orf32, RPRD1B, RPL38, NDUFA10, RPRM, BAT4, RSL1D1.

The method wherein the disease type is OV (Ovarian serous cystadenocarcinoma), and the gene is selected from the group consisting of: KIAA0907, ULK3.

The method wherein the disease type is PAAD (Pancreatic adenocarcinoma), and the gene is selected from the group consisting of: NUAK1, KBTBD4, HMCN1, DSTYK.

The method wherein the disease type is PCPG (Pheochromocytoma and Paraganglioma), and the gene is selected from the group consisting of: CACNA2D1, TP53BP1, KIAA1244, MARCH8, PCDHGC4, ESYT2, DHX15, TECPR1, MAP3K2, TBC1D24, PCDH1, IPO11, MGAT5, TRAM2, ADAM10, GNA11, CBX6, SNURF, RIF1, CNTN1, LMBRD2, CAND1, TRIP12, RC3H2, PAK3, TMCO3, CSNK2A1P, ASB1, AKAP2, ROCK2, NUP155, PIK3C3, KLHDC10, RAB35, GTF2I, HSPA8, FAM49A.

The method wherein the disease type is PRAD (Prostate adenocarcinoma), and the gene is selected from the group consisting of: FEM1B, TGOLN2, SEPT9, MYOCD, LUZP1, TLN1, PIAS1, RNF111, DCBLD2, URB1, ZBTB40, ZNF516, ATXN1L, RHBDD1, HUWE1, VPS13D, ITPR1, NNT, ERC1.

The method wherein the disease type is READ (Rectum adenocarcinoma), and the gene is selected from the group consisting of: FZD4, CD93, DYNC1I2, ENG, ELK3, KDR, FAM101B, PXDN, GIMAP4, F13A1, VCAM1, ARHGAP31, CD34, GNG2, LCP2, VWF, CSF1, GPR116, KIRREL, MMRN2, ETS1, ITGA4, FAM120B.

The method wherein the disease type is SARC (Sarcoma), we found that the mRNAs of the following genes satisfy these criteria: SH3BGRL, SORBS1, MAPK4, LYNX1, MICAL3, AKAP1, LIMS2, RNF38, LOC283174, CAND2, PLIN4, MOAP1, RNF19A, RABGAP1, C5orf4, FRY, ARHGEF17, SETMAR, SSH3, NUMA1, PBX1, TOR1AIP1, TACC2, RAB3D, BBS1, CEP68, GPRASP1, SVIL, CRBN, CRTC3, ZFYVE21, SLMAP, RASL12, SCAPER, STAT5B, ZAK, EZH1.

The method wherein the disease type is SKCM (Skin Cutaneous Melanoma), and the gene is selected from the group consisting of: MLL4, LMTK2, APBB3, C17orf56, LOC388796, ANO8.

The method wherein the disease type is STAD (Stomach adenocarcinoma), and the gene is selected from the group consisting of: KCNMA1, MAST4, FHL1, ATP2B4, TENC1, C20orf194, ASB2, C10orf26, TTC28, FAM13B, ITPKB, GNAO1, FAM129A, ZBTB4, FNBP1, FLNA, CCDC69, STON1, NFASC, PAPLN, ADCY5, LPP, NEGR1, ABI3BP, INPP5B, TNXB, ANGPTL1, ANK2, EPHA3, ZCCHC24, SETBP1, PRICKLE2, LTBP1, RGMA, DARC, KANK2, SYNPO.

The method wherein the disease type is TGCT (Testicular Germ Cell Tumors), and the gene is selected from the group consisting of: ATF6, CTDSP2, MKL2, TEAD1, ZNF407, TRAPPC9, AHDC1, LANCL1, KCTD20, OXR1, SNX1, CSNK1G1, KIAA0247, LDOC1L, EPC1, GRLF1, ABHD2, RAII, ARID1B, ITFG1, MUT, KIAA1737, LAMA2, KIAA1109, CCNI, DIXDC1, C6orf89, RNF144A, APPBP2, KLF12, ZFP91.

The method wherein the disease type is THCA (Thyroid carcinoma), and the gene is selected from the group consisting of: KIAA0495, PHF21A, ZBTB5, SFRS6, NCOA5, ZNF814, IP6K2, IFT140, INTS3, ZNF559, SETD4, TGIF2, VILL, KCNC3, UBE2G2, FBXO9, IPW, DUOXA1, CACNA2D2, EFHC1, FAM189A2, GTF2IRD2P1, KIAA1683, AP4B1, SCAND2, CDRT4, UNKL, NYNRIN, ARMC5, MAPKBP1, USP40, VEGFA, OLFM2, FBF1, TCF7L1, MXD4, IKBKB, POFUT2, BOC, TCF7L2, RMST, TRO.

The method wherein the disease type is THYM (Thymoma), and the gene is selected from the group consisting of: ZFYVE9, LOC399959, SIX1, PDGFC.

The method wherein the disease type is UCEC (Uterine Corpus Endometrial Carcinoma), and the gene is selected from the group consisting of: RNMT, SON, MDN1, CELF1, RIPK1, YLPM1, XRN2, BPTF, RQCD1, PAFAH1B2, BOD1L, SBNO1, RNF169, PIK3R4, LRCH3, DCP1A, SF3A1, SLC9A8, TNRC6A, BRPF3.

The method wherein the disease type is UCS (Uterine Carcinosarcoma), we found that the mRNA of the following gene satisfies these criteria: RHBDF1.

The method wherein the disease type is UVM (Uveal Melanoma), and the gene is selected from the group consisting of: MAP1A, TCIRG1, ECM1, C14orf159, WARS, PCYOX1L.

A further embodiment is directed towards a method of treating a disease in a patient comprising: determining the disease type that is ailing the said patient; determining at least one gene whose abundance is dysregulated in the said patient; determining at least one tRF that is correlated with the at least one dysregulated gene; and administering a therapeutic composition sufficient to modify the abundance of the at least one mRNA corresponding to a gene whos abundance is dysregulated in the said patient. Preferably, the disease is detected by taking a sample from a patient. An appropriate therapeutic composition may be any composition targeted to the regulation of the abundance of the at least on mRNA corresponding to a gene, for example a small molecule, a biologic, an antibody, an antimer, other other material known to those of ordinary skill in the art.

A further embodimner is directed towards a method of treating a disease in a patient comprising: selecting at least one tRF that is transcribed in the ailing tissue and of the said patient; selecting at least one gene that is correlated with the at least one tRF that is transcribed in the ailing tissue of the said patient; and administering a therapeutic composition sufficient to modify the abundance of the at least one gene.

In certain embodiments, a further step comprises collecting an ailing tissue sample from said patient.

In certain embodiments, as described herein, wherein at least one tRF is selected based upon having at least 20 different mRNA correlations for at least the disease being treated, and having no more than 3 different mRNA correlations for another disease not being treated.

In certain embodiments, as described herein, wherein at least one mRNA is selected based upon having at least 20 different tRF correlations for at least the disease being treated, and having no more than 3 different tRF correlations for another disease.

A further embodiment is directed towards a method of treating a patient for a disease of interest by focusing on disease-specific tRFs among those that are correlated with genes or by focusing on disease-specific genes among those that are correlated with tRFs comprising: compiling statistically-significant correlations between tRFs and the mRNAs of genes by analyzing datasets from two or more diseases, one of which is the disease of interest; determining for each tRF the number of correlations with mRNAs in which it participates in the disease of interest; determining for each tRF the number of correlations with mRNAs in which it participates in the one or more diseases other than the disease of interest; subselecting only those tRFs that participate in a high number of correlations with mRNAs in the disease of interest and in a low number of correlations with mRNAs in the one or more diseases other than the disease of interest; determining for each mRNA the number of correlations with tRFs in which it participates in the disease of interest; determining for each mRNA the number of correlations with tRFs in which it participates in the one or more diseases other than the disease of interest; subselecting only those mRNAs that participate in a high number of correlations with tRFs in the disease of interest and in a low number of correlations with tRFs in the one or more diseases other than the disease of interest; choosing at least one of the subselected tRFs; choosing at least one of the subselected mRNAs; and administering a therapeutic composition sufficient to modify the abundance of the at least one chosen tRF or of the at least one chosen mRNA. In preferred embodiments, the disease of interest is cancer. Preferably, where at least one of the one or more diseases other than the disease of interest is cancer. In preferred embodiments, where for each tRF the number of correlations with mRNAs in the disease of interest is at least two times higher than the average number of correlations that this tRF has with mRNAs in the one or more diseases other than the disease of interest. In preferred embodiments, where for each tRF the number of correlations with mRNAs in the disease of interest is at least three times higher than the average number of correlations that this tRF has with mRNAs in the one or more diseases other than the disease of interest. In preferred embodiments, where for each tRF the number of correlations with mRNAs in the disease of interest is at least four times higher than the average number of correlations that this tRF has with mRNAs in the one or more diseases other than the disease of interest. In preferred embodiments, where for each mRNA the number of correlations with tRFs in the disease of interest is at least two times higher than the average number of correlations that this mRNA has with tRFs in the one or more diseases other than the disease of interest. In preferred embodiments, where for each mRNA the number of correlations with tRFs in the disease of interest is at least three times higher than the average number of correlations that this mRNA has with tRFs in the one or more diseases other than the disease of interest. In preferred embodiments, where for each mRNA the number of correlations with tRFs in the disease of interest is at least four times higher than the average number of correlations that this mRNA has with tRFs in the one or more diseases other than the disease of interest.

A further embodiment is directed towards a method of identifying a target for disease treatment by focusing on disease-specific tRFs among those that are correlated with genes or by focusing on disease-specific genes among those that are correlated with tRFs comprising: compiling statistically-significant correlations between tRFs and the mRNAs of genes by analyzing datasets from two or more diseases, one of which is the disease of interest; determining for each tRF the number of correlations with mRNAs in which it participates in the disease of interest; determining for each tRF the number of correlations with mRNAs in which it participates in the one or more diseases other than the disease of interest; subselecting only those tRFs that participate in a high number of correlations with mRNAs in the disease of interest and in a low number of correlations with mRNAs in the one or more diseases other than the disease of interest; determining for each mRNA the number of correlations with tRFs in which it participates in the disease of interest; determining for each mRNA the number of correlations with tRFs in which it participates in the one or more diseases other than the disease of interest; subselecting only those mRNAs that participate in a high number of correlations with tRFs in the disease of interest and in a low number of correlations with tRFs in the one or more diseases other than the disease of interest; choosing at least one of the subselected tRFs; choosing at least one of the subselected mRNAs; and, wherein the correlated tRF's or one or more mRNAs are the targets for treatment. In certain embodiments, we further administer a therapeutic composition sufficient to modify the abundance of the at least one chosen tRF or of the at least one chosen mRNA.

In summary, tRFs and the uncovered associations in which they participate provide an excellent framework in which to develop targeted therapeutics and realize "precision" medicine.

BRIEF DESCRIPTION OF THE DRAWINGS

FIGS. 3A-3B Cleavage points across the tRFs. (A) A schematic that shows the preferences of the 5' termini (white pentagon arrows) and 3' termini (gray chevrons) for 5'-tRFs, 3'-tRFs, and i-tRFs. For clarity purposes, separate schematics show the preferences of the 5' termini and the 3' termini for i-tRFs. The thickness of the arrow or chevron indicates the preference for the corresponding position in a qualitative manner. Groups of arrows are tagged with black-on-gray labels whereas groups of chevrons are tagged with black-on-white labels. The capital X of each label indicates the terminal nucleotide, either 5' or 3': this letter X is preceded (followed, respectively) by the three most frequent dinucleotides found immediately upstream (downstream, respectively) in the mature tRNA for the most abundant tRFs that begin or end at the position. Squares containing white circles indicate positions with known modifications. We stress that these modifications are shown for reference purposes only as it is unclear whether they occur in the tissues and tissue states that are represented by the TCGA datasets we analyzed. (B) Box plots showing the preferences for the starting (left) and ending (right) positions for i-tRFs in LUAD and OV.

DETAILED DESCRIPTION OF THE EMBODIMENTS

Figure 1A:
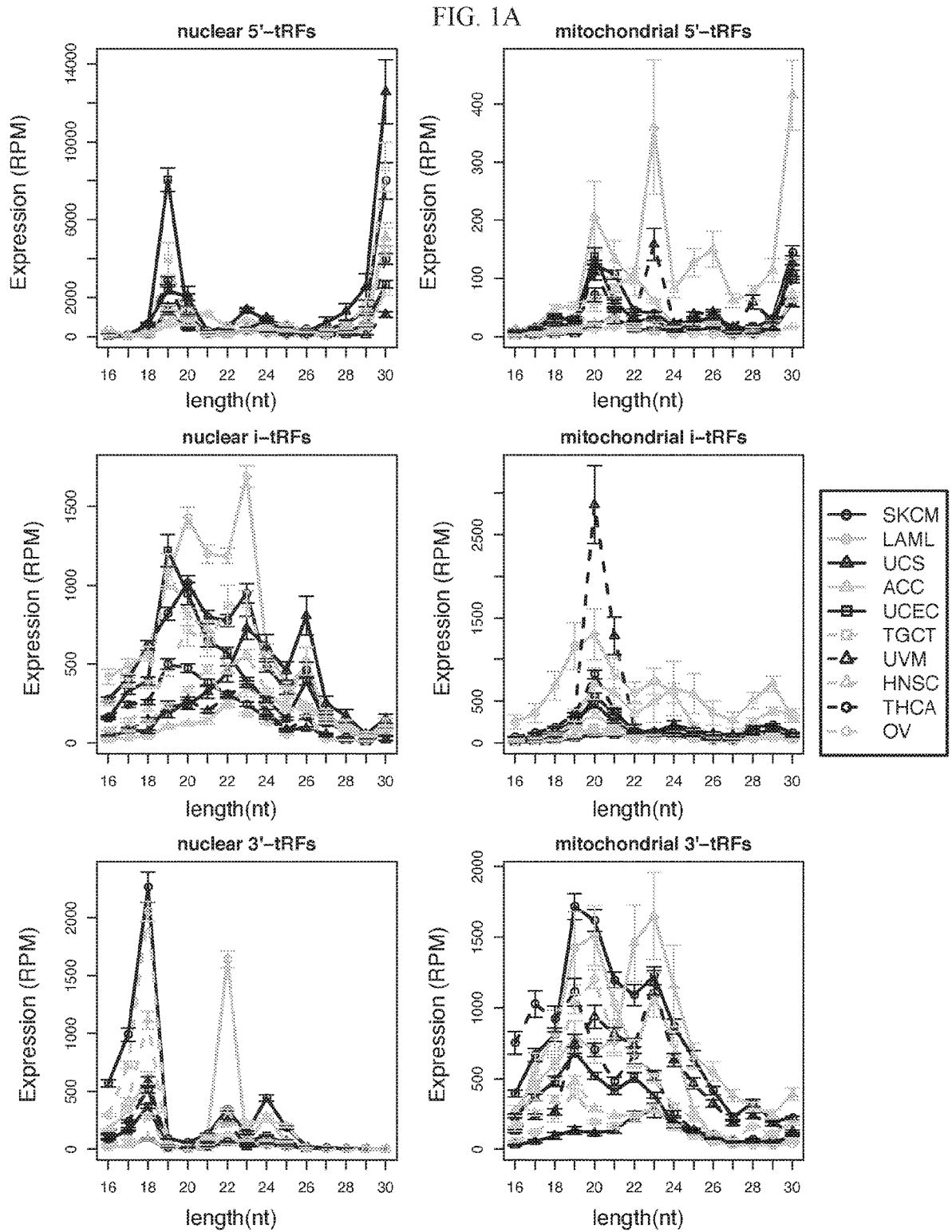
FIGS. 1A-1C tRF distributions by category, length, and abundance. (A) Length distributions of tRFs broken down by type and organelle in 10 of the 32 analyzed cancer types (for each length the mean across samples and the standard error are shown). Each category has a unique and cancer-type-specific distribution. (B) Heatmap and hierarchical clustering (metric: Kendall's tau coefficient) of the expression profiles of the structural categories per origin as the sum of tRF expression that fall in each category. Mitochondrial tRFs are clustered together while nuclear tRFs are split by length. Short nuclear tRFs (<24 nt) are clustered together with the MT tRFs in the bottom half of the heatmap. Longer nuclear tRFs are clustered together in the top half of the heatmap separately from MT tRFs and short nuclear tRFs. This heatmap highlights the observation that tRFs are diverse. (C) A PCA plot showing the clustering for various combinations of tRF type, length, and genome origin, similar to the clustering shown in (B). The correspondence between tRF length and shading of the fill of the used marker is the same for both panels (B) and (C).

Overall explanation of functionality.

While we mined tRFs from all 11,198 datasets, we included in our analyses only the 10,274 datasets that have been "white-listed" by the various consortia of The Cancer Genome Atlas (TCGA): these datasets contain no special annotations in the associated clinical metadata (as of Oct. 28, 2015). Across the 32 cancer types, we identified 20,722 distinct tRFs, 29% of which arise from MT tRNAs. The majority of these fragments belong to the novel category of i-tRFs, i.e. they are wholly internal to the mature tRNAs. The abundances and cleavage patterns of the identified tRFs depend strongly on cancer type. Of note, in all 32 cancer types, we find that tRNA$^{HisGTG}$ produces multiple and abundant 5'-tRFs with a uracil at the −1 position, instead of the expected post-transcriptionally-added guanosine. Strikingly, these −1U His 5'-tRFs are produced in ratios that remain constant across all analyzed normal and cancer samples, a property that makes tRNA$^{HisGTG}$ unique among all tRNAs. We also found numerous tRFs to be negatively correlated with many messenger RNAs (mRNAs) that belong primarily to four universal biological processes: transcription, cell adhesion, chromatin organization and development/morphogenesis. However, the identities of the mRNAs that belong to these processes and are negatively correlated with tRFs differ from cancer to cancer. Notably, the protein products of these mRNAs localize to specific cellular compartments, and do so in a cancer-dependent manner. Moreover, the genomic span of mRNAs that are negatively correlated with tRFs are enriched in multiple categories of repeat elements. Conversely, the genomic span of mRNAs that are positively correlated with tRFs are depleted in repeat elements. These findings suggest novel and far-reaching roles for tRFs and indicate their involvement in system-wide interconnections in the cell.

Results

The tRFs we discovered from all 11,198 datasets of TCGA are available at https://cm.jefferson.edu/tcga-mint-map-profiles. Our analyses focus only on tRFs whose sequences fully overlap a mature tRNA. These tRFs can belong to one of five structural categories (5'-tRFs, i-tRFs, 3'-tRFs, 5'-tRHs and 3'-tRHs). They can also belong to two categories (exclusive and ambiguous) based on their potential genomic origin. In terms of length, all generated tRFs range from 16 to 30 nucleotides (nt). See Methods.

A Multitude of tRFs Across the 32 TCGA Cancer Types

We used our recently developed Threshold-seq algorithm (21) to automatically determine a support threshold for each of the analyzed datasets. Threshold-seq adapts to a dataset's depth of sequencing while being immune to the potential presence of outliers, making it ideal for this purpose. We report tRFs that exceeded Threshold-seq's recommended threshold in at least one of the analyzed datasets. For the range 16-30 nt, we find a total of 20,722 distinct tRFs that exceed threshold. These tRFs comprise 1,717 5'-tRFs, 16,133 i-tRFs, 2,840 3'-tRFs, and 32 5'-tRHs. We note that fragments with lengths larger than 27 nt could be truncated versions of tRFs longer than 30 nt (see Methods). 18,453 of the 20,722 tRFs have lengths between 16 and 27 nt inclusive (=1,395 5'-tRFs, 14,478 i-tRFs, 2,574 3'-tRFs, and six 5'-tRHs). We note that i-tRFs are abundant and very diverse, in agreement with our earlier findings (4,8,22). Of the 20,722 tRFs, 13,904 (67%) are exclusive to tRNA space whereas the remaining 6,818 have ambiguous genomic origin. For more detailed information, see Supp. Table S1.

Figure 12:
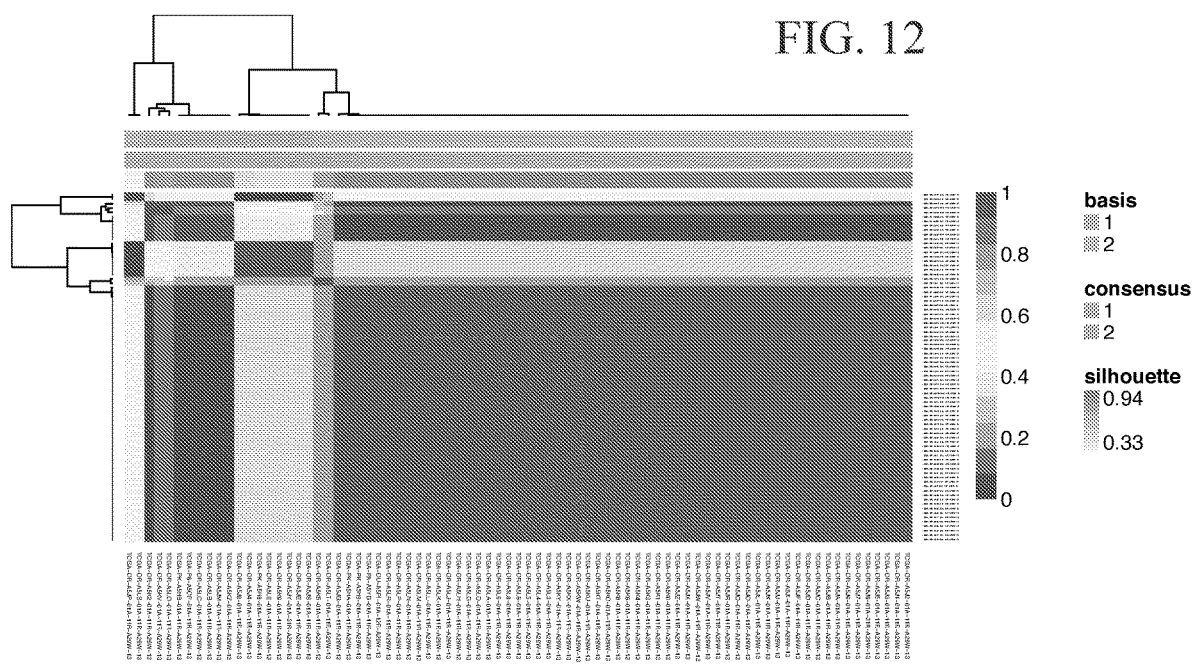
FIG. 12 NMF clustering of samples using the tRF abundance profiles in each cancer type's datasets. Here we show the results obtained for each cancer by applying the NMF method to the tRF abundance profiles. For each of the 32 analyzed cancer types, we show the results for k=1, 2, 3, . . . , 10 clusters.
Figure 12:
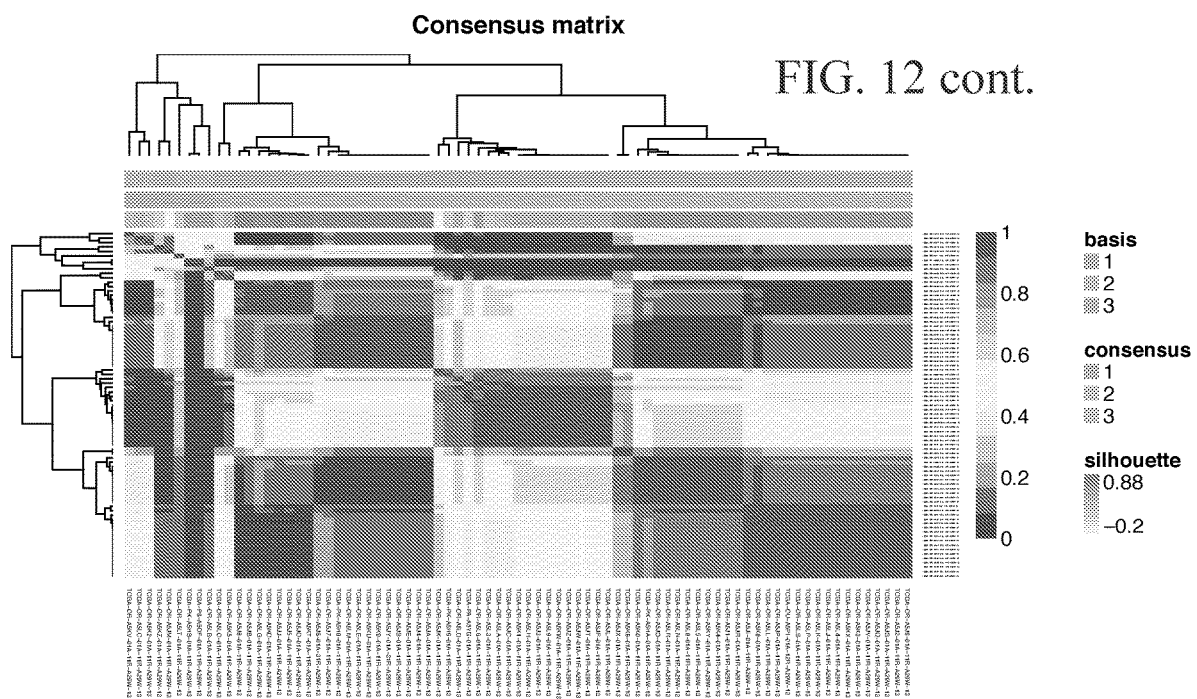
Figure 12:
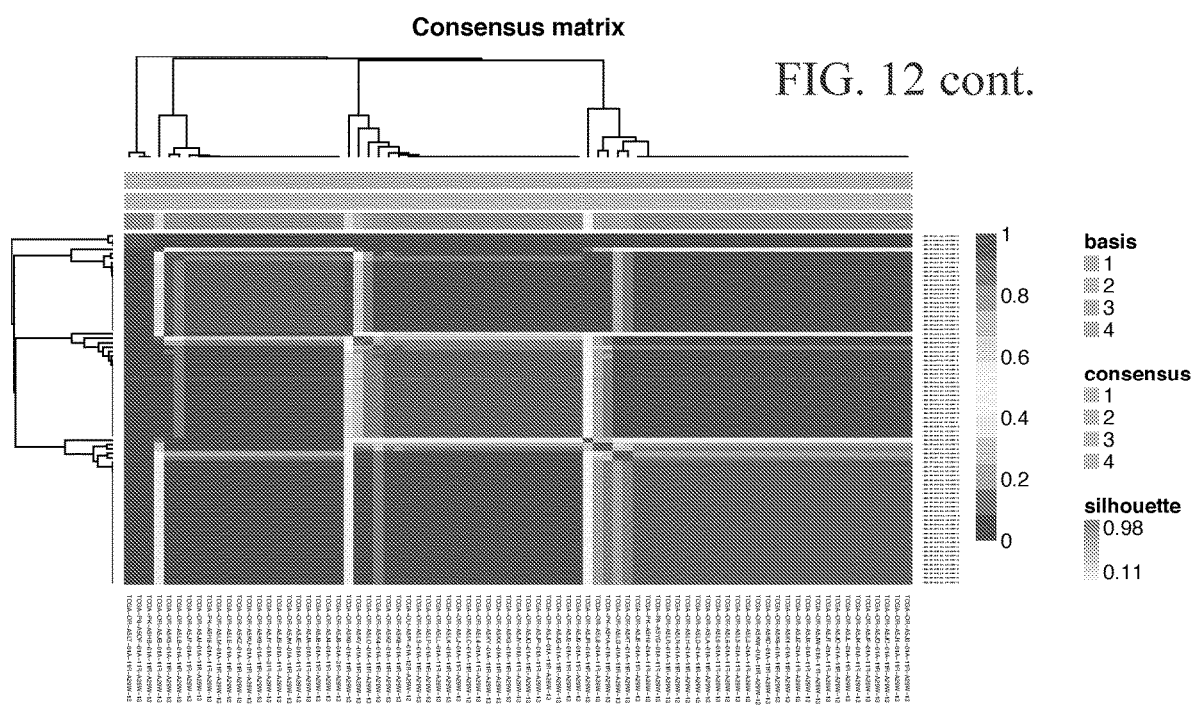
Figure 12:
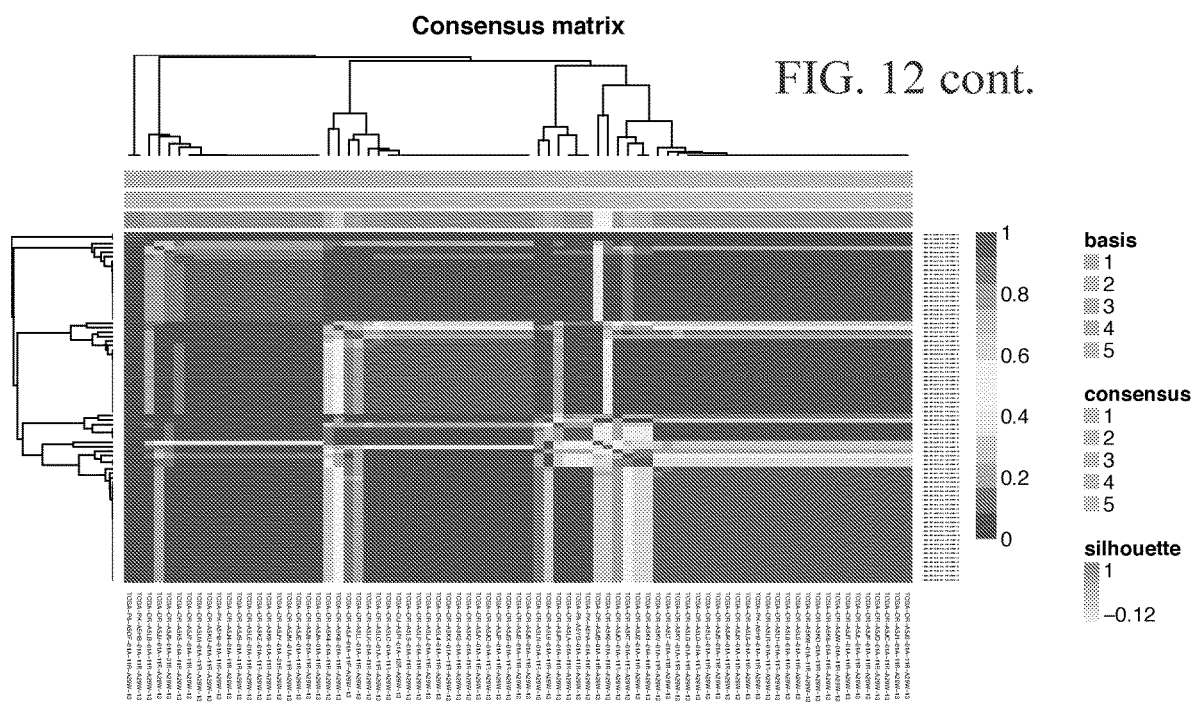
Figure 12:
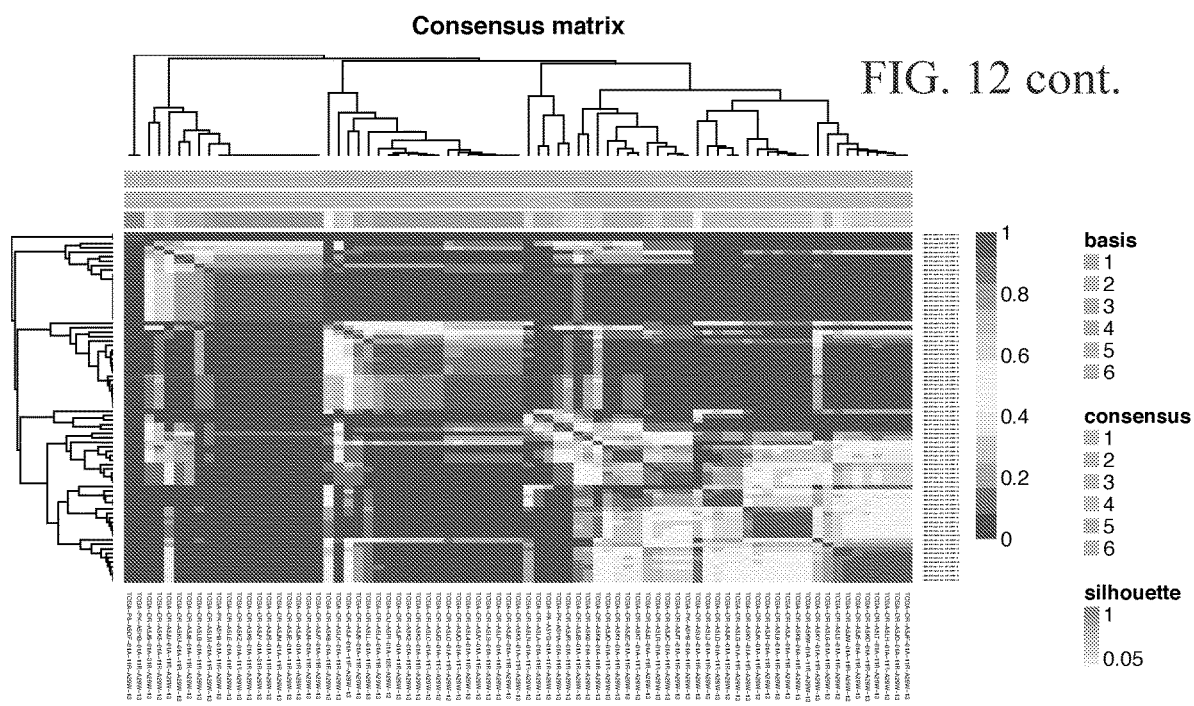
Figure 12:
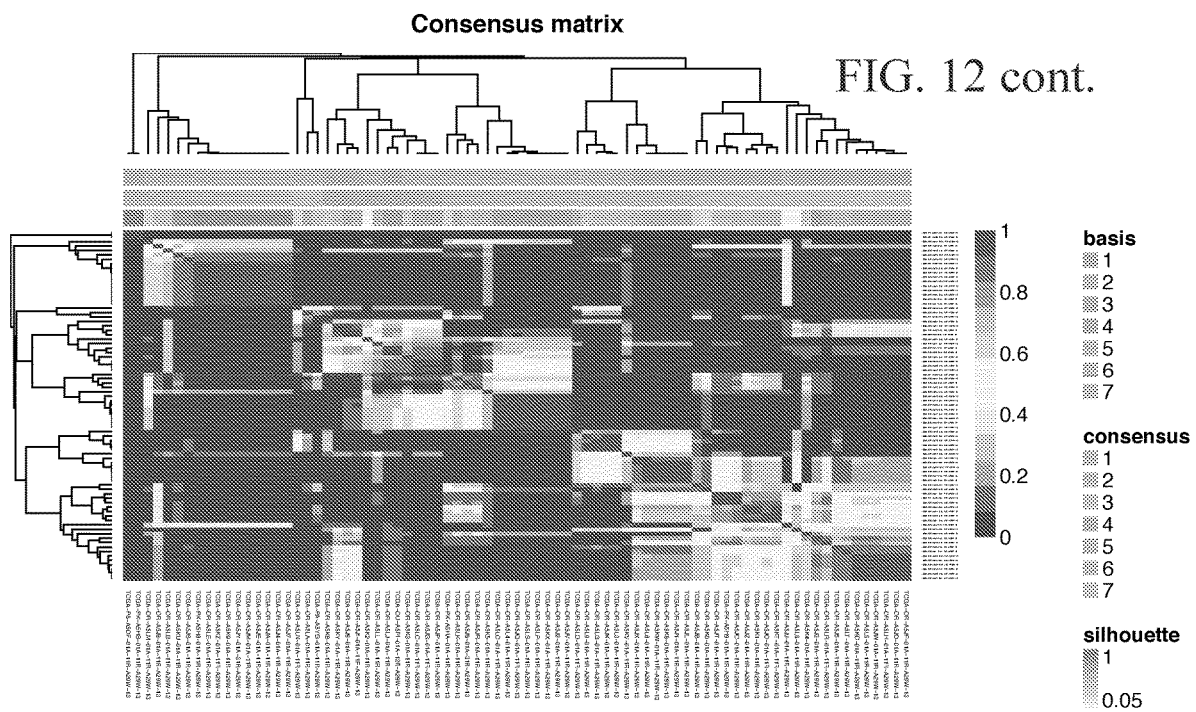
Figure 12:
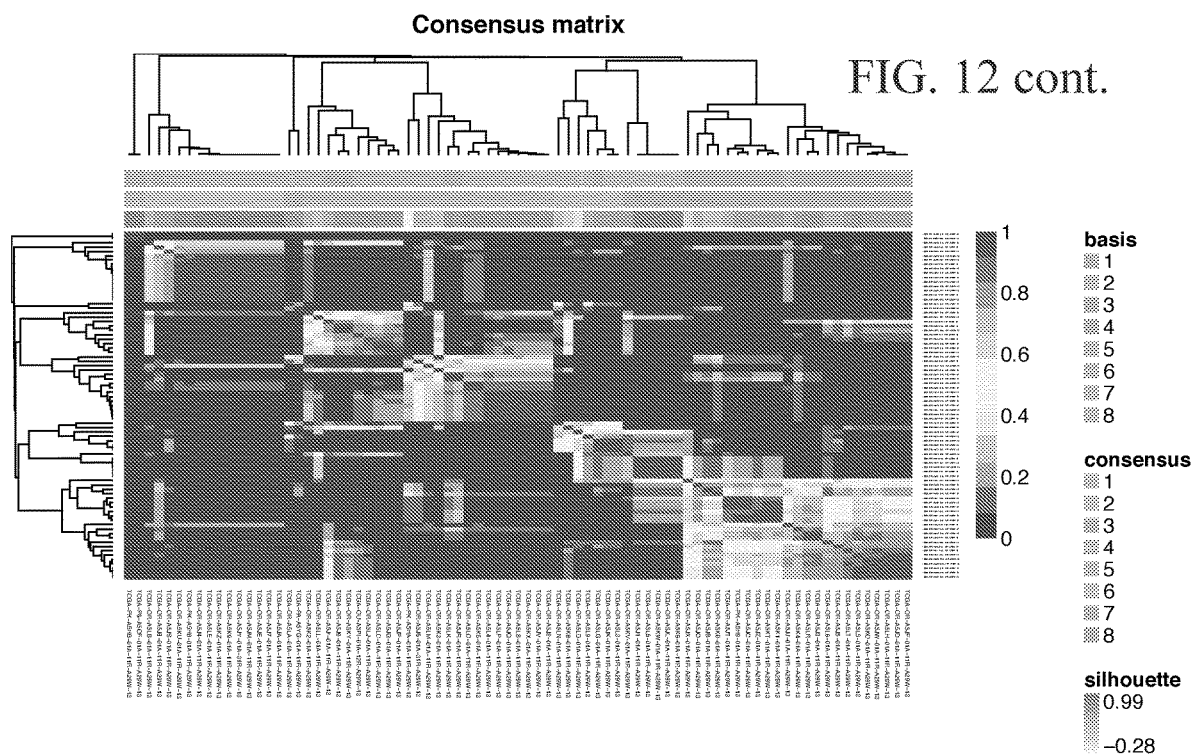
Figure 12:
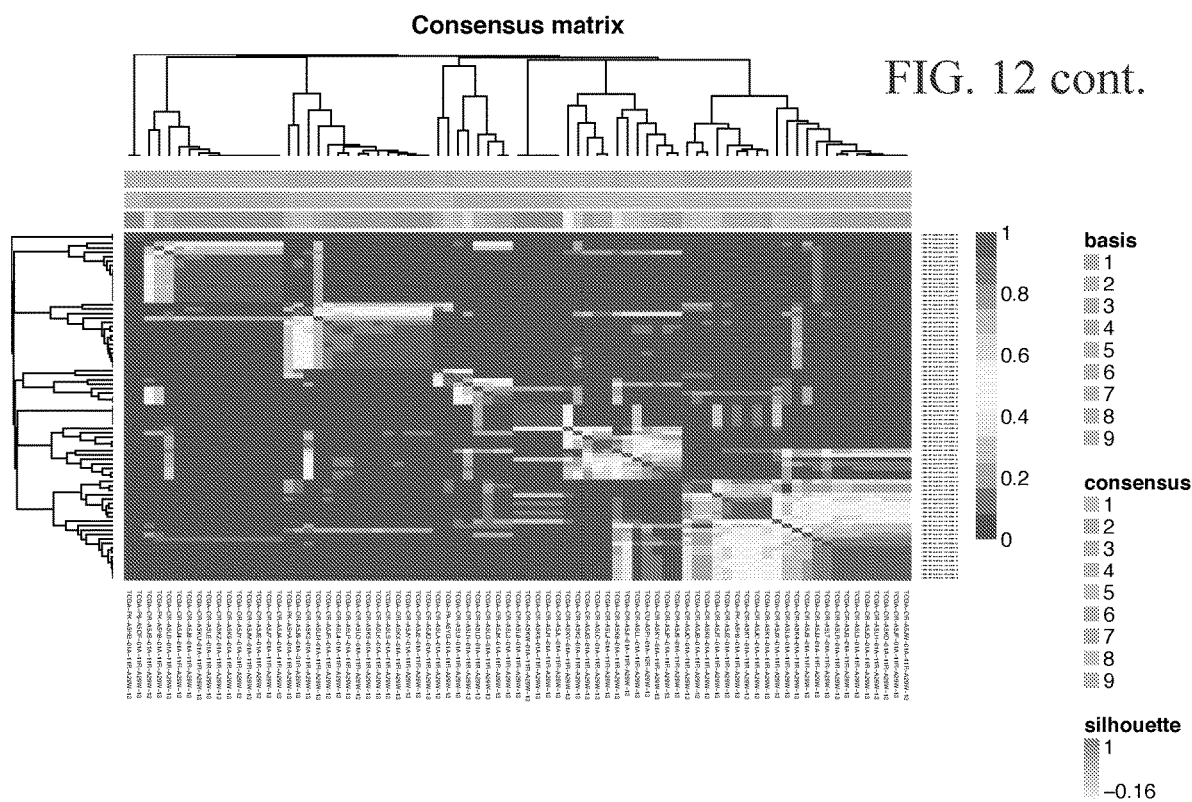
Figure 12:
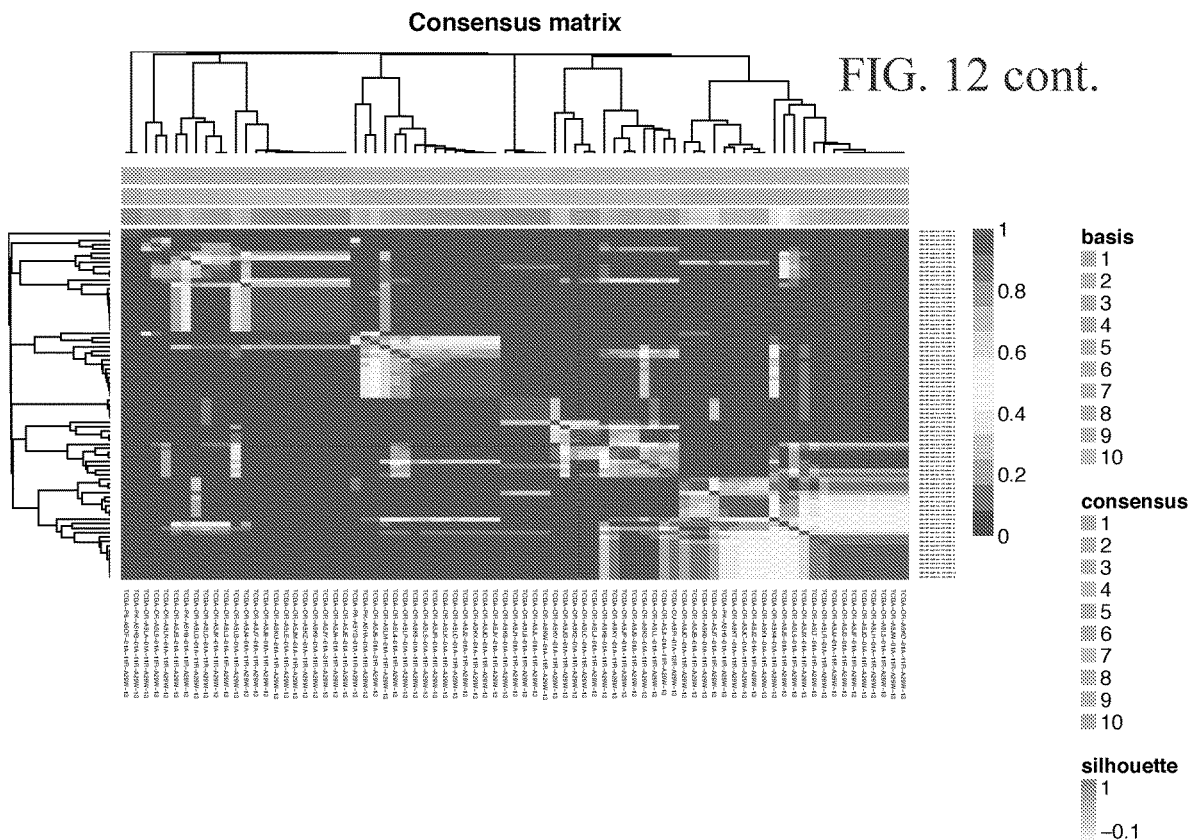

We also adopted the approach of the TCGA working groups and carried out NMF clustering of the datasets in each of the 32 cancer types using tRF profiles instead of miRNA profiles (see Methods). FIG. 12 summarizes the results of the 288 NMF runs (SKCM samples were split into two types whereas GBM was excluded—see Methods).

Nuclear and MT tRFs Exhibit Distinct and Cancer-Dependent Profiles

In previous work, we showed differences in the length and abundance profiles of nucleus-encoded vs. MT-encoded tRFs in healthy individuals from the 1,000 Genomes Project (1KG) (4), breast (4) as well as prostate cancer (8) and liver cancer patients (22) that were not part of the TCGA initiative. These results suggest that different cancer types exhibit different distributions of nucleus-encoded and MT-encoded, respectively, tRFs. Thus, we sought to examine these profiles across all TCGA cancer types.

Figure 1B:
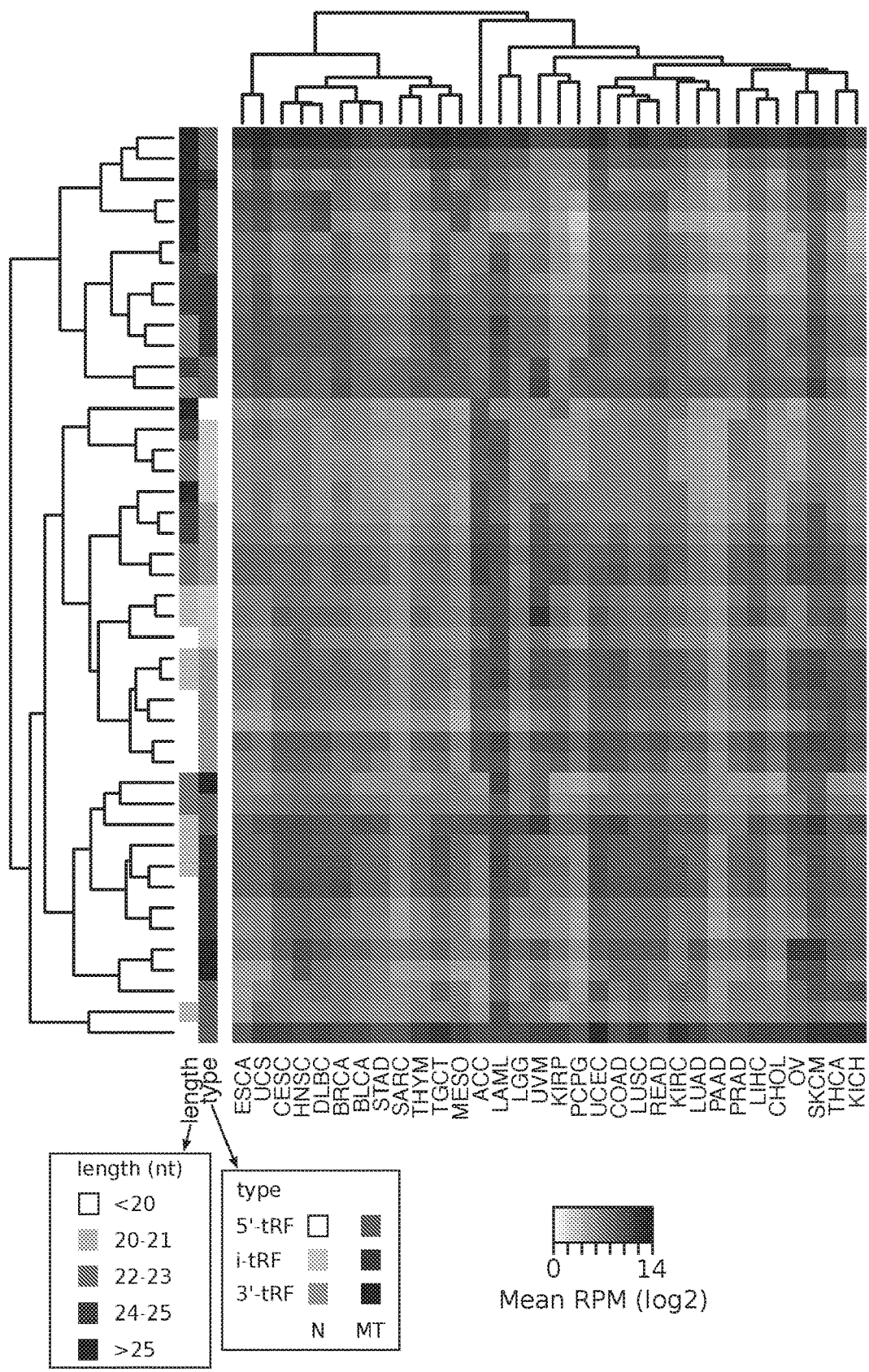
Figure 1C:
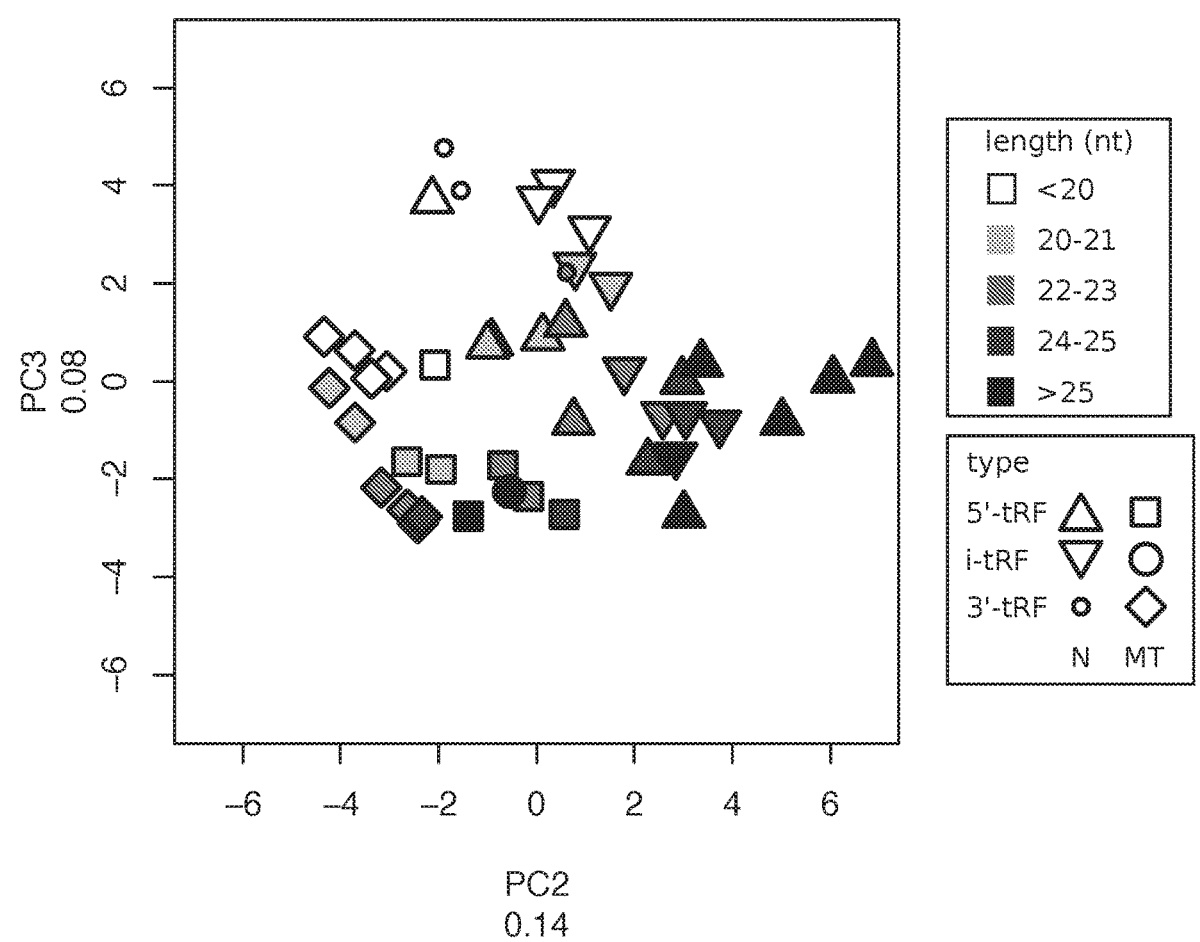
Figure 13:
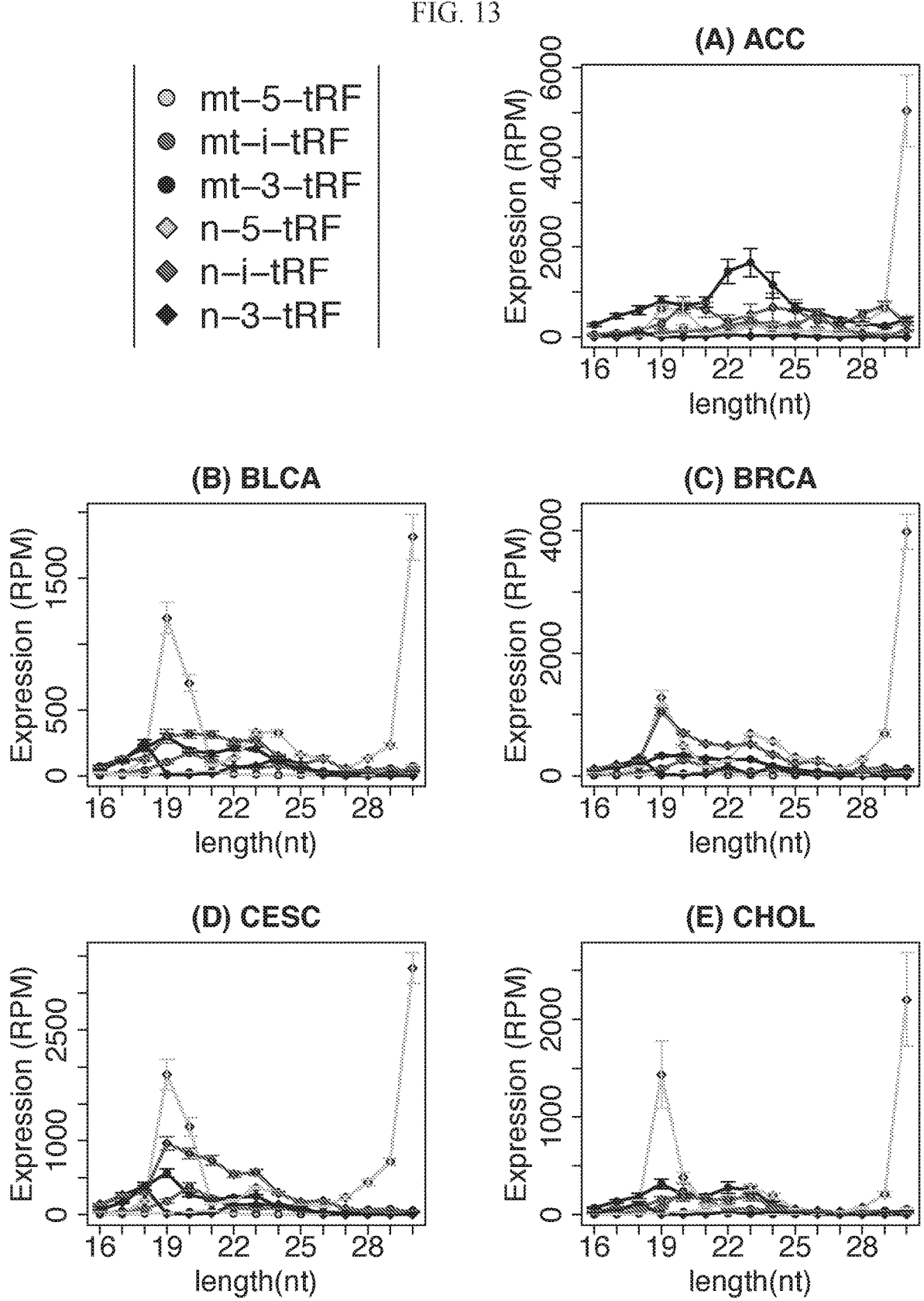
FIG. 13 Distribution of tRF abundance as a function of length and tRF type. Plots showing the distributions of the abundances of the various tRFs as a function of length. The plots are shown separately for each of 32 TCGA cancer types. For each point on a curve a standard error is shown that is derived by analyzing the samples of the corresponding cancer type.
Figure 13:
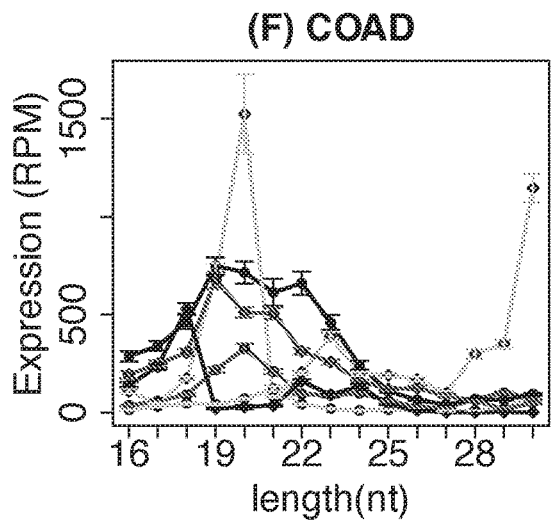
Figure 13:
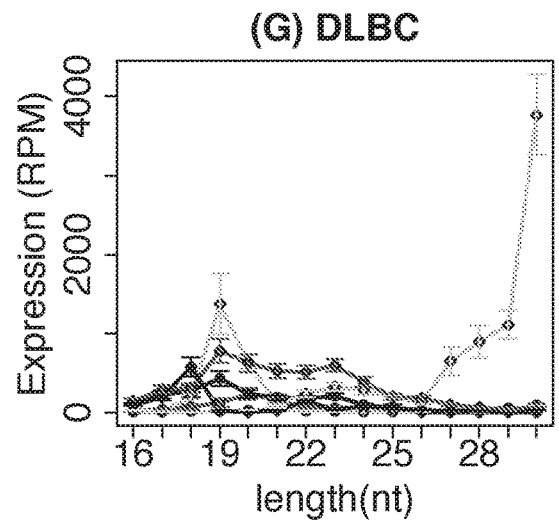
Figure 13:
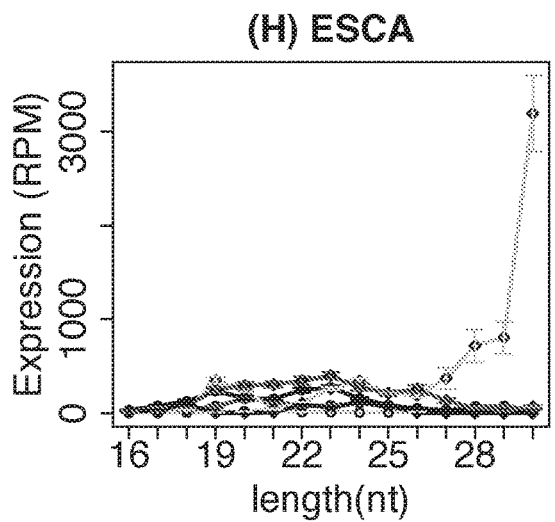
Figure 13:
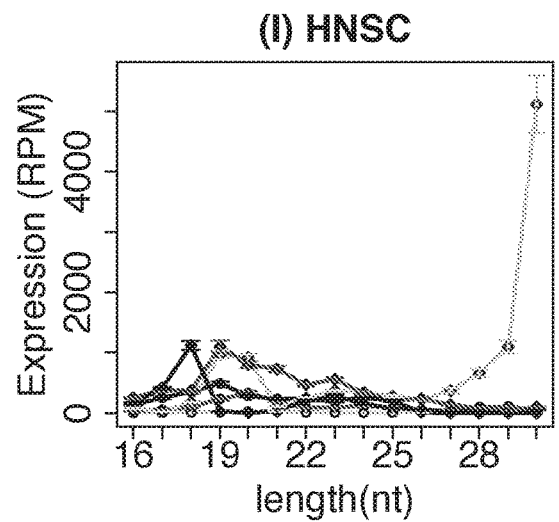
Figure 13:
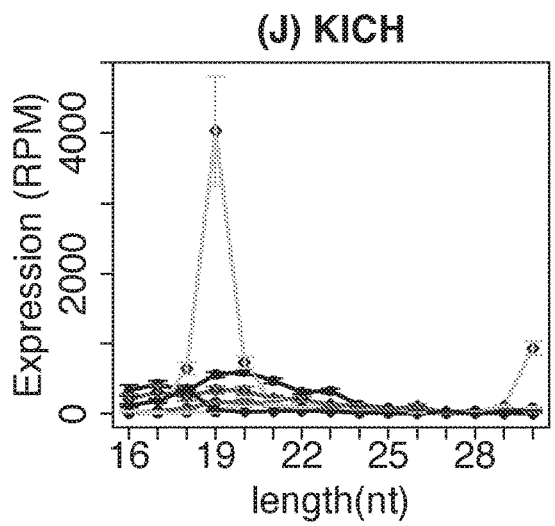
Figure 13:
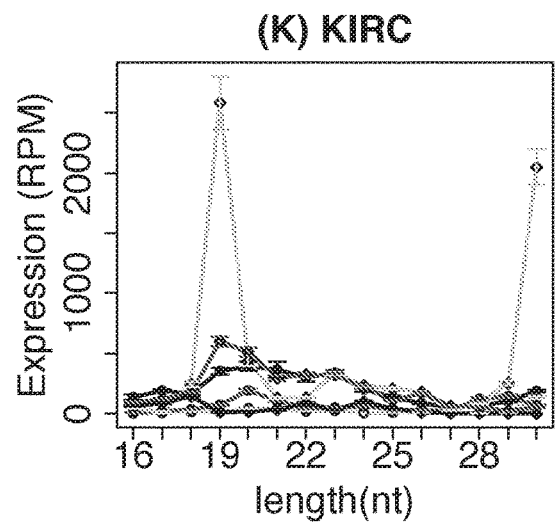
Figure 13:
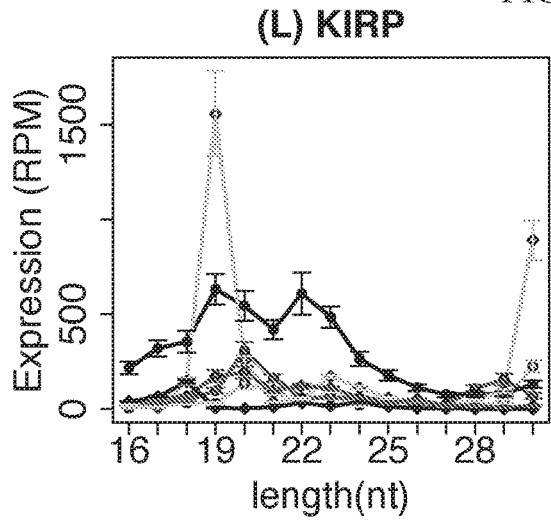
Figure 13:
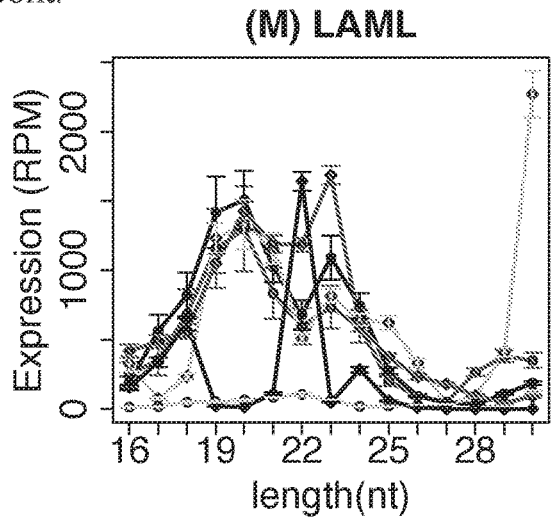
Figure 13:
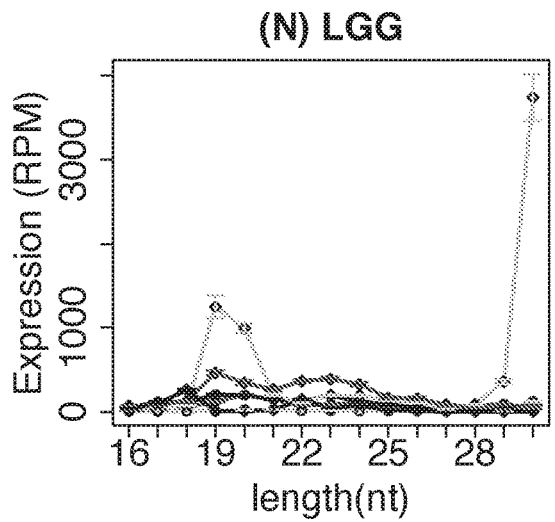
Figure 13:
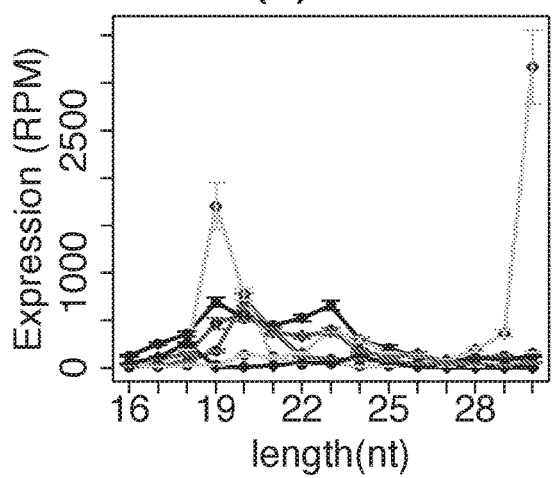
Figure 13:
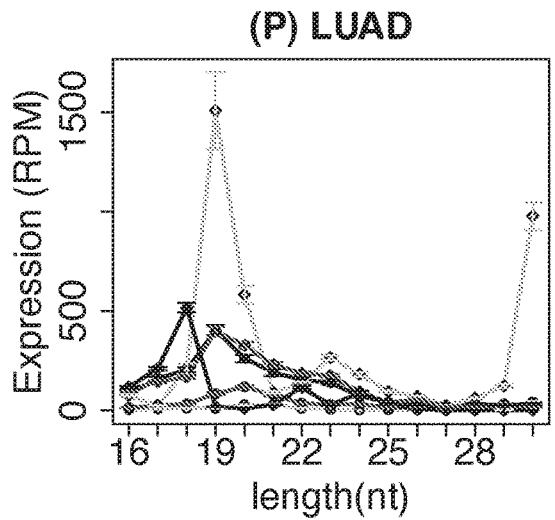
Figure 13:
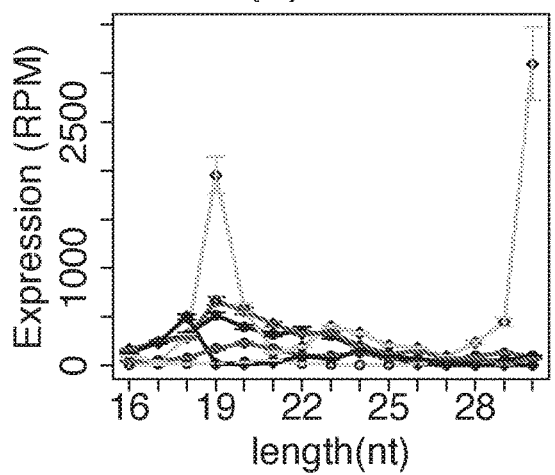
Figure 13:
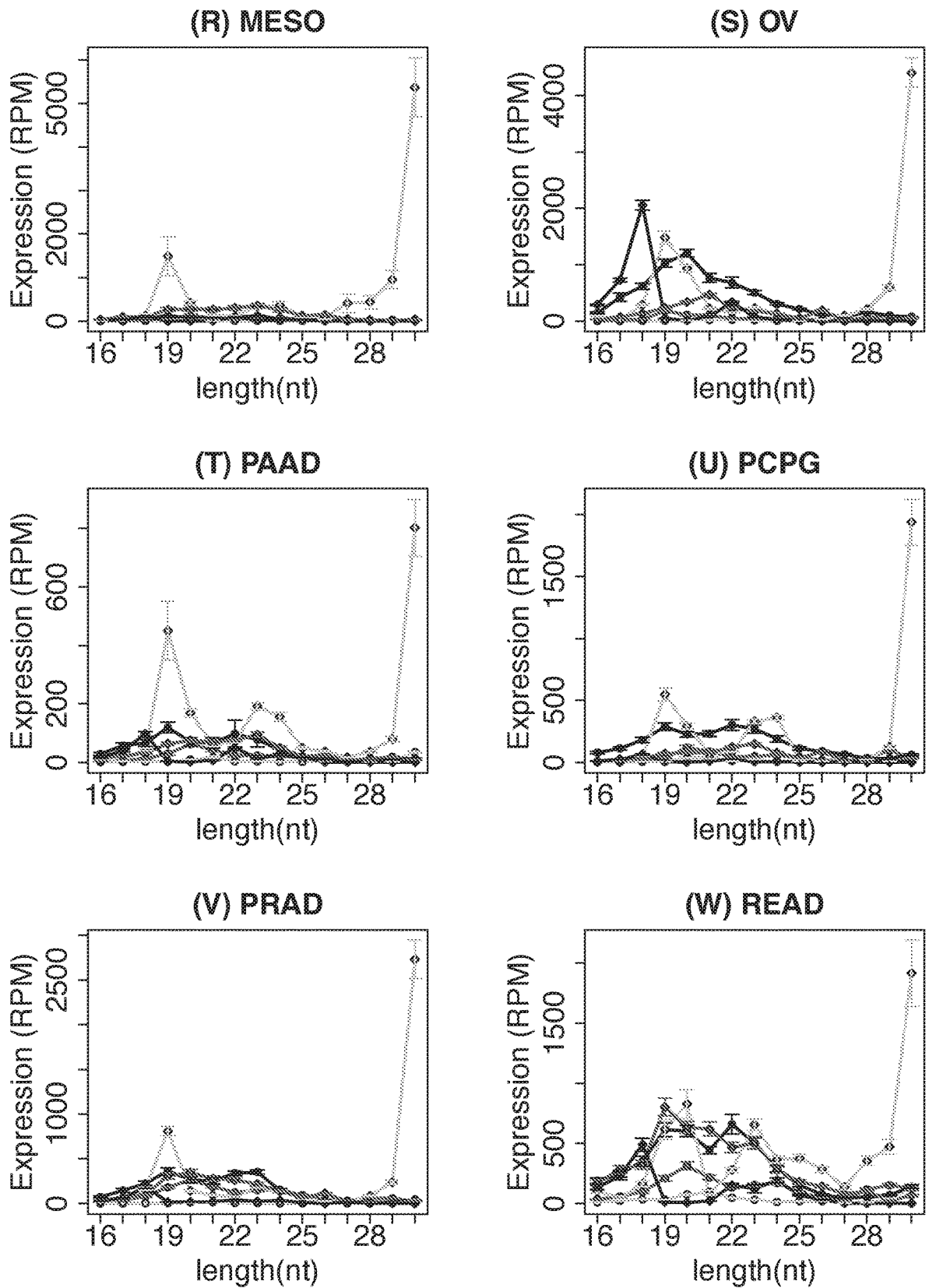
Figure 13:
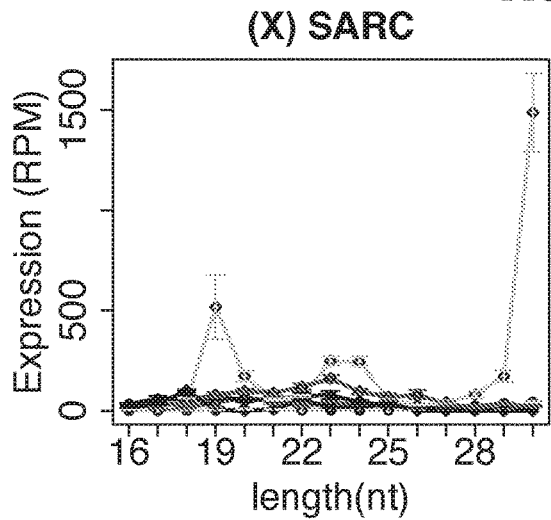
Figure 13:
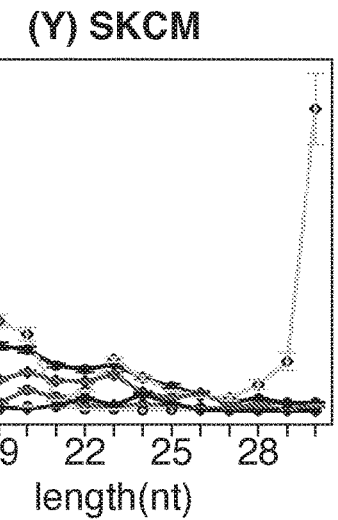
Figure 13:
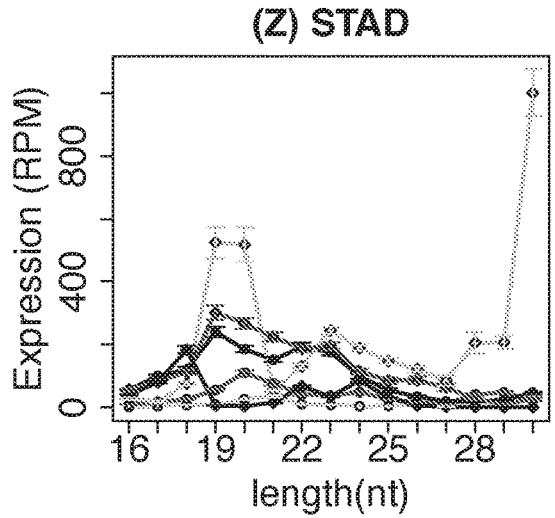
Figure 13:
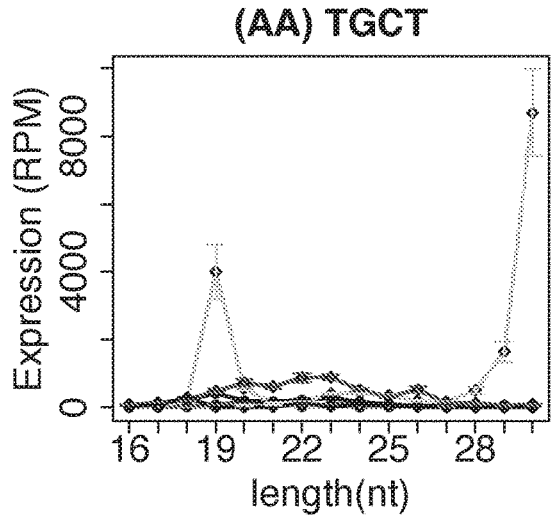
Figure 13:
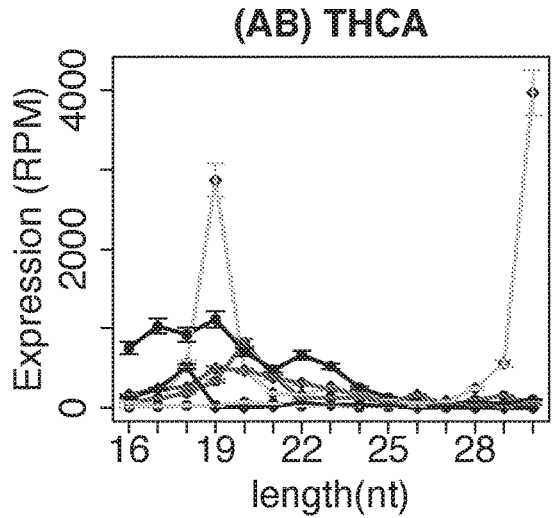
Figure 13:
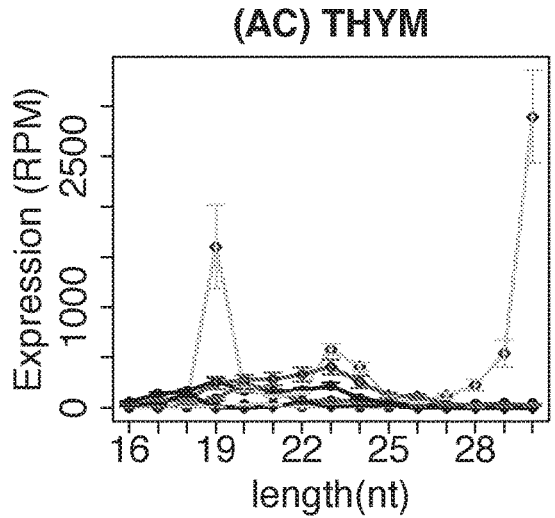
Figure 13:
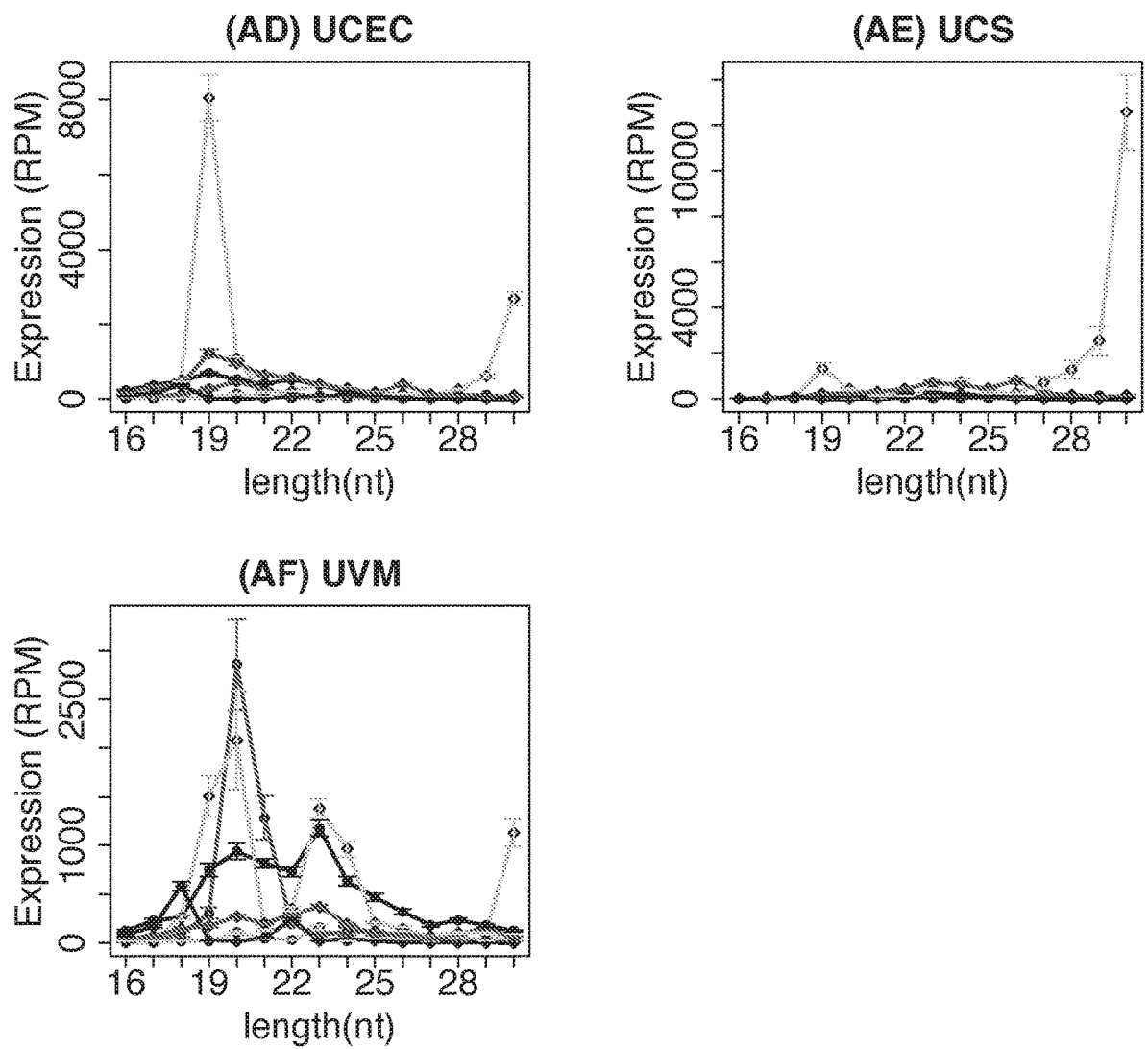

FIG. 1A shows characteristic examples of the length distributions for nucleus- and MT-encoded tRFs and for 10 of the 32 cancer types: AAC, HNSC, LAML, OV, SKCM, THCA, TGCT, UCS, UCEC, and UVM. For a detailed distribution of the different tRF categories in each of the 32 cancer types see FIG. 13 and Supp. Table S2. All distributions show normalized abundances in RPM. There are evident differences in the tRFs' structural type, lengths, nuclear vs. MT origin, and relative abundances. For example, in ACC and UVM, MT tRNAs are sources of comparatively more abundant 5'-tRFs with lengths 20, 23, and 26 nt. Analogously, 30-mer proxies from nuclear tRNAs are the most abundant species in almost all 10 cancers. Also, in SKCM and OV, nuclear tRNAs are much stronger contributors of 3'-tRFs with length 18 nt, when compared to the other eight cancer types. FIG. 1B provides a global view of the structural categories (5'-tRFs, i-tRFs, and 3'-tRFs) and abundances of the populations of tRFs arising from nucleus-encoded and MT-encoded tRNAs across cancer types. The Figure makes the considerable diversity of these molecules clear. FIG. 1C is a Principal Component Analysis (PCA) plot based on the same data and shows clear clusters for various combinations of tRF type, length, and genome of origin, corroborating the results of FIG. 1B. Note that the clusters are explained by tRF length and tRF origin. Specifically, shorter molecules (usually ≤23 nt) are clustered together, separately from longer ones (usually ≥24 nt); additionally, there is clear distinction between tRFs originating in the nucleus from those originating in the MT. These findings indicate that the nuclear and MT tRNAs produce distinctly different populations of tRFs that depend on cancer type.

Isoacceptors Produce tRFs in a Cancer-Dependent Manner

Having established that both nuclear and MT tRNAs are prolific producers of tRFs, we sought to investigate how different tRNA isoacceptors contribute to the abundance profiles of tRFs. We hypothesized that the production of tRFs per isoacceptor is cancer-dependent. To investigate this, we computed the total normalized expression (in RPM) of tRFs that originate from each isoacceptor. We did so separately for each of the 32 cancer types and for each of the 61 nuclear and 20 MT anticodons. This allowed us to tag each isoacceptor with the level of expression of its tRFs on a per cancer basis. We then carried out hierarchical clustering and generated the heatmap of FIG. 2A. Four isoacceptor groups are evident in this Figure. Three isoacceptors, the mitochondrial tRNA$^{ValTAC}$ and the nuclear tRNA$^{HisGTG}$ and tRNA$^{GlyGCC}$, stand out as producing highly-abundant tRFs in all 32 cancer types.

Figure 2A:
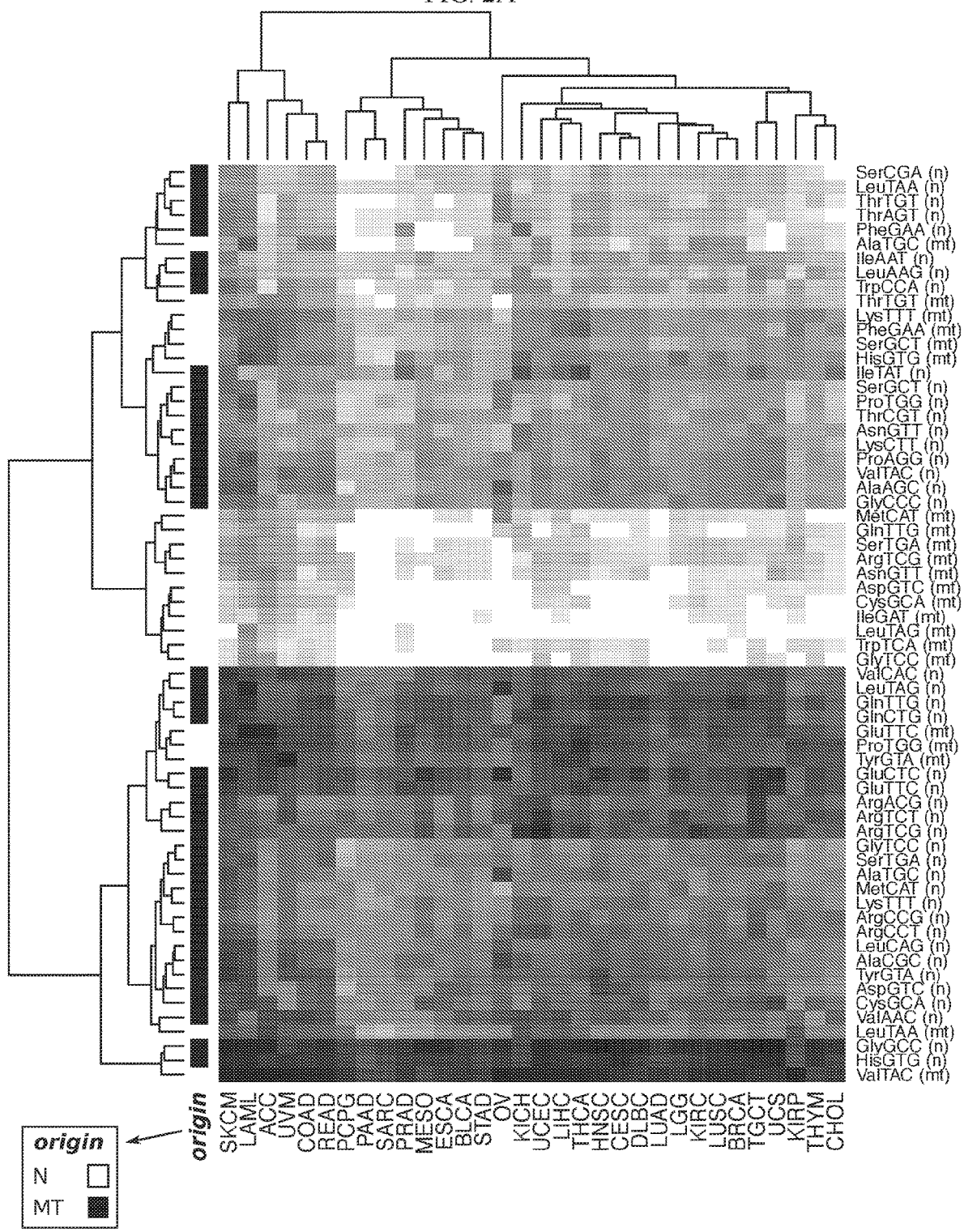
FIGS. 2A-2B Isoacceptor representation among the tRFs. (A) Heatmap and hierarchical clustering (metric: Euclidean distance) of the abundance profile of each isoacceptor, calculated as the sum of the expression of tRFs it produces, in all 32 cancers. Nucleus-encoded isoacceptors are denoted on the side color bar using white, whereas MT ones are denoted in black. (B) Box-plots showing the percentage expression of tRFs from specific isoacceptors across BRCA and UCEC samples. As can be seen, the top tRF-producing isoacceptors differ in the two cancers. The highest-expressed isoacceptor in BRCA is the nuclear tRNA$^{GlyGCC}$ whereas in UCEC it is the MT tRNA$^{ValTAC}$ isoacceptor.
Figure 2B:
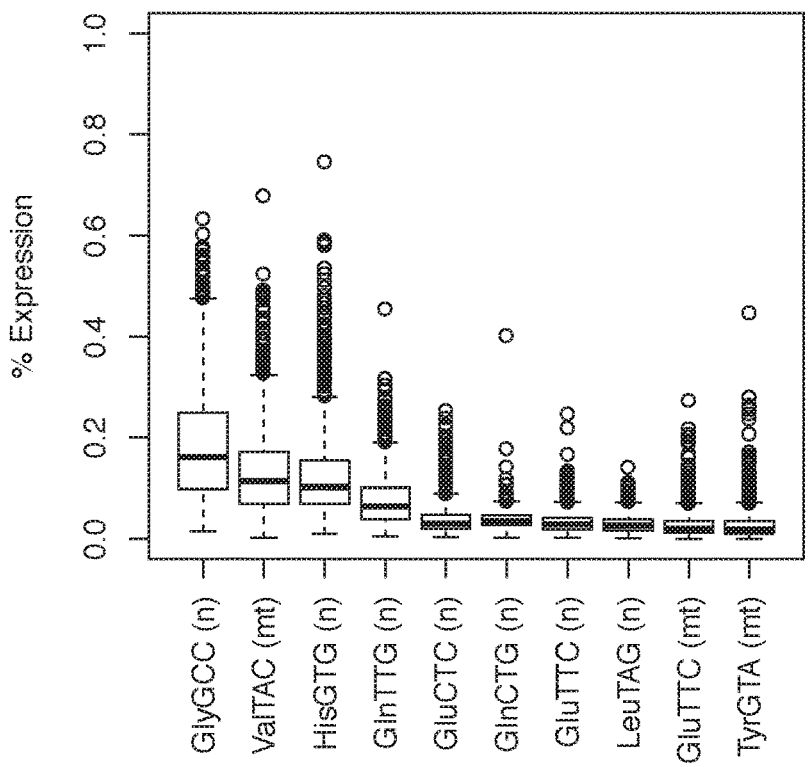

From a cancer standpoint, we note that ACC, LAML, SKCM, UVM, COAD and READ form a distinct branch of the dendrogram (FIG. 2A). All four of these cancers produce abundant tRFs from nearly all of the shown isoacceptors (see FIG. 1 for comparison), albeit with significant expression variation. FIG. 2B highlights the variation in tRF expression across different cancers with the help of BRCA and UCEC. In BRCA, four isoacceptors, tRNA$^{GlyGCC(n)}$, tRNA$^{ValTAC(mt)}$, tRNA$^{HisGTG(n)}$, and tRNA$^{GlnTTG(n)}$ produce most of the tRFs. On the other hand, in UCEC, it is tRFs from tRNA$^{ValTAC(mt)}$, tRNA$^{ArgTCG(n)}$, tRNA$^{GlyGCC(n)}$, and tRNA$^{HisGTG(n)}$ that are expressed abundantly. These findings indicate that the production of tRFs is cancer-type-specific.

The Patterning of tRFs Depends on tRF Category, Isoacceptor, and Cancer Type

In light of the results of the previous section and the dependencies of tRF abundance on cancer type and isoacceptor, we sought to identify cancer-type specific tRNA cleavage patterns. Towards this end, we analyzed "where" tRFs are located with respect to the mature tRNA's origin. We studied all tRFs with above-threshold abundances and lengths between 16 and 27 nt inclusive. As we explain in Methods, we imposed a length limit at 27 nt: as a result, 5'-tRHs and 3'-tRHs are not included in this analysis. To avoid contributions from tRFs of ambiguous origin, which may arise from different biogenesis processes, we focused on only the 3,136 tRFs that are exclusive to tRNA space (see Methods). In the Discussion, we discuss our findings in the context of known modifications across the span of mature tRNAs.

We tracked multiple tRF attributes and did so separately for each of the 32 cancers (see Methods). We show a holistic view of the results in FIG. 3—for the complete set of the histograms for all of the attributes see FIG. 14. Note that we use a white circle to indicate the position of known modifications (m1G9, m3C32, m1G37, and m1A58) in the shown tRNA backbones (23). We stress that we highlight these positions for reference purposes only. Indeed, it is unknown currently whether these modifications occur in the tissues and tissue states that are represented by the TCGA samples.

Figure 3A:
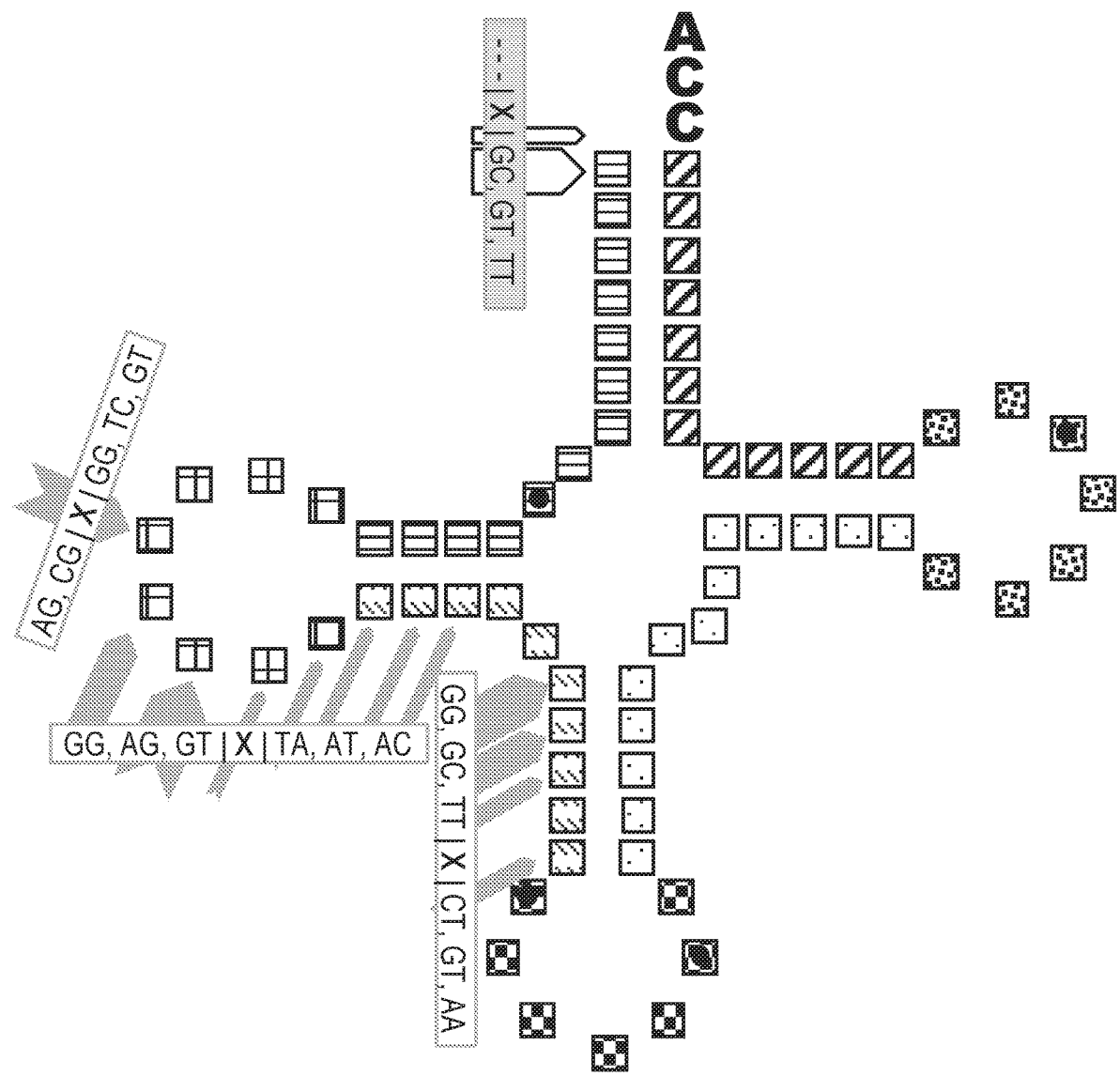
Figure 3A:
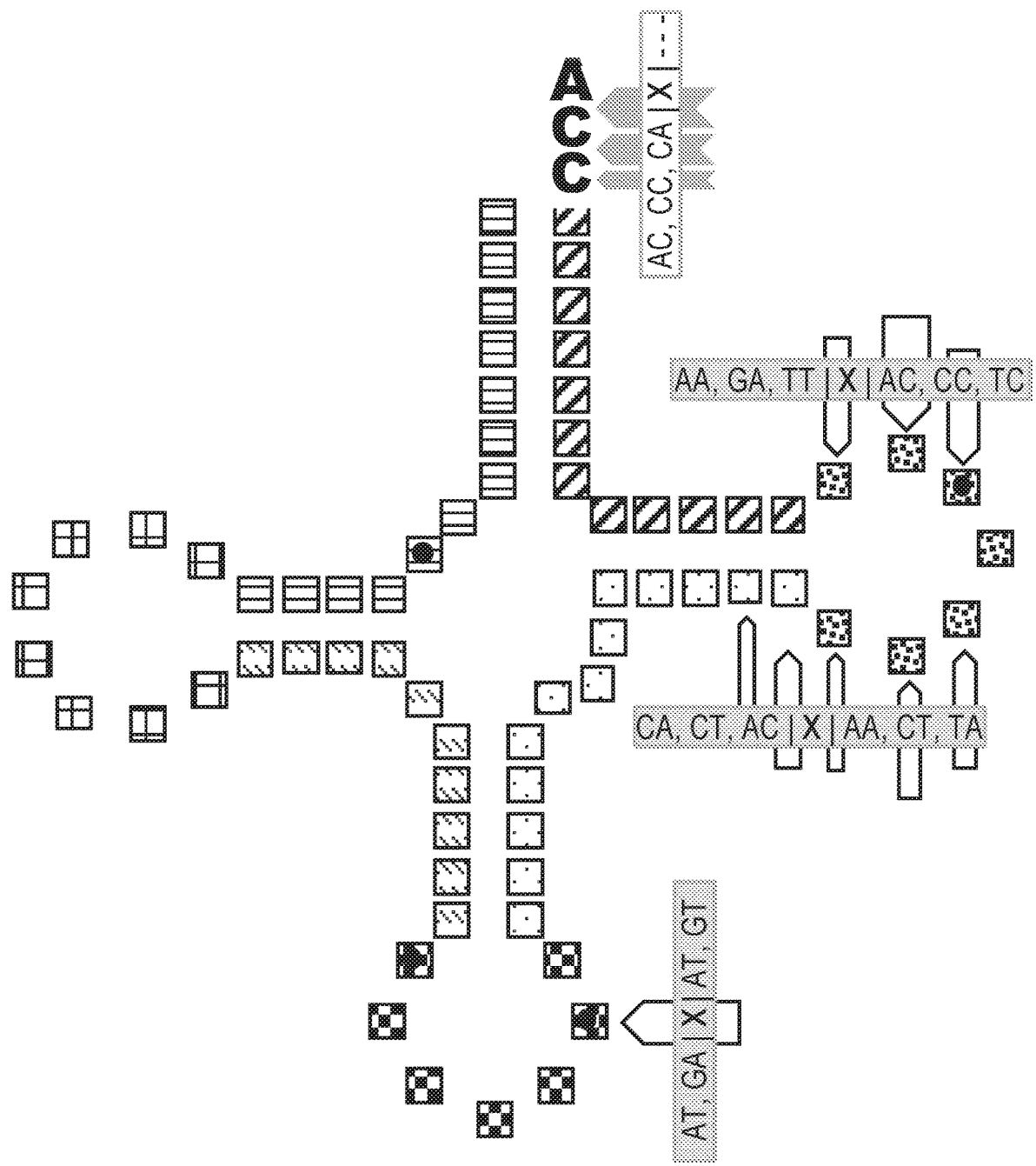
Figure 3A:
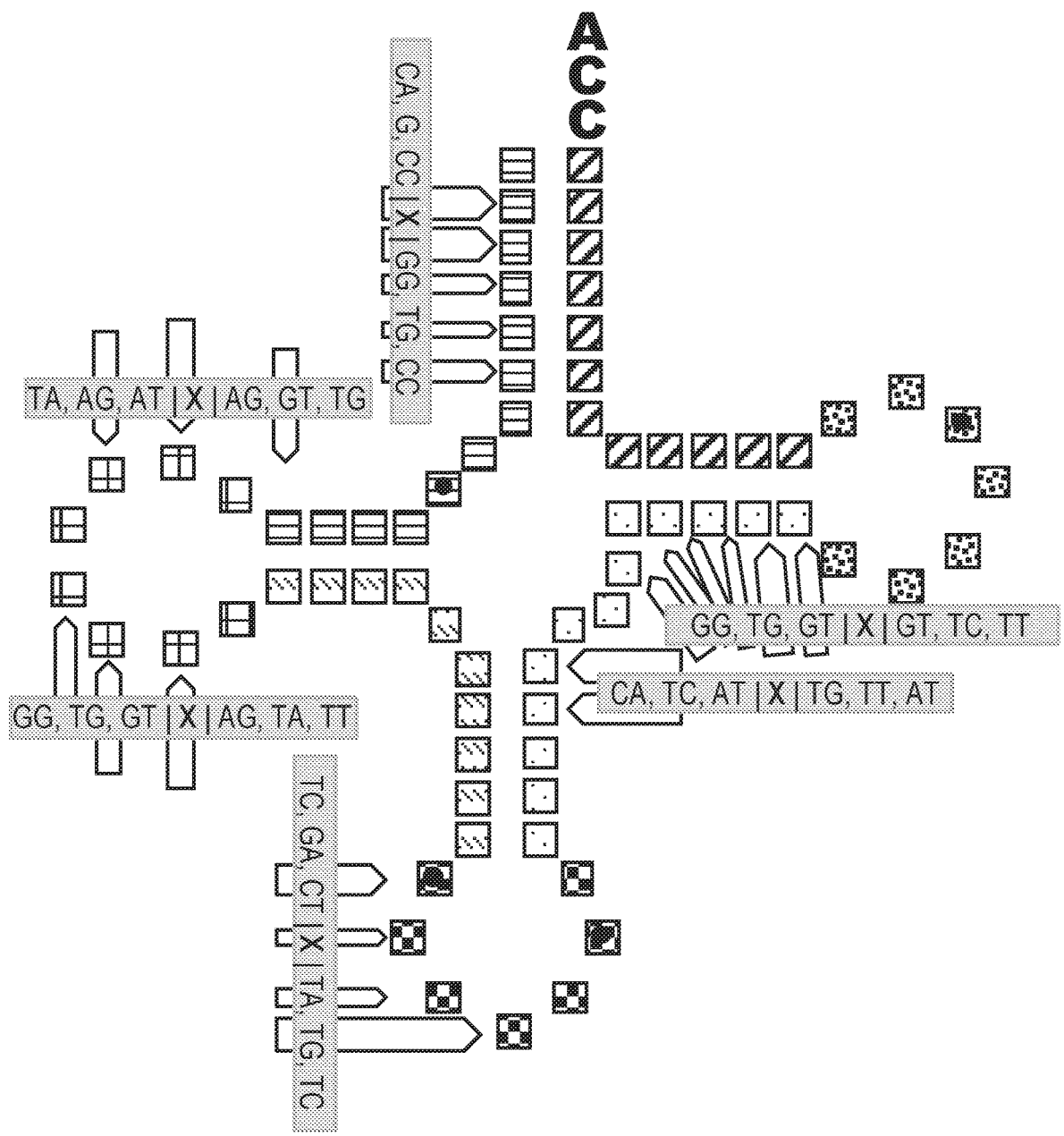
Figure 3A:
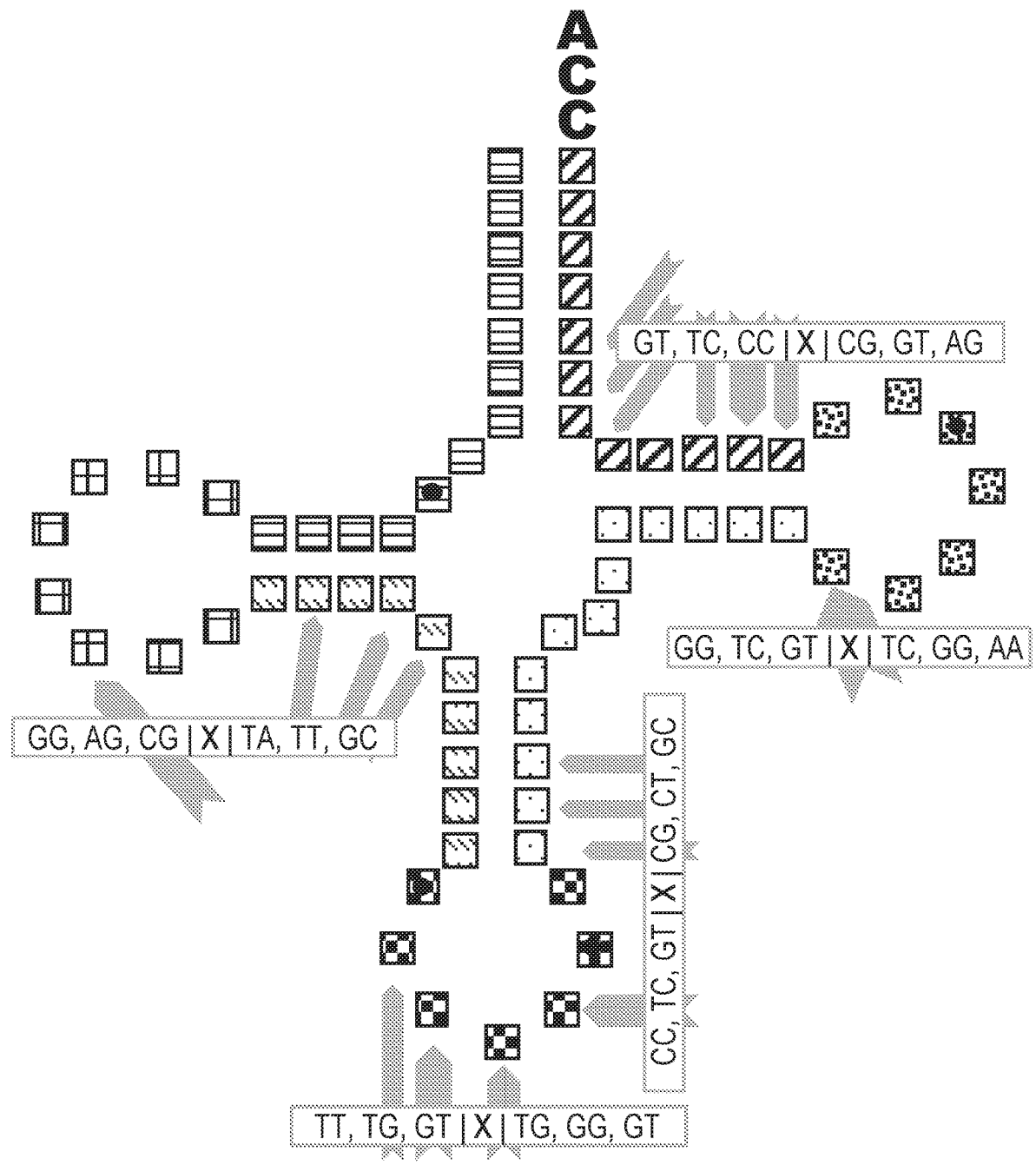

In FIG. 3A we see that the more abundant 5'-tRFs have only moderate preference for the location of their 3' termini, which span virtually all positions from the middle of the D-loop through the beginning of the anticodon loop. Analogously, for the 3'-tRFs, which can terminate at any of the three nucleotides of the non-templated "CCA" addition, their 5' termini begin just before or within the T-loop. We note that the observed preferences across human cancers for the 3' termini of 5'-tRFs, and for the 5' termini of 3'-tRFs respectively, match the preferences that were recently reported for tRFs in the plant A. thaliana (24).

Among the various fragment categories, i-tRFs are the most diverse in both their 5' and 3' termini choices, as we reported recently 4. In theory, i-tRFs can begin and end at every nucleotide of the mature tRNA, except for its 5' end or the CCA tail. However, our detailed analysis revealed that i-tRFs exhibit distinct cleavage patterns in individual cancers. As seen in FIG. 3A, i-tRFs start either close to the 5' end of the tRNA, at the D or the most 5' half of the anticodon loop or between the variable and the T loop. The 3' ends of the i-tRFs also favor specific positions.

We highlight the i-tRF endpoint preferences by examining in more detail the i-tRFs in LUAD and OV (FIG. 3B). In LUAD, comparatively more i-tRFs begin inside the yellow region (D-loop) than do in OV. On the other hand, more i-tRFs begin in the brown region (region C) in OV than do in LUAD. Analogous comments can be made about the i-tRFs' ending positions in LUAD and OV. See also FIG. 14 for more details.

These findings indicate that the manner in which tRFs are cleaved from the respective tRNA depends on the cancer type, on the isodecoder, and on the structural type of the tRF. The findings also argue strongly against the tRFs being random products of tRNA degradation.

Uridylated his(-1) tRFs are Abundant in Human Tissues and Exhibit a Unique Property that is not Affected by Tissue or Tissue State In eukaryotes, before the mature tRNA$^{HisGTG}$ can be recognized by its cognate aminoacyl tRNA synthetase, guanylation of its 5'-terminus by the enzyme THG1 (THG1L in human) is required (25-27). This post-transcriptionally added nucleotide is referred to as the "-1" position and denoted "His(-1)." In recent work with the human breast cancer model cell line BT-474, it was shown that full-length mature tRNAs and 5'-tRHs from tRNA$^{HisGTG}$ also contain a uracil at the His(-1) position (28). To the best of our knowledge, this possibility has not been examined before in human tissues. We therefore sought to profile the His 5'-tRFs and the identity of their -1 nucleotide across all 32 TCGA cancer types.

Our analyses reveal that, in human tissues and across all 32 cancer types, the largest portion of 5'-tRFs from tRNA$^{HisGTG}$ contains a uracil at the His(-1) position—we will refer to them as "-1U 5'-tRFs." A smaller fraction of 5'-tRFs contain an adenine at the His(-1) position, whereas 5'-tRFs with a guanine or cytosine are even fewer. The -1U 5'-tRFs are exclusive to tRNA space and thus can only be produced by isodecoders of tRNA$^{HisGTG}$. However, it cannot be stated with certainty whether these -1U 5'-tRFs arise from cleavage of the precursor or from post-transcriptional modification of the mature tRNA: four of the 12 isodecoders (the one from MT and the three nuclear tRNA-His-GTG-1-

6, tRNA-His-GTG-3-1, tRNA-His-GTG-1-5) contain a T at that location of the DNA template.

Figure 4:
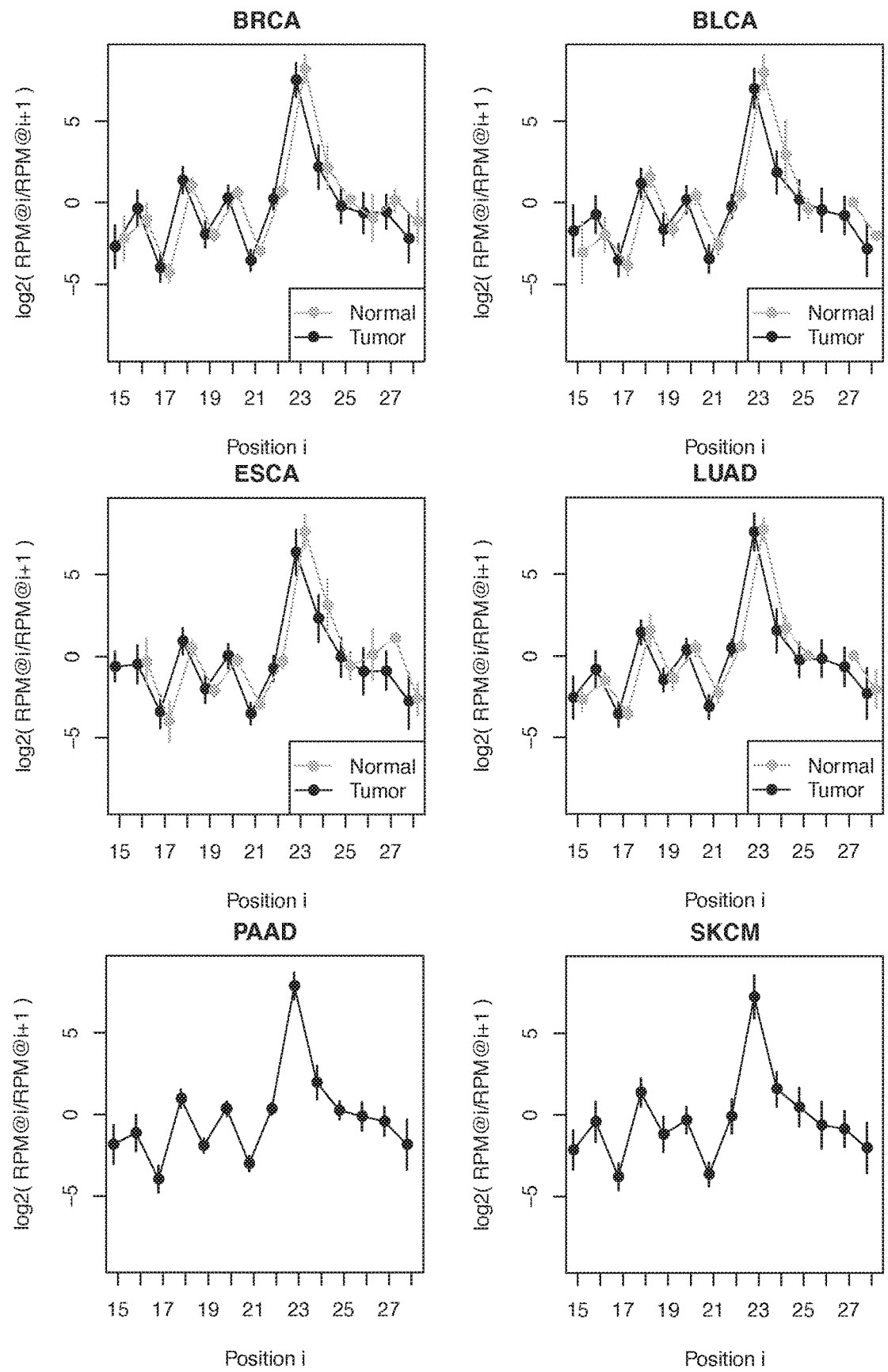
FIG. 4 His(−1U) fragments. Abundance ratios of uridylated His(−1) 5'-tRFs from nuclear tRNA$^{HisGTG}$ that end at consecutive positions within the mature tRNA. The shown ratios for normal (gray) and cancer (black) samples represent 2,635 tumor and samples from six TCGA cancers: BLCA, ESCA, PAAD, BRCA, LUAD, and SKCM. Values are shown only for statistically significant tRFs. Y-axis: log$_2$. At X=i, we plot the ratio "log$_2$ (mean [(RPM of 5'-tRF ending at position i)/(RPM of 5'-tRF ending at position i+1)])." Here, RPM stands for reads-per-million.

Even though the biogenesis of these −1U 5'-tRFs remains elusive, we found their presence in the numerous TCGA RNA-seq datasets and in a cell line (28) intriguing and set out to study their profiles. Examination of −1U 5'-tRFs from tRNA$^{HisGTG}$ across all 32 TCGA cancer types uncovered a striking property for those −1U 5'-tRFs that differ by a single nucleotide in their 3' termini and have lengths between 16 and 24 nt inclusive. In particular, we discovered that as the length of these −1U 5'-tRFs increases, their abundance alternates from low to high to low to high, etc. Specifically, we discovered that the ratio of abundances of these increasingly longer fragments remains constant in all 32 TCGA cancers. Curiously, the pattern of relative abundances was the same for both the normal and the cancer state. Moreover, we found that the pattern is not exhibited by unmodified 5'-tRFs, i.e. by 5'-tRFs that begin at position +1 of the mature tRNA$^{HisGTG}$, to which we refer as +1G 5'-tRFs. FIG. 4 shows the $\log_2$ of the mean ratio of (abundance of −1U 5'-tRF ending at position i)/(abundance of −1U 5'-tRF ending at position i+1), for BLCA, ESCA, PAAD, BRCA, LUAD, and SKCM. If normal samples are available, we report values for both the tumor (black) and normal (light gray) samples. The shown curves are shifted slightly along the X-axis with respect to one another in order to make the details of both curves visible simultaneously.

Figure 15:
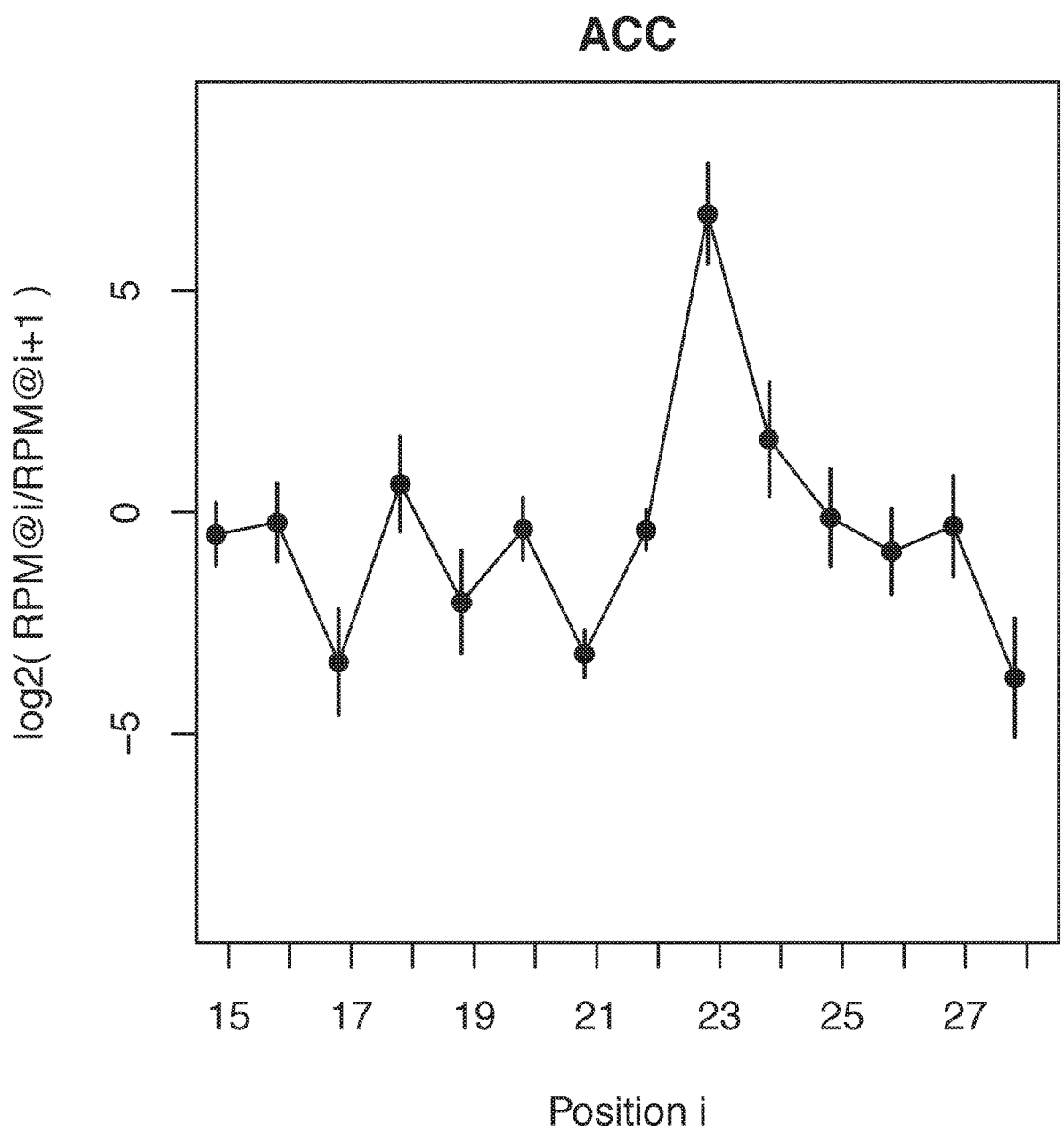
FIG. 15 His(−1)T ratios across TCGA. Plots showing the ratio of His(−1T) tRFs whose 3'-termini end at consecutive position on the mature tRNA$^{HisGTG}$. At abscissa x=i, we plot the value of the ratio $\log_{10}$ (mean (RPM abundance of His(−1T) tRF ending at position i/RPM abundance of His(−1T) tRF ending at position i+1)). Grey curves (when present) represent ratios for normal samples. Black curves represent ratios for tumor samples. The grey and black curves are offset slightly with respect to one another to enable comparisons.
Figure 15:
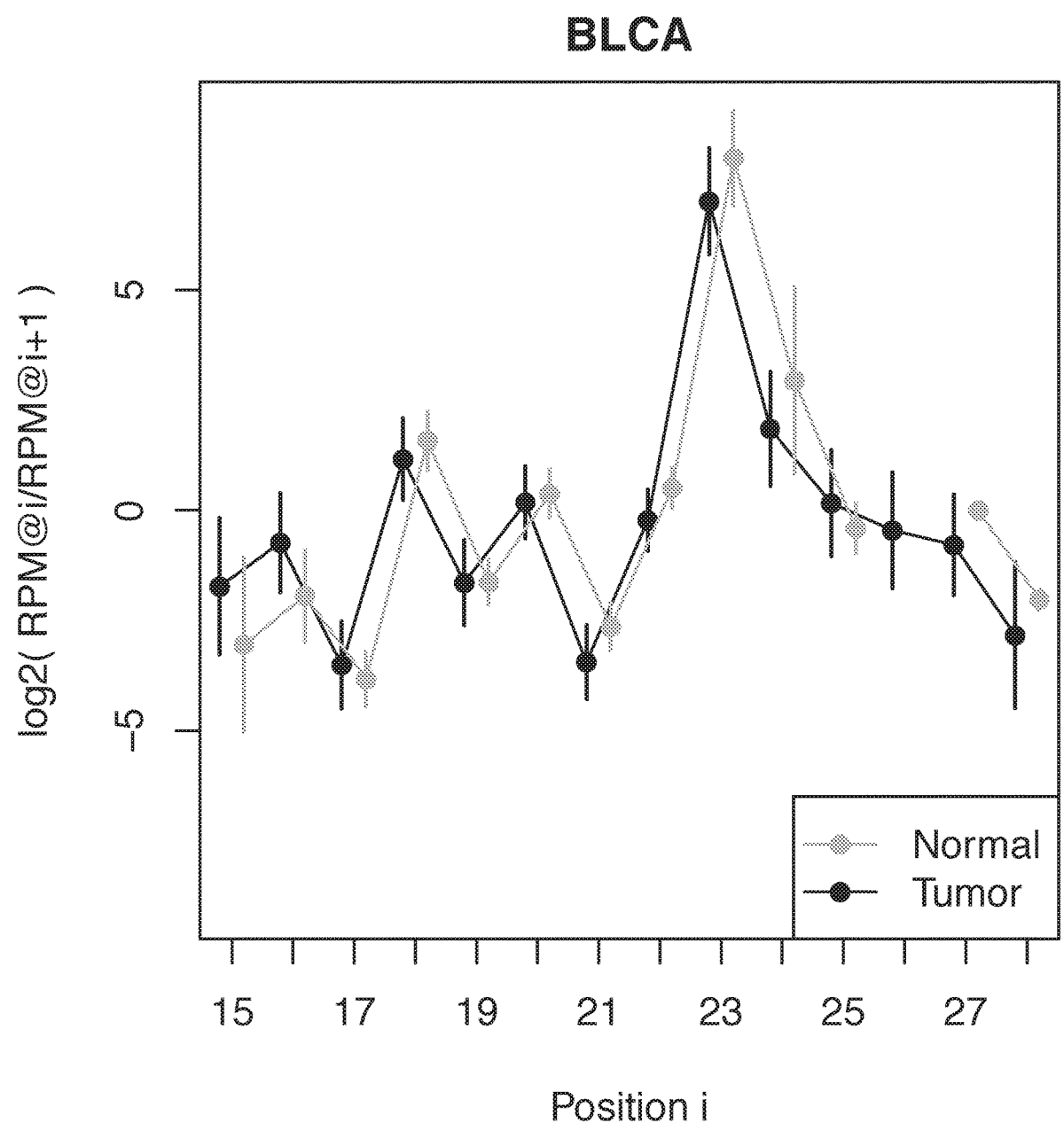
Figure 15:
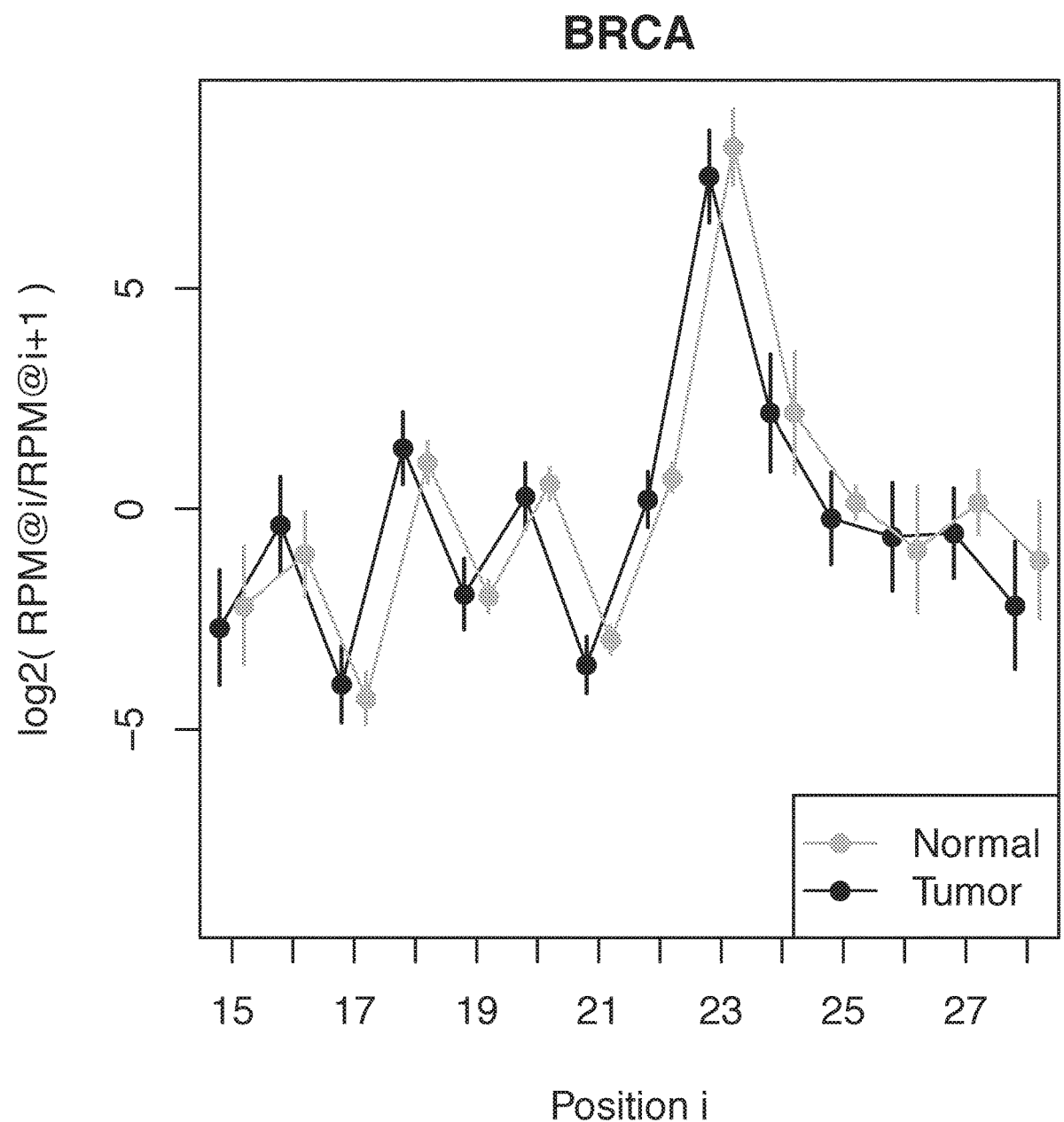
Figure 15:
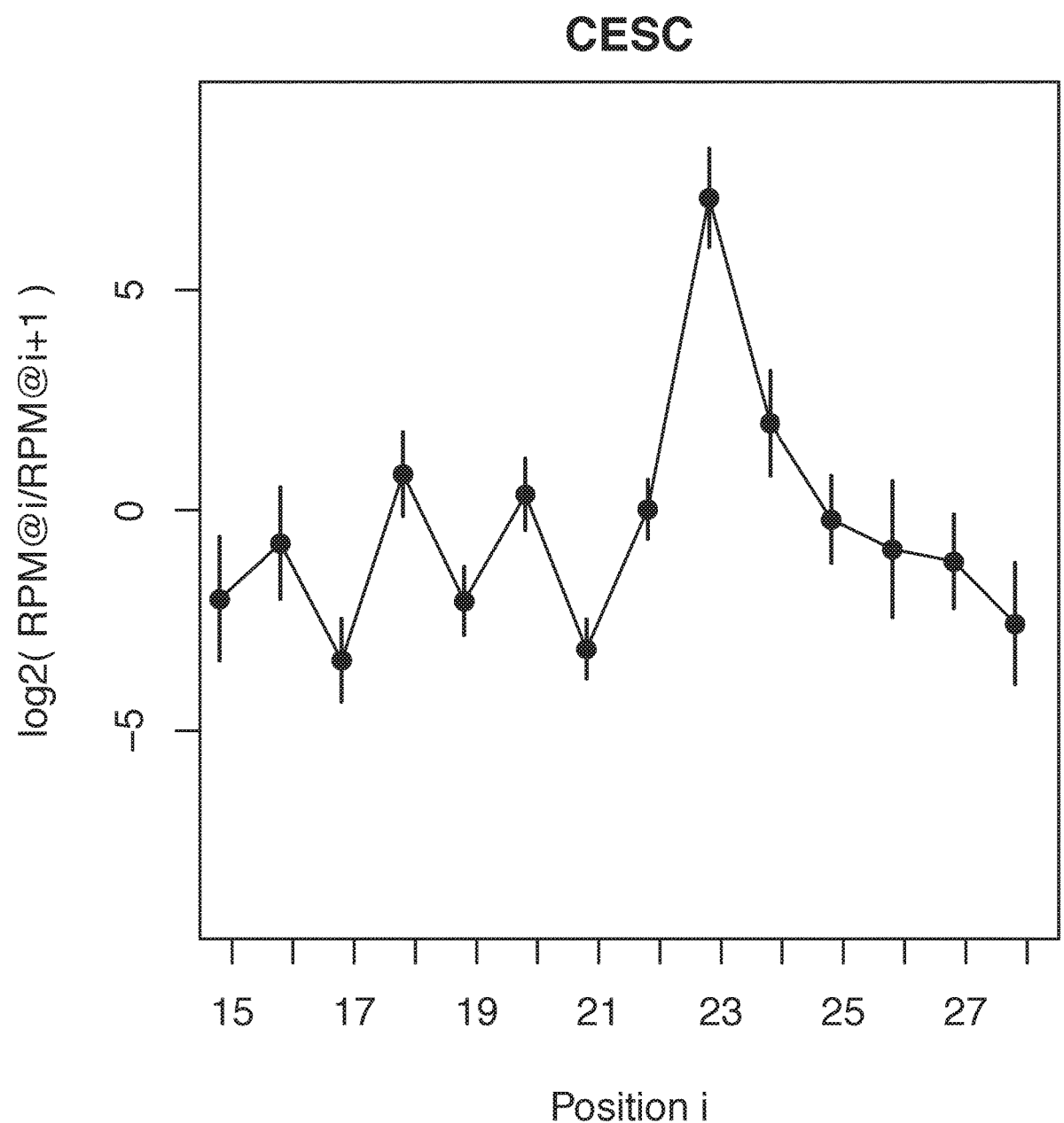
Figure 15:
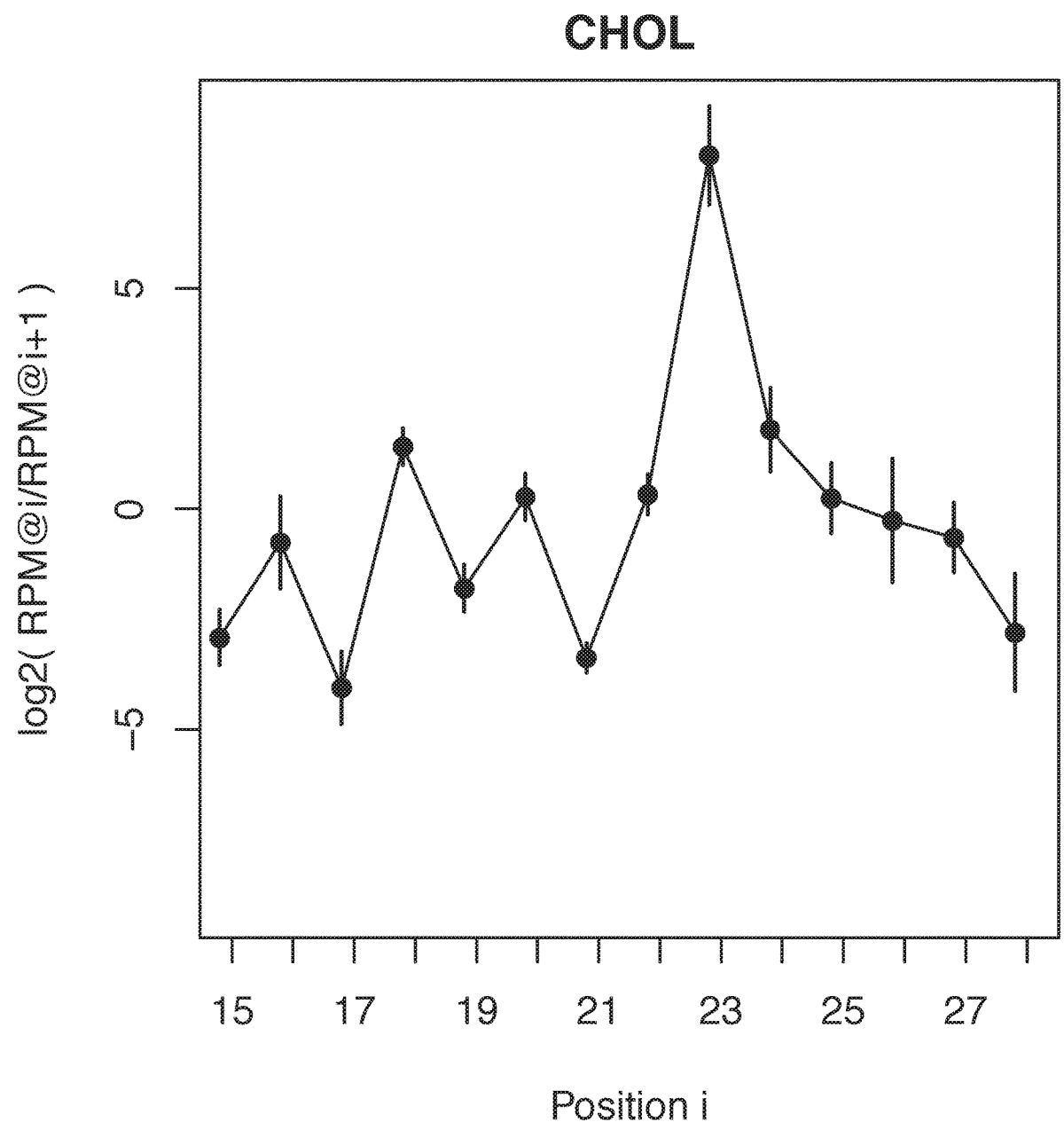
Figure 15:
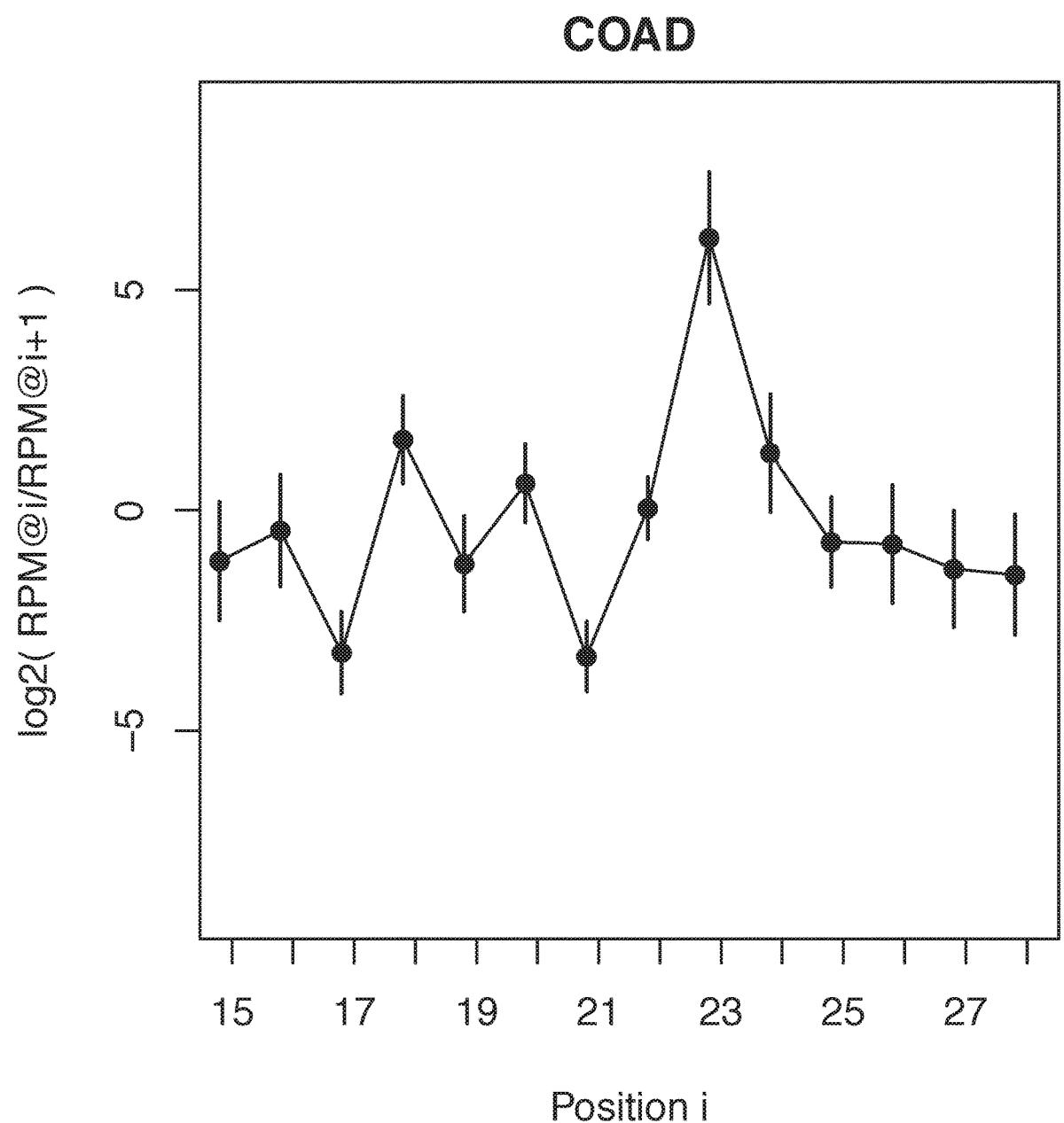
Figure 15:
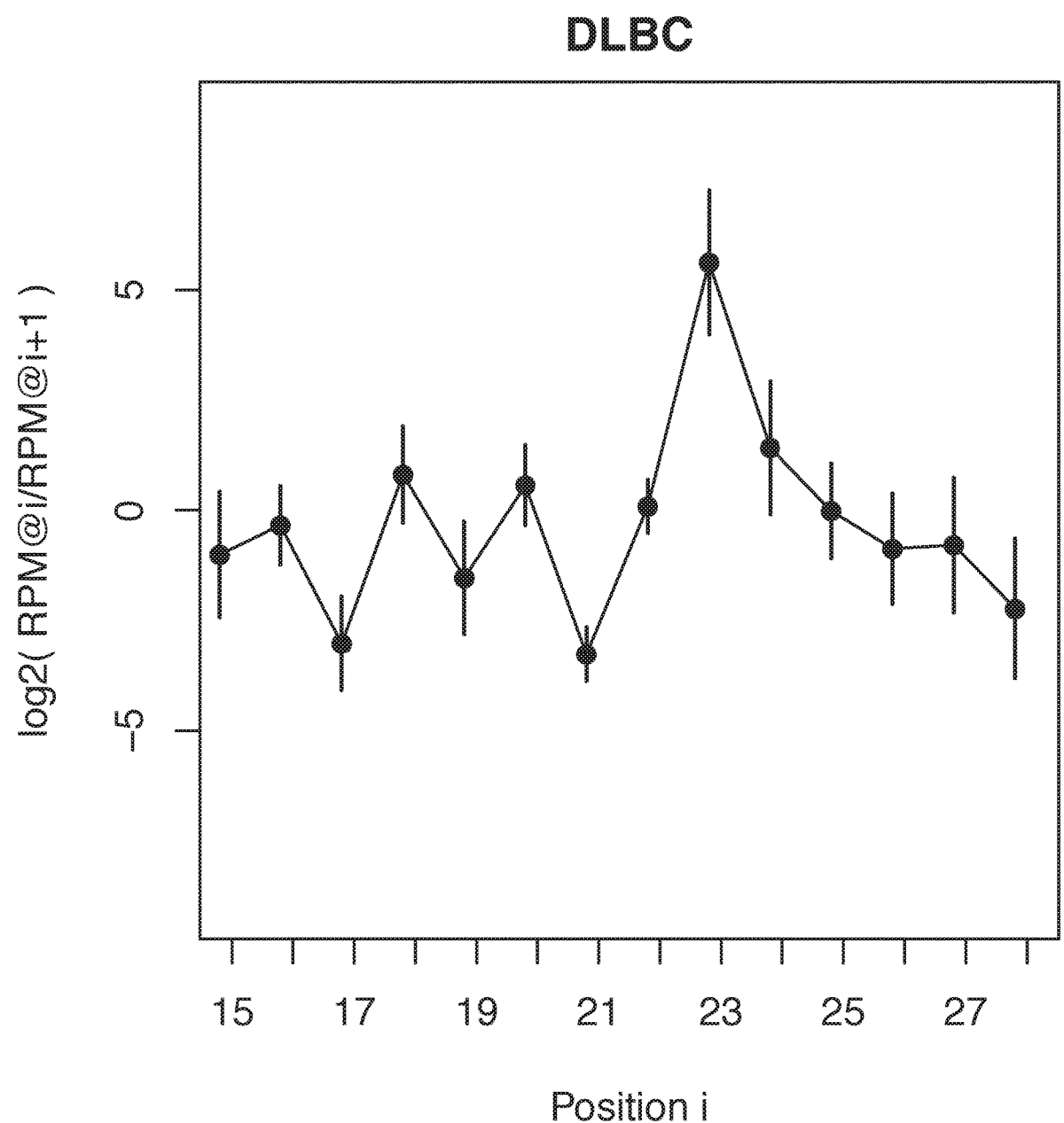
Figure 15:
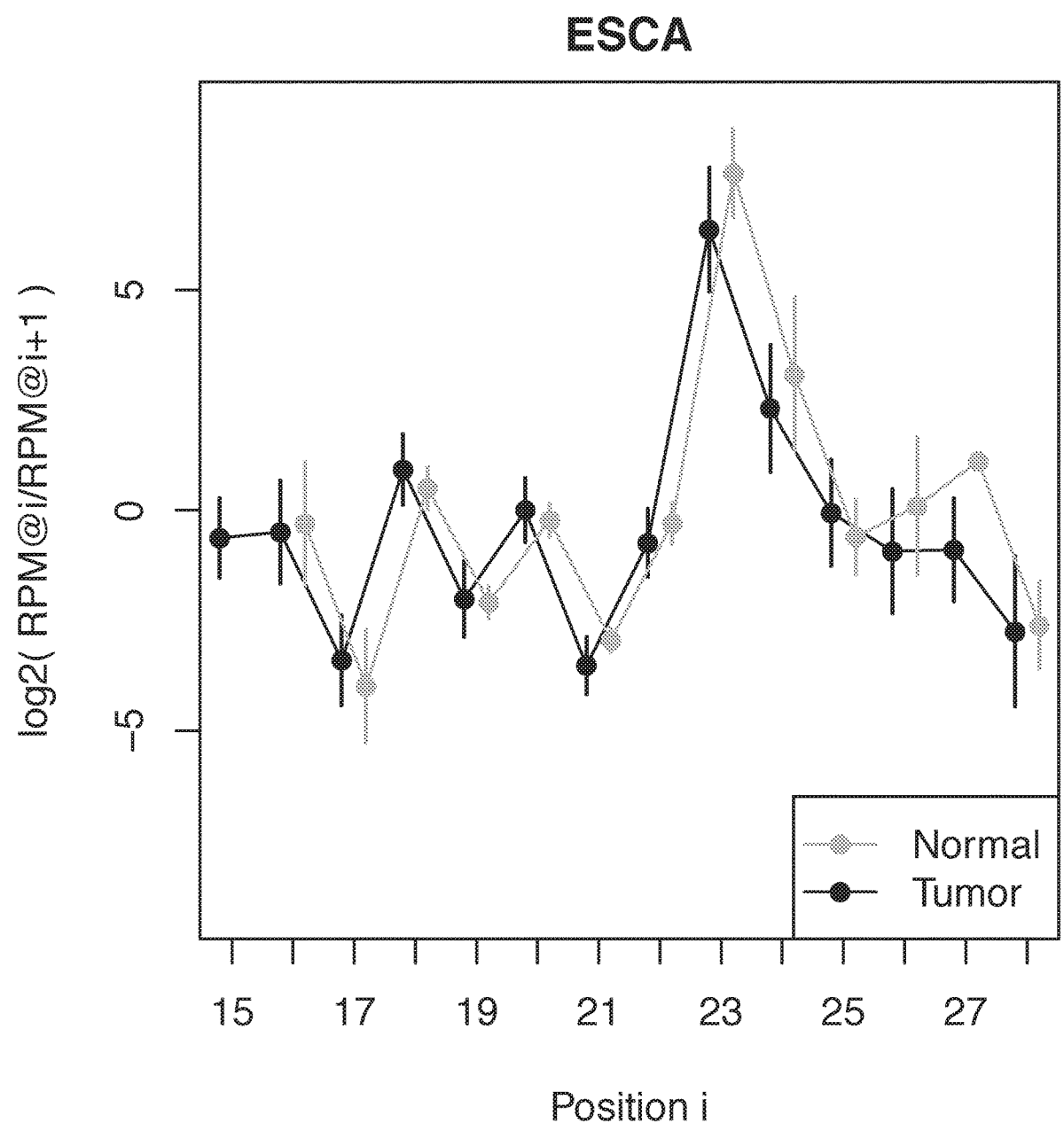
Figure 15:
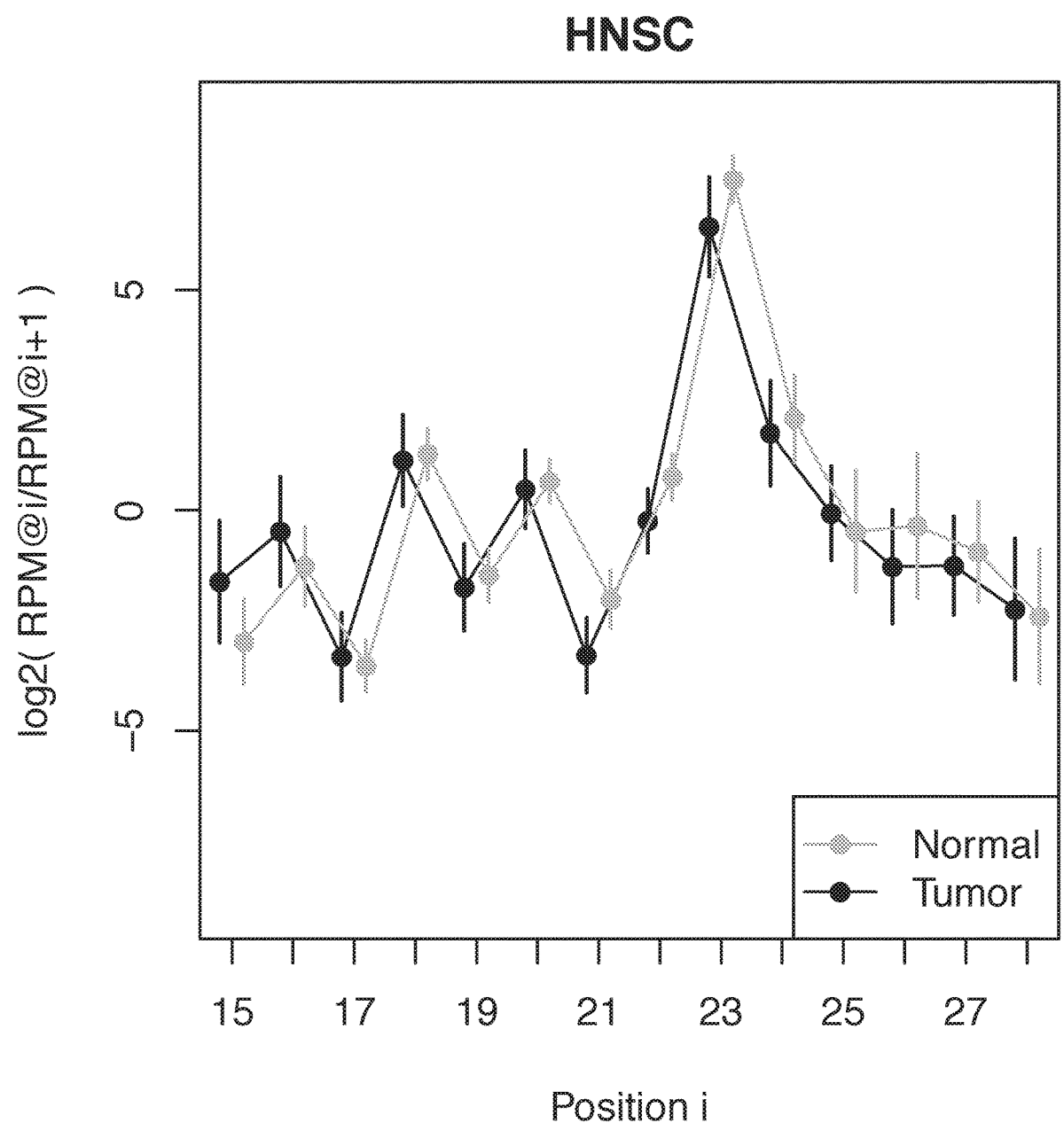
Figure 15:
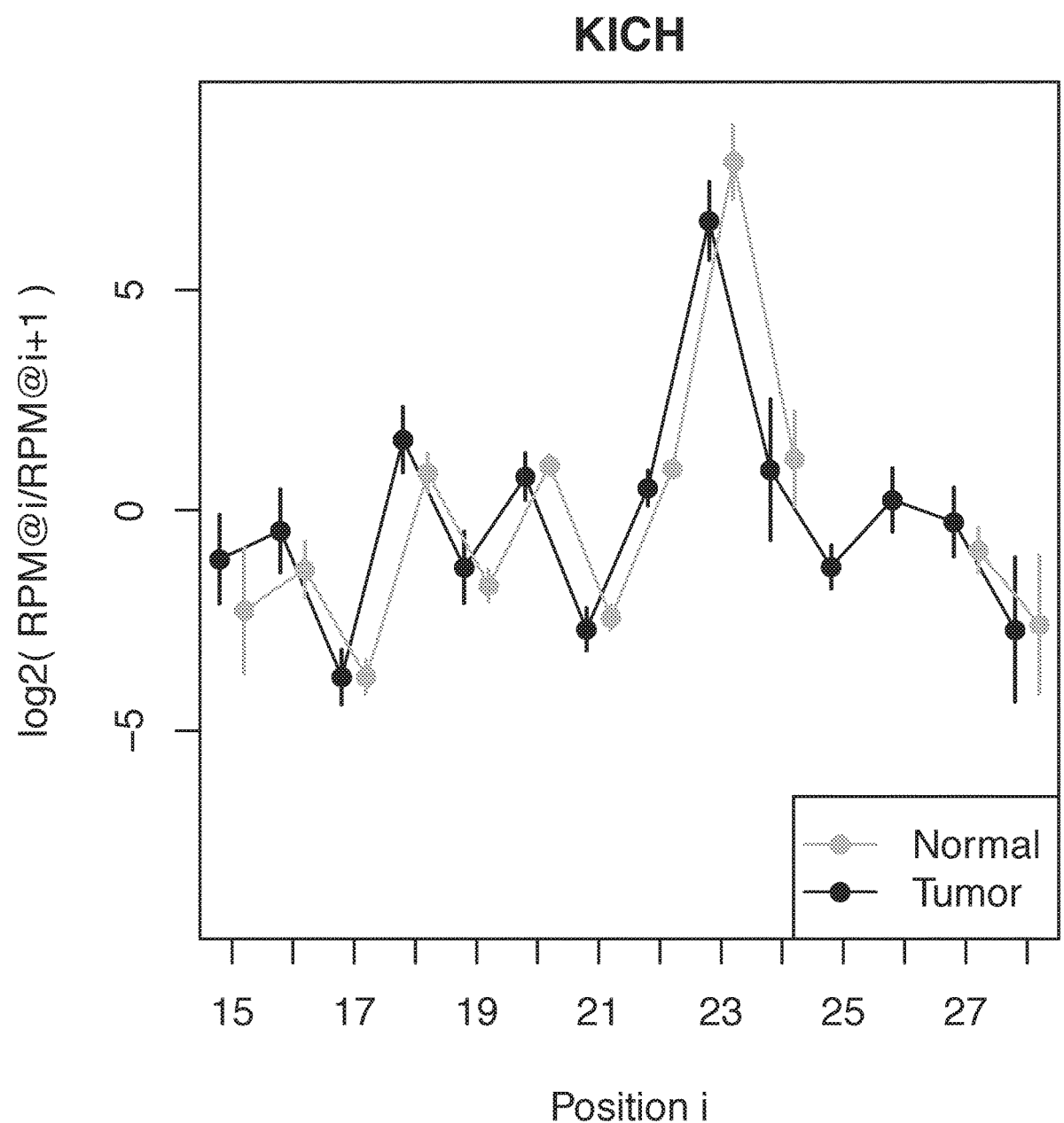
Figure 15:
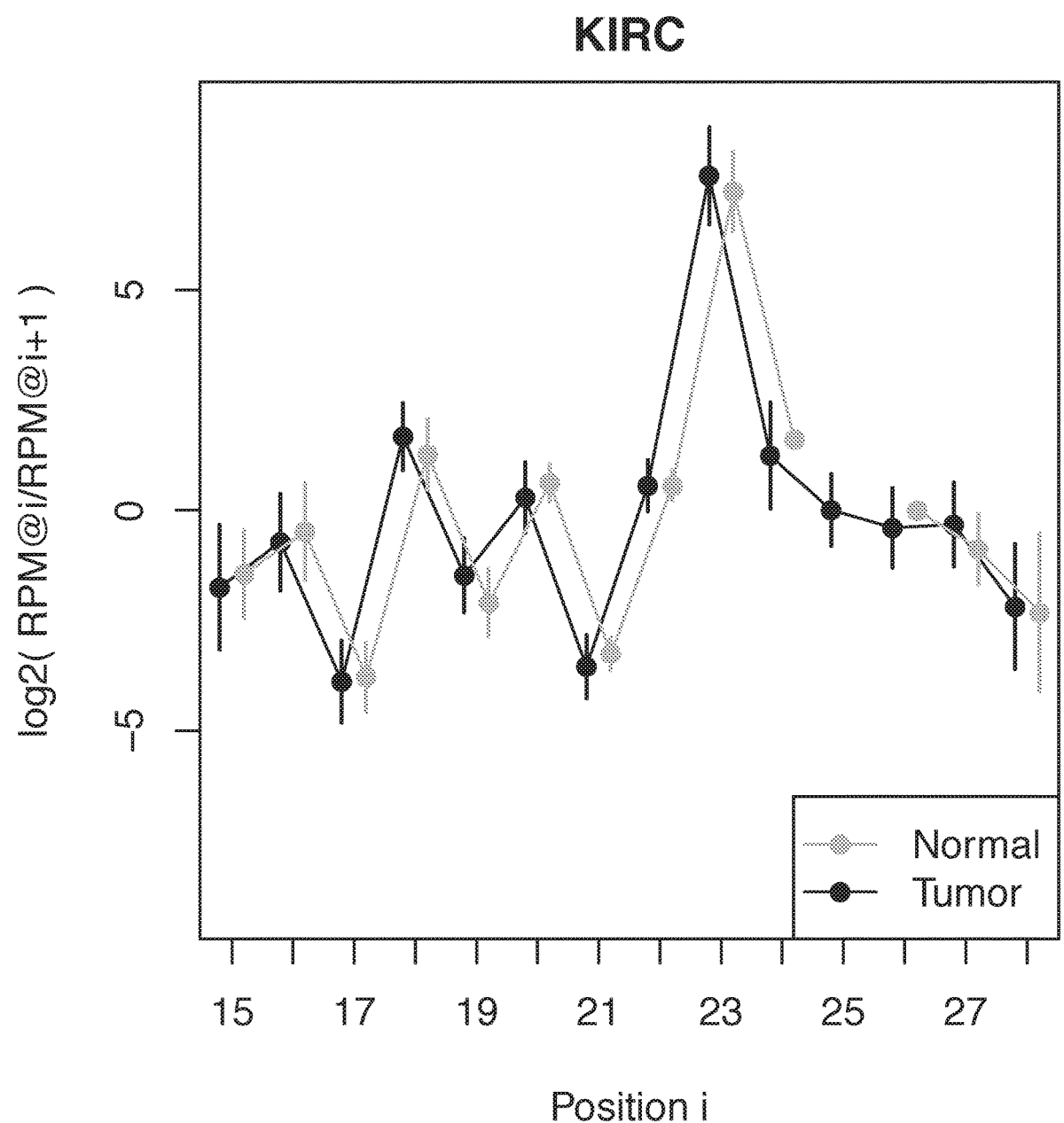
Figure 15:
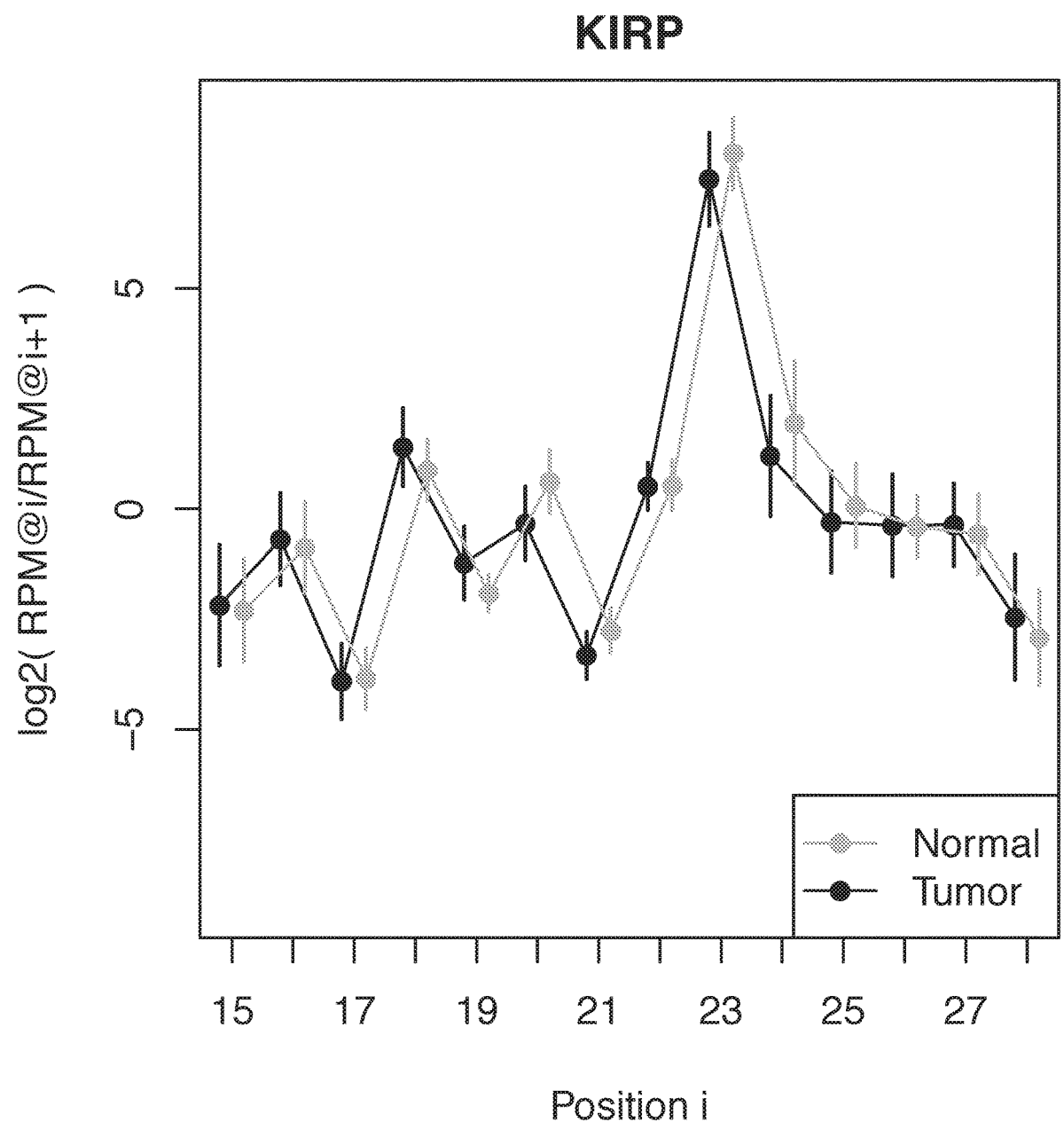
Figure 15:
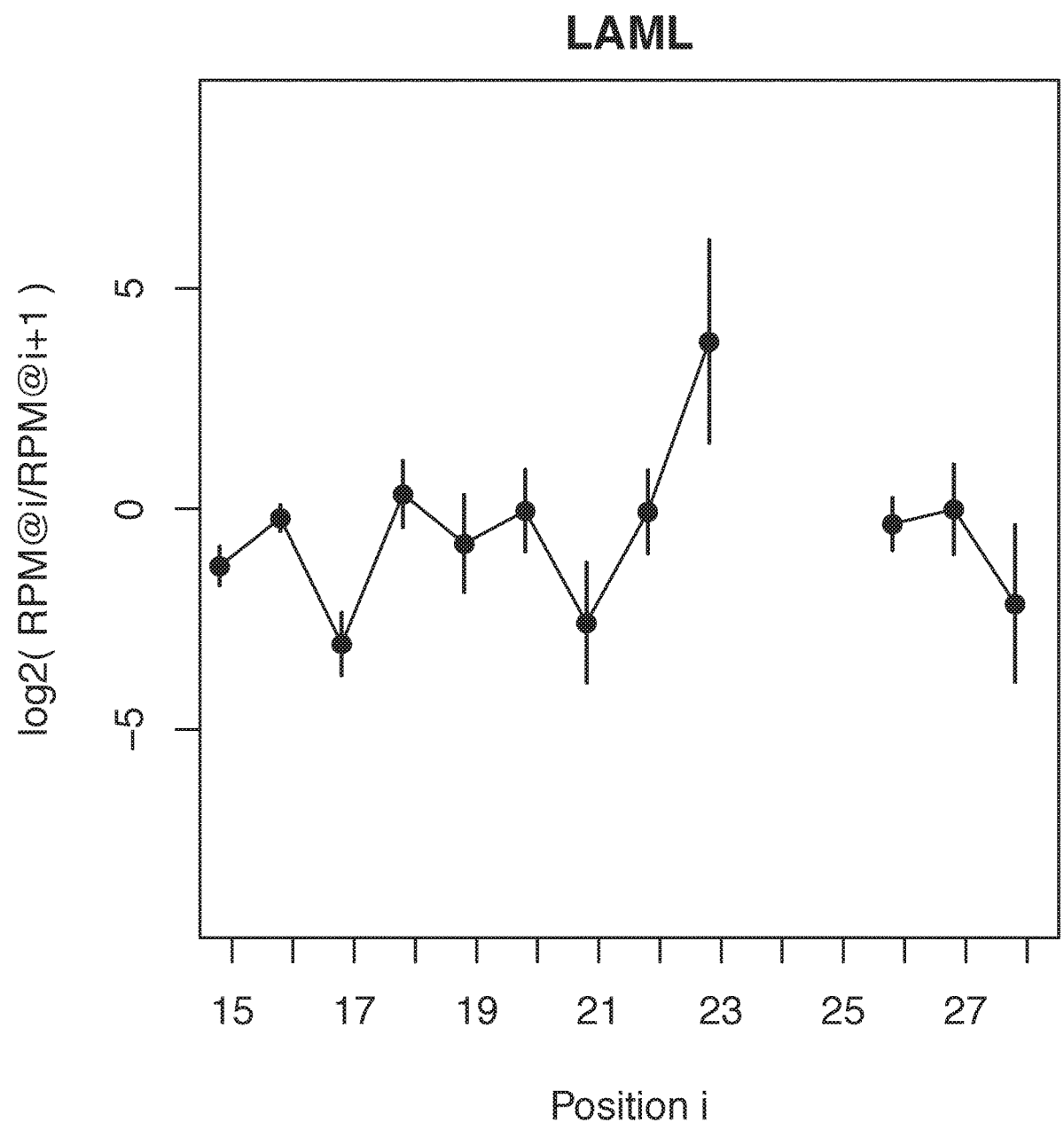
Figure 15:
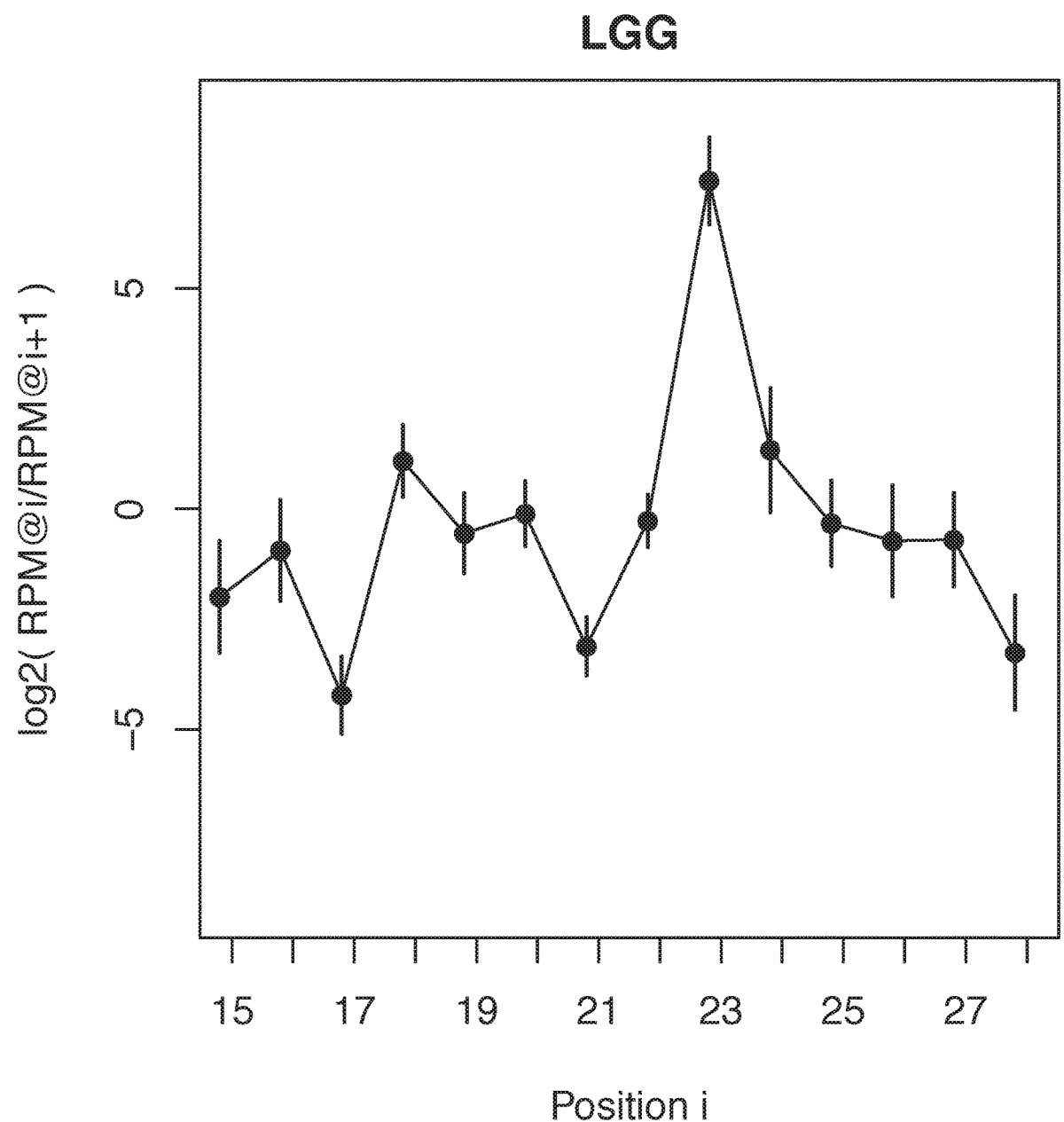
Figure 15:
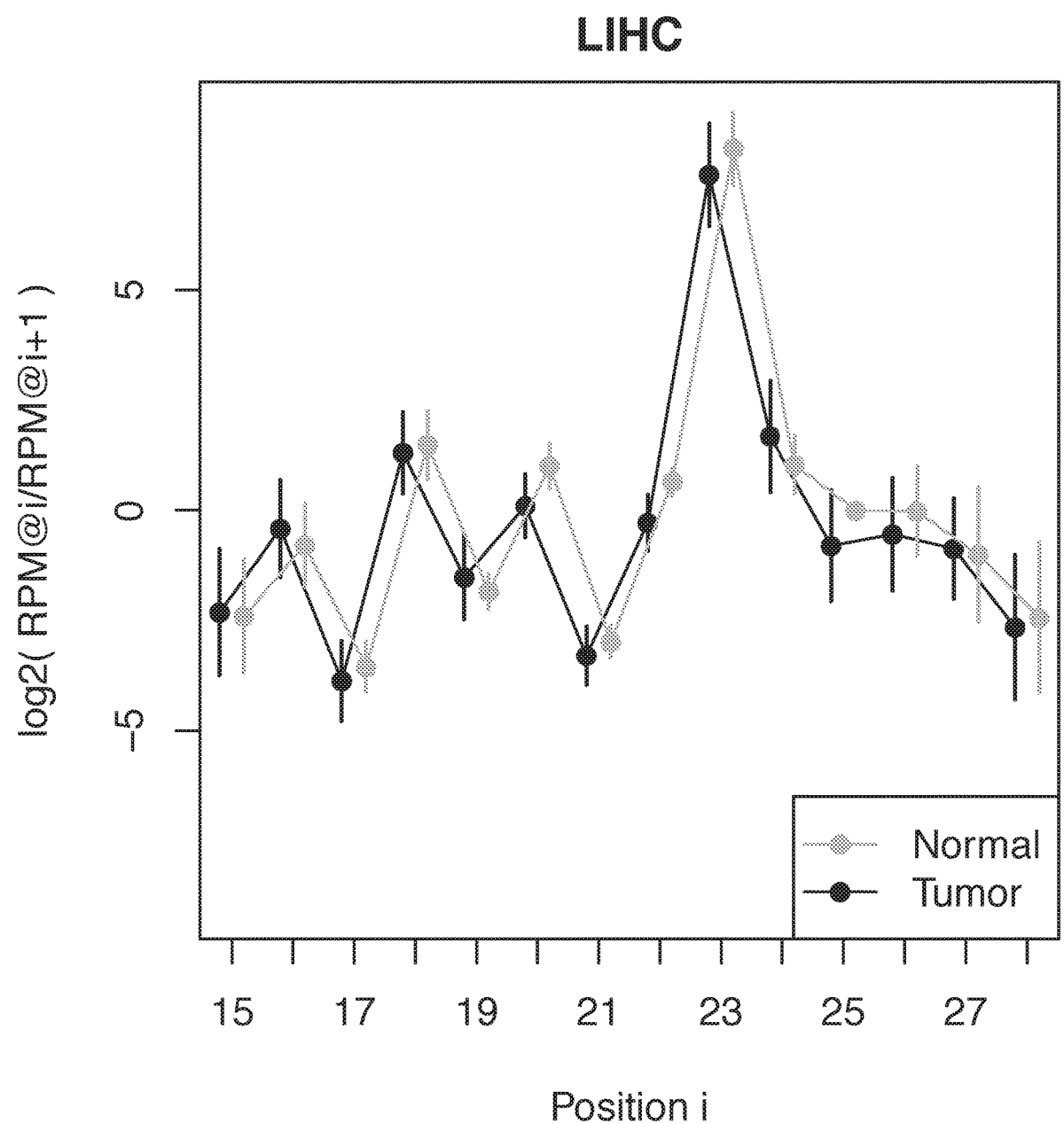
Figure 15:
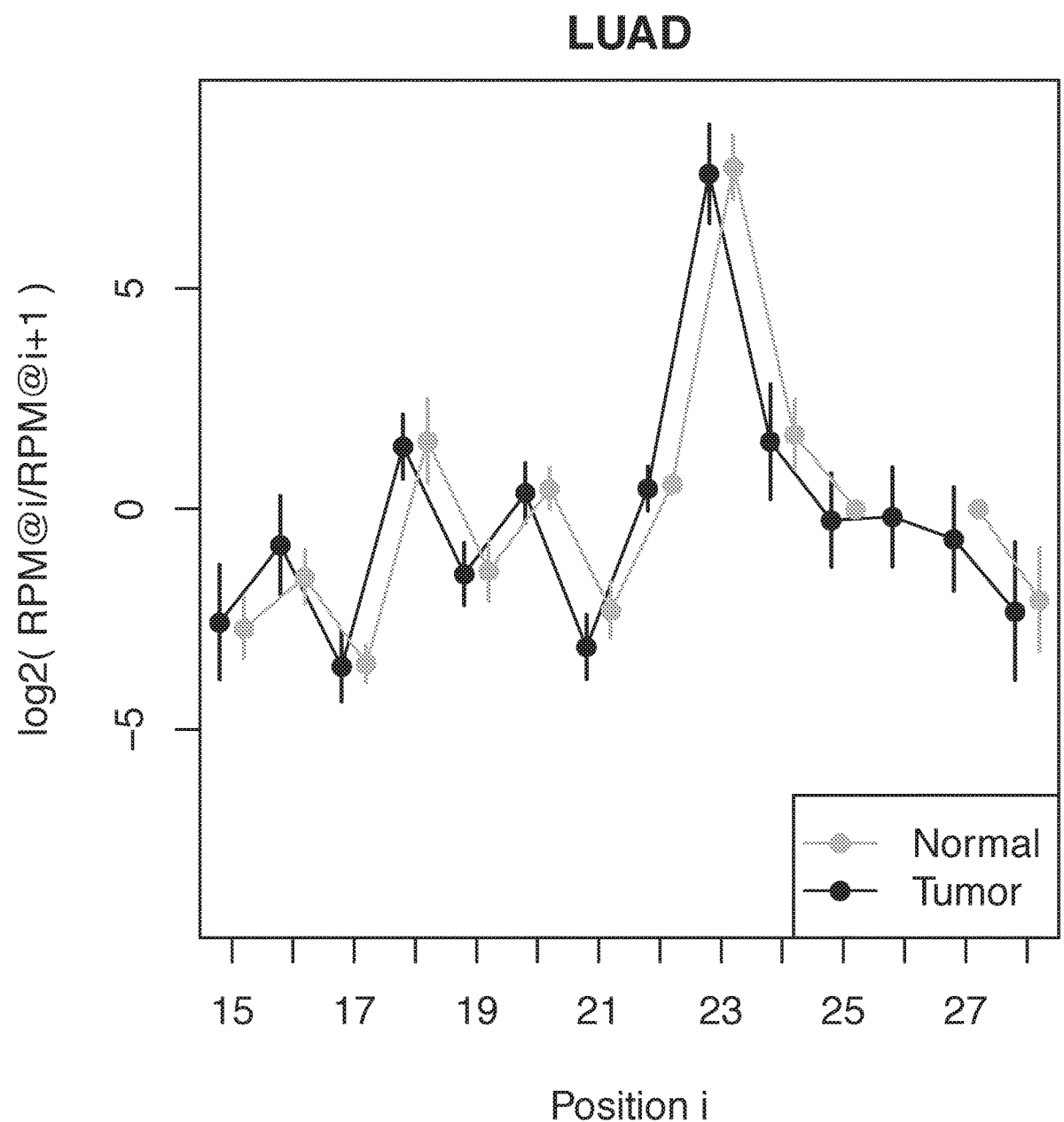
Figure 15:
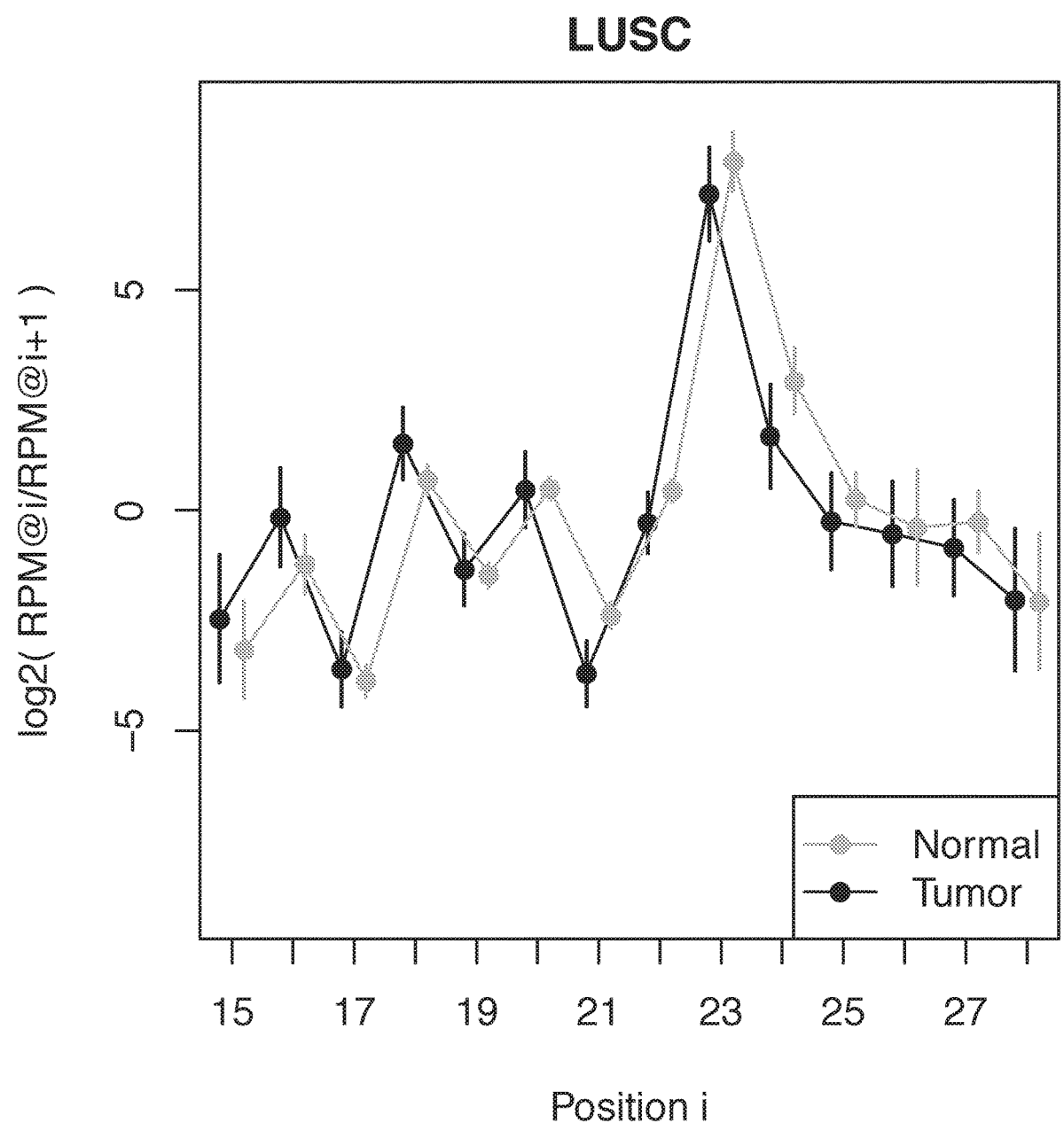
Figure 15:
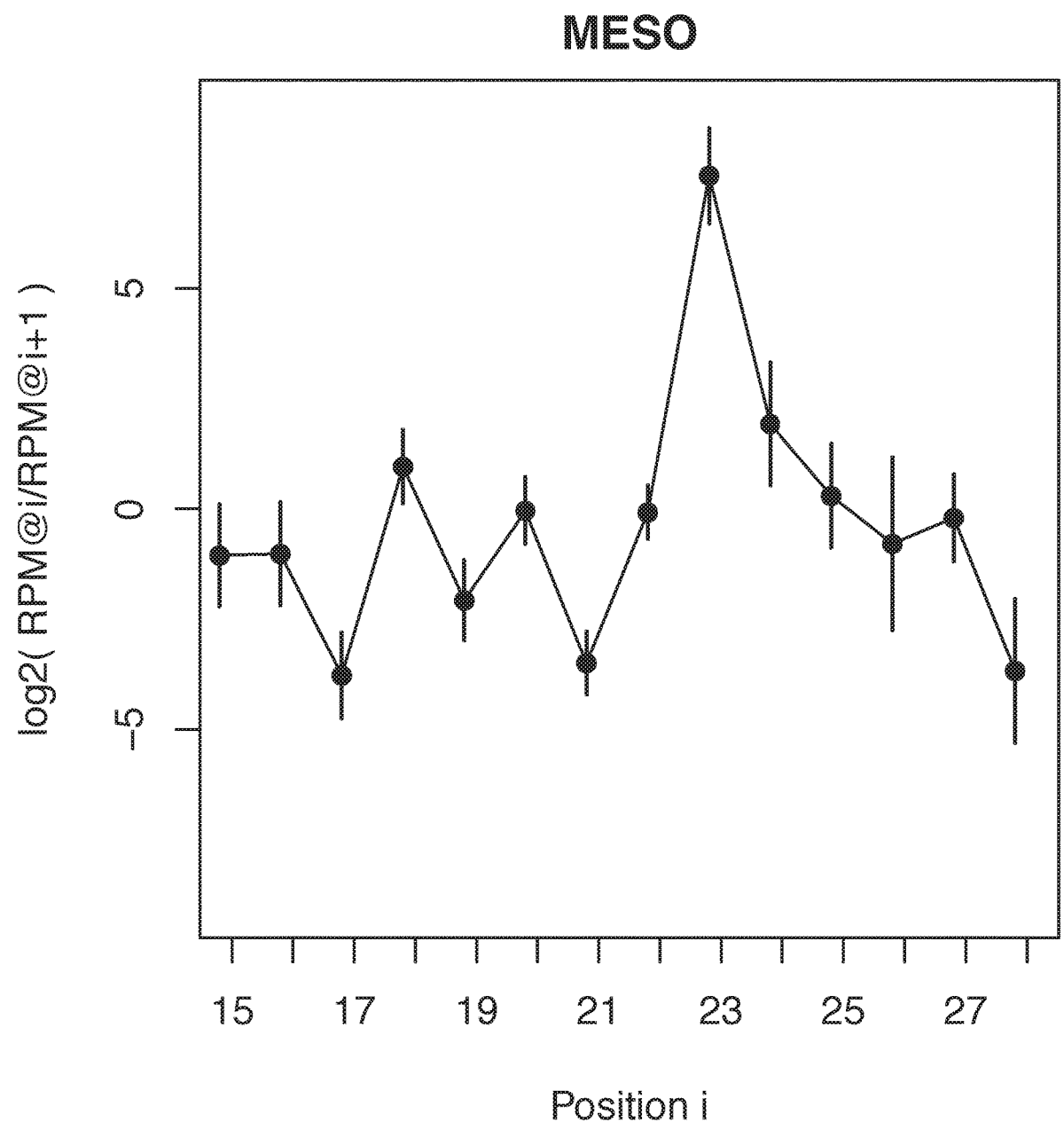
Figure 15:
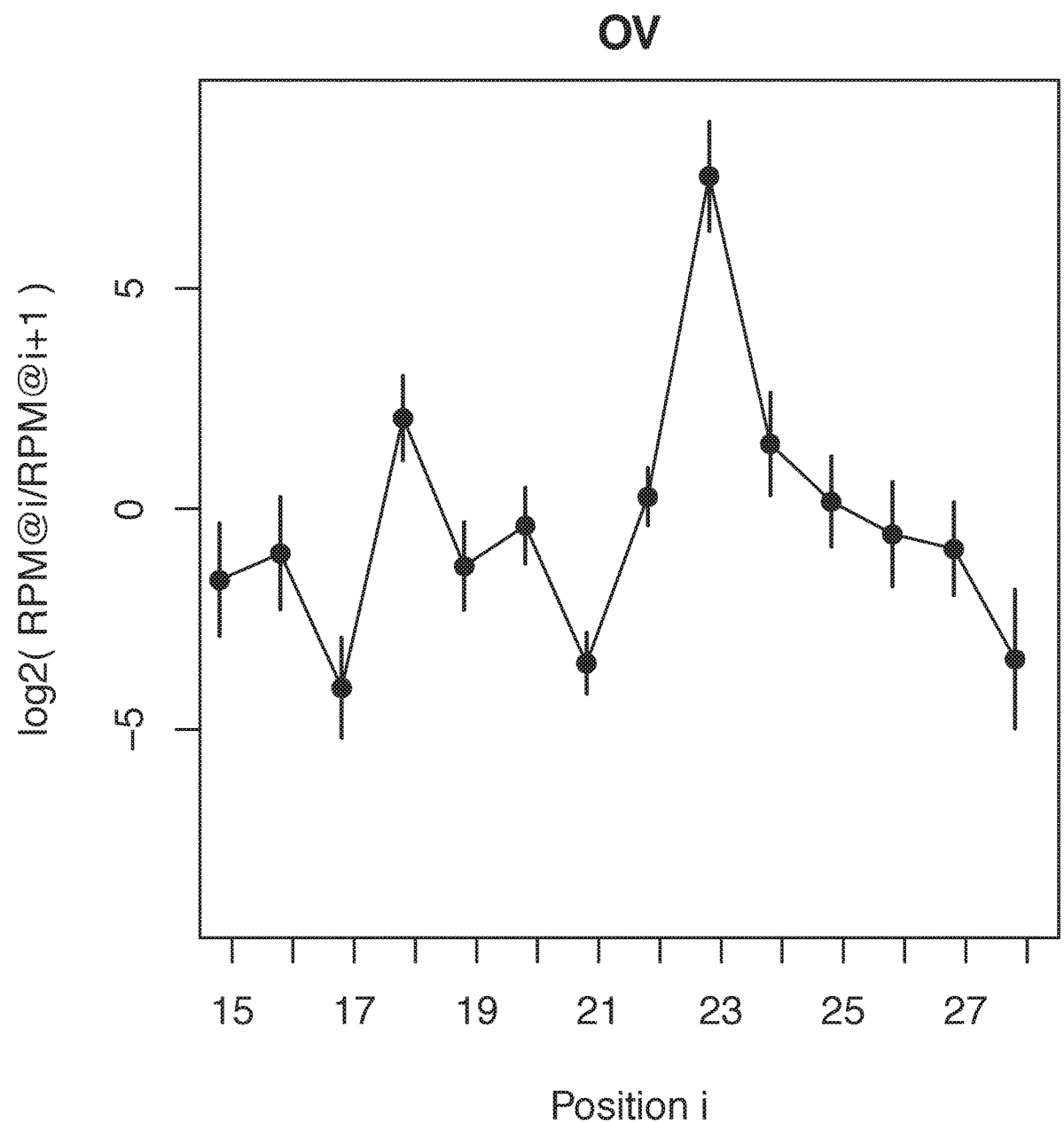
Figure 15:
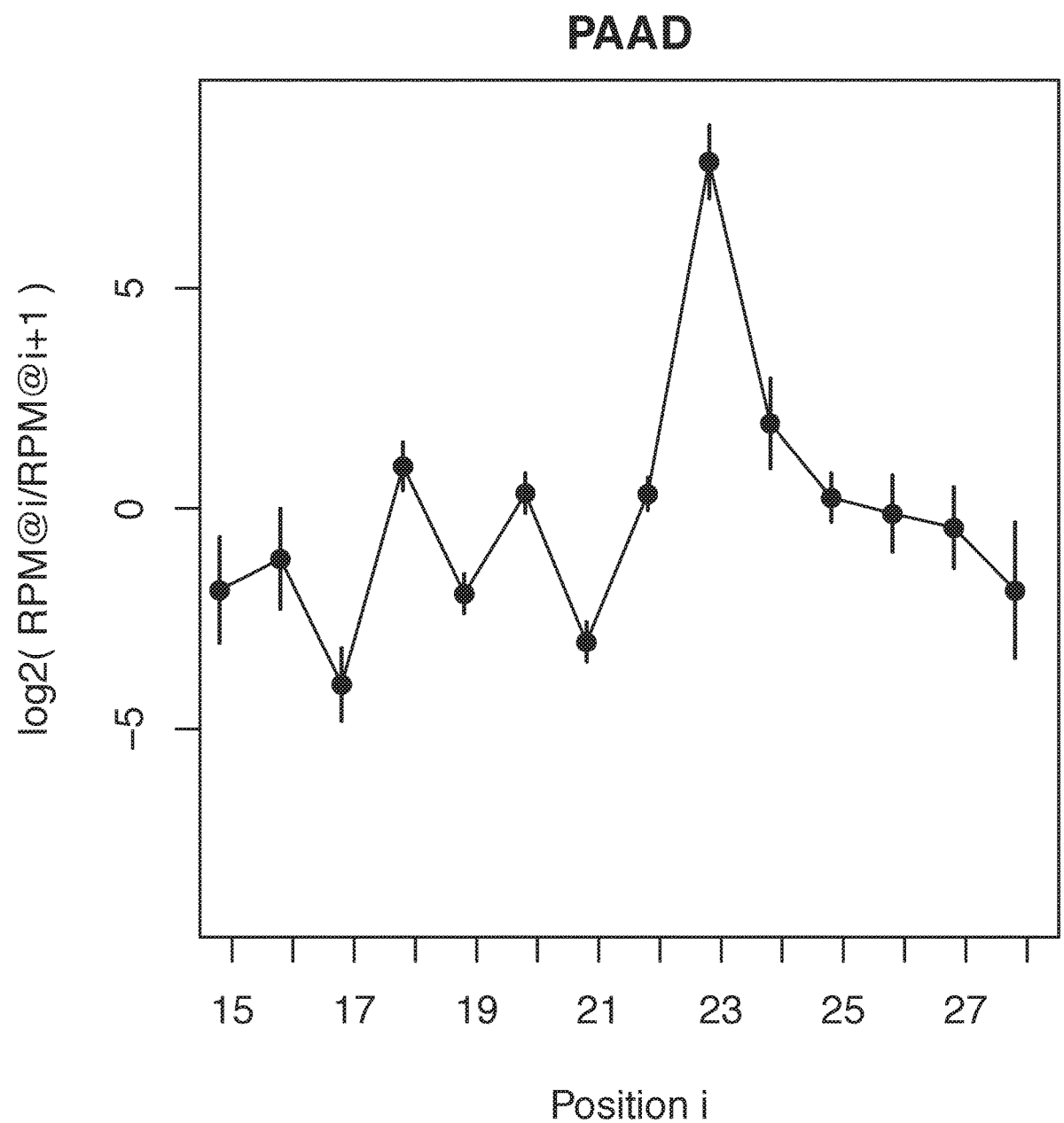
Figure 15:
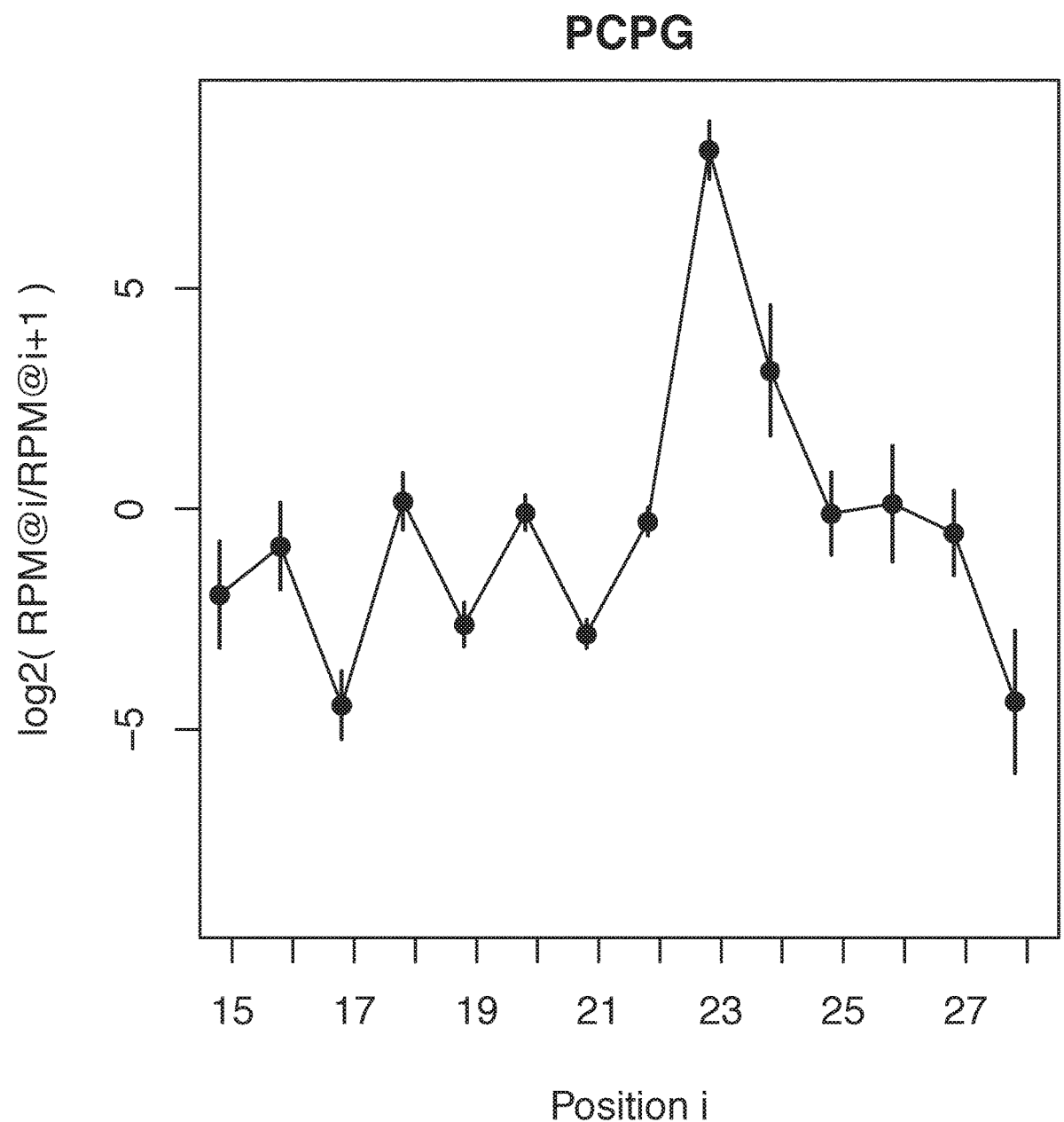
Figure 15:
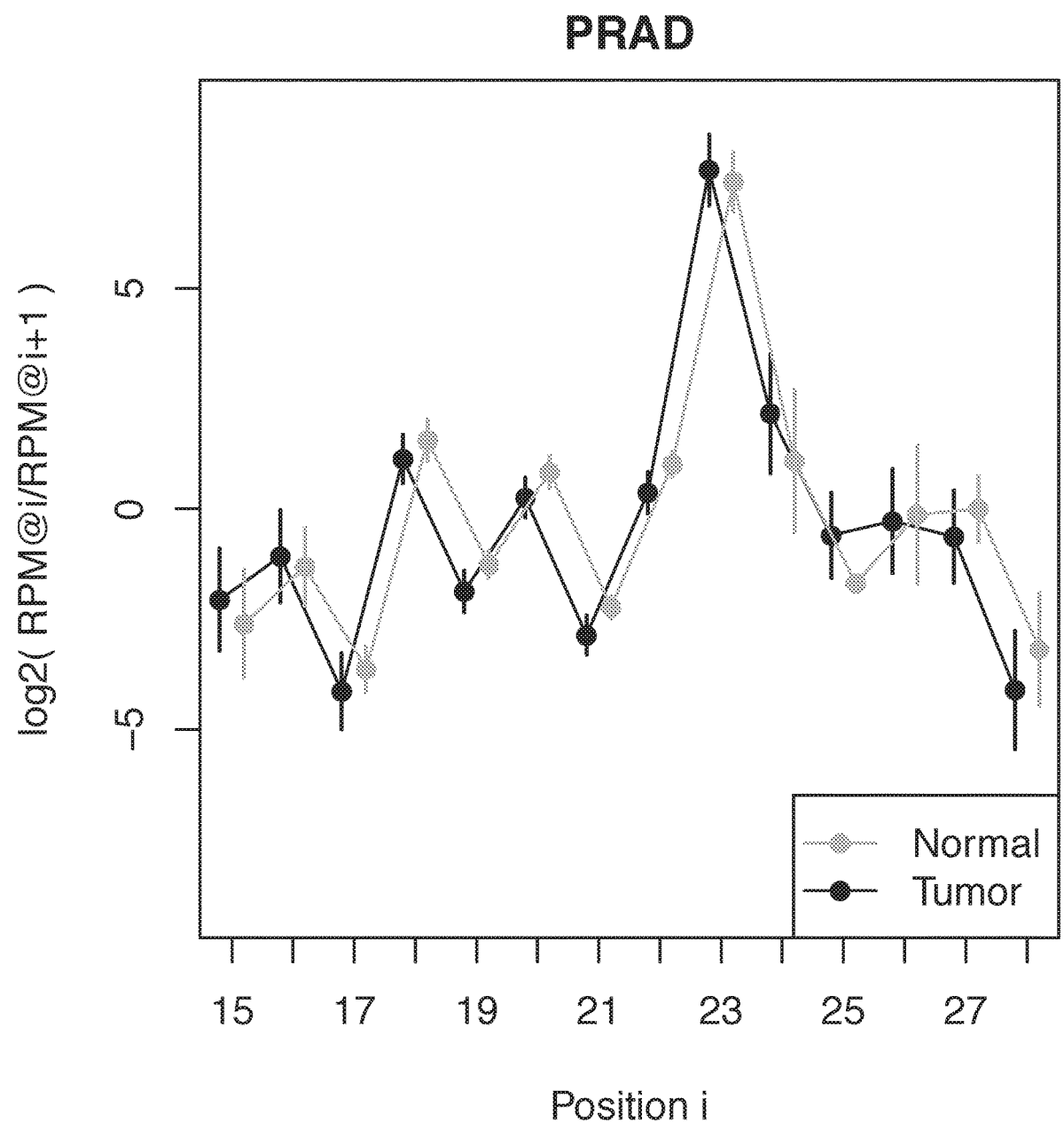
Figure 15:
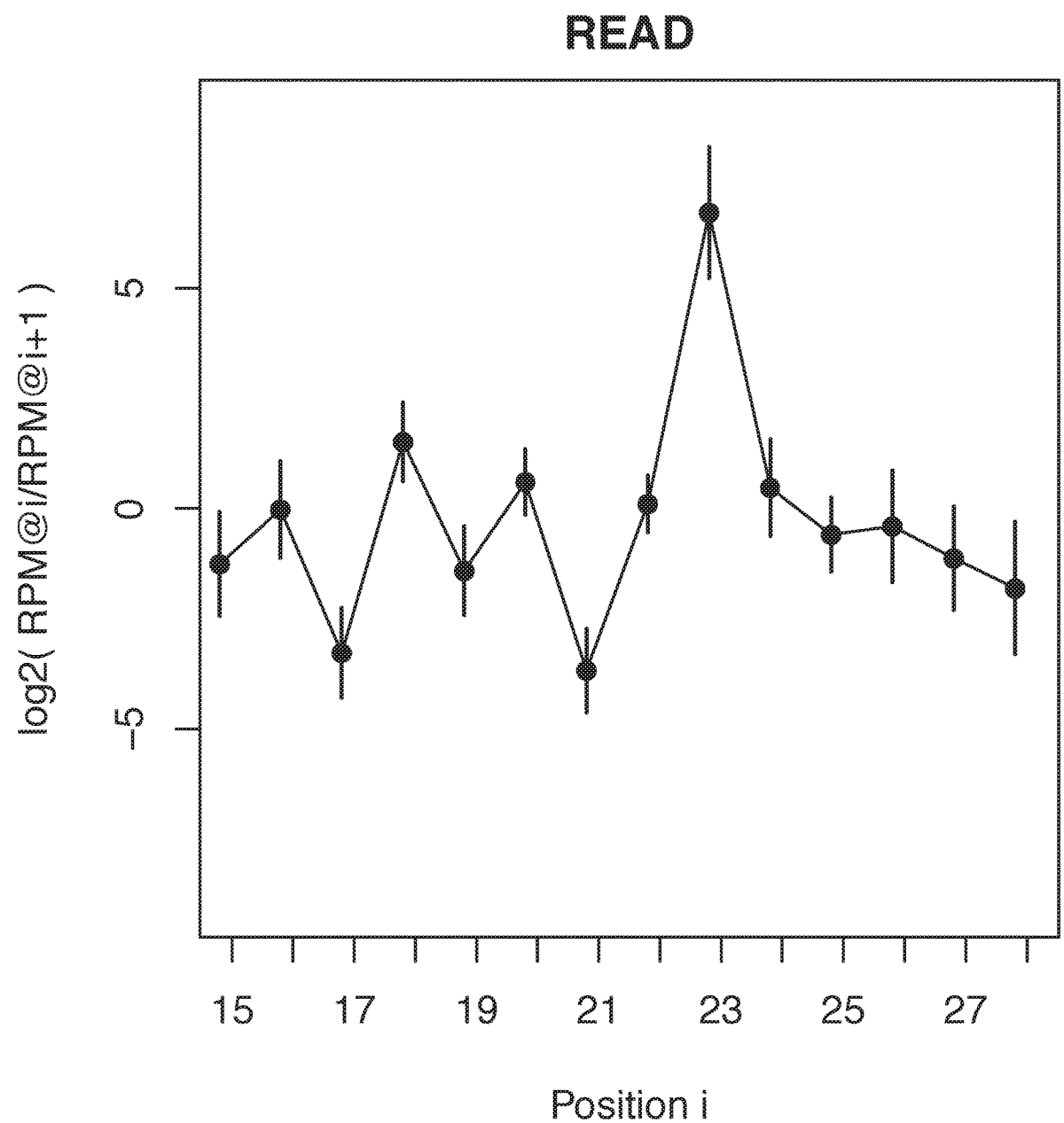
Figure 15:
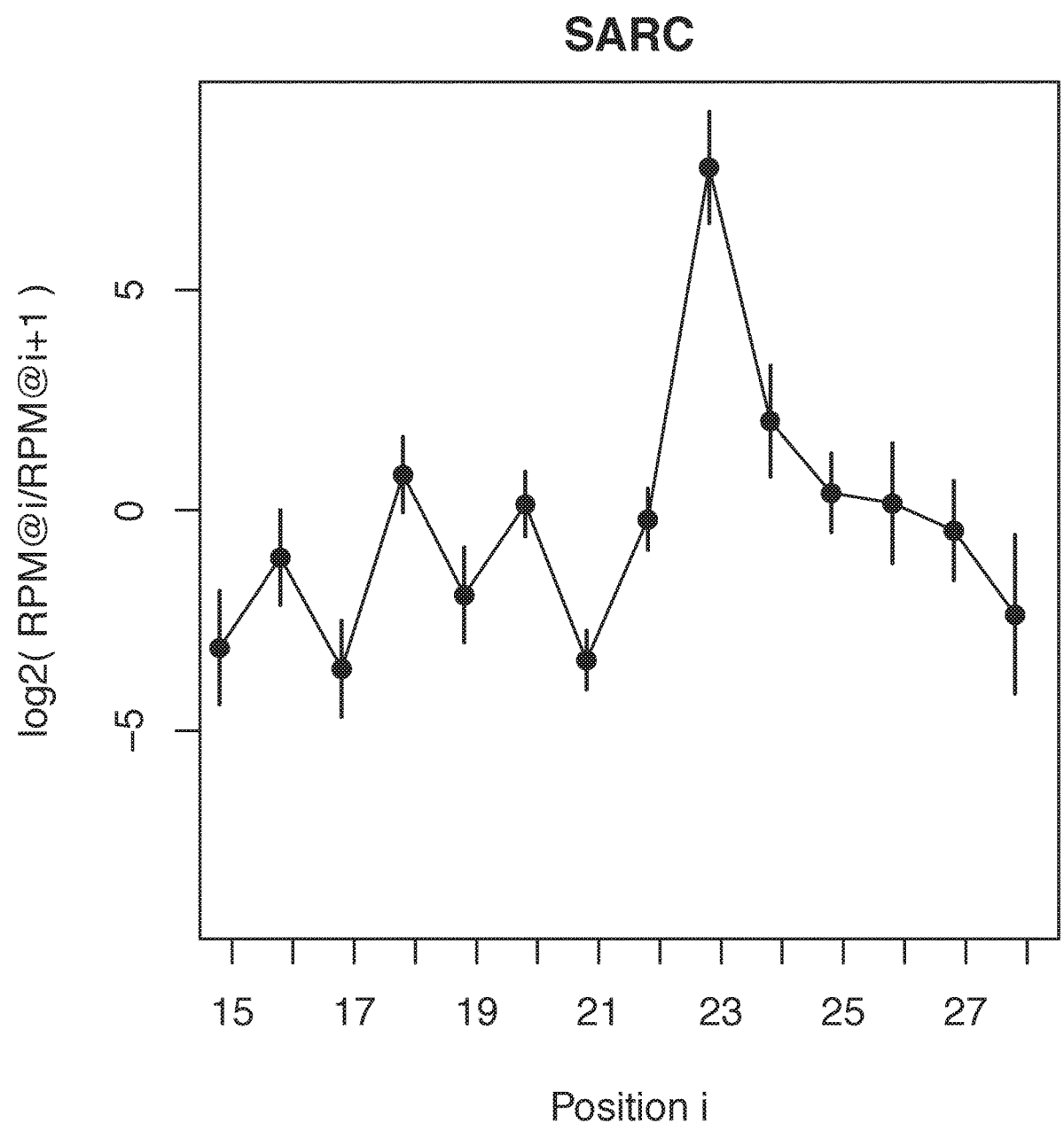
Figure 15:
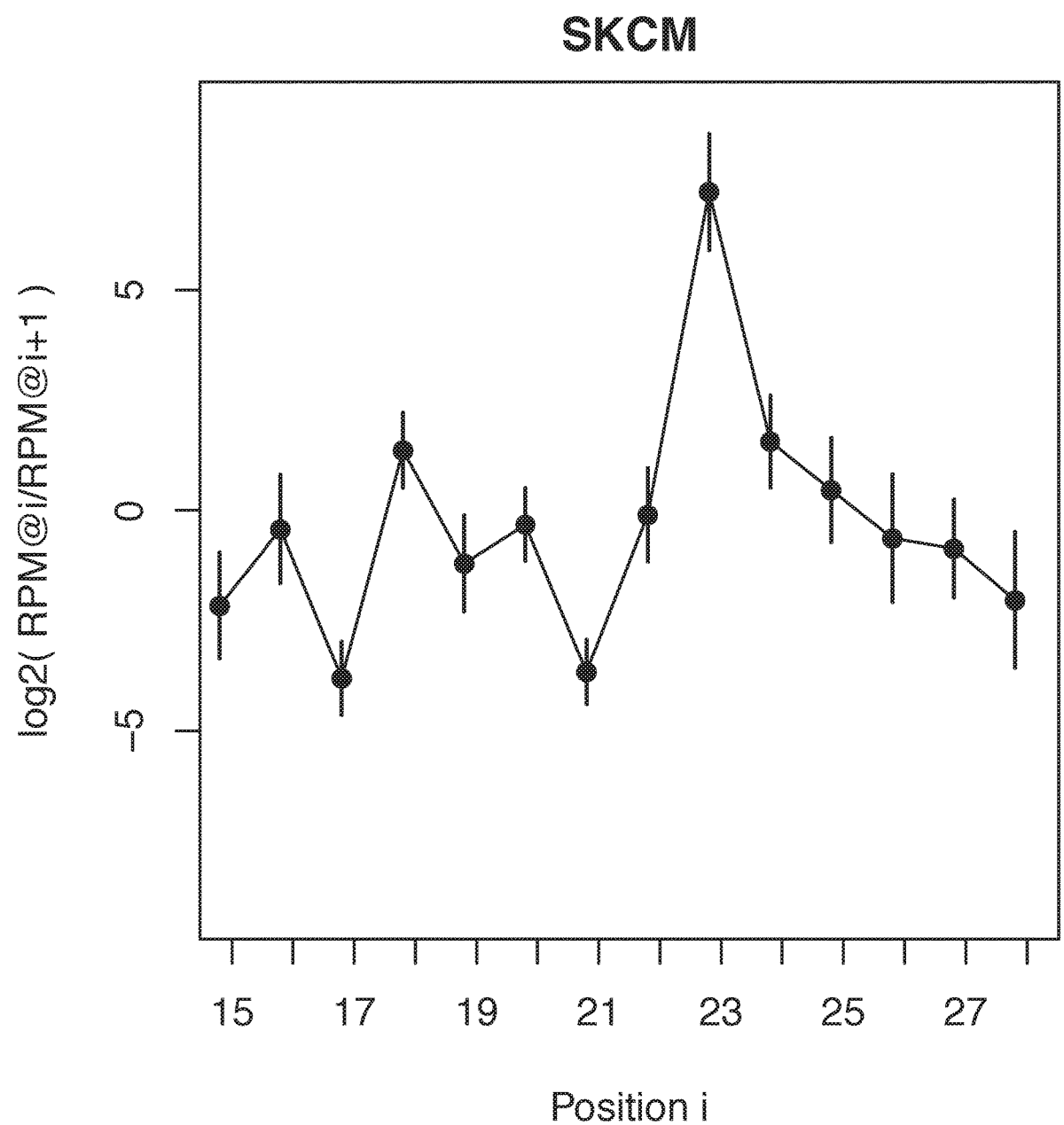
Figure 15:
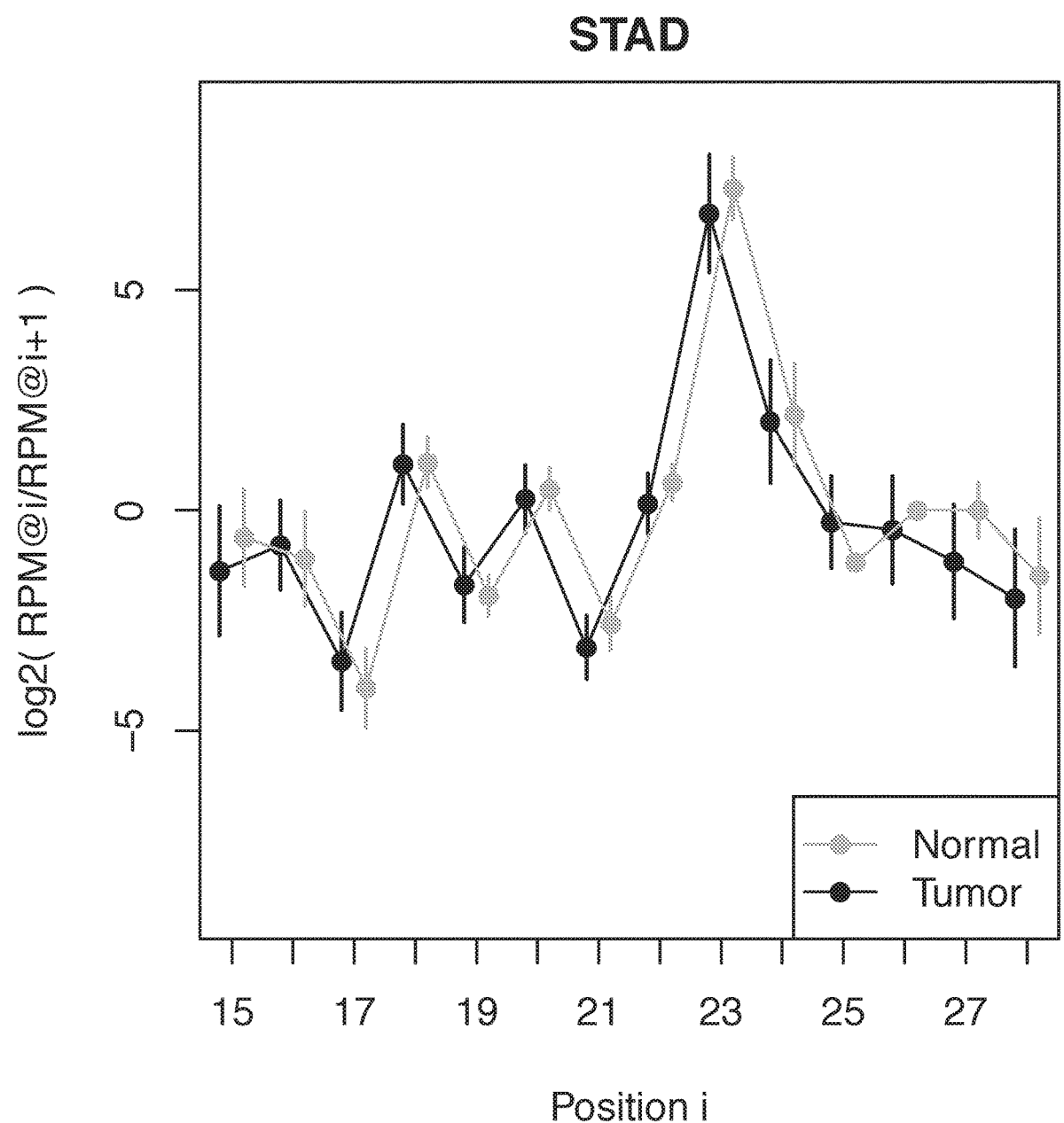
Figure 15:
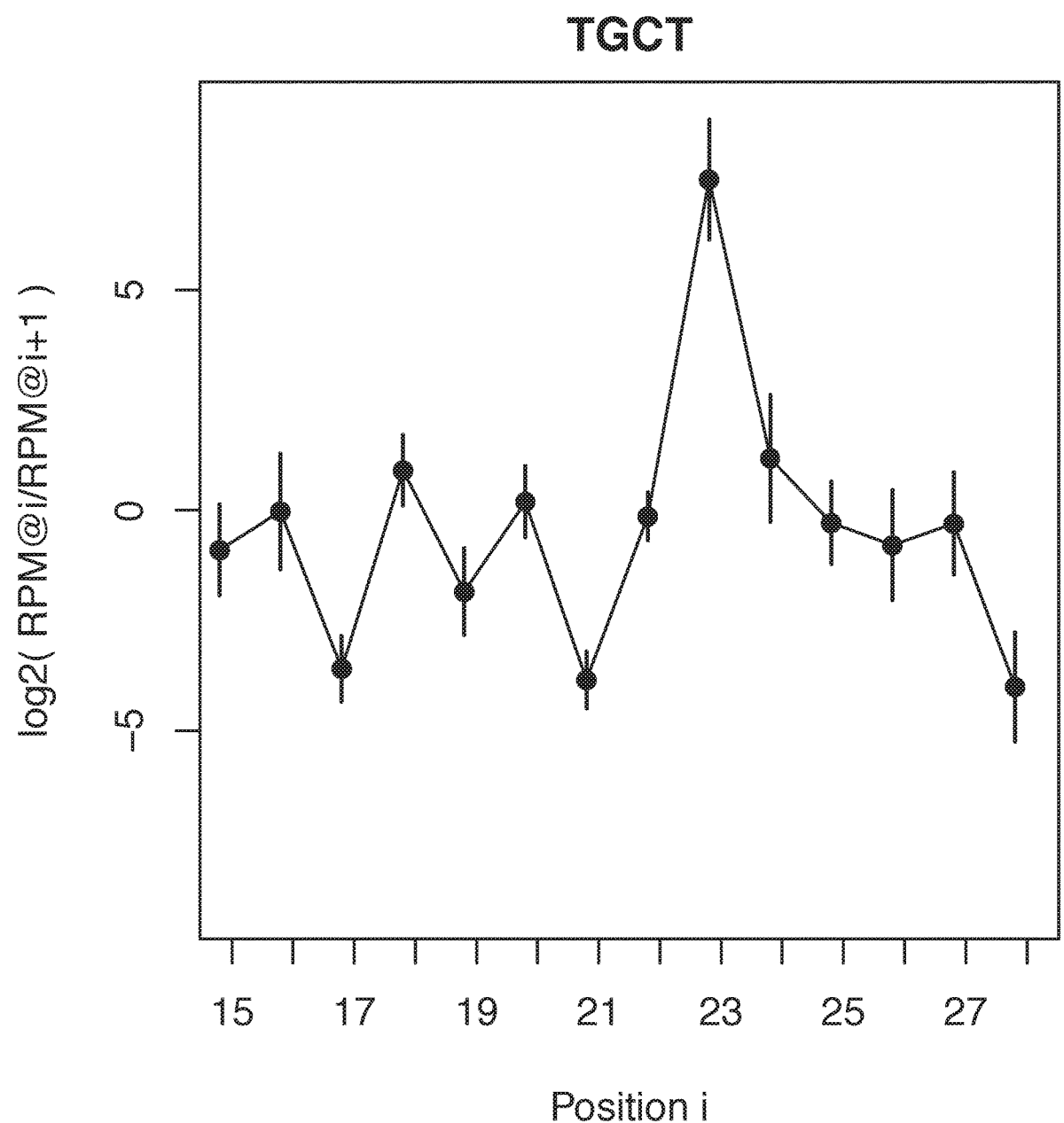
Figure 15:
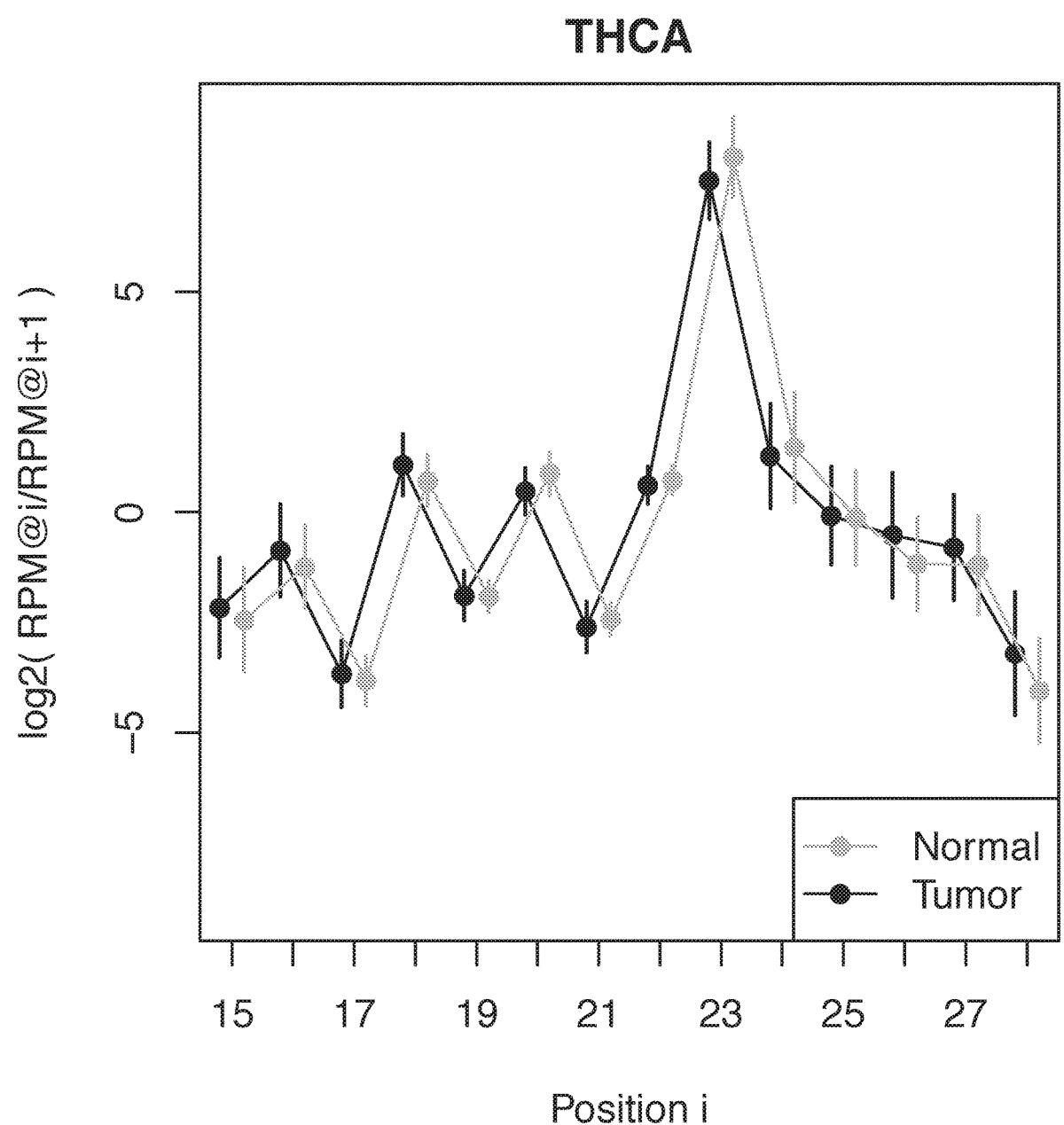
Figure 15:
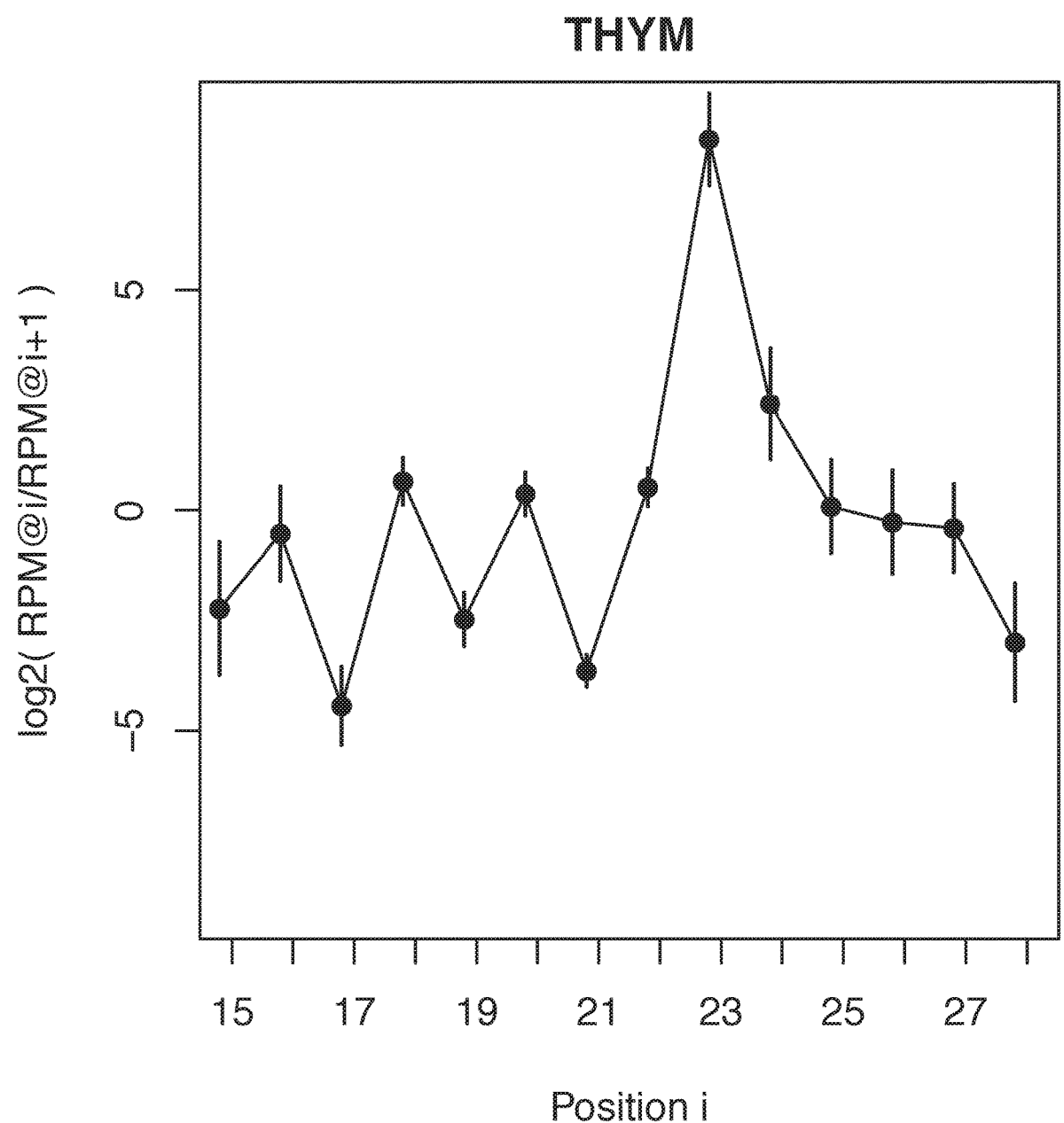
Figure 15:
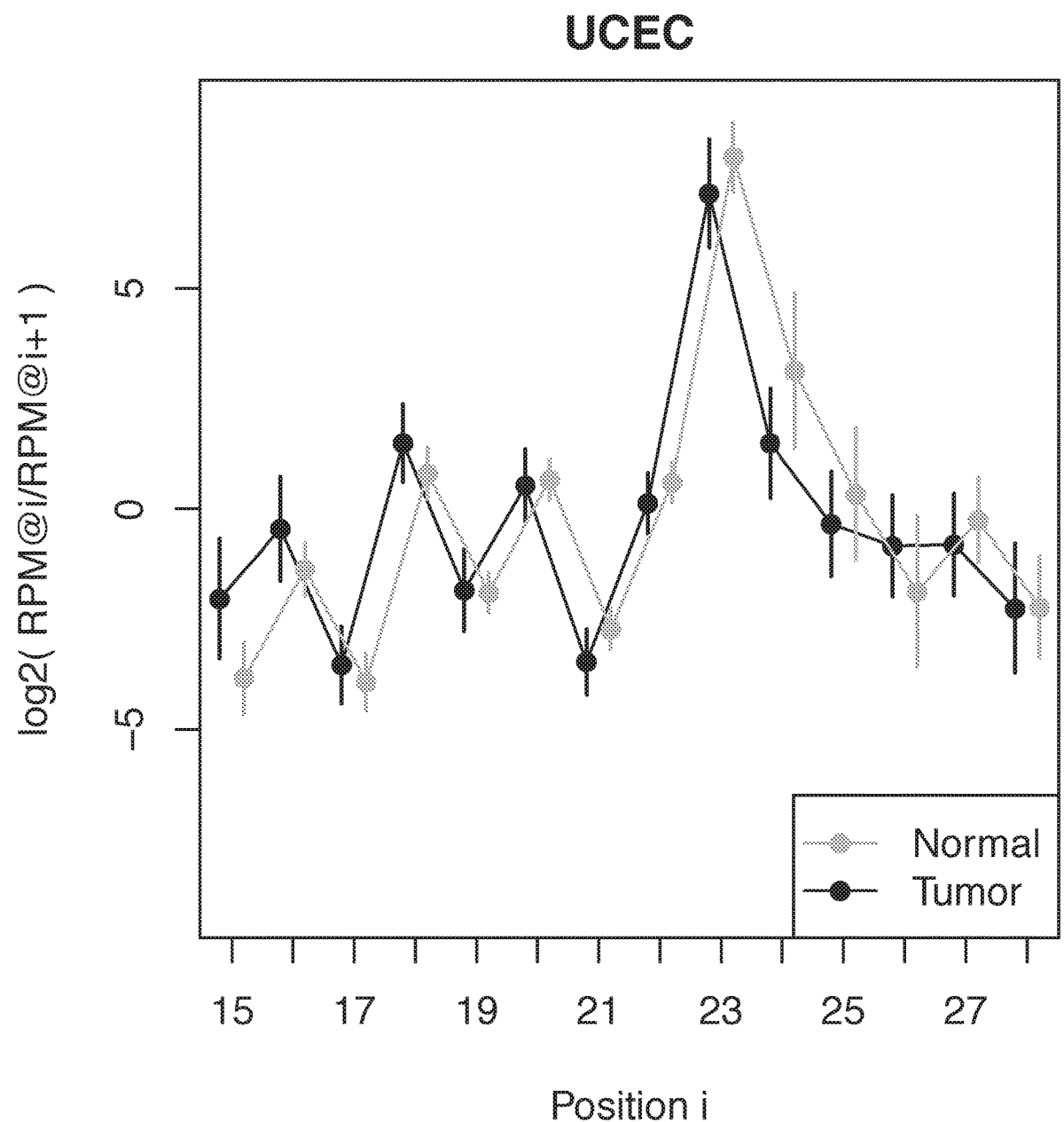
Figure 15:
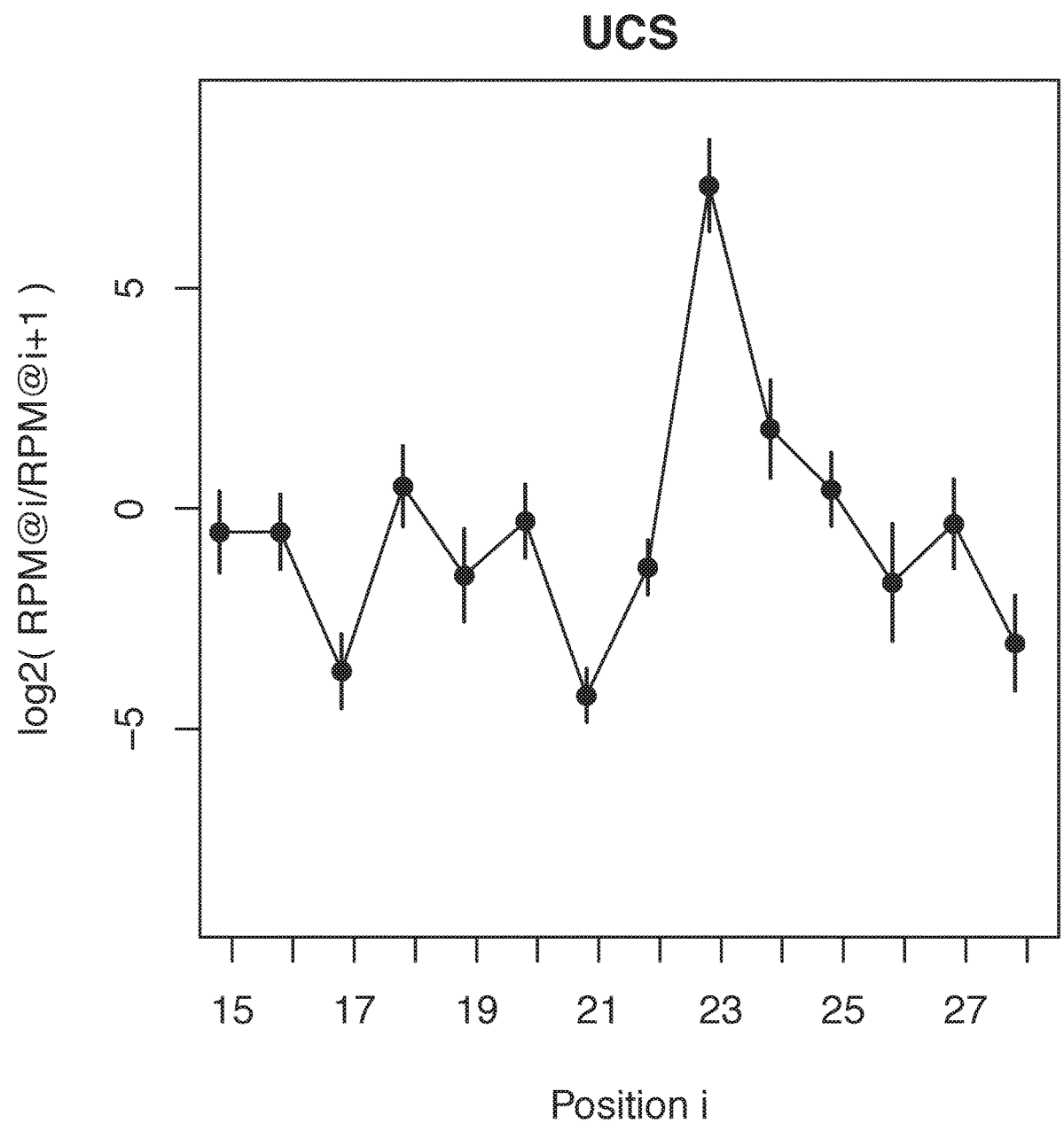
Figure 15:
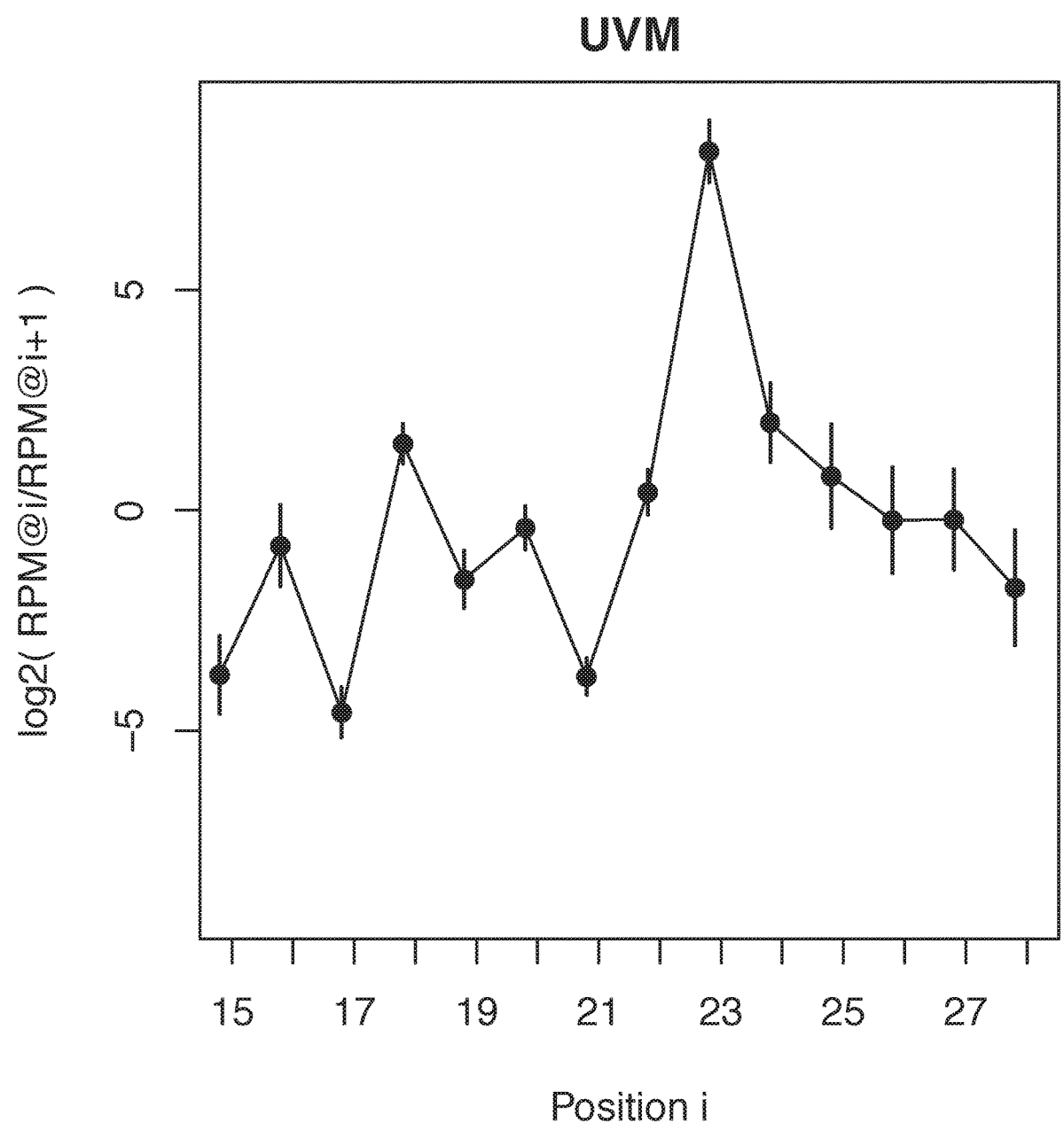

This finding suggests that the biogenesis of uridylated His(−1) 5'-tRFs is under exquisite control and that the specifics of this process are conserved in both health and disease, and across tissues. This conserved relationship suggests that these −1U 5'-tRFs, whether instigators or effectors, participate in cellular process that are common to all cancer types, and, thus, of essential nature. The complete collection of these plots for all 32 cancers can be found in FIG. 15.

System-Level Networks: tRFs are Positively- and Negatively-Correlated with One Another in a Selective Manner As part of the above analyses, we compiled the profiles of tRFs for all 32 cancer types. In our previous work, we found that tRFs from the same anticodon can be clustered in groups that are explained by the position with respect to the mature tRNA and by their lengths (see FIG. 3 of Telonis et al (4)). Here, we expand the analysis to systematically study the correlation patterns among tRFs. For each cancer type, we computed pair-wise correlations (Spearman) between tRFs. We only kept tRF-tRF pairs whose correlation value was ≥0.333 or ≤−0.333 and the associated false discovery rate (FDR) was ≤0.01. Multiple tRFs satisfied these criteria in each of the 32 cancer types.

Figure 16A:
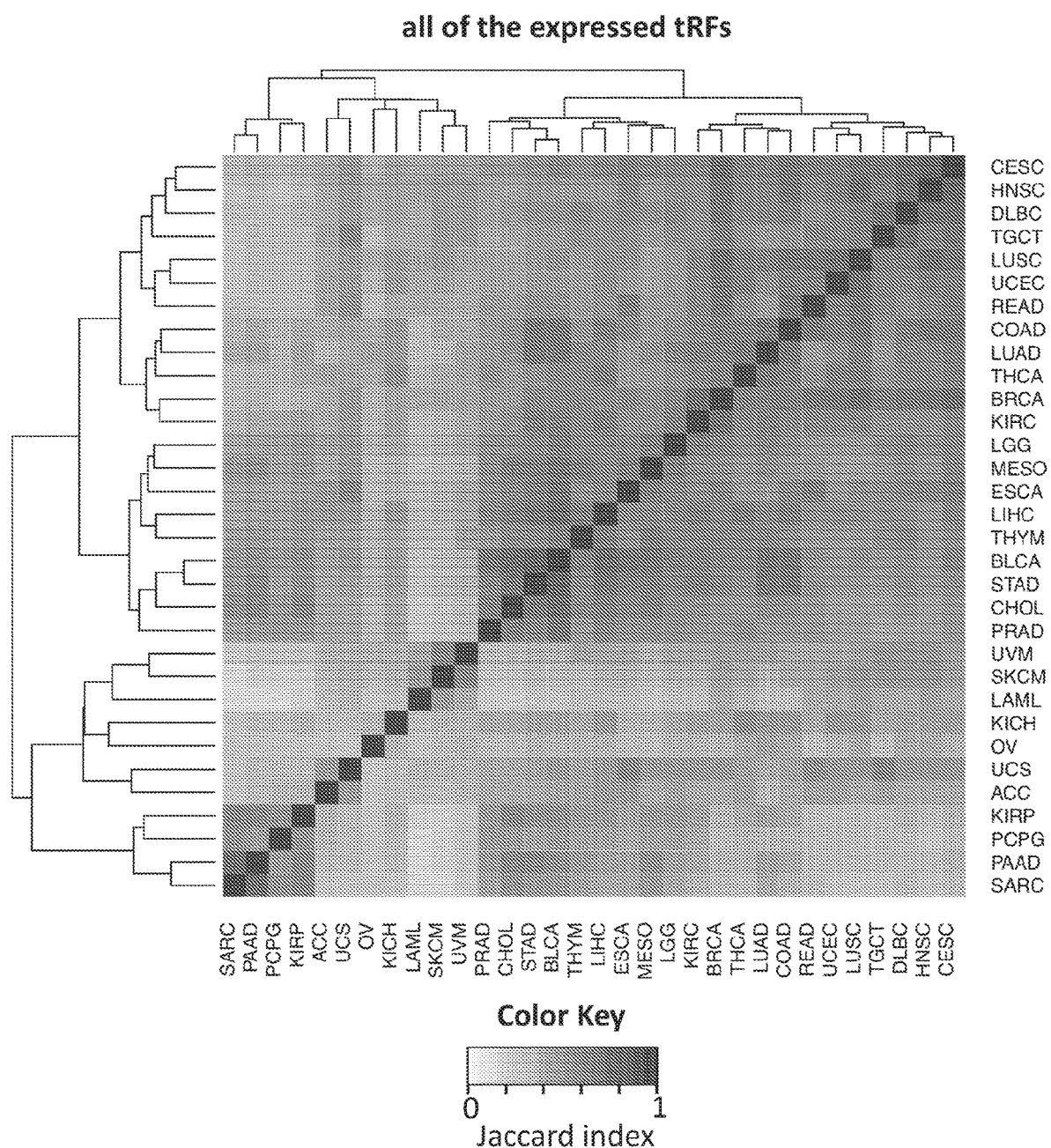
FIG. 16 Jaccard/tRFs vs. tRFs across cancers. Even though any two cancers express largely the same collection of tRFs, the subset of tRFs that are either correlated or anti-correlated with one another differs characteristically across cancers. (A) A heatmap and hierarchical clustering showing what portion of the tRFs that were considered for the correlation analyses in a given cancer are shared between cancer type X and cancer type Y (B) A heatmap and hierarchical clustering showing what portion of the tRFs that participate in statistically significant correlations or anti-correlations with tRFs in a given cancer are shared between cancer type X and cancer type Y.

Analysis of the resulting correlations revealed that the correlated tRFs exhibit notable properties that pertain to the organelle in which the tRFs are produced, the source isoacceptor, the length of the tRF, and the structural type of the tRF (Supp. Table S3). Specifically, we found the following:
  the expressed tRFs remains essentially the same across the 32 analyzed cancer types (FIG. 16A);
  the expressed tRFs that participate in tRF-tRF pairs are characteristically cancer-specific (FIG. 16B);
  tRFs that are positively correlated with one another originate almost exclusively in the same cellular compartment (either both pair members are nuclear tRFs, or, both are MT tRFs);
  tRFs that are negatively correlated with one another originate in different compartments (i.e., one of the tRFs comes from the nucleus and the other from the MT);
  positively-correlated nuclear tRFs frequently arise from distinct isoacceptors;
  positively-correlated MT tRFs frequently arise from the same isoacceptor;
  negatively-correlated tRFs frequently arise from distinct isoacceptors, irrespective of whether they originate in the nucleus or the MT;
  positively-correlated tRFs frequently have similar lengths (length difference <5 nt) and belong to the same structural category;
  negatively-correlated tRFs frequently have different lengths (length difference ≥5 nt) and belong to different structural categories.

A representative list of tRF:tRF pairs (both positively- and negatively-correlated), and their corresponding correlation values and statistical significance, can be found in the Supp. Table S4 for the case of BRCA.

These results indicate that tRFs are a considerably heterogeneous group of molecules. The characteristics of tRFs such as isoacceptor of origin, organelle of origin, length and structural type are important determinants of the types of correlations in which they participate. We stress that, despite these commonalities, the choice of which expressed tRFs participate in positively- or negatively-correlated pairs depends on cancer-type.

System-Level Networks: tRFs are Positively- and Negatively-Correlated with mRNAs and Pathways in a Selective Manner From a functional standpoint, others (10) and we (4) have shown that tRFs can be loaded on Argonaute, just like miRNAs. In fact, such loading was demonstrated to affect the abundance levels of mRNAs (29). To compare and contrast the potential impact of miRNAs and tRFs in the cancer context, we leveraged the available long RNA-seq data of the TCGA repository. As a positive control case, we included miRNAs in these analyses. Specifically, we computed all correlated tRF-mRNA and miRNA-mRNA pairs, and examined their properties across and within cancer types. These analyses were carried out with the understanding that, for both miRNAs and tRFs, these anti-correlations capture both direct interactions and indirect relationships. A representative list of tRF:mRNA pairs (both positively- and negatively-correlated), and their corresponding correlation values and statistical significance, can be found in the Supp. Table S4 for the case of BRCA.

First, we examined whether tRF-mRNA and miRNA-mRNA anti-correlations persist across cancer types. As we computed abundance correlations, we were strict when filtering tRFs to minimize the inclusion of noise in our data. We found that the expressed tRFs, miRNAs, and mRNAs are essentially the same across cancers (Supp. Figures S5A, S6A, and S6B). However, what changes dramatically from one cancer type to the next is the specific manner in which miRNAs and tRFs "partner" with mRNAs to form negatively-correlated pairs. This point is evidenced by the very low off-diagonal support in Supp. Figures S5B, S6C and S6D. Within a cancer, tRFs and miRNAs are frequently negatively correlated with the same mRNAs, as evidenced by the 2×2 mini-matrices across the diagonal in FIG. 17E. This suggests possible synergistic activities by miRNAs and tRFs.

Figure 18A:
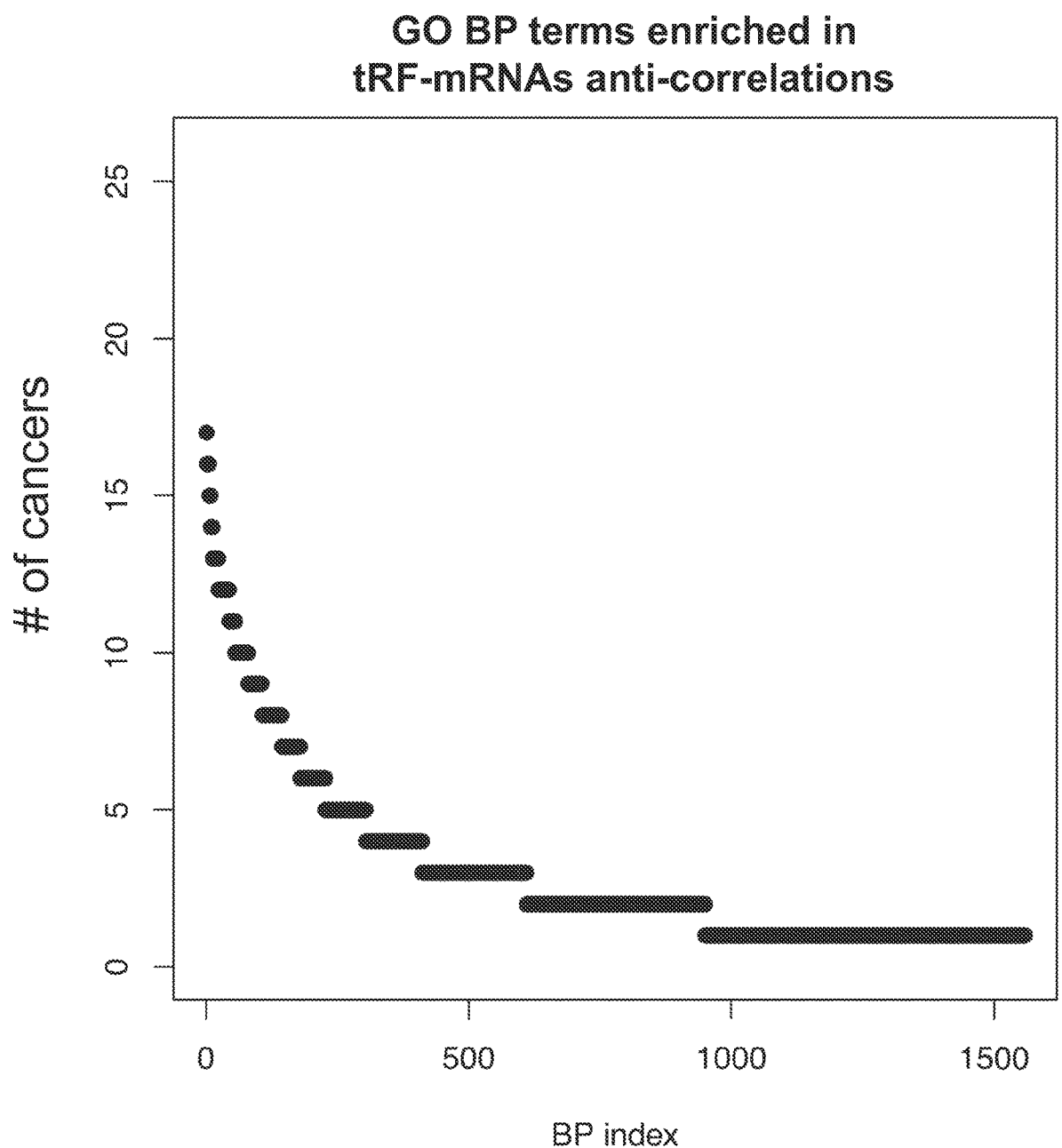
FIG. 18 Distributions across cancers. (A) Distribution of the number of cancers containing an enriched GO BP term that is supported by tRF-mRNA anti-correlations. (B) Distribution of the number of cancers containing an enriched GO BP term that is supported by miRNA-mRNA anti-correlations. (C) Jaccard index for the BP terms enriched for each cancer. (D) Jaccard index among the BP terms showing the overlap in mRNAs/genes. For the construction of the dendrograms in (C) and (D), Euclidean distance was used as a metric.
Figure 18B:
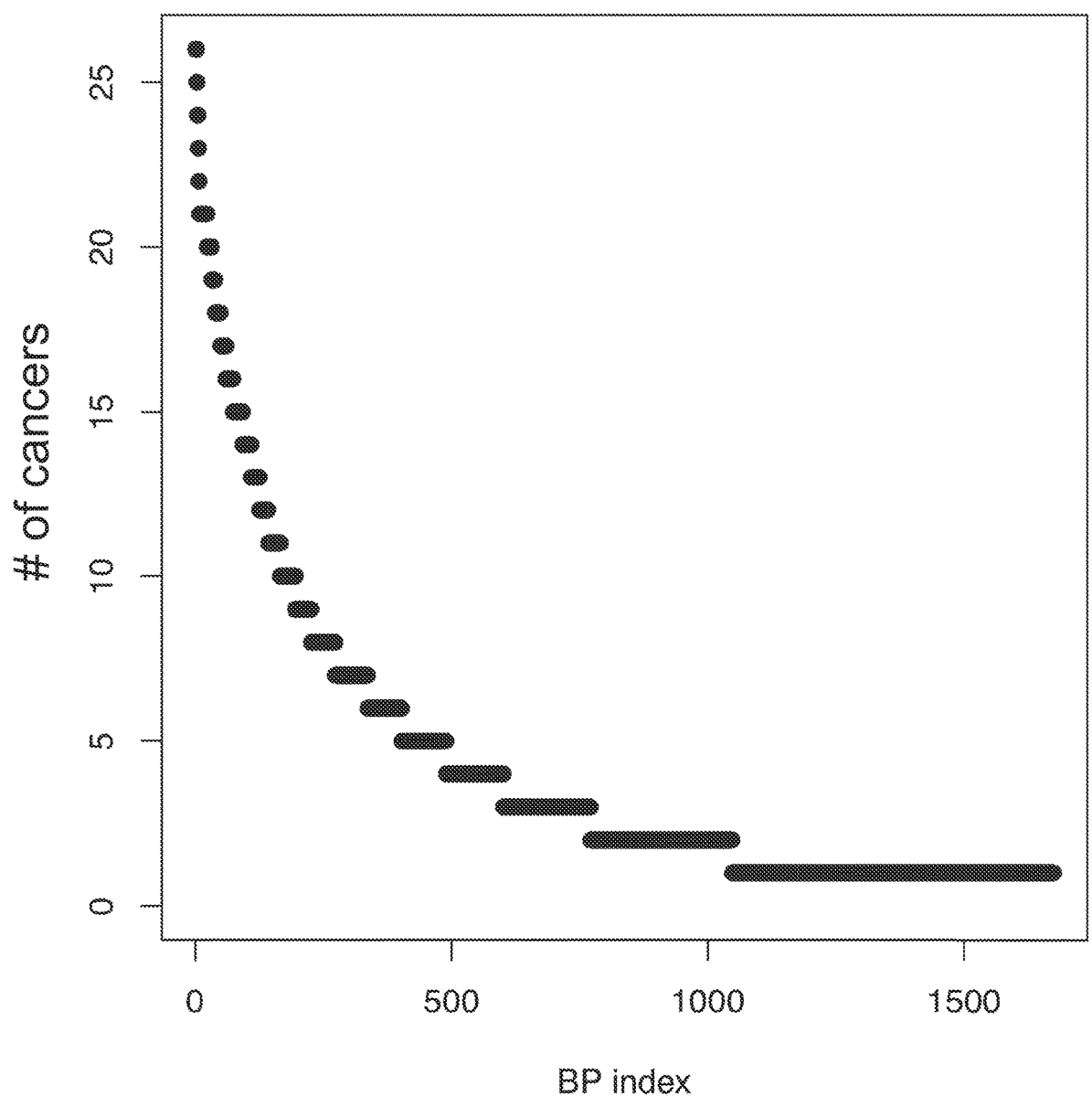
Figure 18C:
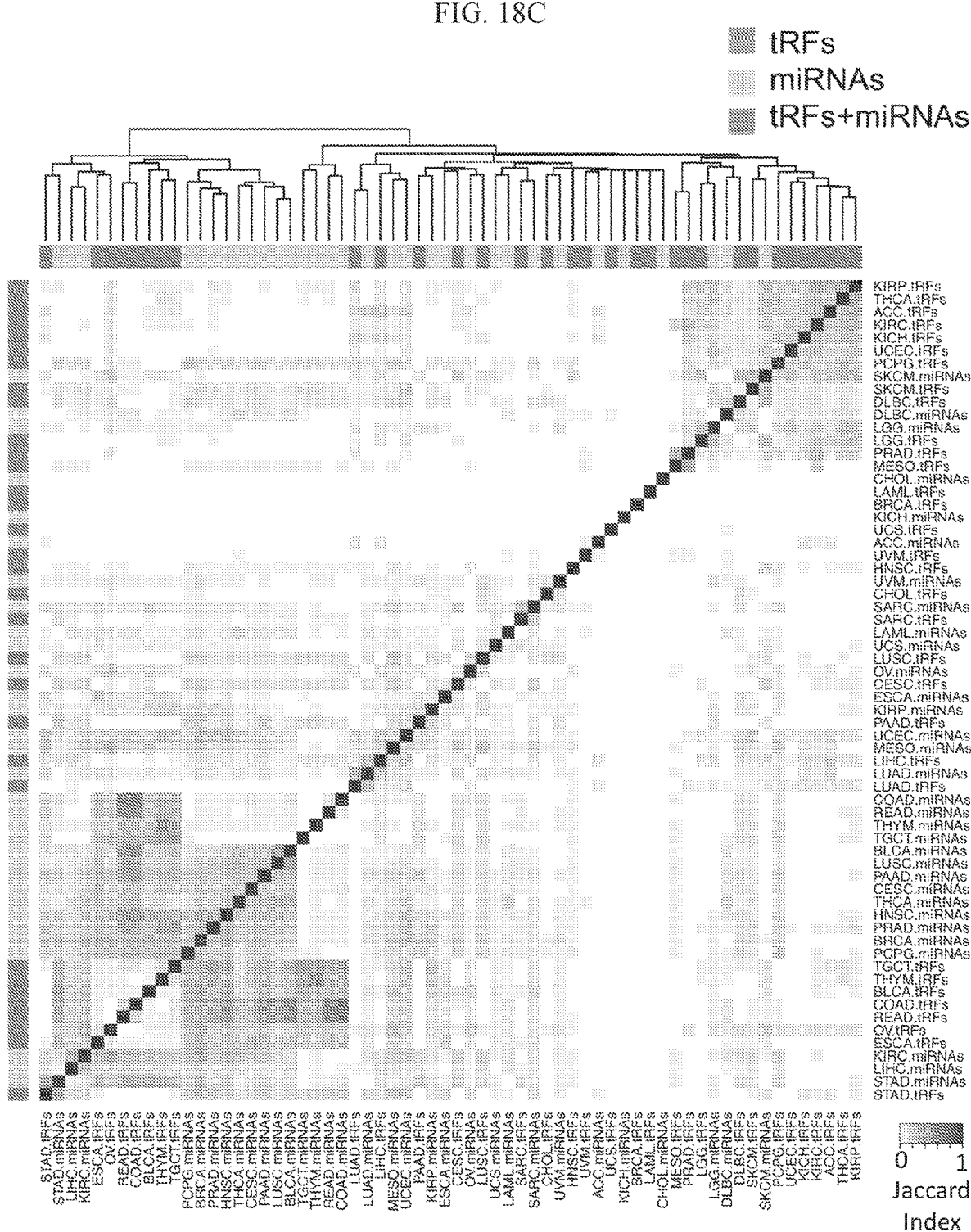
Figure 18D:
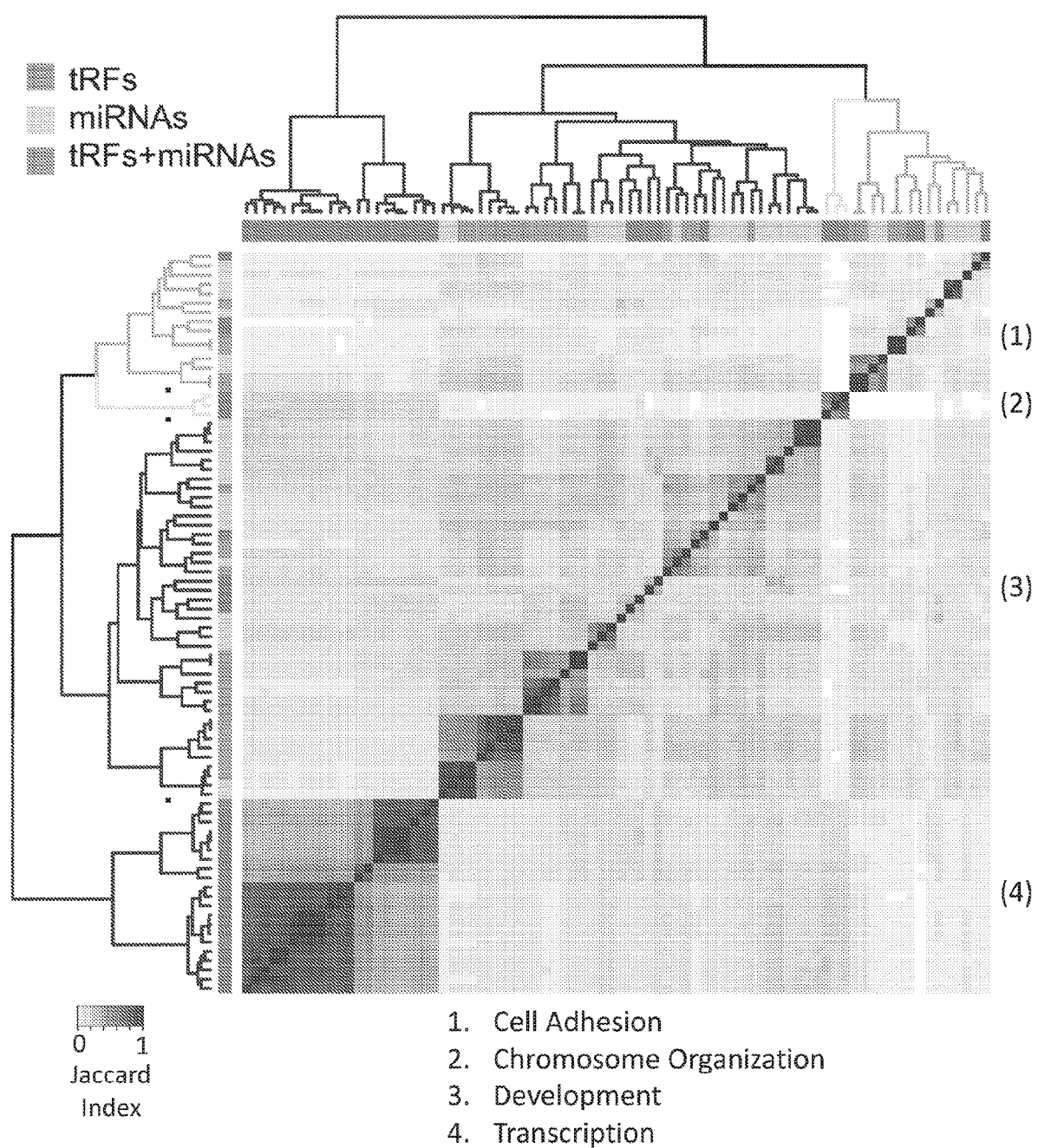

Next, we examined whether the cancer-specificity of the negatively-correlated tRF-mRNA and miRNA-mRNA pairs translate into differences in the underlying pathways. To investigate this possibility, we performed DAVID analysis for each collection of mRNAs in tRF-mRNA pairs in search of enriched Gene Ontology (GO) terms and also KEGG pathways. We observed that the distribution of GO Biological Process (BP) terms as well as of KEGG pathways resembles a power-law distribution with many pathways found uniquely in one cancer-type and relatively fewer pathways appearing in several types (FIGS. 18A-B). For example, "renal cell carcinoma" was found enriched among the mRNAs that are negatively correlated with tRFs in KIRC. However, other enriched KEGG pathways, such as "pathways in cancer" and "proteoglycans in cancer," are universal. Overall, we observed that any two cancers have a smaller overlap in terms of enriched mRNAs (FIG. 18C) compared to enriched pathways (FIG. 18D). This suggests that, although the tRF-mRNA or miRNA-mRNA correlations are cancer-type-specific, the processes that are negatively correlated with tRFs and miRNAs are more general.

We then focused on the GO terms for Biological Processes (BP) that we found to be common to multiple cancer types (Supp. FIGS. S7A and S7B), grouped them into non-redundant clusters (FIG. 18D), and identified four main pathways: (a) Transcription, (b) Development and morphogenesis (abbreviated as "Development"), (c) Chromatin organization, and, (d) Cell adhesion and extracellular matrix organization (abbreviated as "Cell adhesion"). Notably, mRNAs from the "Transcription" and "Chromatin organization" pathways were negatively correlated predominantly with tRFs and exhibited these correlations across the vast majority of cancer types. On the other hand, mRNAs from the other two pathways ("Development" and "Cell adhesion") were negatively correlated with miRNAs, with tRFs or both (FIG. 18D).

Figure 5A:
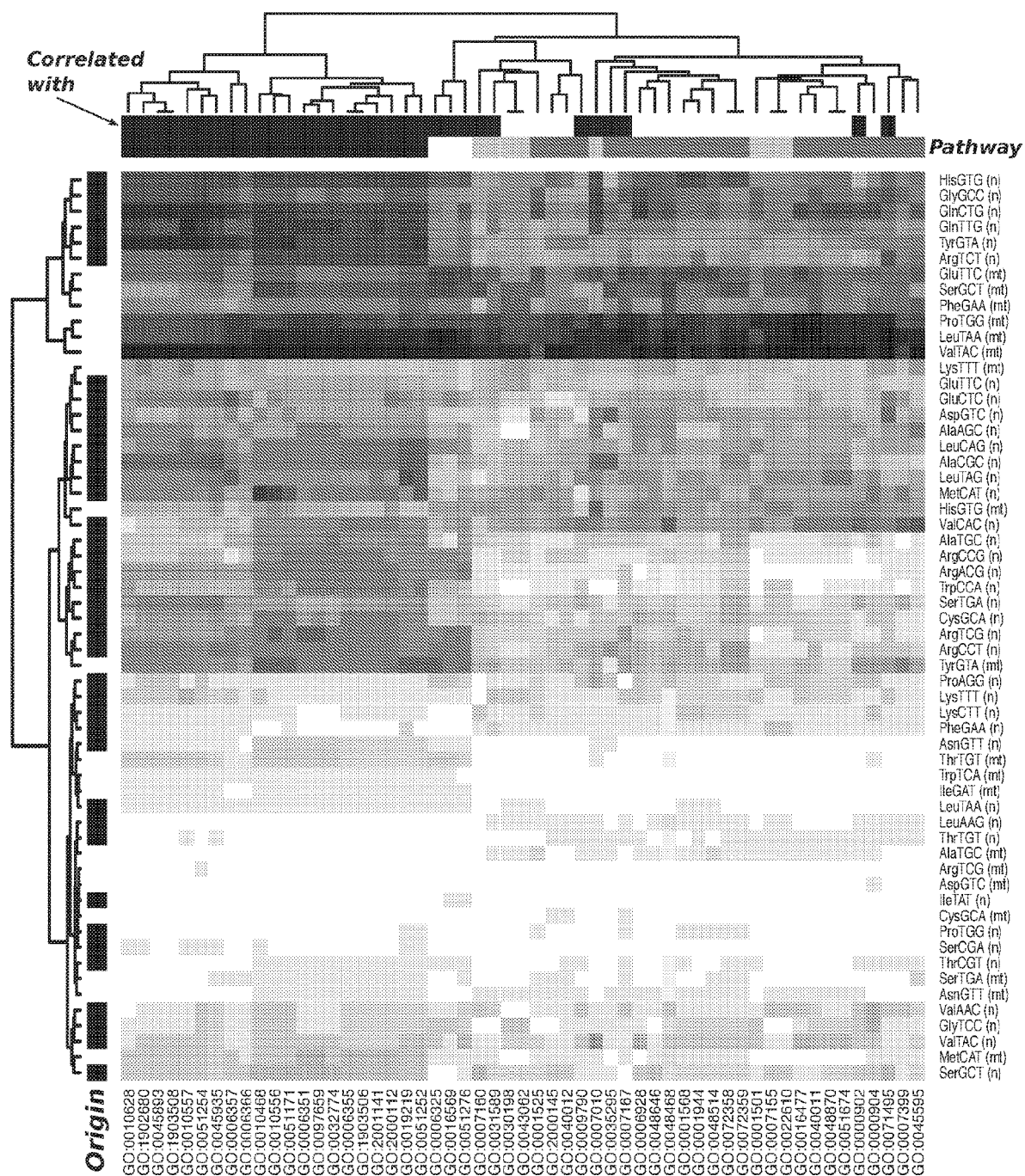
FIGS. 5A-5C Correlations, Compartments and Repeats. (A) Heatmap and hierarchical clustering (metric: Euclidean distance) depicting the fraction of the 32 cancer types in which the shown 58 isoacceptors (rows) are anti-correlated with the listed GO terms (columns). The descriptions for the shown GO terms appear in Supp. Table S6. The same isoacceptors correlated negatively with the same pathways, but not at the gene or tRF level across cancers (FIG. 14). (B) A map showing the localization of the protein products whose mRNAs have positive or negative statistically significant correlations with tRFs. For comparison purposes, we included the localization of the protein products whose mRNAs have positive or negative statistically significant correlations with miRNA isoforms (isomiRs), which we have discussed in previous work (66,71,72). The maps are shown separately for nuclear and MT tRFs and separately for positive and negative correlations. The size of the shown squares corresponds to the number of protein products that localize in the shown compartment. The color of the box represents enrichment (black; Z-score≥2) or depletion (light gray; Z-score≤−2) compared to the expected distribution. (C) Heatmap and hierarchical clustering (metric: Pearson correlation) showing the statistical significance (Z-score) of the enrichment or depletion of fragments from repeat categories in the genomic loci of mRNAs that are anti-correlated with tRFs. Enrichments and depletions are shown separately for the unspliced mRNA (panel A), in the intronic regions (panel B), or in the exonic regions (panel C) of the mRNAs that are positively or negatively correlated with tRFs in each cancer type. Panels B and C maintain the same order of cancers (rows) and repeat elements (columns) as they appear in the heatmap of panel A. The barplots to the right of the heatmaps show the number of cancer types in which each family is found enriched/depleted. A representative list of the tRF-mRNA pairs (both positively-correlated and negatively-correlated), as well as a representative list of the tRF-tRF pairs (both positively-correlated and negatively-correlated) for the case of breast cancer (BRCA) appears in Supp. Table S4. A complete list of all tRF-tRF and tRF-mRNA correlations (both positive and negative) for the remaining TCGA cancers can be generated as described below and as described under "Correlation Analyses" in the Methods section. The latter table also lists the complete list of tRF-tRF pairs (both positively-correlated and negatively-correlated), again separately for each cancer.
Figure 5A:
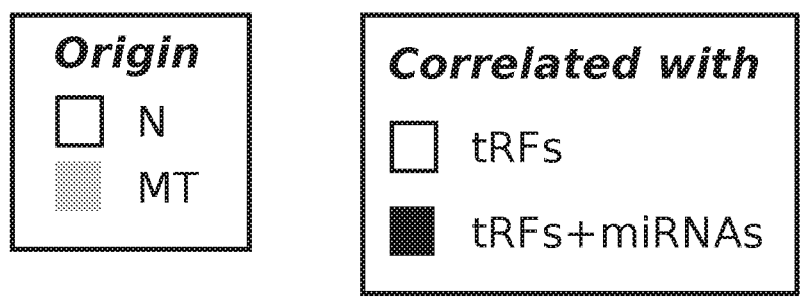
Figure 5A:
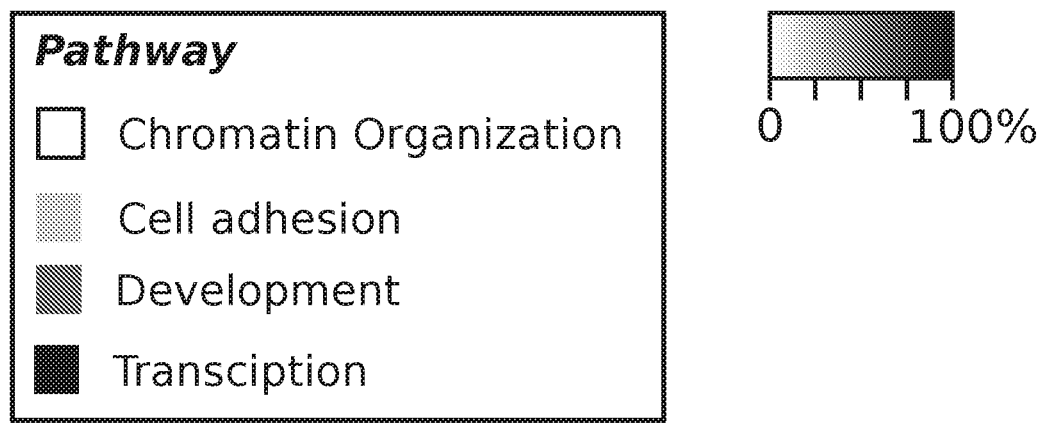

Having established the conserved relationship between these four pathways and the associated tRFs, we examined how often tRFs overlapping isodecoders of a specific isoacceptor are associated with mRNAs from the respective GO term. FIG. 5A shows in heatmap form the fraction of cancer types in which tRFs overlapping a shown isoacceptor are negatively correlated with mRNAs belonging to each pathway.

We see that most tRNA isoacceptors are linked with the same GO terms in many cancer types. The frequency of those correlations does not depend on the tRNA's genome of origin (mitochondrial vs. nuclear) or the encoded amino acid. We also observe that tRFs from several mitochondrial and nuclear isoacceptors are very often negatively correlated with almost all examined GO terms. The mitochondrial ValTAC, LeuTAA and ProTGG isoacceptors are negatively correlated with mRNAs from all shown GO categories (FIG. 5A) in nearly all cancer types: this is true even for pathways whose mRNAs do not have a previously reported mitochondrial link, e.g. "cell adhesion."

Collectively, the above results provide further support to the view that the tRF-mRNA anti-correlations are an integral component of the molecular physiology of cancer, and not random. In fact, the analysis shows that tRF-mRNA anti-correlations parallel miRNA-mRNA anti-correlations (FIG. 5A). It is important to note that the tRF-mRNA anti-correlations comprise tRFs from both the nucleus and the mitochondrion, which in turn indicates that the nuclear and MT genomes marshal the corresponding pathways in a cooperative manner. We will return to this point below and discuss five specific examples after our presentation of MINTbase.

System-Level Networks: tRFs are Linked to the Cellular Destinations of Proteins Encoded by Negatively-Correlated mRNAs Spurred by the numerous statistically significant links between tRFs and miRNAs and pathways, we sought to examine one more facet of these associations, namely the cellular localization of the protein products of the corresponding mRNAs. For this analysis, we treated nuclear tRFs separately from mitochondrial tRFs. We used information from the UniProt database to distinguish among seven destinations: nucleus, cytoplasm, endoplasmic reticulum (ER) or Golgi, mitochondrion, cell membrane, secreted, and "other" organelles (e.g. vesicles, endosomes, etc.). Also, we distinguished between nuclear tRFs and MT tRFs. For comparison purposes, we repeated the cellular destination analysis for the mRNAs in isomiR-mRNA correlations. Note that the protein localization analysis is carried out at the level of isomiRs for more granularity. For both tRFs and isomiRs, we analyzed positive and negative correlations separately.

Figure 5B:
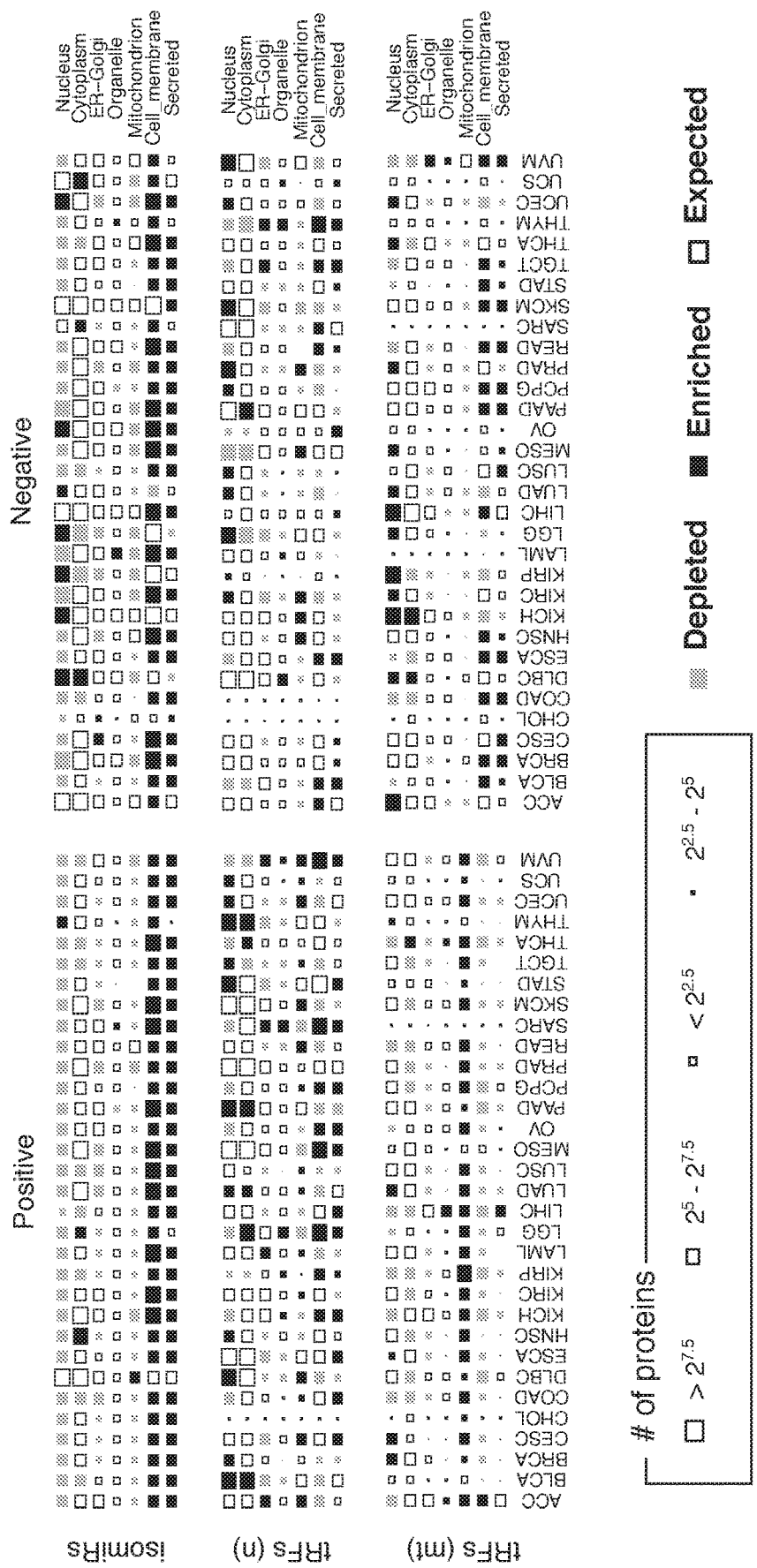

The top row of FIG. 5B shows the results for isomiRs. As can be seen, there are many isomiR-mRNA correlations, as shown by the size of the squares. There is a bimodal behavior with regard to the possible protein destinations and is independent of the correlation sign. In particular, the isomiR-mRNA correlations are enriched (black-filled boxes) in mRNAs whose protein products are destined for the 'cell-membrane' or are 'secreted.' On the other hand, the correlations are depleted (gray-filled boxes) in mRNAs whose protein products are destined for the nucleus. Note that for negatively-correlated mRNAs, the enrichment or depletion of the nucleus among possible destinations exhibits more variability. DLBC, kidney chromophobe (KICH), and KIRP stand out due to their more complicated patterns.

We repeated the same analysis for nuclearly-encoded (FIG. 5B, middle row) and MT-encoded tRFs (FIG. 5B, bottom row), respectively. The dependence on cancer type is more pronounced for tRFs than is for isomiRs. Additionally, the cellular destination pattern is not bimodal anymore. In fact, the proteins produced from mRNAs in tRF-mRNA correlations can reach different combination of the considered destinations in different cancer types. The MT tRFs exhibit a consistent and interesting behavior in almost all cancer types. Specifically, the positive (but not the negative) MT tRF-mRNA correlations, are enriched in mRNAs whose protein products are destined for the MT. On the other hand, the negative (but not the positive) MT tRF-mRNA correlations, are enriched in mRNAs whose protein products either localize to the cell membrane or are secreted. It is worth briefly discussing the results pertaining to the two melanomas, uveal melanoma (UVM) and skin cutaneous melanoma (SKCM). In UVM, nuclear and cytoplasmic proteins are depleted in the set of mRNAs that are positively correlated with nuclear tRFs. However, the mRNAs encoding proteins localizing to these compartments are higher in number and/or enriched in the negative correlations with tRFs. This opposite behavior is also evident for the rest of the compartments in UVM. SKCM provides an example wherein the nuclear and MT tRFs behave differently. In this cancer type, the correlations of MT tRFs with mRNAs are enriched in mRNAs producing proteins that are destined for the cell membrane or are secreted. On the other hand, the correlations of nuclear tRFs with mRNAs are enriched in mRNAs producing proteins that localize to the nucleus.

These results provide strong support to the view that the observed tRF-mRNA pairs are not accidental. In fact, it is reasonable to posit possible synergistic activities between isomiRs and tRFs. Equally importantly, the derived associations suggest that information is transferred across compartments in a manner that is not currently understood.

System-Level Networks: The Genomic Span of mRNAs that are Positively- or Negatively-Correlated with tRFs are Selectively Enriched/Depleted in Specific Repeat Elements In light of our earlier work (30-32) and the more recent findings in mouse that connect fragments from tRNA$^{GlyGCC}$ with the MERVL repeat and mRNAs (15), we hypothesized that a link between tRFs and repeat elements exists in human cancers. Separately for each cancer type, we sought to determine whether the corresponding genomic sequences are enriched or depleted in repeat elements, when the orientation of the repeat is sense to the gene or antisense to it. We examined three collections of sequences: the full (unspliced) genomic span of the corresponding mRNAs; the union of their introns; and, the union of their exons. More specifically, for each of the three collections of sequences, separately for sense and antisense, and for each RepeatMasker (33) category, we determined what fraction of the sequence collection at hand corresponds to embedded instances of the repeat family being considered. For each calculated fraction, we examined whether it is significantly enriched or depleted compared to chance (see Methods).

Figure 5C:
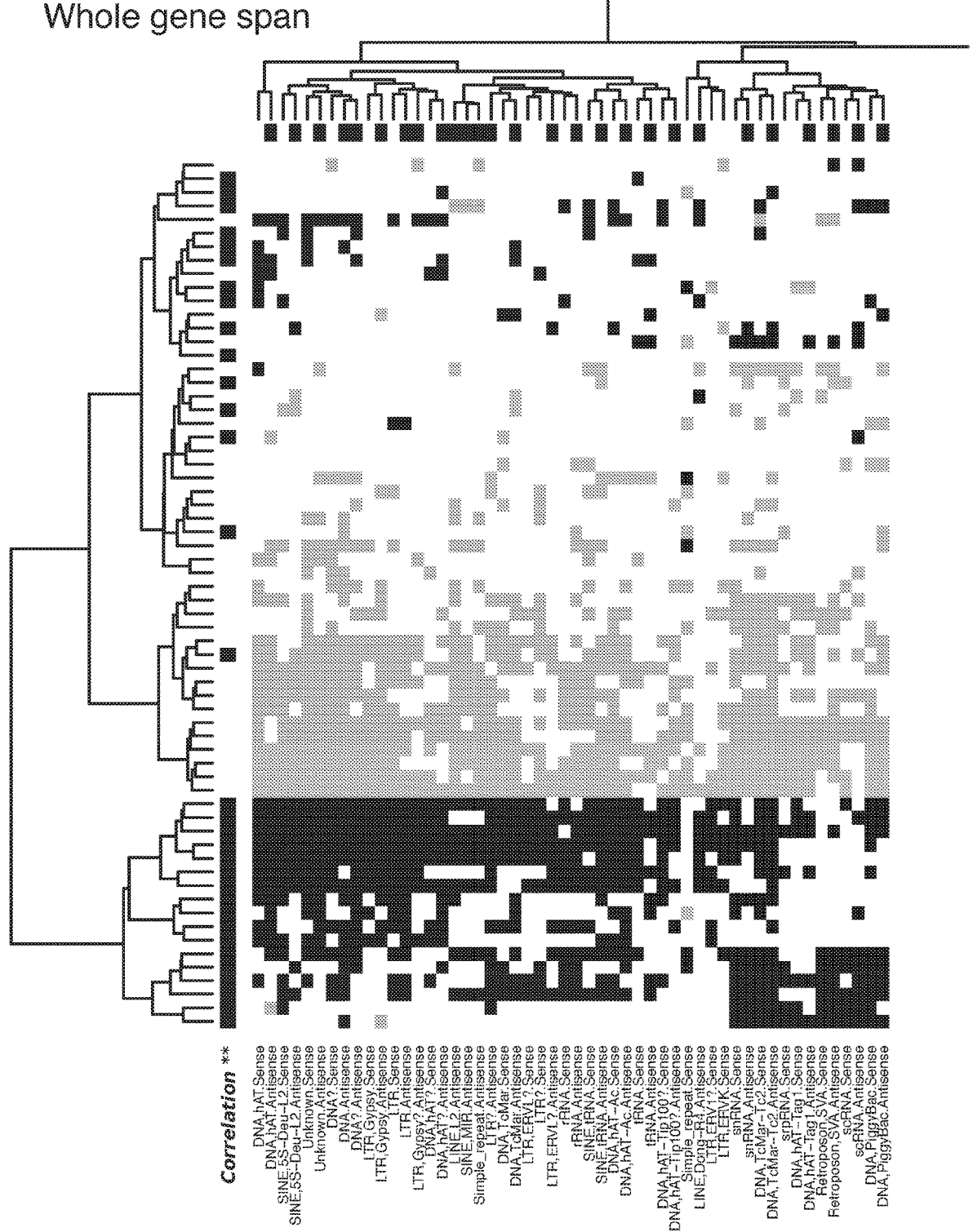
Figure 5C:
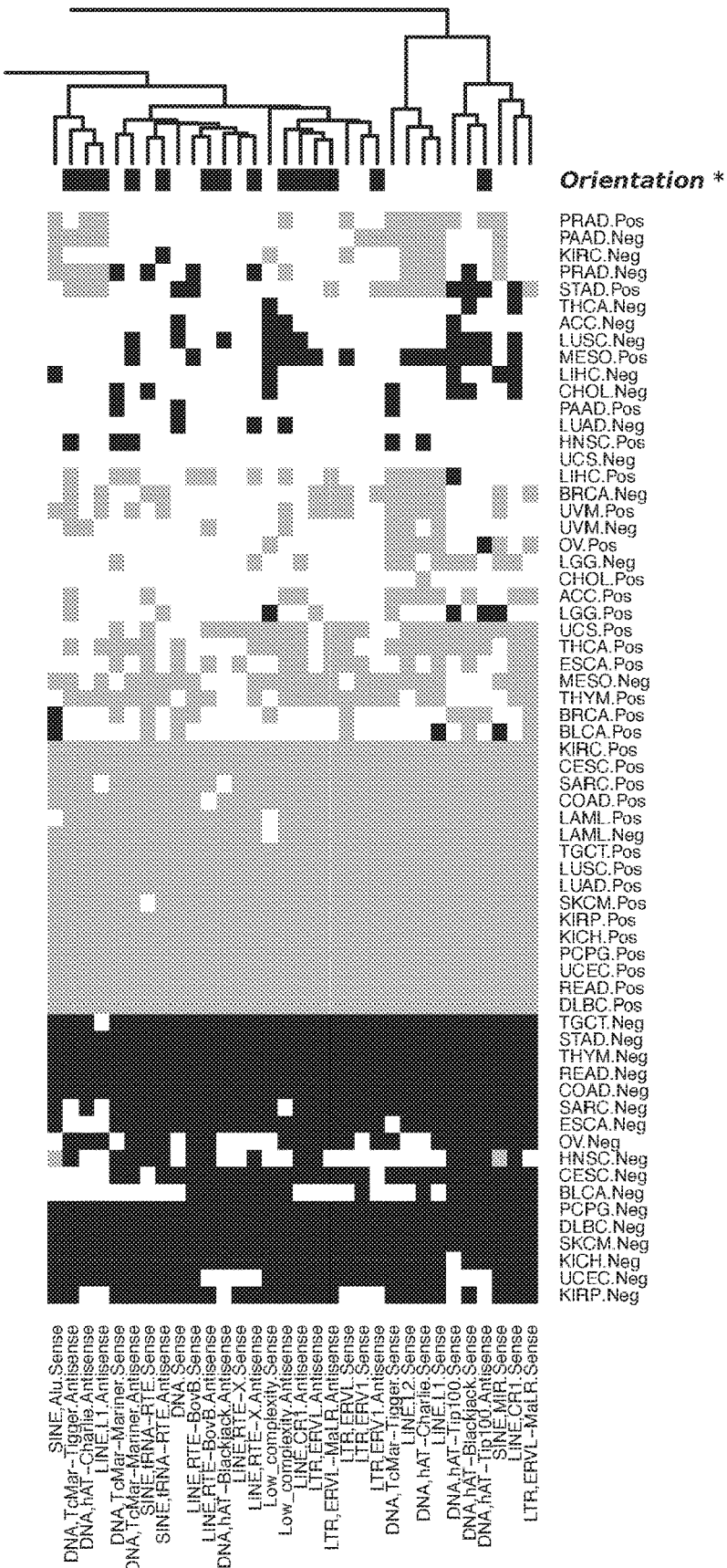
Figure 5C:
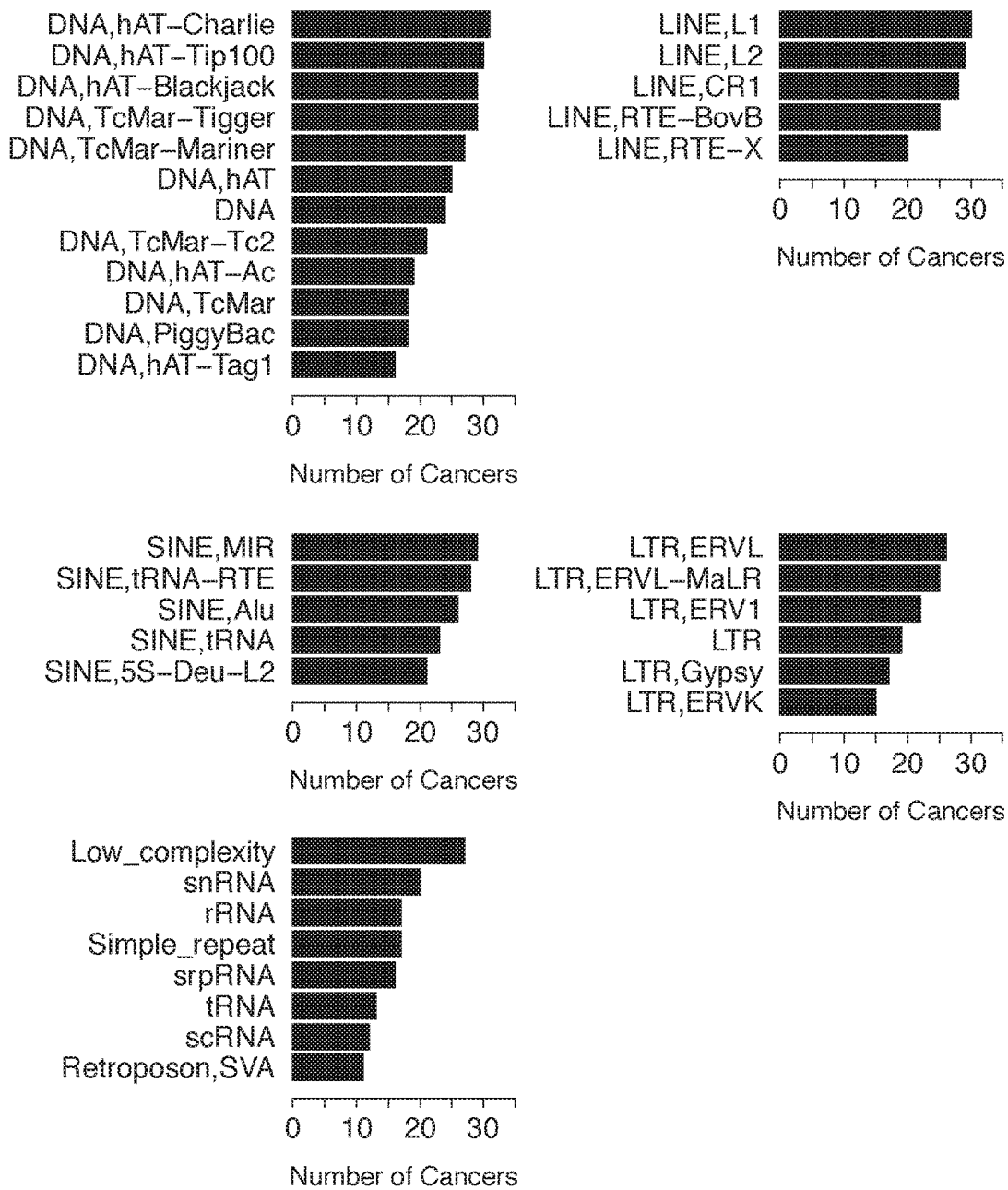
Figure 5C:
Figure 5C:
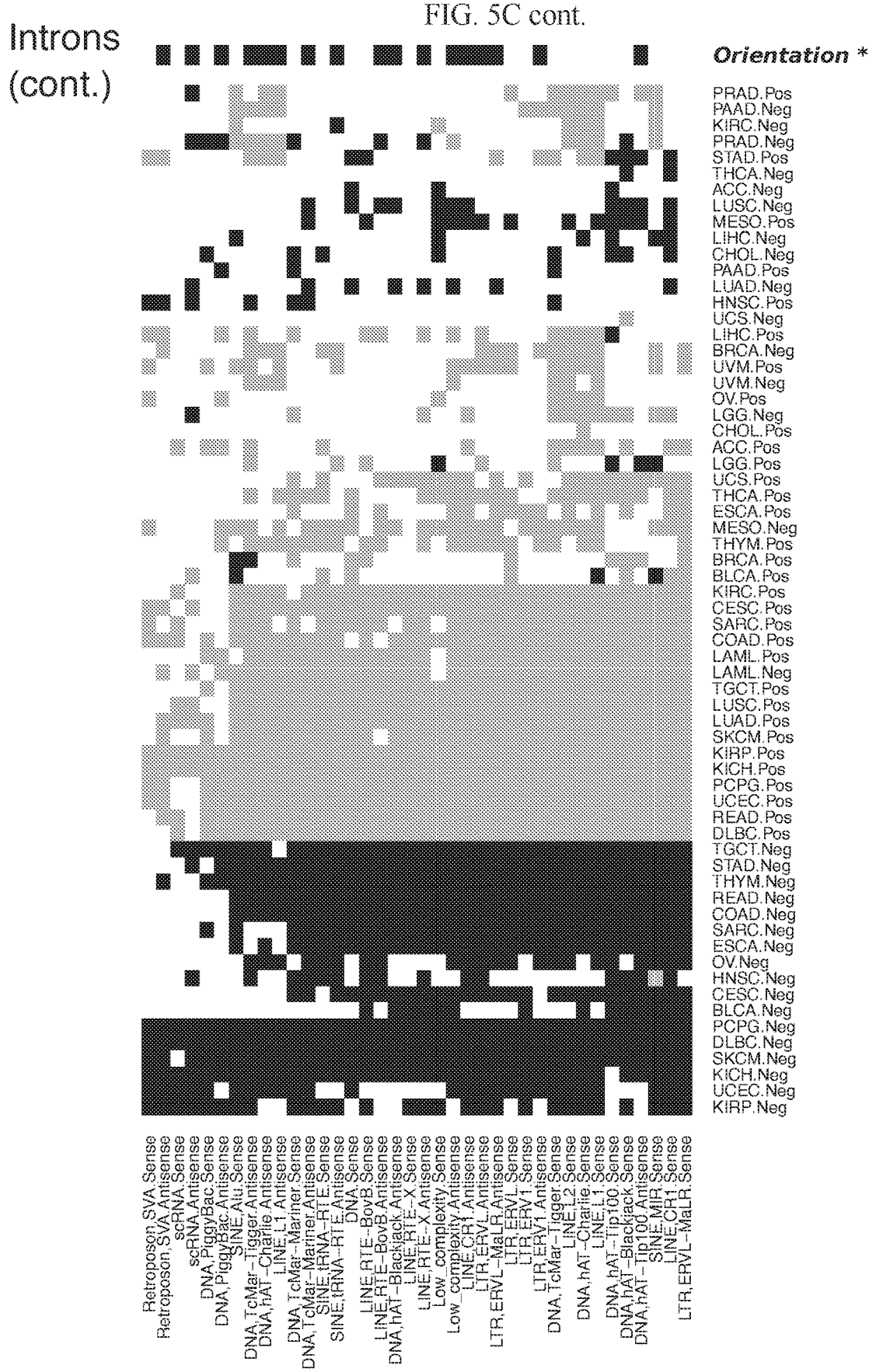
Figure 5C:
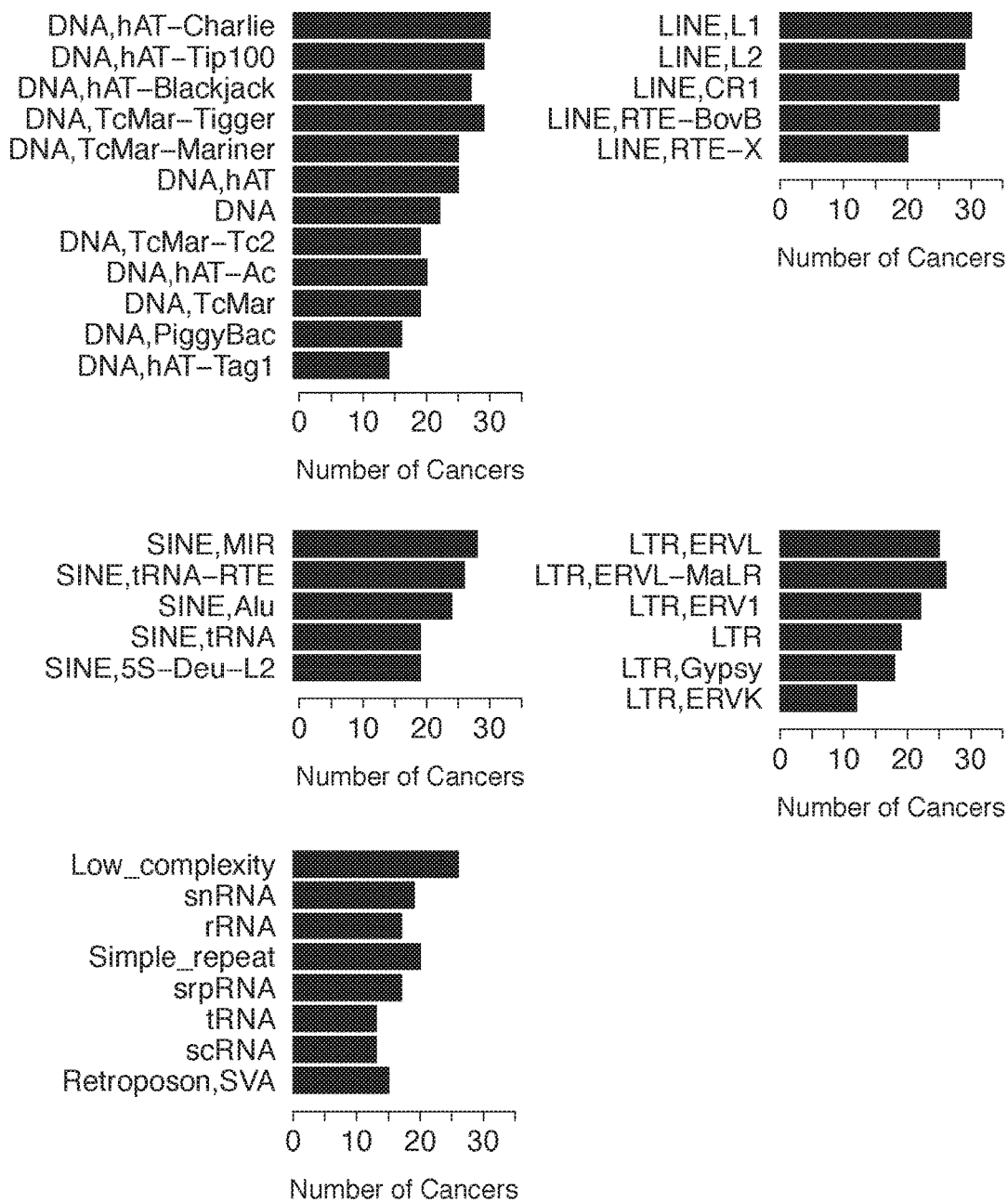
Figure 5C:
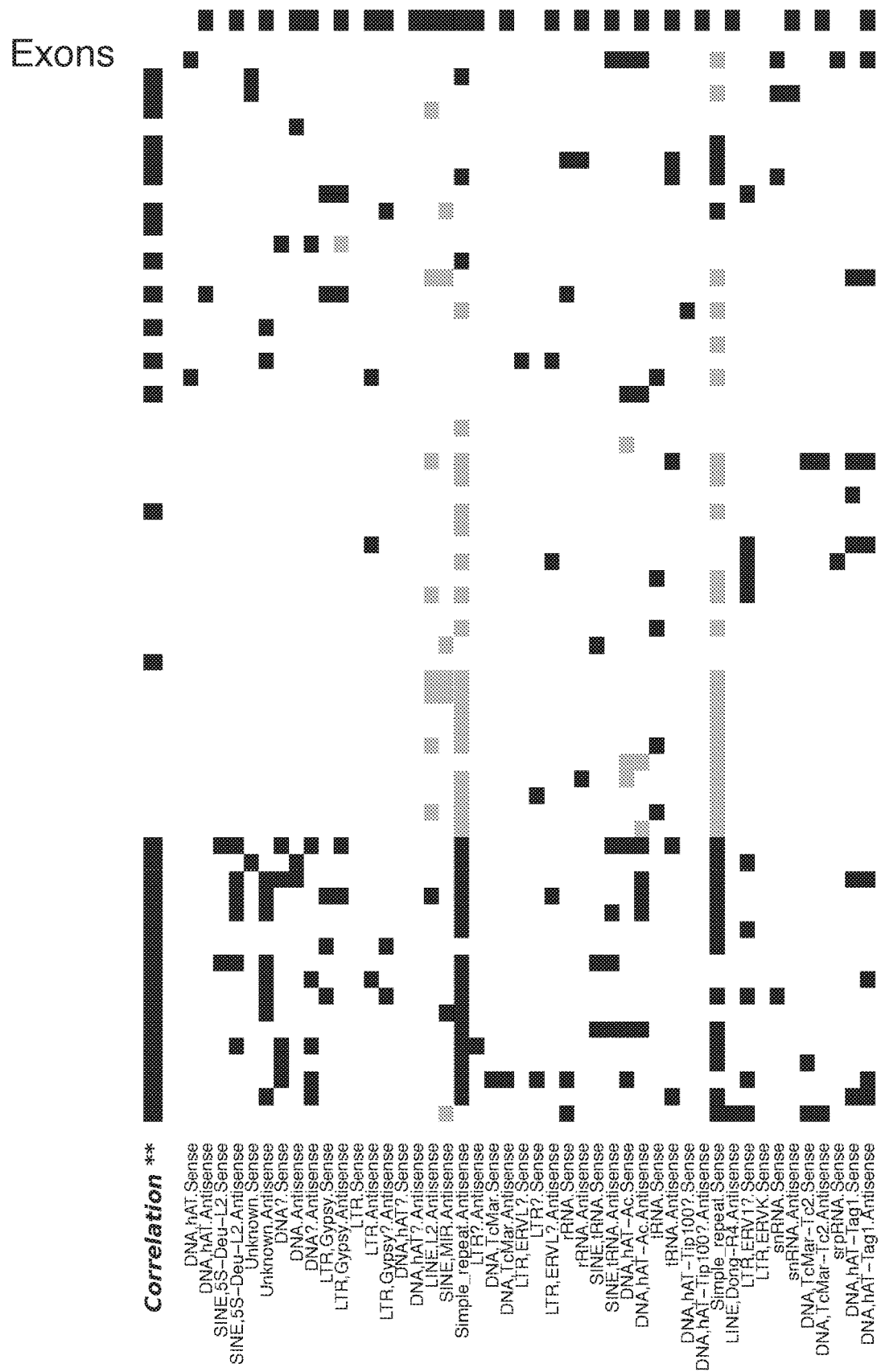
Figure 5C:
Figure 5C:
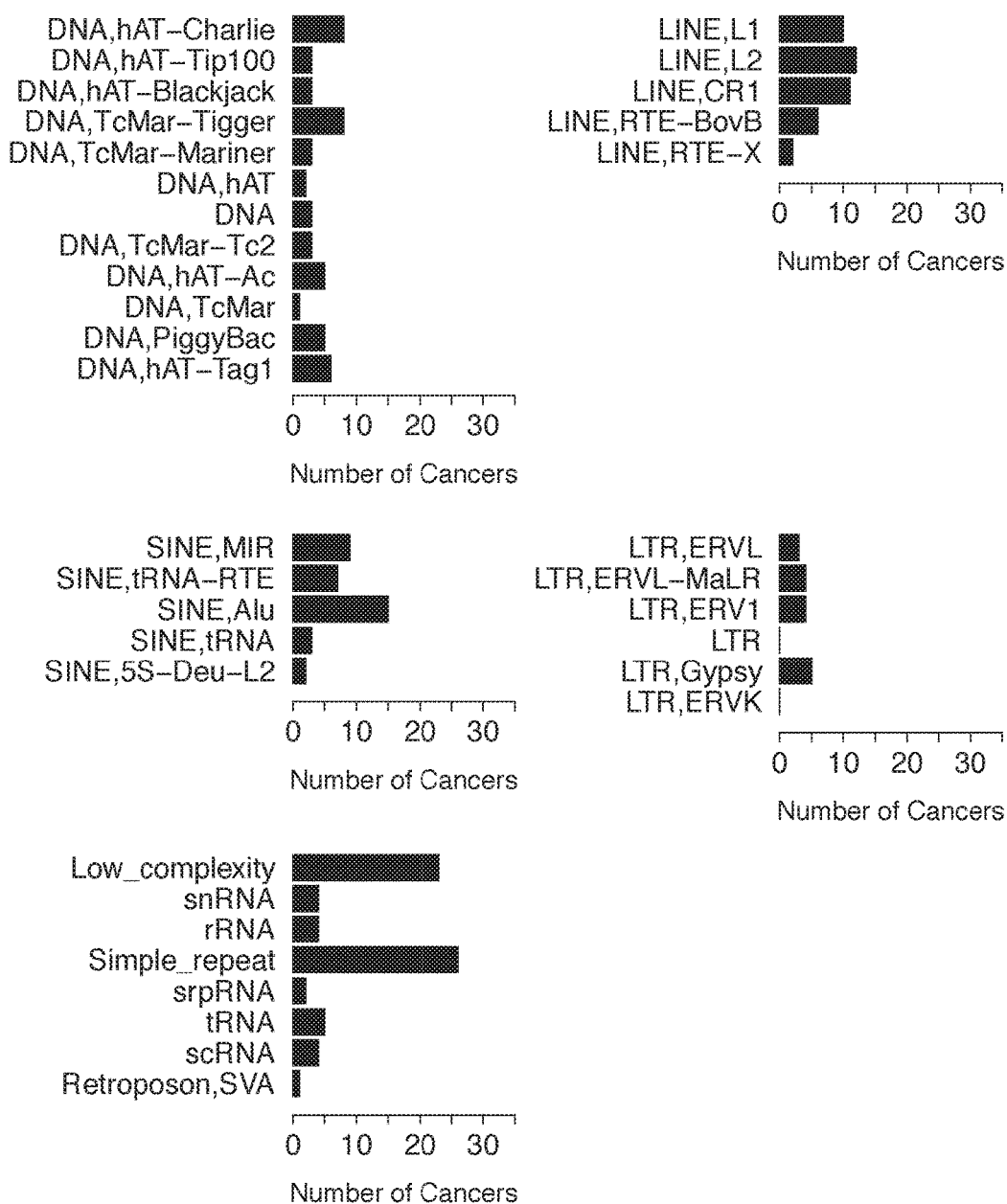

Panel A of FIG. 5C shows a heatmap of the generated z-scores, for all 32 cancer types, for sense and antisense instances of all repeat categories, and, separately for mRNAs that are positively correlated or negatively correlated with tRFs. The very high or very low z-scores strongly argue that these findings are not random. For clarity, only z-scores $\leq-2$ or $\geq+2$ are rendered as light gray and black respectively. As panel A of FIG. 5C makes apparent, in all 32 cancer types, the genomic spans of mRNAs that are either positively or negatively correlated with tRFs exhibit significant enrichment or depletion in repeat elements or their reverse complements.

Our previous studies showed that the distribution of repeats in introns and exons is not random and that repeats in intronic regions appear to reflect functional conservation in the absence of sequence conservation. With that in mind, we repeated the above calculations by separating each unspliced mRNA into its intronic and exonic components shown in panels B and C respectively of FIG. 5C. Interestingly, we find that the introns alone effectively reproduce the above results. Thus, the intronic sequences are responsible for the majority of the observed signal. When we consider only the exonic regions, a lot of the signal effectively disappears (panel C of FIG. 5C).

We also inverted our vantage point. For each RepeatMasker family in turn, we counted the number of cancers in which it was enriched. We did this for the unspliced mRNAs, the intronic regions, and the exonic regions. We find that different combinations of RepeatMasker families are enriched in different cancers: the enriched families include DNA transposons, long interspersed elements (LINE), short interspersed elements (SINE), long terminal repeats (LTR), and other. As can be seen from panels A and B (right column) of FIG. 5C, DNA transposons, LINEs, and the ERVL/ERV1 sub-categories of LTRs are prevalent exclusively in the introns of nearly all of the studied cancers. On the other hand, the ALU sub-category of SINEs, is enriched (in sense) in the exons of one half of the studied cancer types. Considering that many tRFs have repeated genomic instances, it is possible that the correlations we observe are the result of ambiguous tRFs whose multiple genomic instances outside of tRNA space overlap with mRNAs. We examined all possible genomic origins of such tRFs and could not find support for this hypothesis (Methods and FIG. 20).

These results provide additional independent support to our earlier findings that the distribution of repeating sequences in the human genome is not arbitrary (30-32,34). Moreover, the uncovered associations between tRFs and repeat elements strongly implicate the latter in the layer of tRF-mediated regulation of expression in nearly all 32 cancer types.

System-Level Networks: Intra-Cancer Networks of tRFs can be Modulated by a Patient's Sex or a Patient's Race We hypothesized that tRF profiles differ across sex or race boundaries and investigated the matter in two cancer types for which sex-dependent and race-dependent disparities of genetic origin, respectively, have been documented in the literature. Spurring this hypothesis is the above finding that tRFs are strongly associated with tRFs, mRNAs, and proteins that localize to specific cellular compartments.

In the below analysis, we limit ourselves to three of the 32 cancers types contained in TCGA: lung adenocarcinoma (LUAD), the subtype of breast cancer (BRCA) known as "triple negative" (TNBC), and bladder cancer (BLCA). Additional in-depth studies that escape the scope of this presentation will be necessary in order to examine whether the analysis of RNA-seq datasets from other TCGA cancer types supports similar findings. We stress here that mining RNA-seq data is distinctly unlike the task of detecting, e.g., race-based somatic mutations, for which TCGA is well known to be under-powered (35). LUAD and TNBC are examined immediately below from the standpoint of correlations among tRFs. BLCA is examined later in the presentation from the standpoint of sex-dependent tRF-mRNA correlations abundances.

The first of the three cancer types is LUAD. In lung cancer, both sex and race disparities are known to exist. A portion of these disparities can be attributed to differences in the stage and degree of adoption of tobacco smoking (36-41). However, age-adjusted lung cancer incidence rate is higher among black men compared to white. Also, it is roughly equal between black and white women, even though black men and black women have a lower overall exposure to cigarette smoke. These observations suggest that sex and race contribute to these differences (42). Below, we examine only the sex-dependence aspect of LUAD.

The second cancer type that we examine is TNBC. TNBC represents approximately 15-20% of the BRCA cases (43) and is the most aggressive BRCA subtype, characterized by poor prognosis. In the absence of an expressed hormone receptor, chemotherapy continues to remain the only systemic option for TNBC patients (44). TNBC is twice as frequent among B/Aa premenopausal women compared to Wh women (44-49). In what follows, we examine the race-dependence aspect of TNBC.

In each case, we formed networks of tRFs whose expression values were statistically significantly correlated: we only kept relationships with a Spearman correlation $\geq 0.33$ or $\leq -0.33$ and a matching false discovery rate (FDR)$\leq 0.05$. Then, we examined whether and how these networks changed between males and females in LUAD and between White and Black/African American patients with TNBC.

Figure 6A:
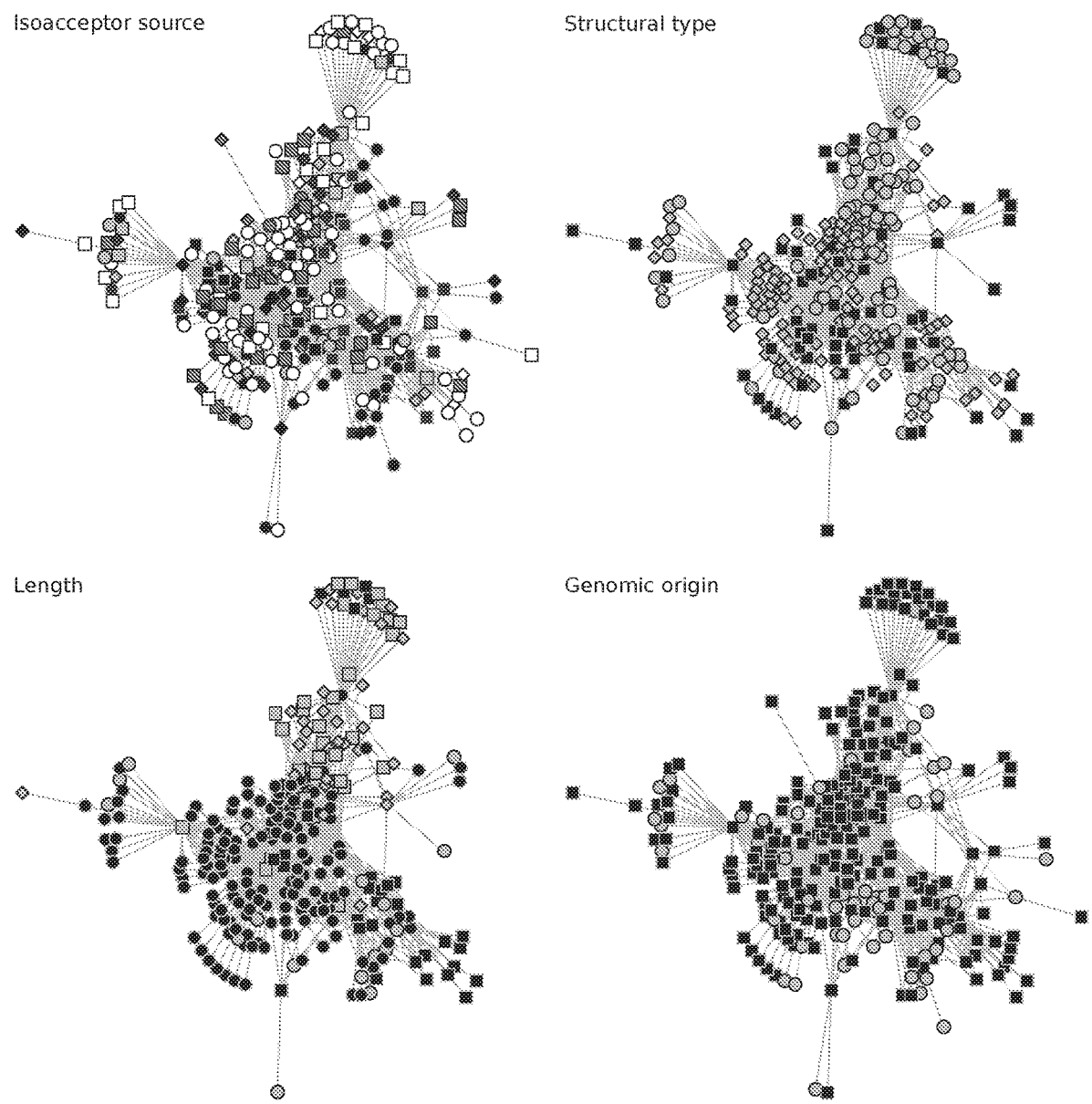
FIG. 6A-E tRF correlations in patients of different sex. Example showing the dependence of the tRF profiles on the sex of patients with lung adenocarcinoma. Shown are the networks of tRF-tRF correlations that are supported LUAD samples from TCGA that belong to either men or women (A), the sub-network of correlations that are present exclusively in samples from male LUAD patients (B), the sub-network of correlations that are present exclusively in samples from female LUAD patients (C), and, finally, the sub-network of correlations that are present in LUAD patients of both sexes (D). Various combinations of shapes and fills/shading capture the source tRNA isoacceptor, the tRFs' structural category, the tRFs' length, and the tRFs' genomic origin (nuclear or MT). Edges between nodes correspond to a Spearman correlation ≤−0.5 (negative correlations) and have an associated FDR≤0.01.
Figure 6B:
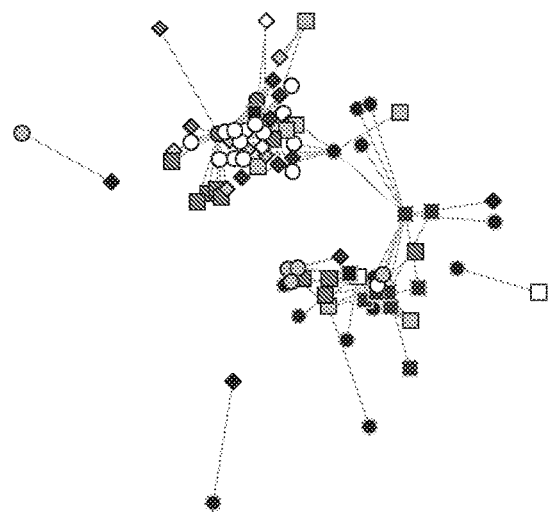
Figure 6B:
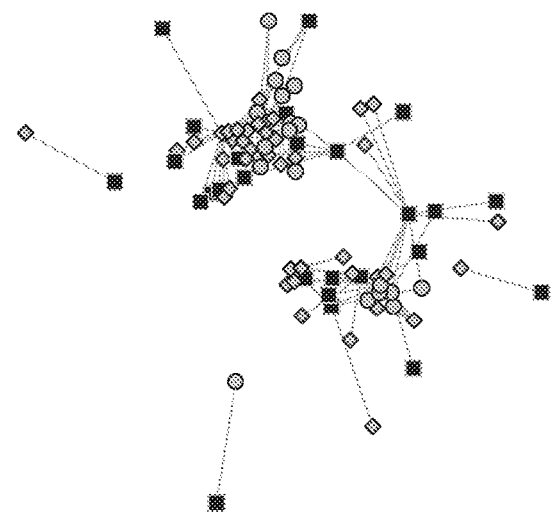
Figure 6B:
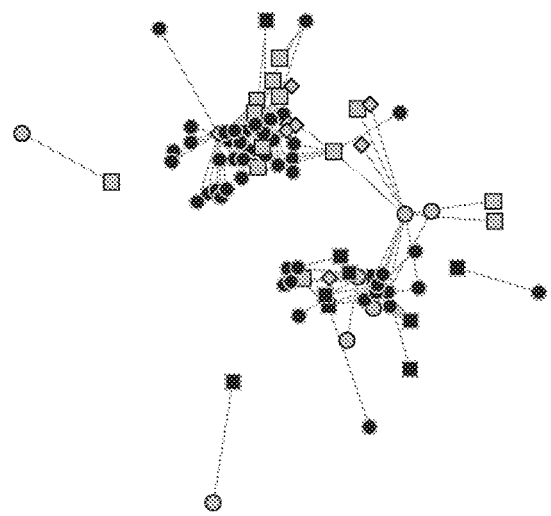
Figure 6B:
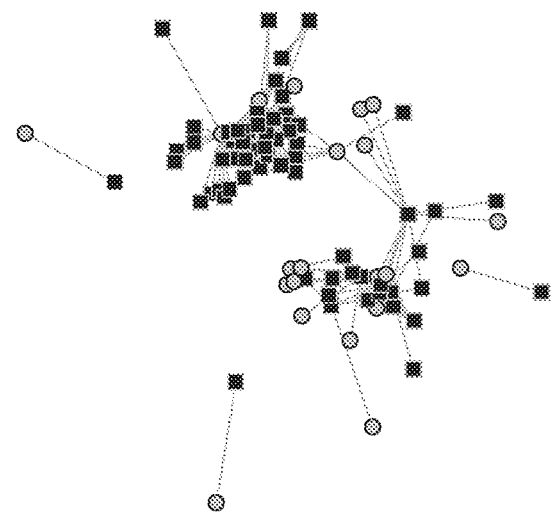
Figure 6C:
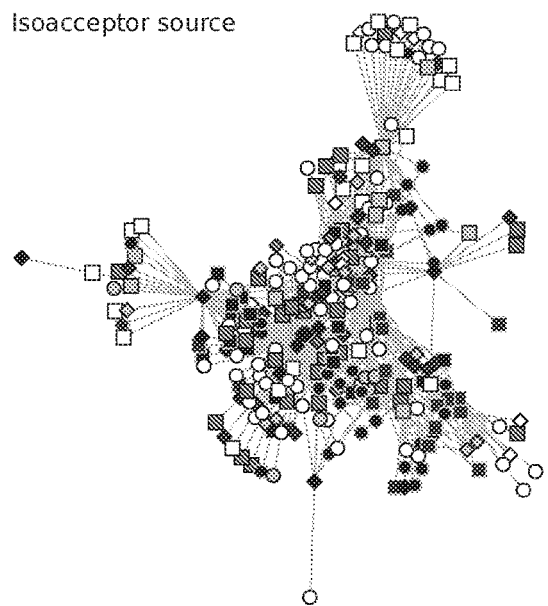
Figure 6C:
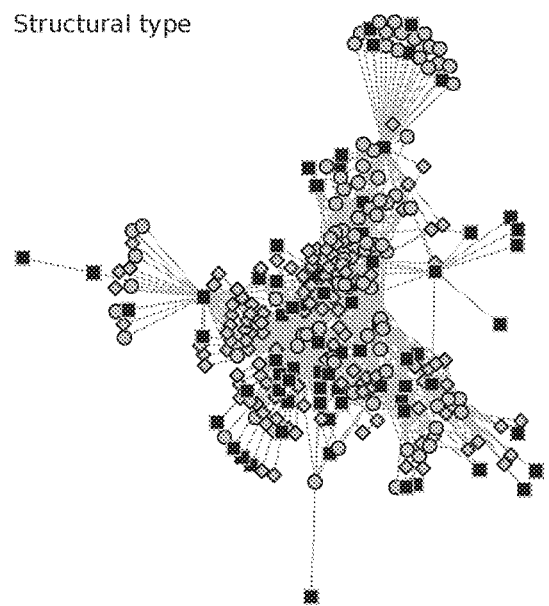
Figure 6C:
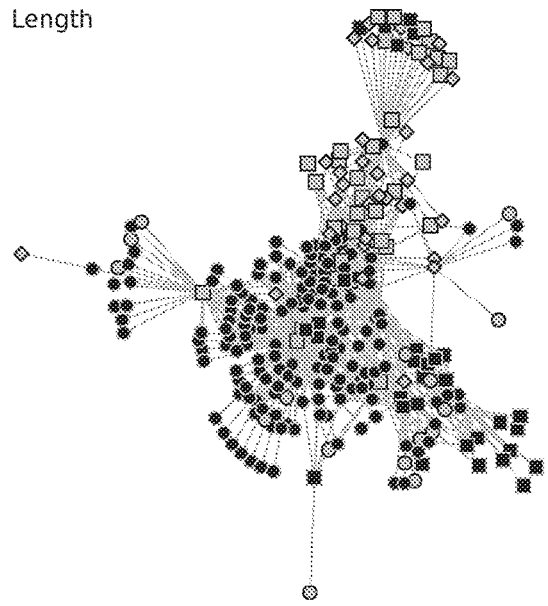
Figure 6C:
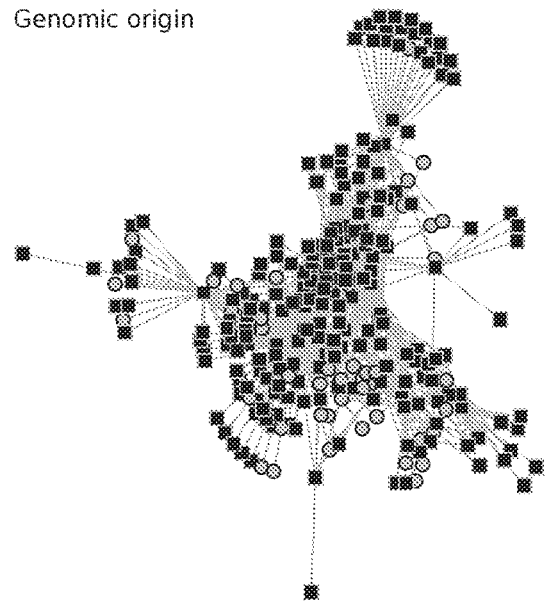
Figure 6D:
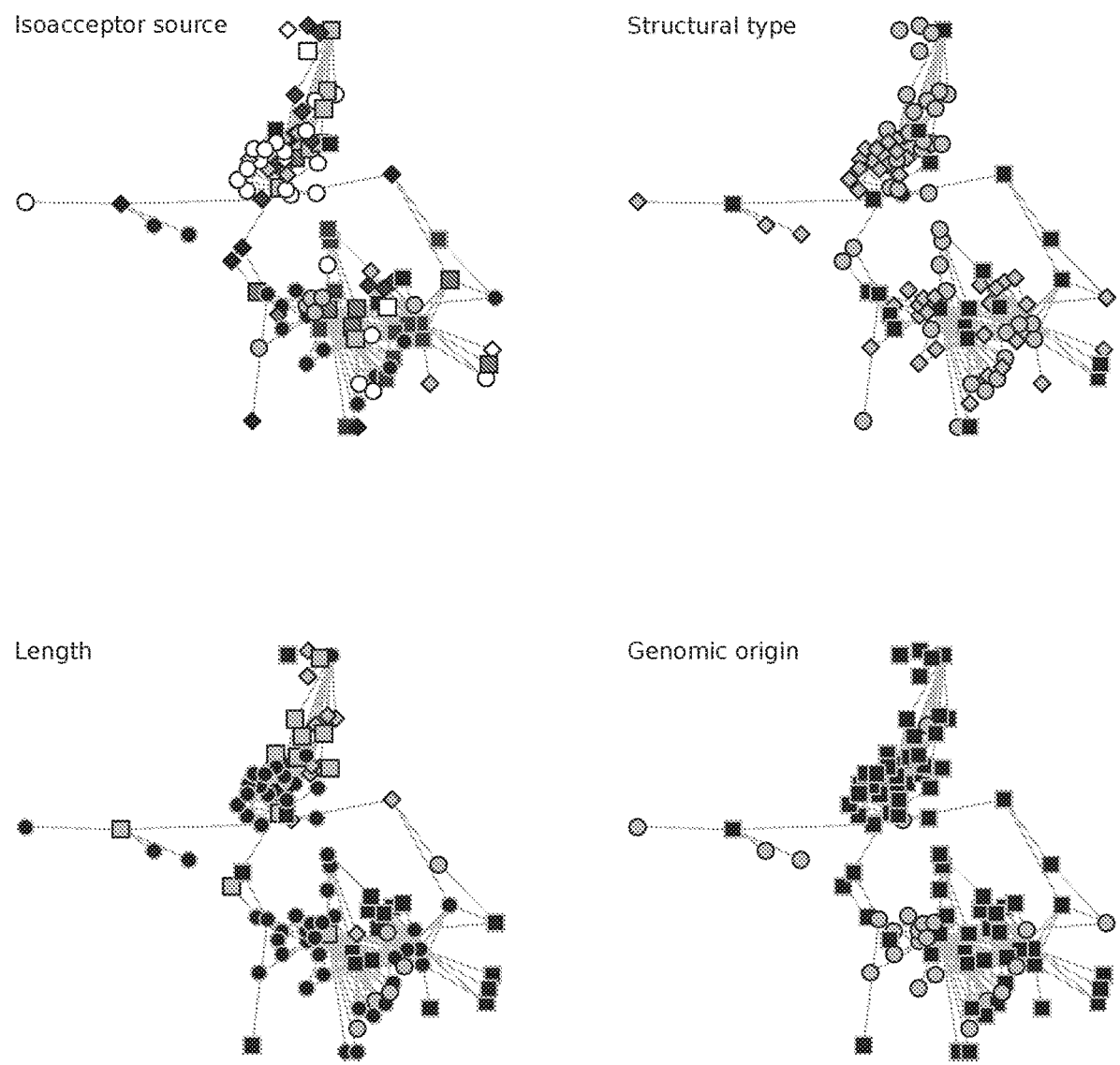
Figure 6E:
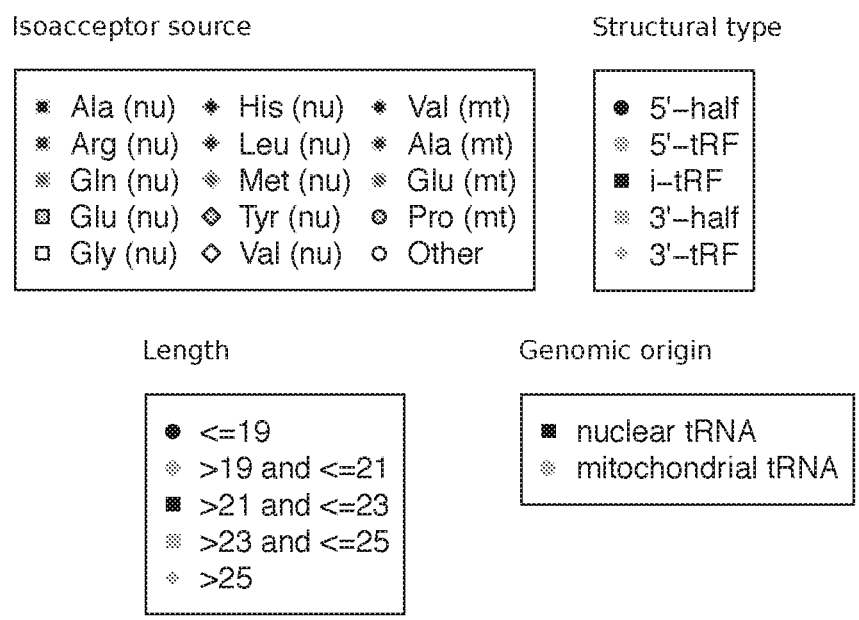

Case: LUAD. We analyzed the lung adenocarcinoma samples from TCGA separately for male and for female patients. FIG. 6A shows the network of negatively correlated tRF pairs that satisfy the correlation value and FDR thresholds mentioned above and are supported by the LUAD samples in TCGA that belong to either male or female patients. The networks are further encoded based on source isoacceptor, structural category of tRF, tRF length, and the tRFs' genome of origin. FIG. 6B shows the subset of edges and vertices that correspond to tRF-tRF correlations that are exclusive to male LUAD patients. FIG. 6C shows the subset of edges and vertices that correspond to tRF-tRF correlations that are exclusive to female LUAD patients. FIG. 6D shows the subset of edges and vertices that correspond to tRF-tRF correlations that are present in both male and female LUAD patients. As can be seen, female LUAD patients exhibit more and more-widespread anti-correlations compared to male patients.

Figure 19:
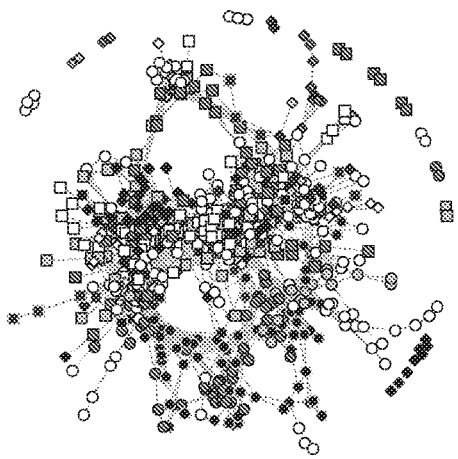
FIG. 19 tRF correlations in TNBC patients of different race. Example of race dependence of tRF correlations in triple negative breast cancer. Shown are the networks of tRF-tRF correlations that are supported by all TNBC samples from TCGA, the sub-network of correlations that are present exclusively in samples from Wh TNBC patients, the sub-network of correlations that are present exclusively in samples from B/Aa TNBC patients, and, finally, the sub-network of correlations that are present in TNBC patients of both races. From left to right, the networks are color-coded by source tRNA, structural category, length, and nuclear/MT origin. Edges between nodes correspond to a Spearman correlation ≥0.5 (positive correlations) and have an associated FDR≤0.01. See also text.
Figure 19:
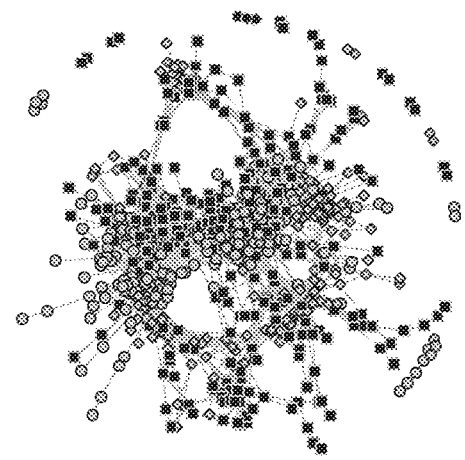
Figure 19:
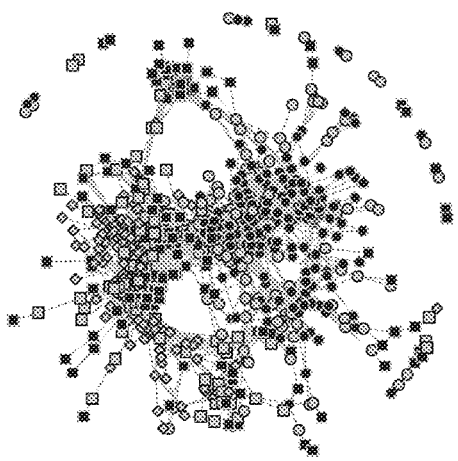
Figure 19:
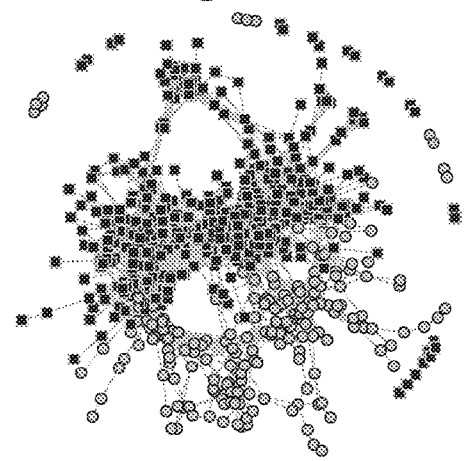
Figure 19:
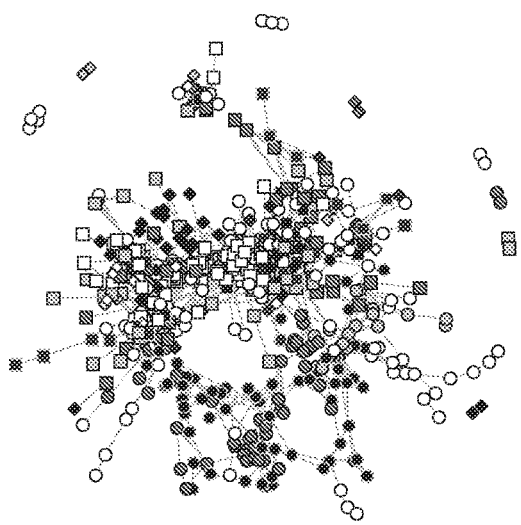
Figure 19:
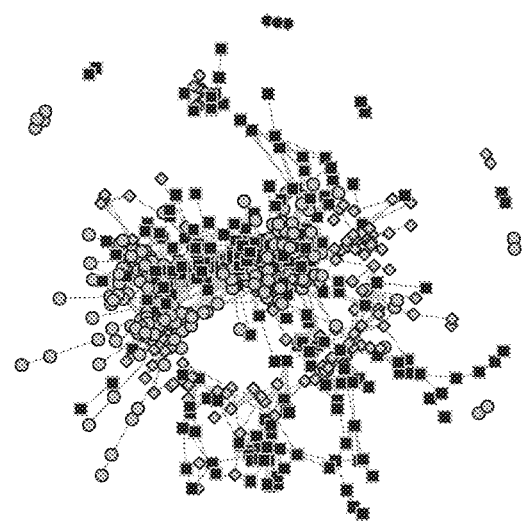
Figure 19:
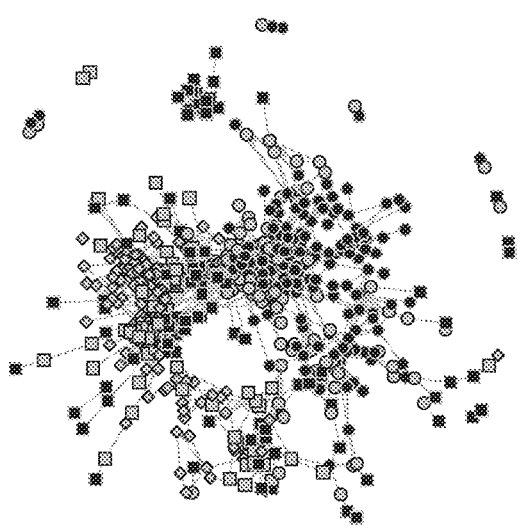
Figure 19:
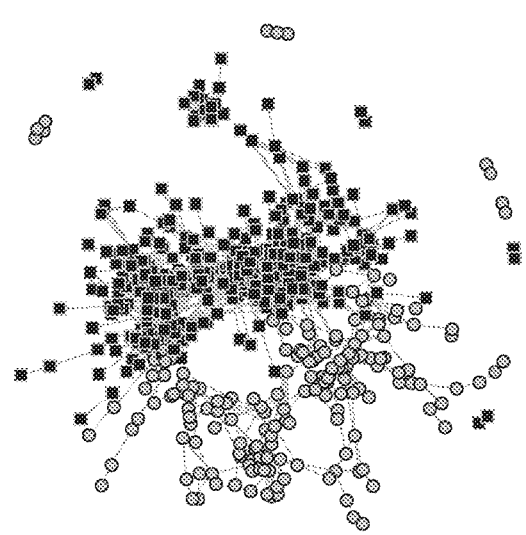
Figure 19:
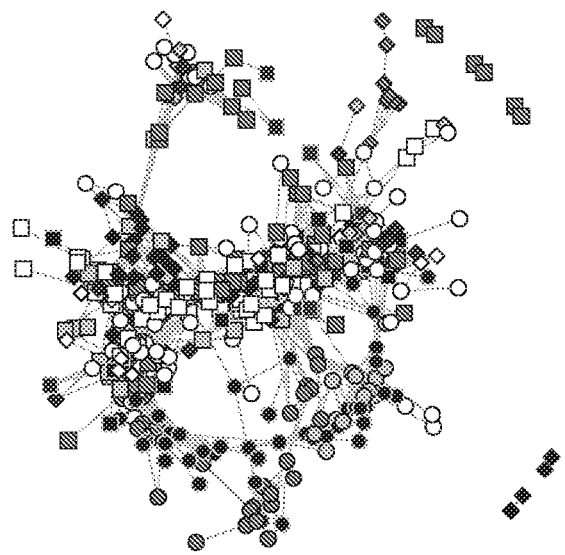
Figure 19:
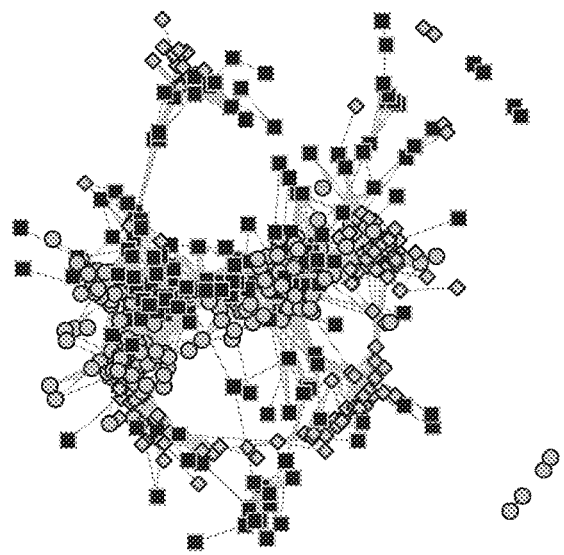
Figure 19:
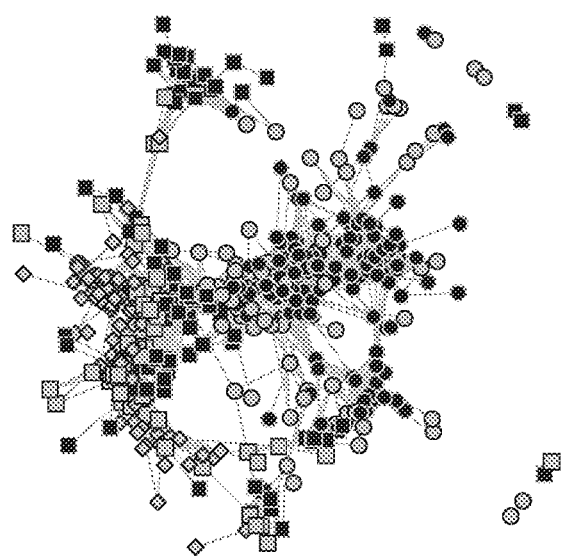
Figure 19:
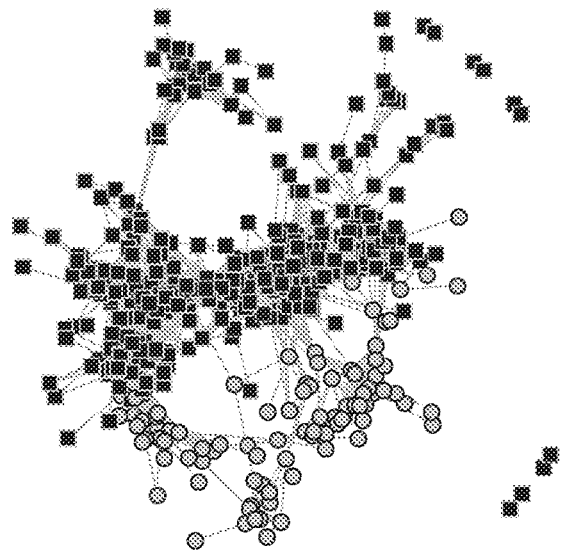
Figure 19:
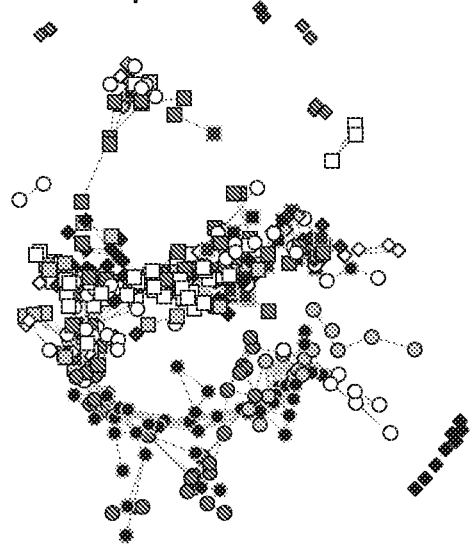
Figure 19:
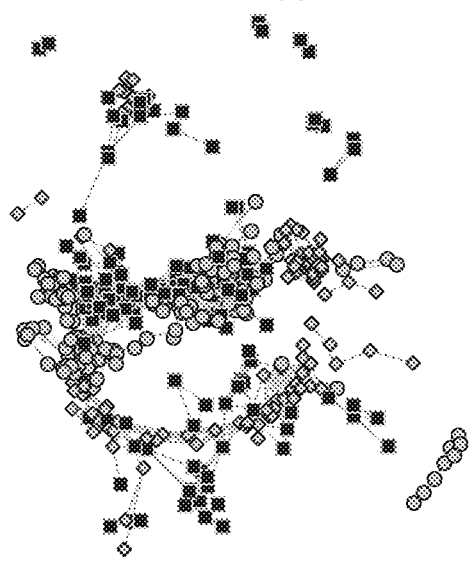
Figure 19:
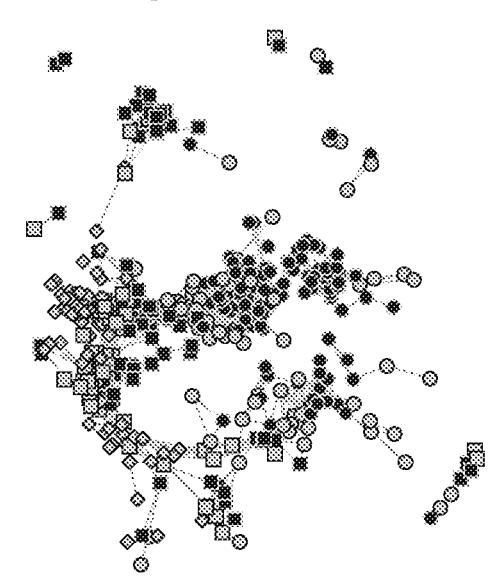
Figure 19:
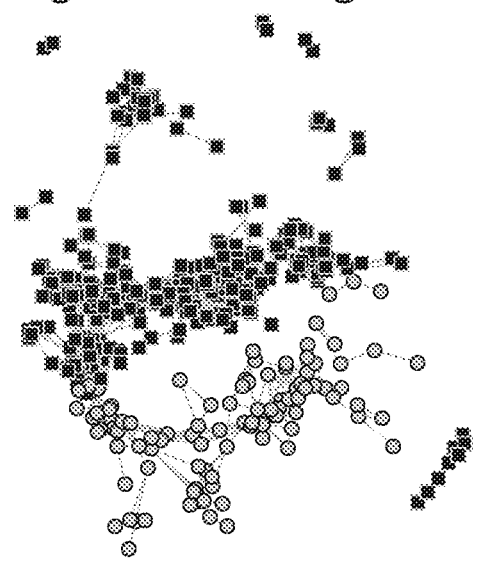

Case: TNBC. We analyzed the TNBC samples from TCGA and created analogous networks. Here, it is the networks of positively-correlated tRF pairs that show characteristic differences between White (Wh) and Black/African American (B/Aa) patients with TNBC (see "Nomenclature/Notation" in Methods). FIG. 19 shows the network of tRF-tRF pairs for all TNBC patients, the subset of the network that is present only in Wh TNBC patients, only in B/Aa TNBC patients, and, in both Wh and B/Aa patients. As in the case of LUAD, there are evident differences in the networks of correlations that are present in the Wh and B/Aa TNBC patients, respectively.

The Discovered TCGA tRFs can be Studied Using a Newly-Added MINTbase Module

We recently reported the development of MINTbase, a framework for storing and studying tRNA fragments 22. MINTbase is both a web-based content repository and a tool for the interactive study of tRFs. Originally, we populated MINTbase with 7,129 unique and statistically significant tRFs that resulted from our analyses of 832 public datasets (4,8,9,22).

We have now extended MINTbase (version 2.0) to include the tRFs that we generated in our analyses of TCGA. With the addition of the tRFs from 32 TCGA cancer types, MINTbase now comprises information about the location, normalized abundances, and expression patterns of 26,531 distinct tRFs compiled by mining a total of 11,719 public datasets from TCGA and elsewhere.

To extend the utility of the repository, we augmented its search capabilities. Specifically, we now allow the user to search using a TCGA cancer abbreviation (e.g. BRCA, PRAD, PAAD, etc.), a descriptive phrase (e.g. breast cancer), one or more structural categories, one or more isoacceptors, a sequence (e.g. GGCTCCGTGGCGCAATGGA), a tRNA name, or a tRNA label, and to combine these choices with a "minimum abundance" criterion. As an example, the following complex Boolean request can be executed by pointing-and-clicking: "retrieve all 5'-tRFs and all i-tRFs that overlap with either the mitochondrial isodecoder of tRNA$^{AspGTC}$ or any of the nuclear isodecoders of tRNA$^{HisGTG}$ and are present in any of the breast cancer samples of MINTbase with abundance ≥25 RPM."

Each of MINTbase's 26,531 tRFs has its own exclusive record that lists all publicly known identifiers for it, information about the isodecoder(s) that contain it, a multiple sequence alignment in the case of multiple tRNA origins, whether the tRF is exclusive to tRNA space (4,8,9), and how many of the MINTbase datasets contain the tRF with an abundance of ≥1.0 RPM.

Figure 7A:
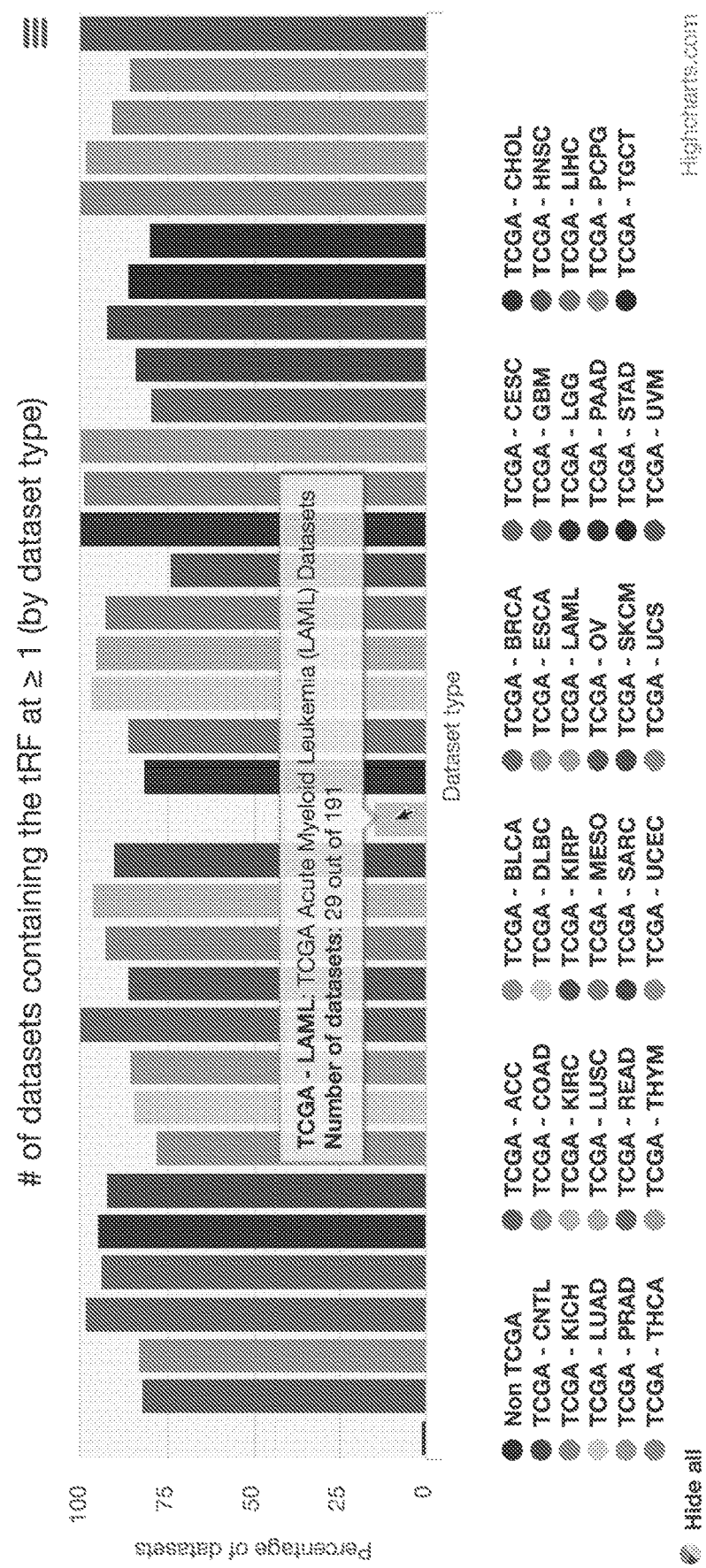
FIGS. 7A-7C v2.0 of MINTbase. We have augmented the interface of MINTbase to enable interactive and detailed exploration of the tRFs contained in it. Here we show three of the four histograms and other information that is available in the record of the His(−1) 5'-tRF TGCCGTGATCGTATAGTGGTT from tRNA$^{HisGTG}$ (note the starting "T"). See text for more details.
Figure 7B:
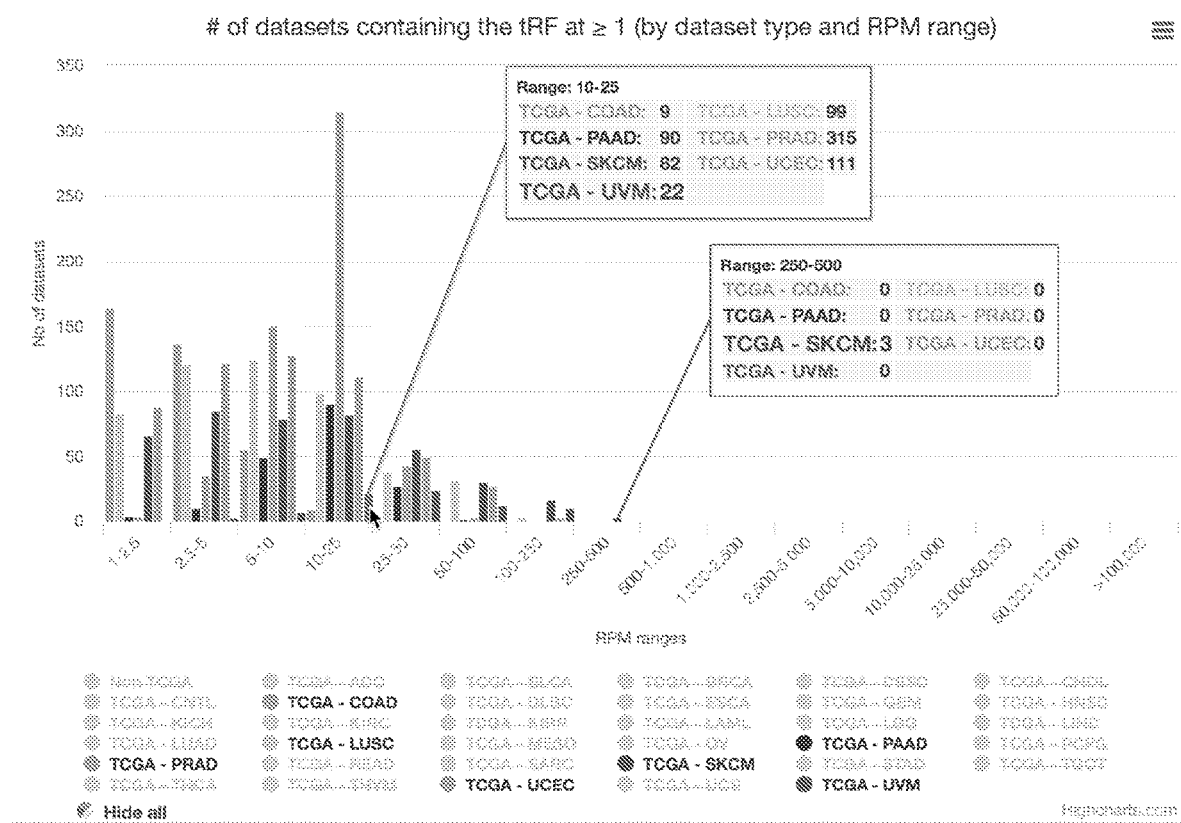
Figure 7C:
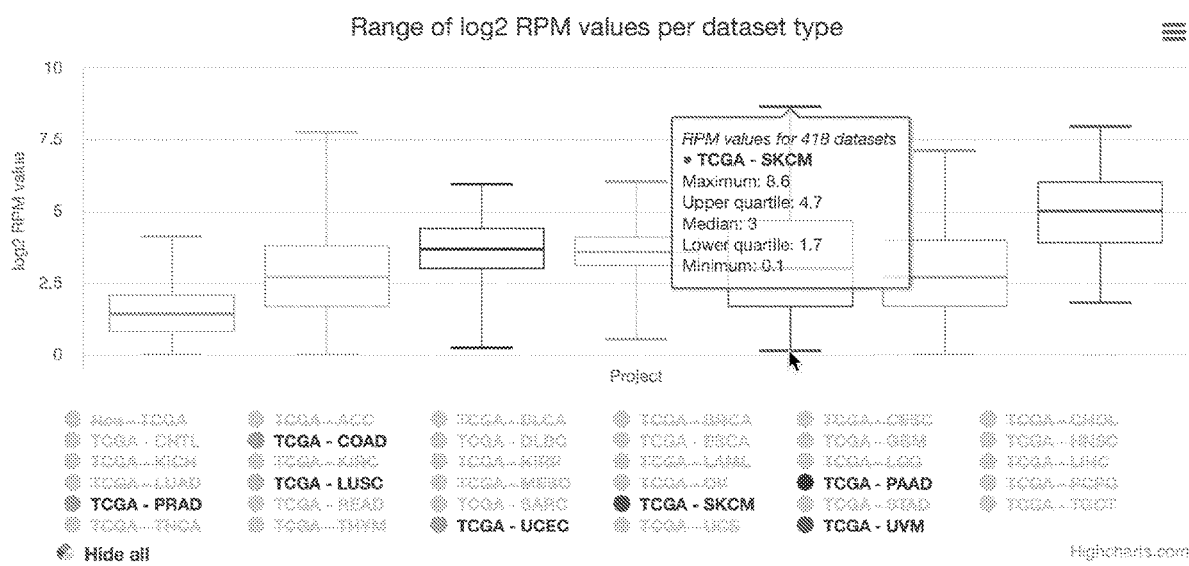

To enable intra-TCGA comparisons as well as comparisons between TCGA and non-TCGA datasets, each tRF record includes four histograms that show: the fraction of datasets containing the tRF in each TCGA cancer type and outside TCGA; the tRF's distribution of abundances in each TCGA cancer type and in non-TCGA datasets; and, two more histograms showing box-plots of the distribution of abundances of the tRF within each TCGA dataset using a linear and a log$_2$ Y-axis, respectively. All four histograms are interactive and allow the user to select which dataset(s) to display. In FIGS. 7A-7C, we show three of the four histograms from the record of the −1U 5'-tRF from tRNA$^{HisGTG}$ with sequence TGCCGTGATCGTATAGTGGTT. FIG. 7A shows that the tRF is present in at least 75% of the samples that are available for 31 of the 32 TCGA cancer types. The only exception is LAML where the fragment appears in only 29 of the 191 datasets. Of the 521 non-TCGA datasets currently contained in MINTbase, the fragment is present in only 8 of them. Across the TCGA datasets in which it is present, this −1U 5'-tRF exhibits a wide range of abundances that reach as high as 1,394.78 RPM in LIHC (not shown). To demonstrate the comparative differences of the fragment's distribution of abundances, we selected and show the histogram bars for PRAD, COAD, LUSC, UCEC, SKCM, PAAD, and UVM (FIG. 7B). For the same set of cancer types, in FIG. 7C, we also show the box-plot of their abundance distributions (note that this panel uses a log$_2$ Y-axis!). To facilitate inclusion in user reports, all these diagrams can be saved in PNG, JPG, PDF or SVG format.

tRF Correlations with mRNAs from Specific Pathways

Figure 9A:
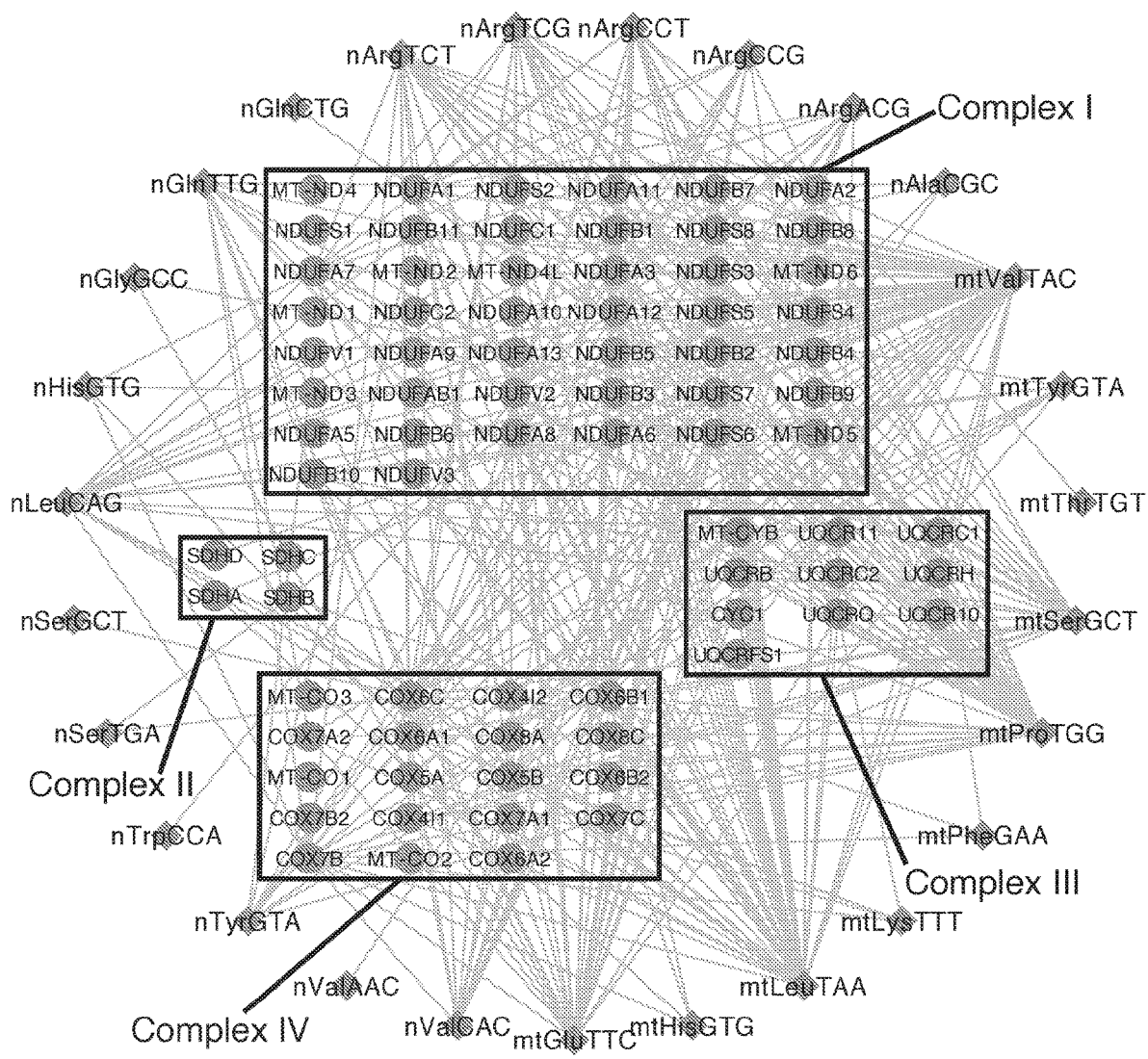
FIGS. 9A-9B Examples of protein complexes whose mRNAs are correlated with tRFs in at least three different cancer types. (A) Oxidative phosphorylation. (B) Ribosome-linked proteins.
Figure 9B:
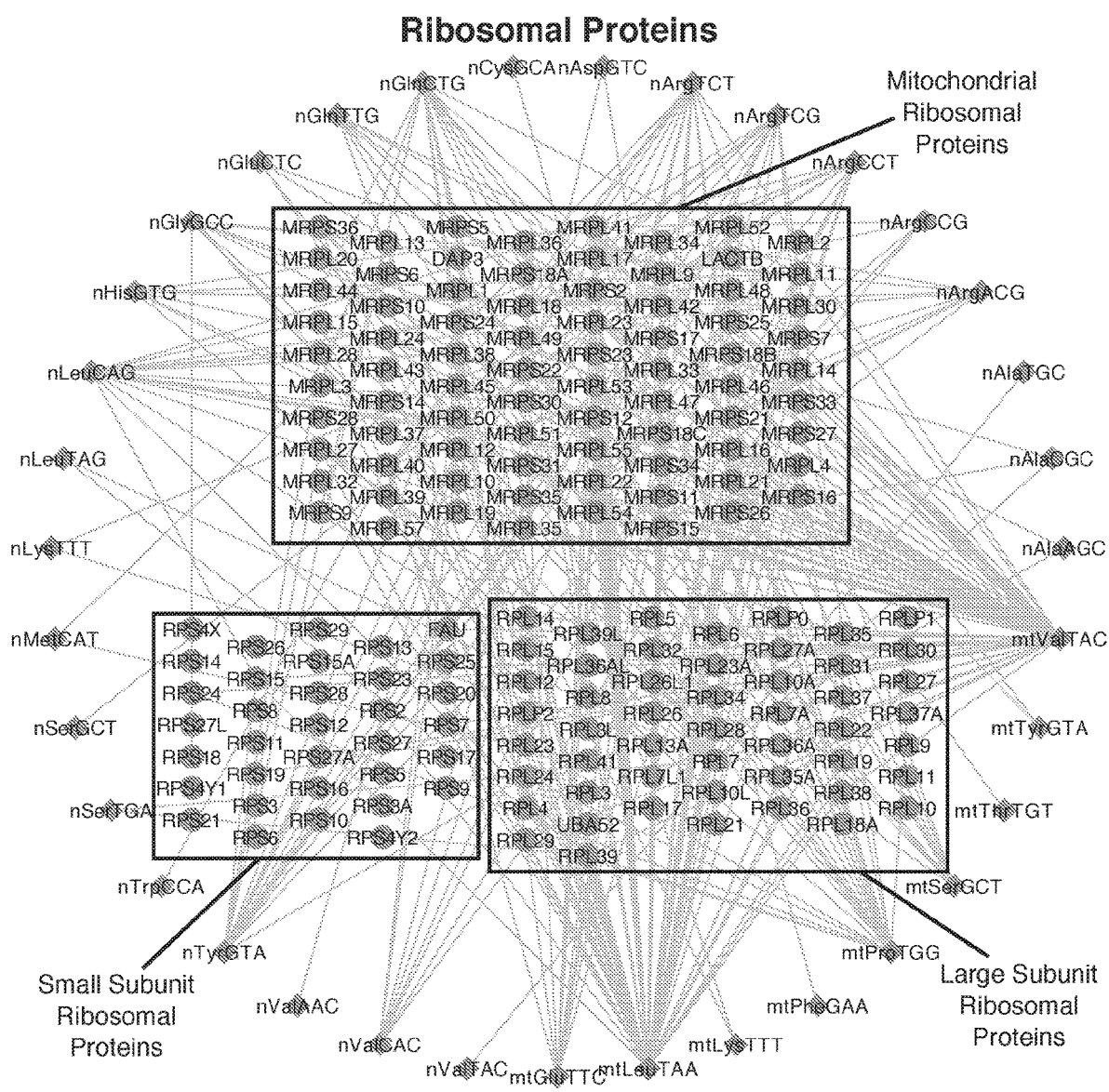

Above, we presented evidence of tRF correlations with mRNAs from specific pathways. Despite differences in the actual tRFs and mRNAs that form the correlations, a considerable number of pathways whose members are correlated with tRFs are common across the 32 cancer types. We highlight this with the help of two specific examples (FIG. 9A-9B). One such pathway, Oxidative Phosphorylation, is found enriched in the tRF-mRNA correlations in 22 of the 32 cancer types. In FIG. 9A, we visualize correlations of tRFs with mRNAs that encode for components of the four complexes of mitochondrial respiration and occur in at least three cancer types. A second pathway involves mRNAs that are linked to the "Ribosome." In FIG. 9B, we visualize correlations of tRFs with mRNAs that correspond to the "small subunit" ribosomal proteins, the "large subunit" ribosomal proteins, or to "mitochondrial" ribosomal proteins. Again, these correlations occur in at least three cancer types.

tRF Correlations with mRNAs that are Cancer-Specific

Figure 10A:
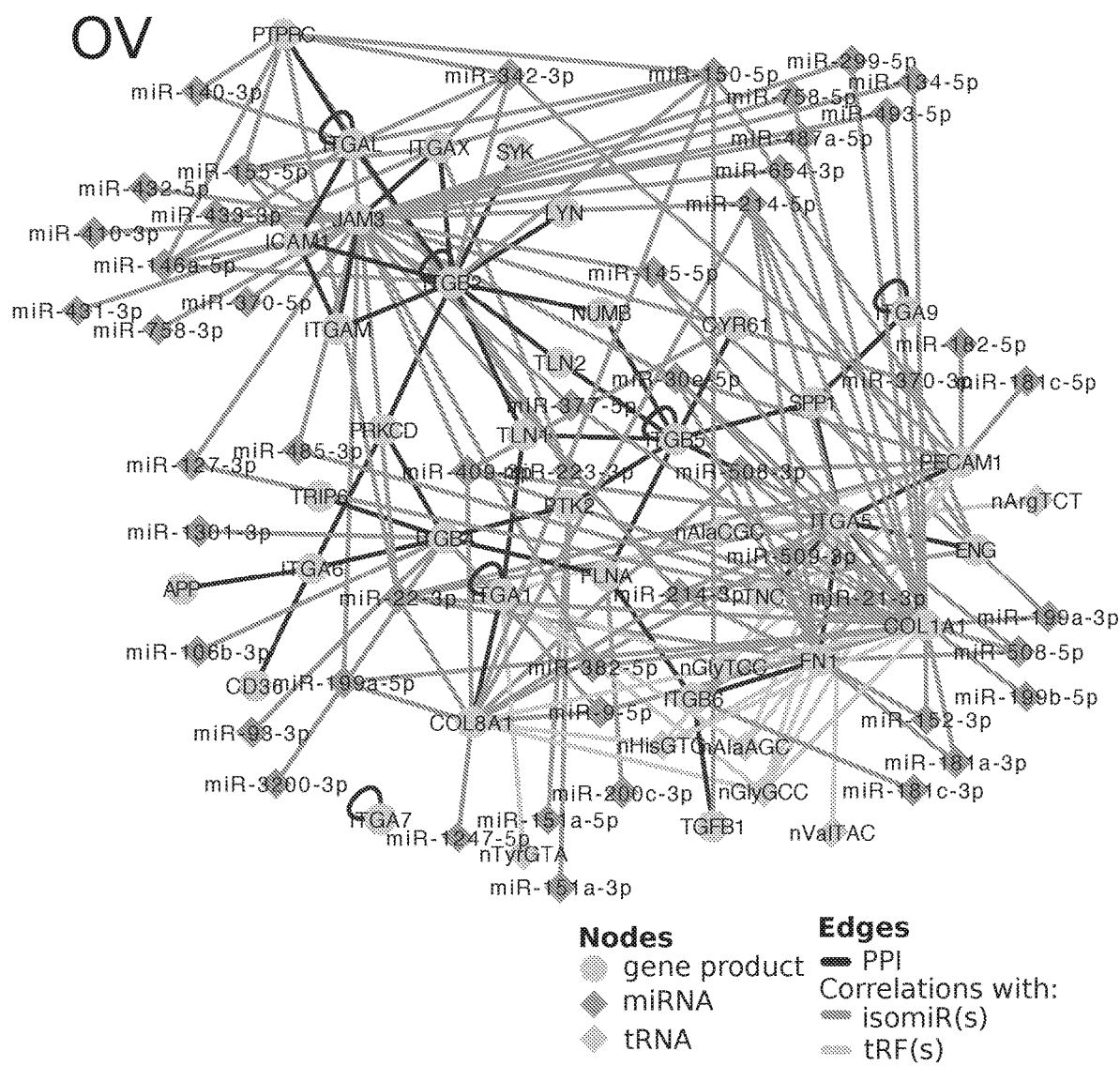
FIGS. 10A-10C Members of the integrin family of proteins associate with tRFs and isomiRs in a cancer-dependent manner. (A) The case of ovarian serous adenocarcinoma (OV). (B) The case of brain lower grade glioma (LGG). (C) The case of acute myeloid leukemia (LAML). Note that in all three cases, we show the same underlying network of protein-protein interactions involving integrins. The nodes labeled with the names of miRNA loci are meant to represent one or more isomiRs from the corresponding locus that are correlated with the corresponding mRNAs. The nodes labeled with the names of tRNA isoacceptors are meant to represent one or more tRFs from the tRNA template that are correlated with the corresponding mRNAs.
Figure 10B:
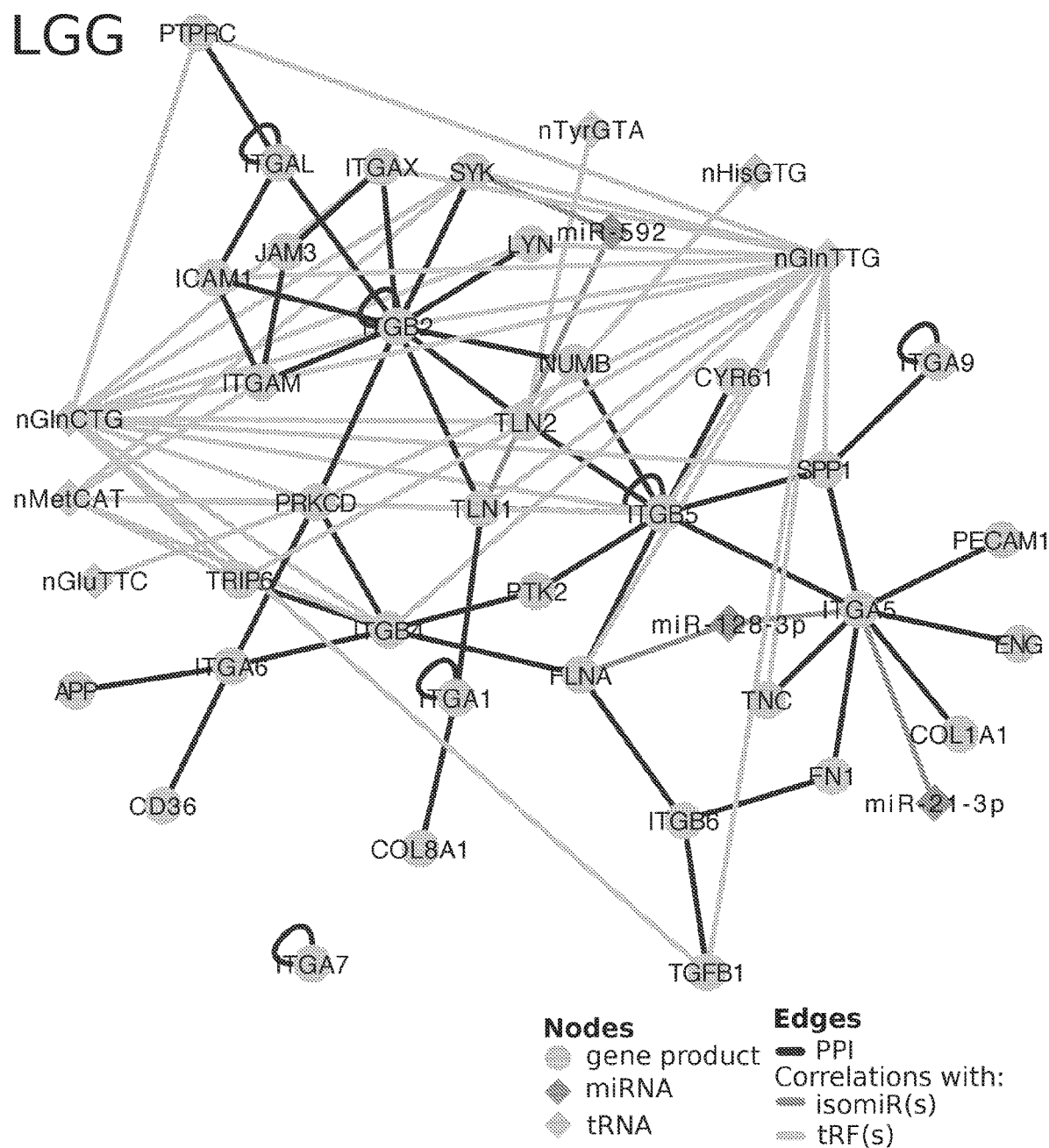
Figure 10C:
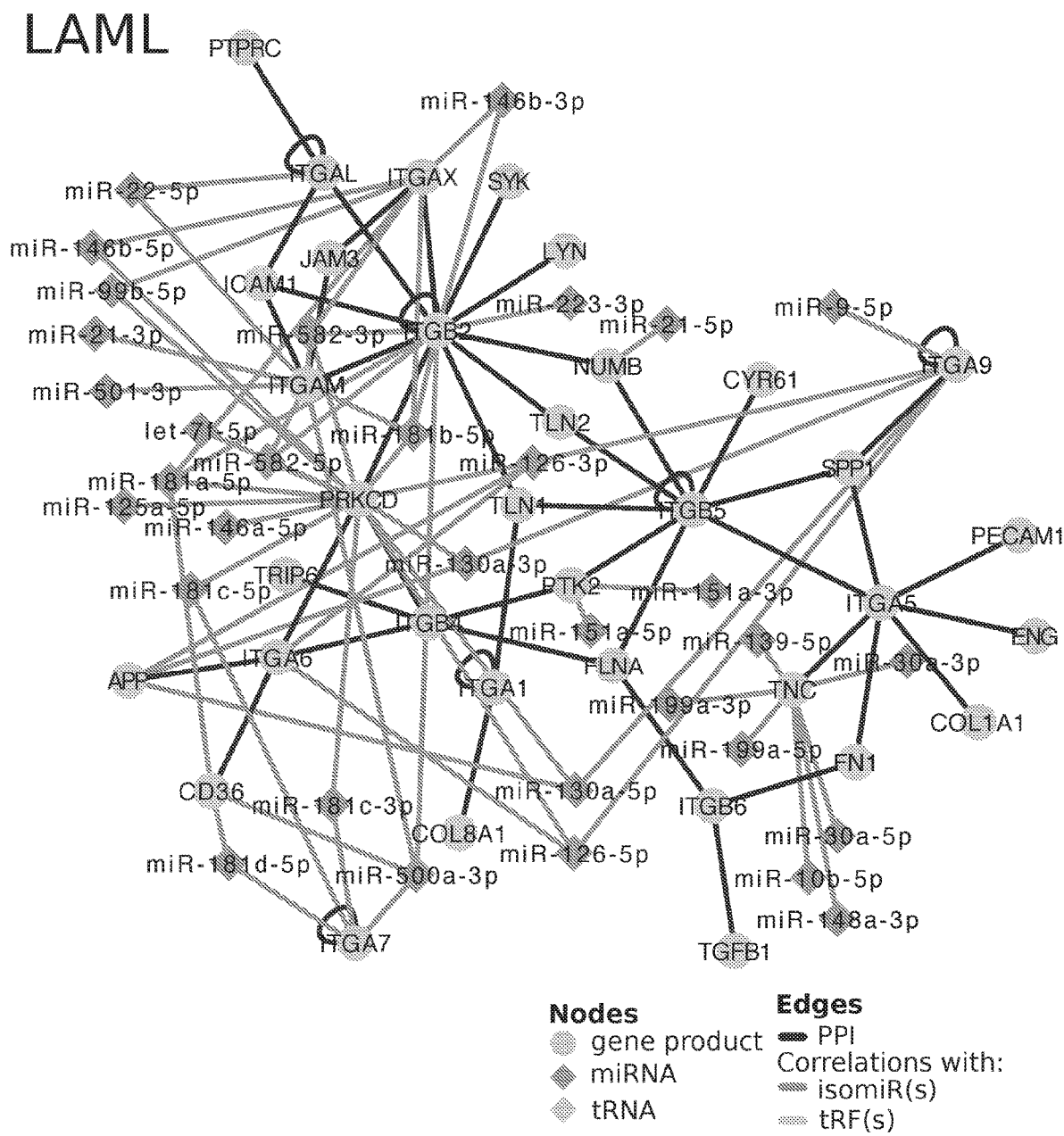

Having shown two examples of tRF-mRNA similarities across cancers, we focus next on an example of tRF correlations with mRNAs that are characteristically cancer-specific. To this end, the integrin family of proteins serves as a good platform. To help highlight the extent of the cancer-dependencies we show differences between in tRF-mRNA and isomiR-mRNA correlations using three different cancers: OV (FIG. 10A), LGG (FIG. 10B) and LAML (FIG. 10C). Note that in all three of these Figures, we show the same underlying network of protein-protein interactions involving integrins, and proteins that interact with integrins. It is important to stress that for clarity purposes, the nodes labeled with the names of miRNA loci are meant to represent one or more isomiRs from the corresponding locus that are correlated with the corresponding mRNAs. Analogously, the nodes labeled with the names of tRNA isoacceptors are meant to represent one or more tRFs from the tRNA template that are correlated with the corresponding mRNAs. As can be seen from FIG. 10A, in OV, isomiRs are involved in comparatively more correlations with the shown mRNAs than tRFs. In LGG, none of the shown correlations involve tRFs. Lastly, in LAML, the correlations with the shown mRNAs involve primarily tRFs. Note also how many more of the family's mRNAs are correlated with tRFs and isomiRs in OV, compared to LGG.

Sex Disparities in BLCA

BLCA is four times more likely to develop in men, yet women present with more advanced disease and have worse survival rates (82-86). This disparity is believed to be due to a differential exposure to carcinogens as well as the result of genetic, anatomical, and hormonal factors. BLCA is also known to depend on a patient's race, with incidence rates in White patients double those in with Black/African Americans, although patients in the latter group have a higher mortality rate (87-91). We are not aware of previous work that examined the possibility of molecular links between these disparities and tRFs.

Figure 11A:
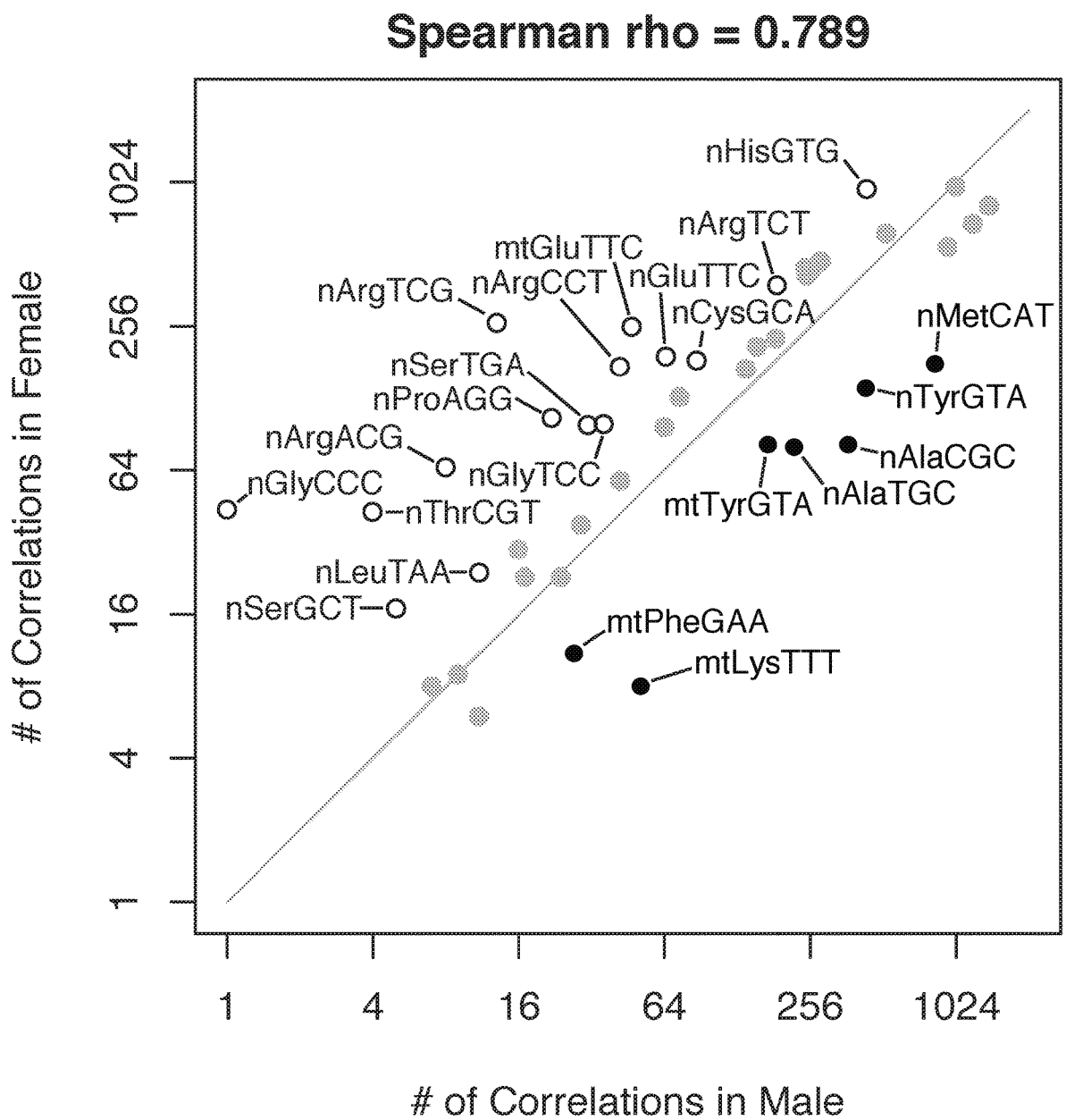
FIGS. 11A-11B Sex-based disparities in bladder urothelial carcinoma (BLCA). (A) Plot showing the number of correlations that the tRFs from each isoacceptor have with mRNAs in each sex in primary tumors of BLCA. The points are denoted with black-filled circles (respectively, white-filled circles) if there are ≥2× correlation in males (respectively, females). Note that this is a $\log_2$-$\log_2$ plot. (B) Protein-Protein interaction network showing cyclin-dependent kinases (CDK), and proteins interacting with CDKs, and the tRFs that interact directly with them reveal differential correlations between male and female BLCA patients. CDKs that are not differentially co-expressed between male and female patients are shown as gray circles.

We correlated tRFs with mRNAs in the BLCA tumor samples from White patients, and did so separately for each sex. A first, rather striking observation pertains to the number of correlations per tRNA isoacceptor, as a function of the patients' sex. As can be seen in FIG. 11A, the same isoacceptor can be associated with markedly different numbers of mRNAs in male (X-axis) and female (Y-axis) BLCA patients. The further away from the diagonal a point is, the higher the disparity in the number of correlated mRNAs. Note how many more isoacceptors are correlated with mRNAs that are more numerous in women than in men (points sit above the diagonal). Isoacceptors for which the difference in the ratio is $\geq 2\times$ (or $\leq \frac{1}{2}\times$) are indicated with black-filled or white-filled circles and are labeled. It is evident that some of the tRFs, e.g. those arising from the nuclear tRNA$^{MetCAT}$ (respectively, the nuclear tRNA$^{HisGTG}$) participate in characteristically more correlations with mRNAs in men (respectively, in women).

We also analyzed tRF-mRNA correlations in BLCA and distinguished between correlations that are present in both male and female patients, and correlations that are present in only one of the two patient groups (only female or only male). One group of mRNAs highlights these sex-based differences: cyclin-dependent kinases (CDK), or proteins interacting with CDKs, exhibit pronounced differences in their correlations with tRFs based on the sex of the patient. This is summarized in FIG. 11B.

Figure 8:
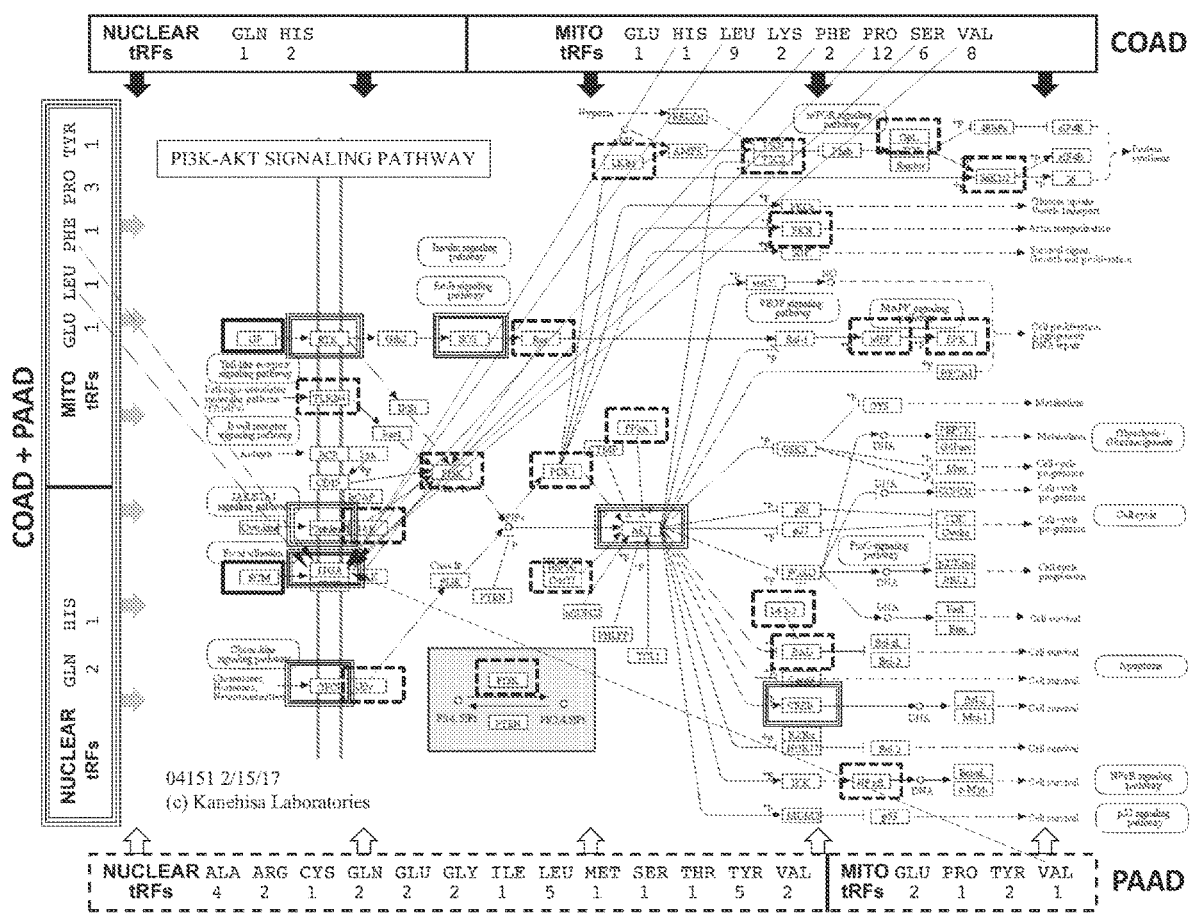
FIG. 8 Correlations between tRFs and the mRNAs of genes belonging to the signal transduction pathway known as "the PI3K-AKT pathway," in colon adenocarcinoma (COAD) and pancreatic adenocarcinoma (PAAD). The solid-line-contour rectangle shows tRFs that are correlated with PI3K-AKT pathway mRNAs in COAD but not in PAAD. The dashed-line-contour rectangle shows the analogous information for PAAD. The compound-line-contour rectangle shows tRFs that are present in and correlated with PI3K-AKT pathway mRNAs in COAD and in PAAD. Note, however, that these tRFs maybe correlated with different mRNAs from this pathway in each cancer and the correlations may have different signs in each cancer, e.g. the tRF:mRNA correlation could be positive in COAD and negative in PAAD.

In our discussion above of FIG. 8, we emphasized that, because of the uncovered cancer dependencies, it is important to know the cancer type in order to establish the context in which a tRF could interact with a mRNA, and also determine whether a tRF and an mRNA are positively- or negatively-correlated. As already mentioned, the therapeutic intervention would aim to counterbalance the mRNA deregulation. For a given tRF:mRNA correlation, this counterbalancing could be achieved by modulating the abundance of the tRF, by modulating the abundance of the mRNA, or by modulating the abundance of one or more tRFs or of one or more mRNAs simultaneously.

With that in mind, and as a case in point, we focused on the negatively-correlated tRF-mRNA pairs among those that we generated from our analysis of the TCGA datasets. Note that even though we focus on negatively-correlated pairs, the analysis extends trivially to positively-correlated pairs and the methodology is the same.

First, among the negatively-correlated tRF-mRNA pairs that are present in a given cancer i we identified those tRFs that participate in correlations with at least 20 different mRNAs. The threshold T, in this case "20," was chosen arbitrarily and can be changed and optimized as needed. For each tRF that exceeded the threshold T in cancer i, we identified the number of mRNAs with which the tRF forms negative correlations in each of the remaining cancers (in this case, 31 cancers) and computed the average A of negative correlations across these other cancers. Of the tRFs that exceeded threshold T in cancer i we sub-selected and kept only those for which A was not more than a second threshold t: in this case, we selected t to be 3—this threshold t can again be changed and optimized as needed. By selecting a large value for threshold T and a small value for threshold t we seek to identify those tRFs that participate in $\geq T$ negative-correlated tRF-mRNA pairs in cancer i and $\leq t$ such pairs on average in the remaining cancers under consideration, i.e. in comparatively fewer pairs in the other cancers. For the thresholds we selected here, the emerging tRFs participate in at least six times more negative correlations with mRNAs in cancer i than the average number of correlations in the remaining cancers. Clearly, the higher the difference between T and t, the more specific the tRF under consideration is for cancer i.

We carried out this analysis for each of the 32 TCGA cancers in turn, using a value of 20 for T and a value of 3 for t. Thusly, we identified, separately for each TCGA cancer, a number of tRFs that participate in cancer-specific negative correlations with mRNAs and could serve as targets of therapeutic intervention. The same methodology could be repeated using different thresholds, or by focusing on positively-correlated tRF-mRNA pairs, or by focusing on positively-as well as negatively correlated tRF-mRNA pairs. Accordingly, these following sequences can be utilized in methods of treatment.

For ACC (Adrenocortical carcinoma), we found that the tRFs with sequences SEQ 1 through SEQ 31 satisfy these criteria.

For BLCA (Bladder Urothelial Carcinoma), we found that the tRFs with sequences SEQ 32 through SEQ 40 satisfy these criteria.

For BRCA (Breast invasive carcinoma), we found that the tRFs with sequences SEQ 41 through SEQ 58 satisfy these criteria.

For CESC (Cervical squamous cell carcinoma and endocervical adenocarcinoma), we found that the tRFs with sequences SEQ 59 through SEQ 71 satisfy these criteria.

For COAD (Colon adenocarcinoma), we found that the tRFs with sequences SEQ 72 through SEQ 77 satisfy these criteria.

For DLBC (Lymphoid Neoplasm Diffuse Large B-cell Lymphoma), we found that the tRFs with sequences SEQ 78 through SEQ 88 satisfy these criteria.

For ESCA (Esophageal carcinoma), we found that the tRFs with sequences SEQ 89 through SEQ 94 satisfy these criteria.

For HNSC (Head and Neck squamous cell carcinoma), we found that the tRFs with sequences SEQ 95 through SEQ 109 satisfy these criteria.

For KICH (Kidney Chromophobe), we found that the tRFs with sequences SEQ 110 through SEQ 120 satisfy these criteria.

For KIRC (Kidney renal clear cell carcinoma), we found that the tRFs with sequences SEQ 121 through SEQ 128 satisfy these criteria.

For KIRP (Kidney renal papillary cell carcinoma), we found that the tRFs with sequences SEQ 129 through SEQ 132 satisfy these criteria.

For LAML (Acute Myeloid Leukemia), we found that the tRFs with sequences SEQ 133 through SEQ 165 satisfy these criteria.

For LGG (Brain Lower Grade Glioma), we found that the tRFs with sequences SEQ 166 through SEQ 180 satisfy these criteria.

For LIHC (Liver hepatocellular carcinoma), we found that the tRFs with sequences SEQ 181 through SEQ 186 satisfy these criteria.

For LUAD (Lung adenocarcinoma), we found that the tRFs with sequences SEQ 187 through SEQ 194 satisfy these criteria.

For LUSC (Lung squamous cell carcinoma), we found that the tRFs with sequences SEQ 195 through SEQ 217 satisfy these criteria.

For MESO (Mesothelioma), we found that the tRFs with sequences SEQ 218 through SEQ 235 satisfy these criteria.

For OV (Ovarian serous cystadenocarcinoma), we found that the tRF with sequence SEQ 236 satisfies these criteria.

For PAAD (Pancreatic adenocarcinoma), we found that the tRFs with sequences SEQ 237 through SEQ 242 satisfy these criteria.

For PCPG (Pheochromocytoma and Paraganglioma), we found that the tRFs with sequences SEQ 243 through SEQ 251 satisfy these criteria.

For PRAD (Prostate adenocarcinoma), we found that the tRFs with sequences SEQ 252 through SEQ 261 satisfy these criteria.

For READ (Rectum adenocarcinoma), we found that the tRFs with sequences SEQ 262 through SEQ 270 satisfy these criteria.

For SARC (Sarcoma), we found that the tRFs with sequences SEQ 271 through SEQ 275 satisfy these criteria.

For SKCM (Skin Cutaneous Melanoma), we found that the tRFs with sequences SEQ 276 through SEQ 283 satisfy these criteria.

For STAD (Stomach adenocarcinoma), we found that the tRFs with sequences SEQ 284 through SEQ 291 satisfy these criteria.

For TGCT (Testicular Germ Cell Tumors), we found that the tRFs with sequences SEQ 292 through SEQ 308 satisfy these criteria.

For THCA (Thyroid carcinoma), we found that the tRFs with sequences SEQ 309 through SEQ 324 satisfy these criteria.

For THYM (Thymoma), we found that the tRFs with sequences SEQ 325 through SEQ 331 satisfy these criteria.

For UCEC (Uterine Corpus Endometrial Carcinoma), we found that the tRFs with sequences SEQ 332 through SEQ 344 satisfy these criteria.

For UVM (Uveal Melanoma), we found that the tRFs with sequences SEQ 345 through SEQ 372 satisfy these criteria.

In each of these cancer types, a possible therapeutic intervention would comprise modulating the abundance of one or more of the corresponding tRFs. The modulation would comprise increasing the abundance of one or more of these tRFs, decrease the abundance of one or more of these tRFs, or a combination.

Second, we also reversed our vantage point as follows. Among the negatively-correlated tRF-mRNA pairs that are present in a given cancer i we identified those mRNAs that participated in correlations with at least 20 different tRFs. The threshold T, in this case "20," was chosen arbitrarily and can be changed and optimized as needed. For each mRNA that exceeded the threshold T in cancer i, we identified the number of tRFs with which the mRNA forms negative correlations in each of the remaining cancers (in this case, 31 cancers) and computed the average number A of negative correlations across these other cancers. Of the mRNAs that exceeded threshold T in cancer i we sub-selected and kept only those for which A was not more than a second threshold t: in this case, we selected t to be 3—this threshold t can again be changed and optimized as needed. By selecting a large value for threshold T and a small value for threshold t we seek to identify those mRNAs that participate in ≥T negative-correlated tRF-mRNA pairs in cancer i and ≤t such pairs on average in the remaining cancers under considerations, i.e. in comparatively fewer pairs in the other cancers. For the thresholds we selected here, the emerging mRNAs participate in at least six times more negative correlations with tRFs in cancer i than the average number of correlations in the remaining cancers. Clearly, the higher the difference between T and t, the more specific the mRNA under consideration is for cancer i.

We carried out this analysis for each of the 32 TCGA cancers in turn, using a value of 20 for T and a value of 3 for t. Thusly, we identified, separately for each TCGA cancer, a number of mRNAs that participate in cancer-specific negative correlations with tRFs and could serve as targets of therapeutic intervention. The same methodology could be repeated using different thresholds, or by focusing on positively-correlated tRF-mRNA pairs, or by focusing on positively-as well as negatively correlated tRF-mRNA pairs.

For ACC (Adrenocortical carcinoma), we found that the mRNAs of the following genes satisfy these criteria: CSDC2, CSGALNACT1, RERG, PCMTD1, PLCB3, YEATS2, BIRC2, MVP, MYST3, ARL6IP5, TRANK1, TMEM45A, ACVR1, PGCP, VCL, MSRA, C10orf54, DCUN1D3, CTDSPL2, SIK2, TMCO6, SRCAP, TMEM159, PLEKHO2, HLA-E, TAX1BP3, C11orf75, RCE1, NDRG4, MR1, MARK2, FAM21B, HLA-B, RBL2, CABC1.

For BLCA (Bladder Urothelial Carcinoma), we found that the mRNAs of the following genes satisfy these criteria: ACTG2, TGFBR3, PRELP, RERE, OSR1, TCEAL1, NNAT, GCOM1, MMP2, MYST4, SYNPO2, C16orf45, FYCO1, MYH11, CSRP1, MEIS2, ACTA2, CLU, LOXL1, IGFBP4, TXNIP, SLIT3, CHRDL2, MYL9.

For BRCA (Breast invasive carcinoma), we found that the mRNAs of the following genes satisfy these criteria: CRTC1, CALCOCO1, SLC27A1, CROCC, PGPEP1, PSD4, TBC1D17, PHF15, ARAP1, TNFRSF14, NISCH, MED16, RGS12, MYO15B, AGXT2L2, RFX1, C21orf2, NEURL4, TPCN1, HOOK2, LTBP3, SPHK2, ABTB1, ABCD4, ZBTB48, CIRBP, CYTH2, ZNF446, PHF1, RPS9, MZF1, FAM160A2, KIF13B, GLTSCR2, WDR81, SH2B1, RHOBTB2, CRY2, LTBP4, HDAC7, ZNF219, MUM1, RBM5, RAPGEF3, CCDC9.

For CESC (Cervical squamous cell carcinoma and endocervical adenocarcinoma), we found that the mRNAs of the following genes satisfy these criteria: NBPF10, JRK, SMG5, ALDH1A2, MFAP4, ZFYVE1, CDC42BPB, ENTPD4, IGF1, ZFYVE26, APOLD1, LOC200030, KIAA0430, UBN1, VASH1, RANBP10, WDR37, MGP, MON1B, CNN1, MAT2A, PGR, KIAA0100, C14orf21, HCFC1, LRP10, DIDO1, FBXL18, ATP6V0A1, RGS2, MLXIP, TRIM56, CTGF, KIAA0284, DES, SFRP4, PDPK1, TAOK2, SMCR8, CLN8, UNC119B, TRIM25, CYB561D1, TBC1D2B, DNAJC5, CRAMP1L, ZNF646, ZC3HAV1, KHNYN, PSKH1, RGS1.

For COAD (Colon adenocarcinoma), we found that the mRNAs of the following genes satisfy these criteria: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL10RA, HEG1, HIPK3, NEXN, TMEM140, AMOTL1, A2M, TIE1, AKT3, CD163, LPHN2, OSMR, CSF1R, DAAM2, IL1R1,

GPC6, SLC8A1, FBN1, GNB4, GPNMB, DOCK2, KIAA1462, CSF2RB, MYO5A, S1PR1, ARHGEF6.

For DLBC (Lymphoid Neoplasm Diffuse Large B-cell Lymphoma), we found that the mRNAs of the following genes satisfy these criteria: GOLGA2, DCHS1, CLDND1, CSRNP2, FRMD8, SLCO2A1, ARHGAP23, NID1, DUSP7, TBC1D20, YAP1, WDR82, TMEM43, TJP1, CARD8, ZNF213, KIAA0232, EPAS1, VPS11, PHC1, SKI, DAG1, ANKRD40, FAT1, PHF12.

For ESCA (Esophageal carcinoma), we found that the mRNAs of the following genes satisfy these criteria: SSC5D, PDLIM3, CELF2, TIMP3, ABCC9, CALD1, COL8A1, GREM1, THBS4, PRUNE2, TMEM47, PBXIP1, PLN, CCDC80, C7, PODN, DDR2, PPP1R12B, MRVI1, LMOD1, C7orf58, HSPB7, TAGLN, PPP1R16B, GFRA1, LOC728264, SGCD, PGM5.

For HNSC (Head and Neck squamous cell carcinoma), we found that the mRNAs of the following genes satisfy these criteria: GABBR1, C14orf179, METT11D1, C6orf125, ZNF692, FKBP2, FAM113A, LOC388789, TAZ, WASH3P, CDK5RAP3, PLBD2, SDR39U1, CPT1B, UBL5, C14orf2, LOC146880, THAP3, ANKRD13D, C12orf47, ATP5E, ATPIF1, SYF2, C8orf59, WASH7P, NPIPL3, CDK10, C1orf151, MRPS21, C19orf60, C7orf47, CENPT, GAS5, KIFC2, NFIC, RPL39, UQCRB, COX6C, LUC7L, CCS, COMMD6, ZNF133, SNHG12, C11orf31, NPEPL1.

For KICH (Kidney Chromophobe), we found that the mRNAs of the following genes satisfy these criteria: BMPR1A, EXT1, TFAM, PDCD11, MTIF2, POLR3A, MAPK8, PRDX3, COQ5.

For KIRC (Kidney renal clear cell carcinoma), we found that the mRNAs of the following genes satisfy these criteria: ARHGAP19, KIAA1671, KIAA0754, KIAA1147, ZNF45, KLF13, MYO9A, FUT11, ASH1L, KIF13A, TUBGCP3, MTF1, FAM168A.

For KIRP (Kidney renal papillary cell carcinoma), we found that the mRNAs of the following genes satisfy these criteria: GLCCI1, CDK13, POGZ, UBN2, CREBZF, NPHP3, VEZF1, CHD1, YPEL2, LRRC37B2, GPATCH8, ENC1, TTC18, C11orf61, RSBN1L, EFNB2, PHIP, RBAK, SPEN, RBM9, SMURF2, ZNF264, ZNF587, PTPN12, TPBG, RBM33, DMTF1, CCNT2, ARID4B, ARGLU1, CREB1, KIAA0753, BTAF1, C17orf85, RLF, MLL5, ZFC3H1, ZNF160, PRPF38B, SETD5, ARRDC4, HOOK3, RC3H1, MLL3, RNF207, MAP3K1, PLEKHH2, CCDC57, DAPK1, LUC7L3.

For LAML (Acute Myeloid Leukemia), we found that the mRNAs of the following genes satisfy these criteria: SUPT5H, SKIV2L, IKBKG, HGS, MIB2, MED15, STK25, ANAPC2, RHOT2, SFI1, CUL9, ARHGEF1, GTPBP2, KIAA0892, MBD1, UCKL1, DHX16, ZFYVE27, APBA3, PI4 KB, C19orf6, SPSB3, CAPN10, FLYWCH1, ATG4B, CDC37, LZTR1, MAN2C1, C1orf63, DVL1, EDC4, DHX34, PCNXL3, EXOC3, FUK, FBXL6, LMF2, HDAC10, E4F1, TSC2, ZDHHC8, CPSF3L, FAM160B2, CLCN7, LRRC14, D2HGDH, ZNF335, FHOD1, SOLH, ZBTB17, POLRMT, SLC26A1, KIAA0415, SELO, SAPS2, NME3, KLHL36, SCYL1, USP19, DGKZ, CYHR1, ATG2A, VPS16, XAB2, ACTR5, ZNF76, ATP13A1, RNF31, GPN2, MUS81, FAM73B, TTC15, CXXC1, TRMT2A, WDR8, PTGES2, TELO2, RFNG, SLC39A13.

For LGG (Brain Lower Grade Glioma), we found that the mRNA of the following gene satisfies these criteria: EXD3.

For LIHC (Liver hepatocellular carcinoma), we found that the mRNA of the following gene satisfies these criteria: DYRK2.

For LUAD (Lung adenocarcinoma), we found that the mRNAs of the following genes satisfy these criteria: CROCCL1, RHPN1, ABCA7, RGL3, PDXDC2, ENGASE, ATG16L2, CSAD, TTLL3, ARHGEF12, ANKS3, LOC100132287, SGSM2, HEXDC, LPIN3, ACCS, PLEKHM1P, ANO9, ELMOD3, KIAA0895L, AP1G2, ACAP3, ECHDC2, NXF1, JMJD7-PLA2G4B, TMEM175, CCDC64B, ANKMY1.

For LUSC (Lung squamous cell carcinoma), we found that the mRNAs of the following genes satisfy these criteria: PKD1, CHKB-CPT1B, WDR90, MACF1, RBM6, LENG8, TAF1C, COL16A1, CAPN12, RBM39, ACIN1, FNBP4, PILRB, DMPK, SFRS5, AHSA2, RBM25, PLCG1, SNRNP70, NCRNA00201, GIGYF1, SRRM2, GOLGA8B, ZGPAT, RTEL1, COL27A1, MAPK8IP3, PABPC1L, HSPG2, AKAP13, LRP1, NKTR, ATAD3B, TUBGCP6, ZNF276, MICALL2, CLCN6, NSUN5P2, NEAT1, LAMA5, CHD2, PPP1R12C, FAM193B, NPIP, CDK11A, STX16, LTBP2, LOC91316, NBEAL2, FLJ45340, LRDD, CCDC88B, GOLGA8A.

For MESO (Mesothelioma), we found that the mRNAs of the following genes satisfy these criteria: C15orf40, SNUPN, CHTF8, CLNS1A, CSNK1D, DPF2, PCIF1, DNAJC4, SECISBP2, C5orf32, RPRD1B, RPL38, NDUFA10, RPRM, BAT4, RSL1D1.

For OV (Ovarian serous cystadenocarcinoma), we found that the mRNAs of the following genes satisfy these criteria: KIAA0907, ULK3.

For PAAD (Pancreatic adenocarcinoma), we found that the mRNAs of the following genes satisfy these criteria: NUAK1, KBTBD4, HMCN1, DSTYK.

For PCPG (Pheochromocytoma and Paraganglioma), we found that the mRNAs of the following genes satisfy these criteria: CACNA2D1, TP53BP1, KIAA1244, MARCH8, PCDHGC4, ESYT2, DHX15, TECPR1, MAP3K2, TBC1D24, PCDH1, IPO11, MGAT5, TRAM2, ADAM10, GNA11, CBX6, SNURF, RIF1, CNTN1, LMBRD2, CAND1, TRIP12, RC3H2, PAK3, TMCO3, CSNK2A1P, ASB1, AKAP2, ROCK2, NUP155, PIK3C3, KLHDC10, RAB35, GTF2I, HSPA8, FAM49A.

For PRAD (Prostate adenocarcinoma), we found that the mRNAs of the following genes satisfy these criteria: FEM1B, TGOLN2, SEPT9, MYOCD, LUZP1, TLN1, PIAS1, RNF111, DCBLD2, URB1, ZBTB40, ZNF516, ATXN1L, RHBDD1, HUWE1, VPS13D, ITPR1, NNT, ERC1.

For READ (Rectum adenocarcinoma), we found that the mRNAs of the following genes satisfy these criteria: FZD4, CD93, DYNC1I2, ENG, ELK3, KDR, FAM101B, PXDN, GIMAP4, F13A1, VCAM1, ARHGAP31, CD34, GNG2, LCP2, VWF, CSF1, GPR116, KIRREL, MMRN2, ETS1, ITGA4, FAM120B.

For SARC (Sarcoma), we found that the mRNAs of the following genes satisfy these criteria: SH3BGRL, SORBS1, MAPK4, LYNX1, MICAL3, AKAP1, LIMS2, RNF38, LOC283174, CAND2, PLIN4, MOAP1, RNF19A, RABGAP1, C5orf4, FRY, ARHGEF17, SETMAR, SSH3, NUMA1, PBX1, TOR1AIP1, TACC2, RAB3D, BBS1, CEP68, GPRASP1, SVIL, CRBN, CRTC3, ZFYVE21, SLMAP, RASL12, SCAPER, STAT5B, ZAK, EZH1.

For SKCM (Skin Cutaneous Melanoma), we found that the mRNAs of the following genes satisfy these criteria: MLL4, LMTK2, APBB3, C17orf56, LOC388796, ANO8.

For STAD (Stomach adenocarcinoma), we found that the mRNAs of the following genes satisfy these criteria: KCNMA1, MAST4, FHL1, ATP2B4, TENC1, C20orf194, ASB2, C10orf26, TTC28, FAM13B, ITPKB, GNAO1, FAM129A, ZBTB4, FNBP1, FLNA, CCDC69, STON1, NFASC, PAPLN, ADCY5, LPP, NEGR1, ABI3BP, INPP5B, TNXB, ANGPTL1, ANK2, EPHA3, ZCCHC24, SETBP1, PRICKLE2, LTBP1, RGMA, DARC, KANK2, SYNPO.

For TGCT (Testicular Germ Cell Tumors), we found that the mRNAs of the following genes satisfy these criteria: ATF6, CTDSP2, MKL2, TEAD1, ZNF407, TRAPPC9, AHDC1, LANCL1, KCTD20, OXR1, SNX1, CSNK1G1, KIAA0247, LDOC1L, EPC1, GRLF1, ABHD2, RAIl, ARID1B, ITFG1, MUT, KIAA1737, LAMA2, KIAA1109, CCNI, DIXDC1, C6orf89, RNF144A, APPBP2, KLF12, ZFP91.

For THCA (Thyroid carcinoma), we found that the mRNAs of the following genes satisfy these criteria: KIAA0495, PHF21A, ZBTB5, SFRS6, NCOA5, ZNF814, IP6K2, IFT140, INTS3, ZNF559, SETD4, TGIF2, VILL, KCNC3, UBE2G2, FBXO9, IPW, DUOXA1, CACNA2D2, EFHC1, FAM189A2, GTF2IRD2P1, KIAA1683, AP4B1, SCAND2, CDRT4, UNKL, NYNRIN, ARMC5, MAPKBP1, USP40, VEGFA, OLFM2, FBF1, TCF7L1, MXD4, IKBKB, POFUT2, BOC, TCF7L2, RMST, TRO.

For THYM (Thymoma), we found that the mRNAs of the following genes satisfy these criteria: ZFYVE9, LOC399959, SIX1, PDGFC.

For UCEC (Uterine Corpus Endometrial Carcinoma), we found that the mRNAs of the following genes satisfy these criteria: RNMT, SON, MDN1, CELF1, RIPK1, YLPM1, XRN2, BPTF, RQCD1, PAFAH1B2, BOD1L, SBNO1, RNF169, PIK3R4, LRCH3, DCP1A, SF3A1, SLC9A8, TNRC6A, BRPF3.

For UCS (Uterine Carcinosarcoma), we found that the mRNA of the following gene satisfies these criteria: RHBDF1.

For UVM (Uveal Melanoma), we found that the mRNAs of the following genes satisfy these criteria: MAP1A, TCIRG1, ECM1, C14orf159, WARS, PCYOX1L.

In each of these cancer types, a possible therapeutic intervention would comprise modulating the abundance of one or more of the corresponding mRNAs. The modulation would comprise increasing the abundance of one or more of these mRNAs, decrease the abundance of one or more of these mRNAs, or a combination.

Lastly, yet another possible therapeutic intervention would comprise modulating the abundance of one or more of the above-mentioned cancer-specific tRFs in combination with modulating the abundance of one or more of the above-mentioned cancer-specific mRNAs.

Discussion

We carried out a comprehensive mining of 11,198 datasets from TCGA in search of statistically significant tRNA fragments. 10,274 of these datasets representing 32 human cancer types had associated records that are devoid of any special annotations ("whitelisted") and entered our downstream analyses. We found that nearly all tRNAs exhibit cancer-specific cleavage patterns. Additionally, we found that nucleus-encoded and MT-encoded tRNAs exhibit distinctly different behavior vis-à-vis to patterning and the abundance of the tRFs they generate. tRNA$^{HisGTG}$ represents an exception in that it gives rise to a specific collection of 5'-tRFs that contain a uracil in their −1 position (instead of the expected guanosine). The relative abundances of these −1U 5'-tRFs exhibit ratios that are maintained constant across all examined cancer types and in both health and disease. The analyses also revealed wide-ranging associations between tRFs on one hand, and mRNAs and proteins on the other. Many of the (positive and negative) associations involve partners that cross organelle boundaries: for example, they involve tRFs that arise from nucleus-encoded tRNAs and mRNAs whose proteins localize in the MT; or, tRFs that arise from MT-encoded tRNAs and mRNAs whose proteins localize in the nucleus. These associations provide new insights to understanding the layer of post-transcriptional regulation. Moreover, in the short term, these relationships suggest intriguing novel viewpoints from which to study inter-organelle communication. In the longer term, there is great potential in leveraging these relationships to develop novel diagnostics and novel therapeutics that are tuned to individual cancers.

We note that we carried out our study with full understanding that the presence of documented modifications across the span of tRNAs (50-56) has the potential to pause or stop reverse transcription. Two recently reported methods (57,58) introduced a demethylation step that was shown to improve the enumeration of tRFs for some isoacceptors. It is conceivable that the 20,722 tRFs we have identified are but a subset of a larger class of tRFs that are active in cancer tissues. By studying the TCGA datasets, we work with the best and most comprehensive datasets that are available for the time being. Even though these datasets are arguably incomplete, they remain invaluable in helping us shed a first light on important characteristics of tRFs across tissues.

A key finding of the analysis is the diversity of the identified tRFs. We mined a total of 20,722 tRFs that range widely in terms of abundance, length, structural type, and the location of their 5' and 3' termini. The tRFs also depend on the identity of the corresponding template isodecoder/isoacceptor (10,59) and the identity of the genome (nuclear vs. mitochondrial) hosting the tRNAs from which the tRFs arise (22). The type of the cancer that is analyzed each time further modulates these tRF attributes; we will return to this point below. Given that our computational pipeline complements other available methods by exhibiting superior sensitivity and specificity (60), our results significantly enrich the publicly available data with new information that can be readily exploited in future studies.

Approximately one third of all identified tRFs are of ambiguous origin. In other words, if one examines the entirety of the human genome, the sequences of these tRFs can be found within annotated tRNAs as well as at loci that contain only partial instances (e.g., one half or one third) of mature tRNA sequences (4,9,22). Some of these loci resemble full-length tRNAs (4,61) whereas other loci correspond to partial tRNAs, repeat elements or mRNAs (4), and, possibly, non-transcribing sequences. Recognizing this complication, in parallel work, we designed and implemented MINTmap (60), a freely-available tool that facilitates the identification of tRFs of ambiguous genomic provenance. Strictly speaking, ambiguous tRFs require special attention, particularly when experimental work is being considered, as they cannot be linked unequivocally to transcription from a tRNA template. We provided examples of non-exclusive tRFs that are correlated with mRNAs containing an embedded instance of the corresponding tRF. Even though there were few such examples in TCGA, they warrant caution because their biogenesis may not be linked to tRNA transcripts.

The 22 mitochondrial tRNAs were found to be very strong contributors to the pool of distinct tRFs, when compared to the 610 nucleus-encoded tRNAs. In fact, 29% of all discovered tRFs derive from the 22 MT tRNAs (Supp. Table S1). This finding mirrors our previous results (4,8,9,22) and extends them to the numerous human tissues that are part of TCGA. Moreover, MT-tRNA-derived tRFs show marked differences when compared with the nuclear-tRNA-derived tRFs. Indeed, for a given cancer type, the mitochondrial tRFs differ from their nuclear counterparts in length, relative abundances, dominant structural category, etc.

Figure 2B:
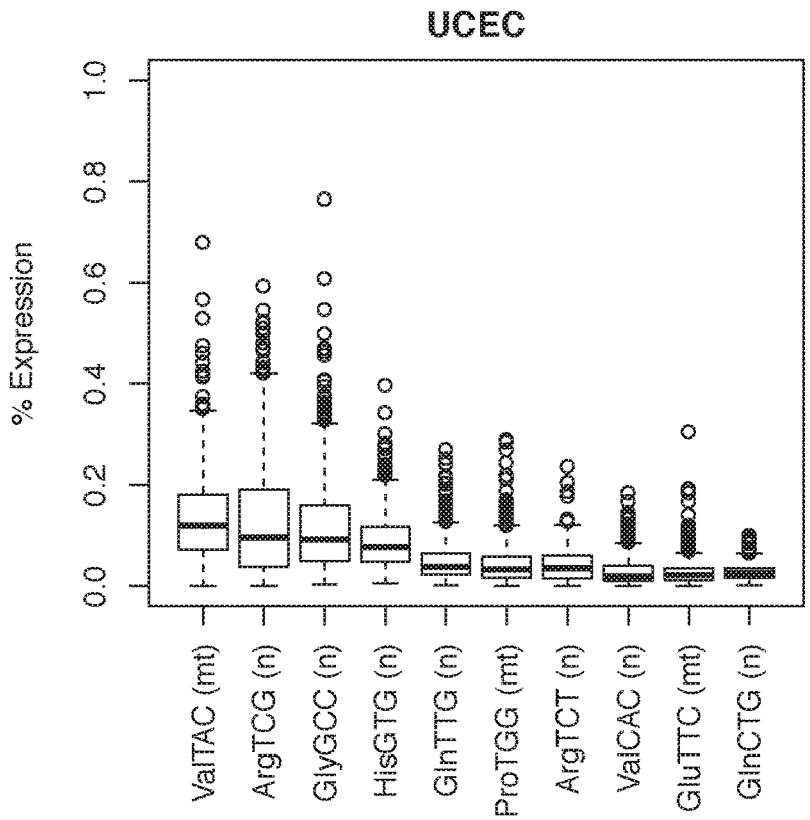

Even when we confine ourselves to a specific genome, i.e., nuclear or MT, we find a strong dependence of the tRF populations on the identity of the parental isoacceptor. These populations change across cancer types and are characterized by differences in the structural type of the produced tRFs (FIG. 1), the identity of the isoacceptor that produces most distinct tRFs (FIG. 2), and the relative abundances of the tRFs (Supp. Table S3).

Moreover, the tRF populations show cancer-dependent differences with regard to the specific endpoints that are favored by tRFs of a given structural type (Supp. Table S3). Even if we ignore this cancer-dependence and look at the structural types holistically, it is evident that the 3' termini of 5'-tRFs and the 5' termini of 3'-tRFs span a large number of choices (FIG. 3). Notably, these preferences are very similar to what was reported recently for the plant *A. thaliana* (24), which suggests common underlying biogenetic mechanisms and, possibly, functions. Furthermore, the cancer-dependence of the observed fragments suggests a tissue-specific dimension in the biogenesis of tRFs. This notion is supported, at least in part, by recent results showing that the channeling of tRNAs into the miRNA Dicer-Ago pathway depends on the structure of the RNA molecule (62). Given that RNA folding is a dynamic process (63), we posit that the observed differences in tRF cleavage patterns among tissues are caused by differences in each tissue's molecular physiology.

The i-tRFs, a novel structural type that we discovered recently (4), exhibit the largest diversity in TCGA. i-tRFs represent more than 75% of the 20,722 identified tRFs. As FIG. 3 shows, i-tRFs have a multitude of preferred starting and ending positions. The choice of these endpoints strongly depends on cancer type (Supp. Table S3).

Despite the pronounced dependence of tRF profiles on cancer type, some isoacceptors stand out by producing tRFs with profiles that remain exceptionally consistent in healthy and diseased tissues, and across all cancer types. Of note here is the nuclear tRNA$^{HisGTG}$ that produces −1U 5'-tRFs with lengths that range between 16 and 22 nt and have abundances that are characterized by a unique property. Specifically, the abundances of −1U 5'-tRFs with 3' termini that differ by a single nt (all these tRFs share the same 5' terminus) alternate between high and low, whereas their ratios remain constant across all analyzed normal and cancer samples, and all 32 cancer types. The resulting 'see-saw' pattern spans a limited and persistent range of ratios that can be seen in FIG. 4 and FIG. 14. It should be stressed, however, that even though the ratios of these −1U tRFs remains constant, their absolute abundances do change from cancer type to cancer type. We did not find any other isoacceptors whose tRFs exhibited this unusual behavior. The exquisite stability of these ratios across tissues, and the uniqueness of tRNA$^{HisGTG}$ in this regard among tRNAs, leads us to conjecture that these −1U 5'-tRFs participate in fundamental cellular processes that are currently unknown.

Of equal importance is the finding that across all human tissues that we examined, the 5'-tRFs from tRNA$^{HisGTG}$ contain primarily a uracil at the His(−1) position. This is a new and unexpected finding, because the mature tRNA$^{HisGTG}$ requires guanylation of its 5'-terminus before it can be recognized by its cognate aminoacyl tRNA synthetase. By comparison, the levels of 5'-tRFs from tRNA$^{HisGTG}$ with G, A, or C at the −1 position were low. Recent work with the human breast cancer model cell line BT-474 suggests that −1U 5'-tRFs from the tRNA$^{HisGTG}$ locus arise from the mature tRNA (28). However, it is unclear for the time being whether the −1U 5'-tRFs that we discovered in the multitude of human tissues that we analyzed above arise from the processing of the mature tRNA$^{HisGTG}$ or its precursor. Further complicating this determination is the fact that the DNA template at four of the 12 genomic loci encoding isodecoders of tRNA$^{HisGTG}$ contains a T at the −1 position.

Figure 16B:
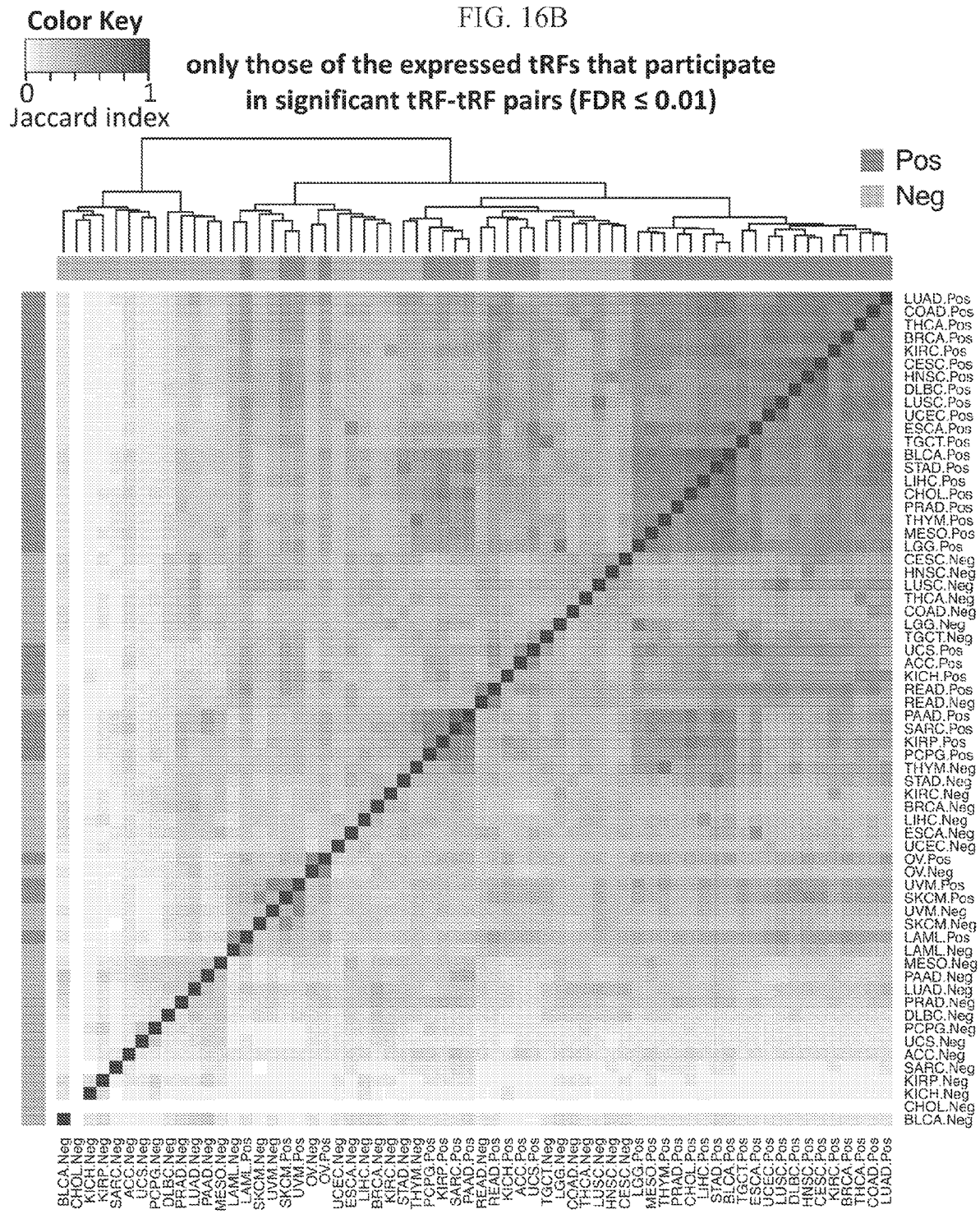
Figure 17C:
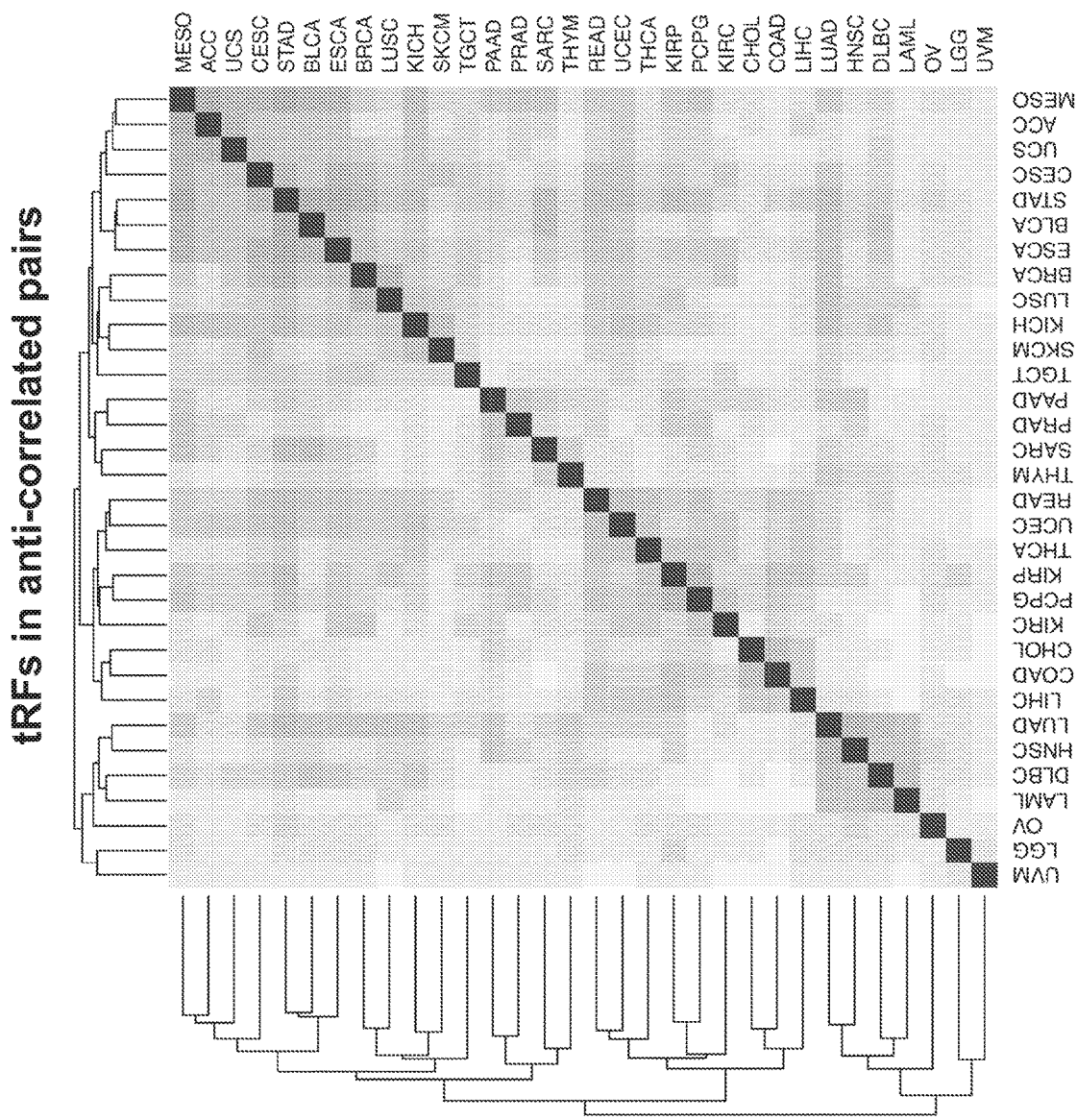
FIG. 17 Jaccard/tRFs vs. mRNAs and miRNAs vs mRNAs across cancers. Even though any two cancers express largely the same collection of tRFs, miRNAs and mRNAs, the subset of tRFs and miRNAs that are anti-correlated with mRNAs differs characteristically across cancers. (A-B) Heatmaps and hierarchical clusterings (metric: Euclidean distance) showing what portion of the miRNAs (A) or mRNAs (B) that were considered for the correlation analyses are shared between any two cancer types. (C) Heatmap and hierarchical clustering (metric: Euclidean distance) showing what portion of the tRFs that are anti-correlated with mRNAs in cancer type X are also anti-correlated with mRNAs in cancer type Y (D) Heatmap and hierarchical clustering (metric: Euclidean distance) showing what portion of the miRNAs that are statistically significantly anti-correlated with mRNAs in cancer type X are also anti-correlated with mRNAs in cancer type Y (E) Heatmap and hierarchical clustering (metric: Euclidean distance) showing what portion of the mRNAs that are statistically significantly anti-correlated with tRFs or miRNAs in cancer type X are also anti-correlated with tRFs or miRNAs in cancer type Y.
Figure 17E:
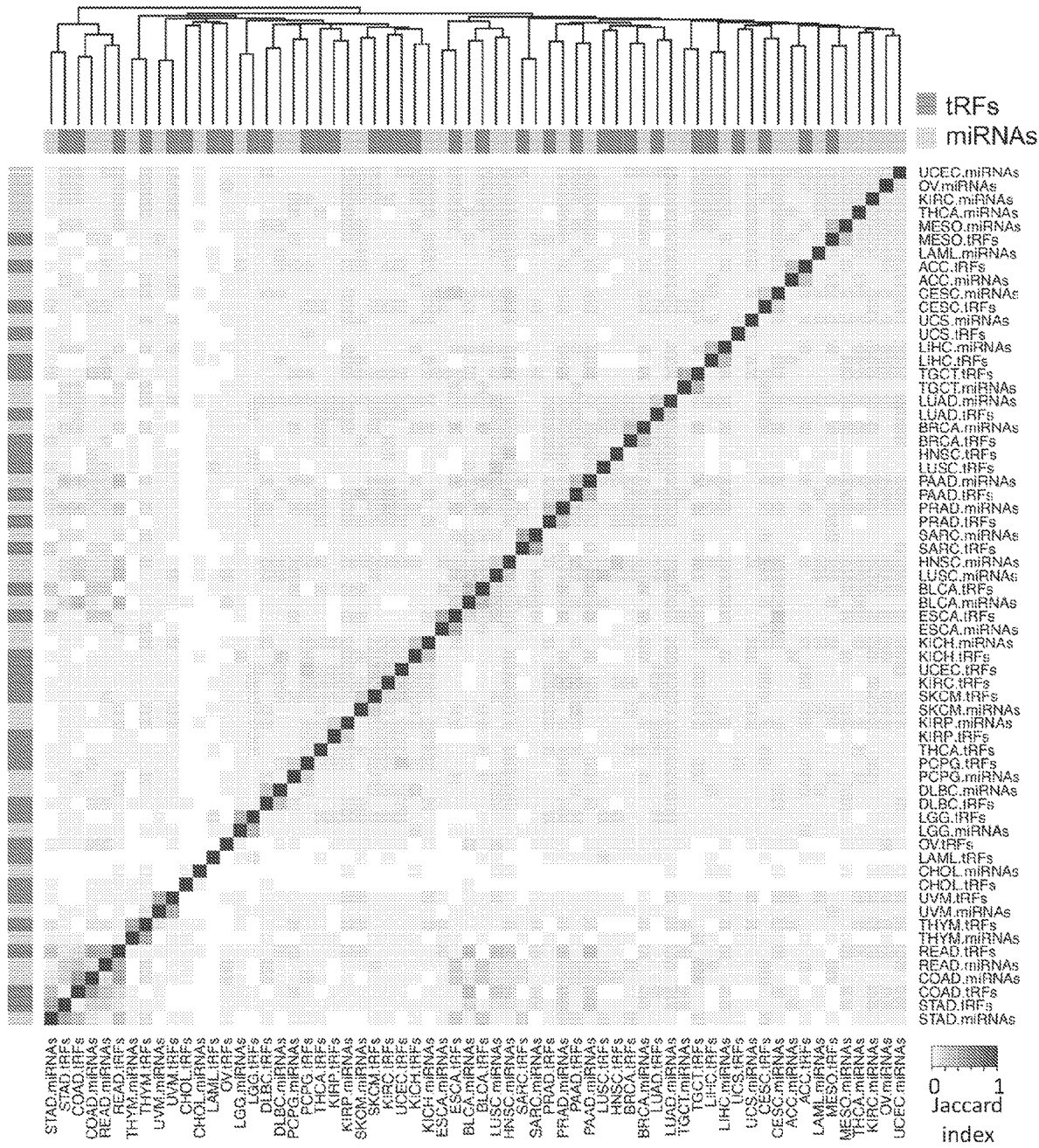

Given the nascent nature of this field and the apparent diversity and context-specific nature of the tRFs, it is not surprising that very little is known currently about their functional roles. With that in mind, we placed particular emphasis on leveraging the TCGA datasets to shed as much light as possible on this question. First, we found pairs of tRFs that are correlated across samples. Within a given cancer type, the same tRFs were found correlated across all available samples. However, different groups of tRFs were correlated across cancers (FIG. 16B). We then extended this analysis to protein-coding transcripts and found a very rich repertoire of negative correlations involving tRFs and specific mRNAs. These tRF-mRNA anti-correlations depended strongly on cancer type (FIG. 17E). Earlier reports by others and us provided evidence of tRFs acting like miRNAs via Argonaute loading (4,10,29). In light of this, we also identified the group of mRNAs that are negatively correlated with miRNAs. The miRNA-mRNA anti-correlations depended strongly on cancer type as well (FIG. 17E).

We wish to stress one point here. It is entirely possible that direct molecular coupling drives some of the uncovered correlations. However, in the absence of any additional information, it will be prudent to treat these relationships as associations. For example, these associations could result from a common upstream regulator, from belonging to the same pathway, or because some tRFs arise from the same precursor transcript. Considering the apparent diversity across cancer types, it appears that it will be necessary to unravel the mechanisms underlying the correlation patterns separately for each cancer. Moreover, the presented analysis makes it evident that tRFs have tissue-specific roles that are also more diverse than those of miRNAs (see below). Regarding the diversity in function, Ago-loaded tRFs are but one of multiple facets of tRF biology. Indeed, one should also recognize the interaction of tRFs with other RNA binding proteins and with the translation machinery (1,5,64).

Even though the specific mRNAs that are found associated with tRFs differ between cancer types, the pathways to which these mRNAs belong show striking similarities across cancers. This observation is supported through a DAVID analysis of gene ontology terms that reveal four super-groups: cell adhesion, chromatin organization, and developmental processes (FIG. 18D). Additionally, our analysis generated several observations that were reported recently in the literature. For example, we found several correlations involving tRFs from isoacceptors of Gly, Asp, Glu, and Tyr with the mRNAs of HMGA1, CD151, CD97 and TIMP3: these mRNAs were recently reported to be controlled by tRFs from these tRNAs in a YBX1-dependent manner (64). Additionally, we enumerated more than 3,000 correlations of tRFs with ribosomal proteins, either mitochondrial or cytoplasmic, as well as more than 100 correlations of tRFs with aminoacyl tRNA synthetases, particularly IARS and MARS, which is in agreement with previous work in the field (5,65).

We examined at the isoacceptor level the correlations of the above-mentioned four super-groups of mRNAs with tRFs. We split the mRNAs into those that are negatively correlated with tRFs only and those that are negatively correlated with both tRFs and miRNAs in the same cancer type. In each case, we computed the fraction of the 32 cancer types supporting a specific "tRF isoacceptor—GO term" or a specific "miRNA+tRF isoacceptor—GO term" relationship. This revealed a tight coupling of specific isoacceptors with specific GO categories that persists across multiple cancer types (FIG. 5A), but is manifested by different tRF-mRNA pairings in each cancer (FIG. 17E). This suggests the existence of a previously unrecognized tight coupling between MT and nuclear processes.

The seeming diversity of negatively-correlated tRFs and mRNAs in the face of persistent relationships between tRFs and pathways made us examine the cellular localization of proteins whose mRNAs are negatively correlated exclusively with either miRNAs or tRFs. Specifically, in the case of miRNAs we examined the individual isomiRs that are produced by the various miRNA loci that are transcribed in the TCGA samples that we analyzed. Juxtaposing the findings for isomiRs and tRFs, and doing so separately for positive and negative correlations, revealed a striking dichotomy (FIG. 5B). Specifically, we found that the localization patterns of proteins produced by mRNAs that are correlated with isomiRs are largely unchanged across the 32 cancer types. On the other hand, proteins produced by mRNAs that are correlated with tRFs show localization patterns that depend strongly on cancer type.

It is important to note here that, by comparison to miRNAs, the mechanisms of biogenesis and function of tRFs remain poorly understood for the most part. Nonetheless, as we mentioned above, it is known that short tRFs are loaded on Argonaute and act like miRNAs. With that in mind, let us assume for the moment that the uncovered anti-correlations imply tRF-mediated regulatory events that mirror the action of miRNAs on mRNAs. Then, our findings (FIG. 5A) suggest an intriguing "division of labor" where some mRNAs are regulated solely by miRNAs, some solely by tRFs, and some by both miRNAs and tRFs. This synergistic hypothesis is further supported by the findings that are summarized by FIG. 5B and indicate that tRFs are likely involved in cell-type-dependent interactions, analogously to what we reported previously for miRNAs (66). An instance of this dynamic and context-dependent network of interactions was shown for tRFs from tRNA$^{Gln}$ that interact with YBX1 in breast cancer cell lines (64) but not in cervical cancer cell lines (65).

Earlier (30-32) and more recent work (15) on the non-random placement of repeat elements on the genome as well as the finding that repeat elements become demethylated as stem cell differentiation progresses (67), led us to examine one more possibility. Specifically, we examined possible associations between tRFs and the sequence composition of the genomic loci for mRNAs participating in these identified positive and negative correlations. We analyzed unspliced mRNAs separately from their intronic and exonic regions. We also distinguished between repeat elements that are sense with regard to the studied sequences and ones that are antisense. We found a strong enrichment of sense repeats in the mRNAs that are anti-correlated with tRFs with the bulk of the signal being contributed by the intronic regions of these mRNAs (FIG. 5C). The observed enrichments depend strongly on cancer type, and on the category of the embedded repeats. The fact that tRFs have different correlations with repeat elements in different cancer types suggests a complex system-wide interaction network and a compendium of associated molecular events that differ from cancer type to cancer type. Currently, the roles of repeat elements in human cancers are not understood. However, the observed enrichments are statistically significant (p-val≤0.001). Thus, it is reasonable to assume that these wide-ranging associations are actively leveraged by the cancer cell (68) in ways that remain to be elucidated.

We note that several of the GO terms that are part of the four general pathways we described above (cell adhesion, chromatin organization, and developmental processes) are significantly over-represented in the group of genes that overlap with Alu elements (32). Our results on the link of tRFs with repeat elements come on the heels of two recent and related publications. First, tRFs from the tRNA$^{GlyGCC}$ isoacceptor were shown to repress expression of genes associated with the retroelement MERVL in mice (15). Second, tRFs were shown to increase in *Arabidopsis* pollen in a Dicer-dependent manner and to specifically target transposable elements (69). It is unclear currently whether the tRFs in human cancers act in a way similar to what is suggested in plants, i.e. to suppress transposon activity. Notably, the fact that tRFs have different correlations with repeat elements in different cancer types suggests a complex system-wide interaction network and a compendium of associated molecular events that differ from cancer type to cancer type. These correlations and data could start shedding light on the peculiar roles of repeat elements in human diseases and cancers (70).

Figure 11B:
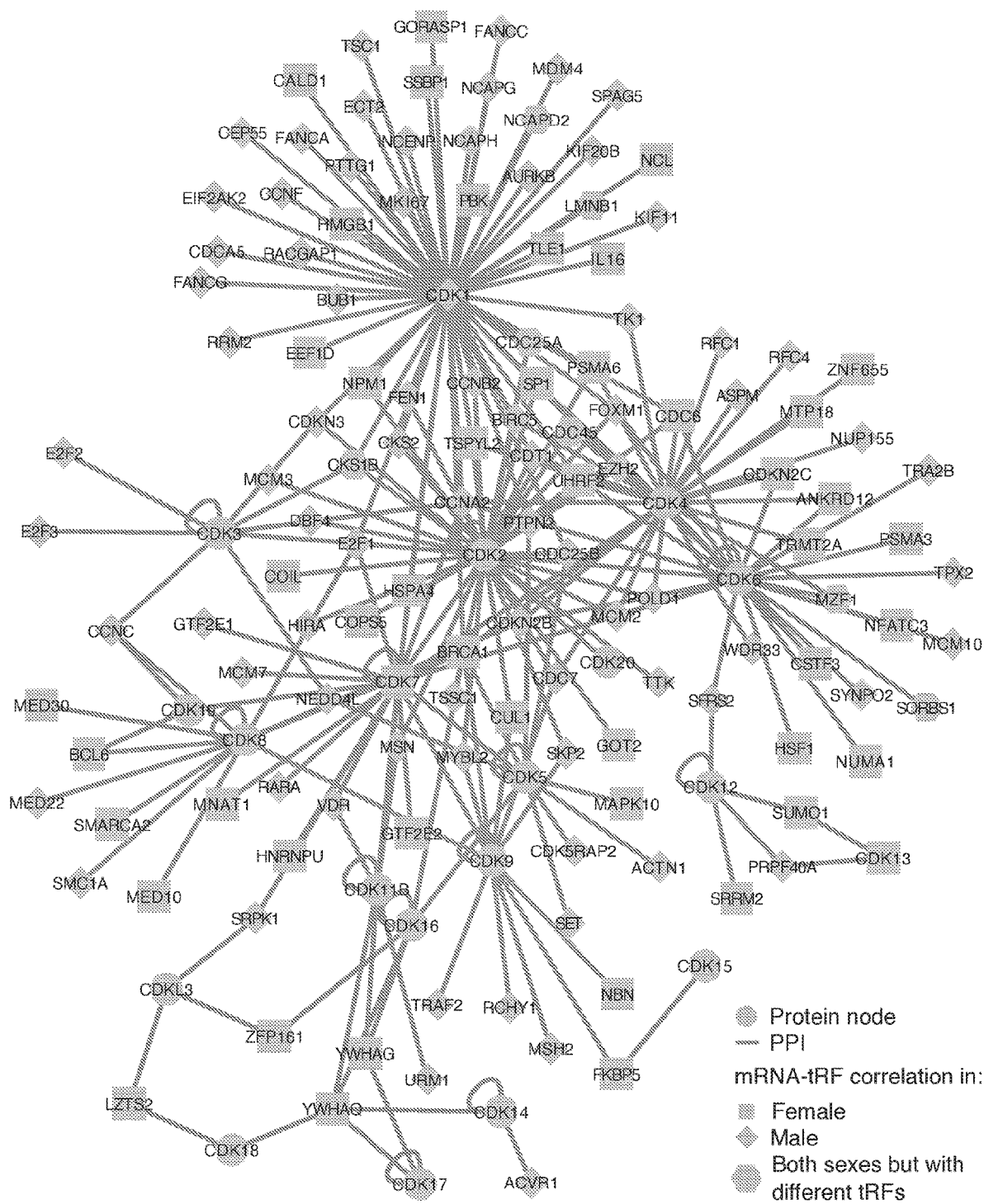

Previously, we demonstrated for miRNA isoforms that their abundance profiles in human tissues depend on a person's sex, population origin, and race (71), as well as on tissue, tissue state and disease subtype (72). We also demonstrated that miRNAs are not unique in this regard and that tRNA fragments have the exact same dependency on sex, population origin, race, tissue, tissue state and disease subtype (4,9). Working with the TCGA samples we had the opportunity to evaluate the possibility that similar dependencies might exist in LUAD, TNBC, and BLCA. In the case of LUAD, we highlighted a dependency of tRF profiles on sex (FIG. 6). In the case of TNBC, we highlighted a dependency of tRF profiles on the patient's race (FIG. 19). In the case of BLCA, the sex-dependent correlations that emerged are striking: we found that specific isoacceptors have a propensity for producing tRFs whose correlations with mRNAs depend strongly on the patient's sex (FIG. 11A). In terms of pathways, we found the greatest differences in genes regulating the cell cycle (FIG. 11B). These findings suggest the likely involvement of tRFs in the molecular events underlying sex-based disparities in BLCA.

Considering the emergence of tRFs as regulatory molecules in their own right, such dependencies are expected to modulate the regulatory events underlying a given disease in ways that have not been previously considered.

The multitude and diversity of the uncovered tRFs, and the multiplicity of associations between tRNA fragments and various cancers, suggest that a lot more work will be required before the community can improve its understanding of the roles of tRFs in the cancer context. To facilitate investigations, we enhanced our MINTbase repository (22) with a module that is specific to TCGA. The module provides access to all of the tRFs that we mined from TCGA. Importantly, the module permits very involved interactions with the contents of MINTbase by allowing elaborate search requests that require only minimal effort on the part of the user. We stress that although the TCGA portion of MINTbase is static, its non-TCGA portion is dynamic and growing steadily through the contributions of tRF profiles by different research teams. We designed the TCGA module in a way that permits users to compare TCGA findings with the ever-growing non-TCGA data.

In summary, analysis of the entirety of the TCGA repository revealed a very rich population of tRNA fragments. The identities and relative abundances of these fragments depend on cancer type. They also depend on the identity of the parental isoacceptor. Yet, tRF profiles remain essentially constant within samples of the same cancer type, underscoring the constitutive nature of these fragments. These tRFs exhibit strong associations with one another and with other molecular types such as mRNAs (and, by extension, miRNAs) suggesting the existence of numerous regulatory interactions that await discovery and characterization.

Methods

Datasets 11,198 short RNA datasets were downloaded on Oct. 16, 2015 from TCGA's Cancer Genomic Hub (CGHub). We used datasets from both normal and tumor samples, which are identified by their TCGA barcode tag (01A, 01B and 01C for tumor; 11A, 11B and 11C for normal). These datasets already had adaptors trimmed and were converted back to FASTQ format using BamUtil's bam2FastQ tool (http://genome.sph.umich.edu/wiki/BamUtil—version 1.0.10). For each of these datasets, tRF profiles were generated using MINTmap60 and default settings. These profiles have been incorporated in MINTbase22.

Our analyses focused exclusively on whitelisted datasets. Generally, non-whitelisted samples are marked for withdrawal by the various TCGA projects for reasons that range from incorrect pathologic diagnosis to exclusion on the basis of patient medication history. Clinical metadata were downloaded from TCGA's data portal on Oct. 28, 2015. To help eliminate problematic and outlier samples that were identified by the various TCGA working groups, only datasets that did not have any special annotation notes within the clinical metadata were included (n=10,274).

The Various Categories of tRFs

In terms of structural type, the tRFs overlapping a mature tRNA sequence fall in one of five possible categories (1,60): a) 5'-tRNA halves or '5'-tRHs' (5,6,73,74); b) 3'-tRNA halves or '3'-tRHs' (2,75,76); c) 5'-tRFs2,75,76; d) 3'-tRFs2, 75,76; and, e) the "internal tRFs" or "i-tRFs" that we discovered and reported recently (4).

In terms of genomic origin, we characterize tRFs as "exclusive" or "ambiguous." The sequences of exclusive tRFs are encountered only within the span of mature CCA-containing tRNAs, and appear nowhere else on the genome. Ambiguous tRFs on the other hand have sequences that can be found both in mature tRNAs (the "tRNA space") and elsewhere on the genome. We recently published a methodology and standalone tool that automates the mining of tRFs from human RNA-seq datasets and automatically tags them as exclusive or ambiguous (60). Our analyses were based on both exclusive and ambiguous tRFs.

In terms of length, we generated tRFs with lengths between 16 and 30 nt inclusive. It is important to note here that the short RNA-seq profiles for the samples of the TCGA repository were generated by running deep-sequencing for 30 cycles. Although adequate for miRNAs, 30 cycles will generate inaccurate profiles for those tRFs that are longer than 30 nt. In the various TCGA datasets, these longer tRFs appear truncated and, thus, are represented in the TCGA as "30-mers." Our parallel work (7) as well as our previous analyses of TCGA from BRCA subtypes (4), and of non-TCGA datasets from prostate cancer (8) and liver cancer (22) show that there exist many distinct tRFs with length >30 nt that are very abundant. Moreover, in the case of TCGA BRCA, we found that the "30-mer" tRFs are differentially abundant between normal breast and BRCA (4), suggesting an association with disease states. We note that the adapter cutting step may have shortened artificially long tRFs into "30-mers", a problem that does not arise when analyzing shorter molecules such as miRNAs (77). Most of the analyses described below were based on tRFs with lengths 16-27 nt. Lest we miss potential important associations, we included tRFs with length 28-30 nt in those instances where doing so was warranted.

Nomenclature and Notation

We adhere to NIH/TCGA's definition of race: White (Wh) refers to person with origins in any of the original peoples of the far Europe, the Middle East, or North Africa; and Black or African American (B/Aa) refers to persons with origins in any of the black racial groups of Africa. Based on the provided information, the majority of TCGA samples are from either Wh or B/Aa donors. Smaller groups of samples were obtained from donors who are: a) American Indian or Alaska Native (i.e., persons having origins in any of the original peoples of North and South America, including Central America, and who maintain tribal affiliation or community attachment), b) Asian (i.e. persons having origins in any of the original peoples of the Far East, Southeast Asia, or the Indian subcontinent including, e.g., Cambodia, China, India, Japan, Korea, Malaysia, Pakistan, the Philippine Islands, Thailand, and Vietnam); and, c) Native Hawaiian or other Pacific Islander (i.e., persons having origins in any of the original peoples of Hawaii, Guam, Samoa, or other Pacific Islands).

tRNA Cleavage Patterns

For each of the 32 cancer types, we examined the following attributes:

location within the mature tRNA of the tRFs' 5' termini;
nucleotide composition within a rolling dinucleotide window that surrounds the 5' termini (positions −2/−1, −1/5'terminus, 5'-terminus/+1, +1/+2);
location within the mature tRNA of the tRFs' 3' termini;
nucleotide composition within a rolling-dinucleotide window surrounding the 3' termini, as above; and,
location of the tRFs' 5' and 3' termini with respect to the mature tRNA endpoints and upstream-stem or downstream-stem of the nearest loop (D, anticodon, or T), as applicable.

Support for each of the attributes was calculated using tRFs above threshold. For each attribute, and for the cancer being studied, we calculated its normalized support in two ways: a) by considering only distinct tRF sequences ignoring their abundance; and, b) by repeating the analysis taking into account the abundance of the tRFs.

Figure 14:
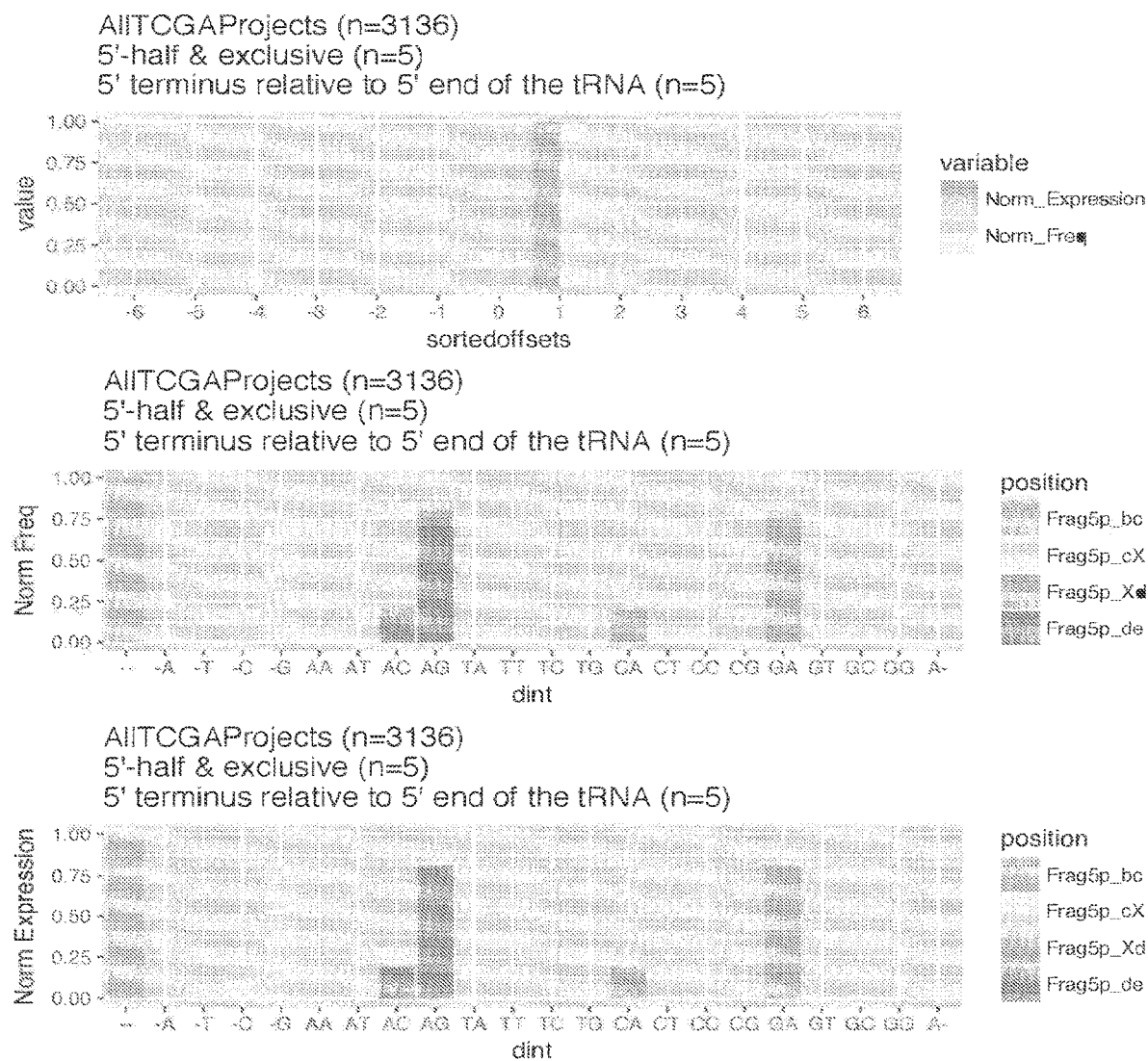
FIG. 14 Location and features of cleavage points. Plots showing how the identified tRFs are distributed along the length of mature tRNAs. The results are shown separately for each tRF structural type and separately for the tRFs' 5' and 3' termini. Moreover, the plots show the relative position of the tRFs with regard to recognizable landmarks along the mature tRNA including: its 5' end; the 5' end of the D-loop; the 3' end of the D-loop; the 5' end of the A-loop; the 3' end of the A-loop; the 5' end of the T-loop; the 3' end of the T-loop; and, the mature tRNA's 3' end. In each case, we report additionally the dinucleotide composition of the mature tRNA at the position at hand. In all cases, the plots are reported in two ways: considering normalized abundance of the tRFs; and, considering the diversity of the tRFs independent of their abundance. The plots are shown separately for each of 32 TCGA cancer types.
Figure 14:
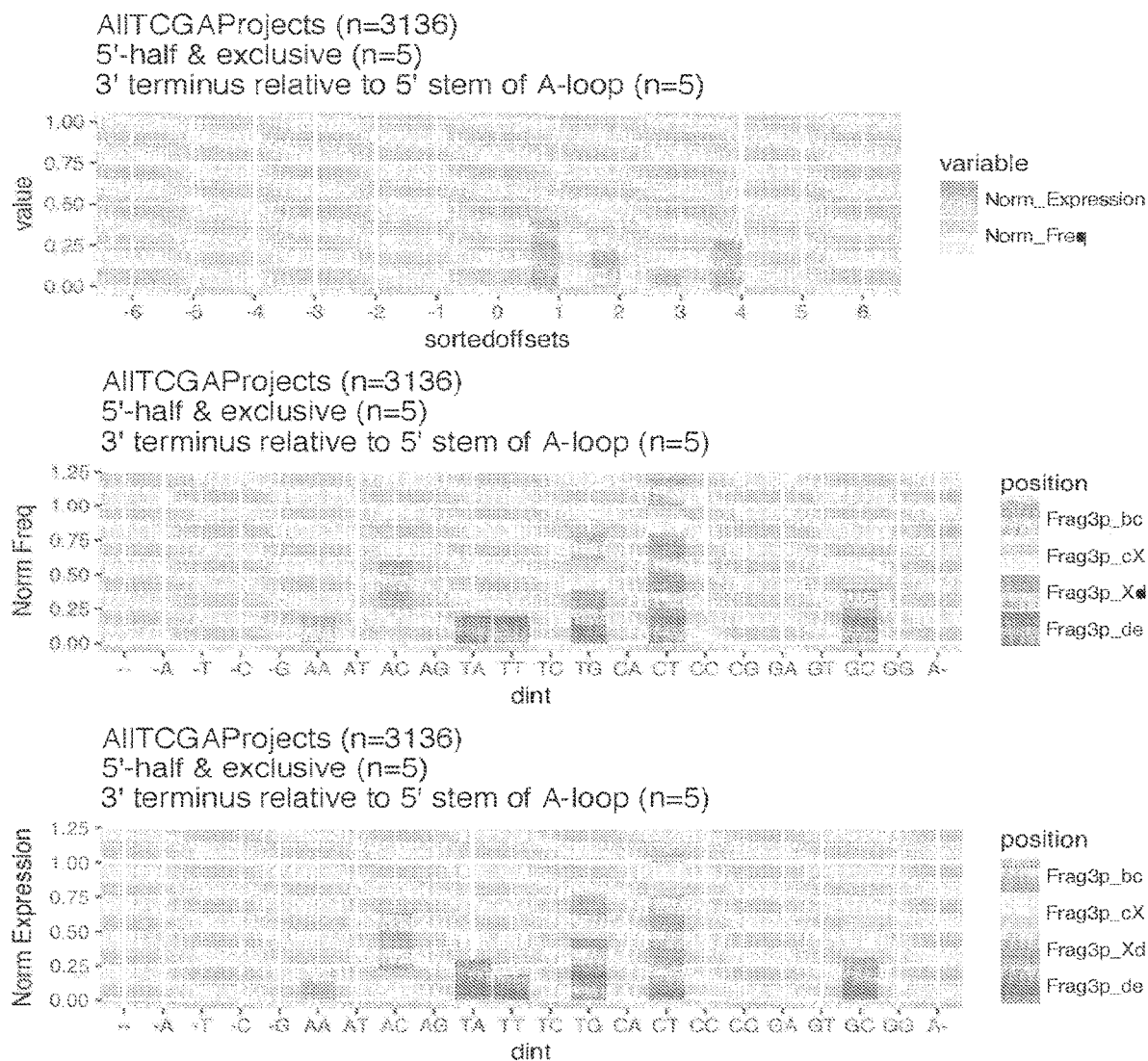
Figure 14:
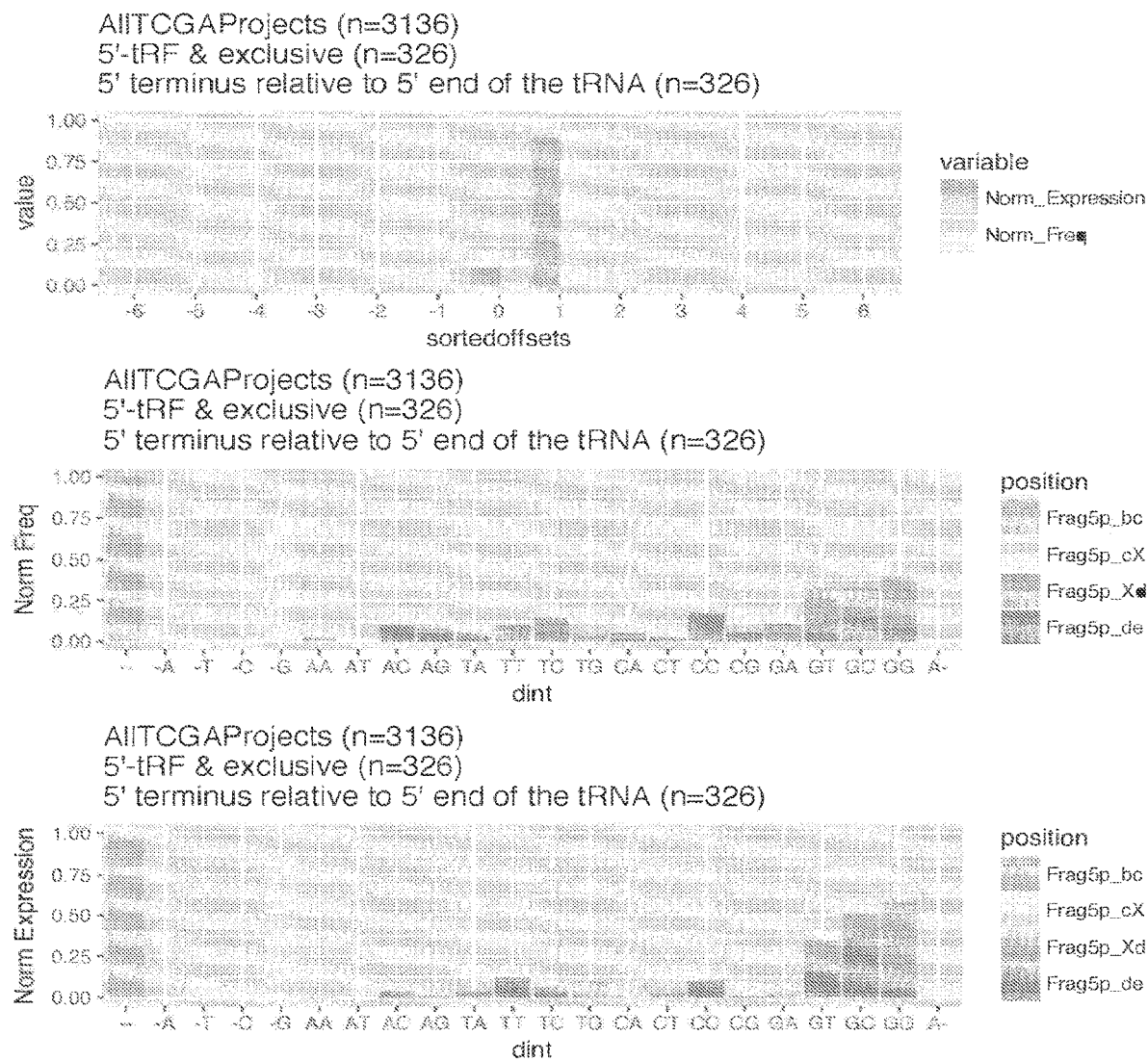
Figure 14:
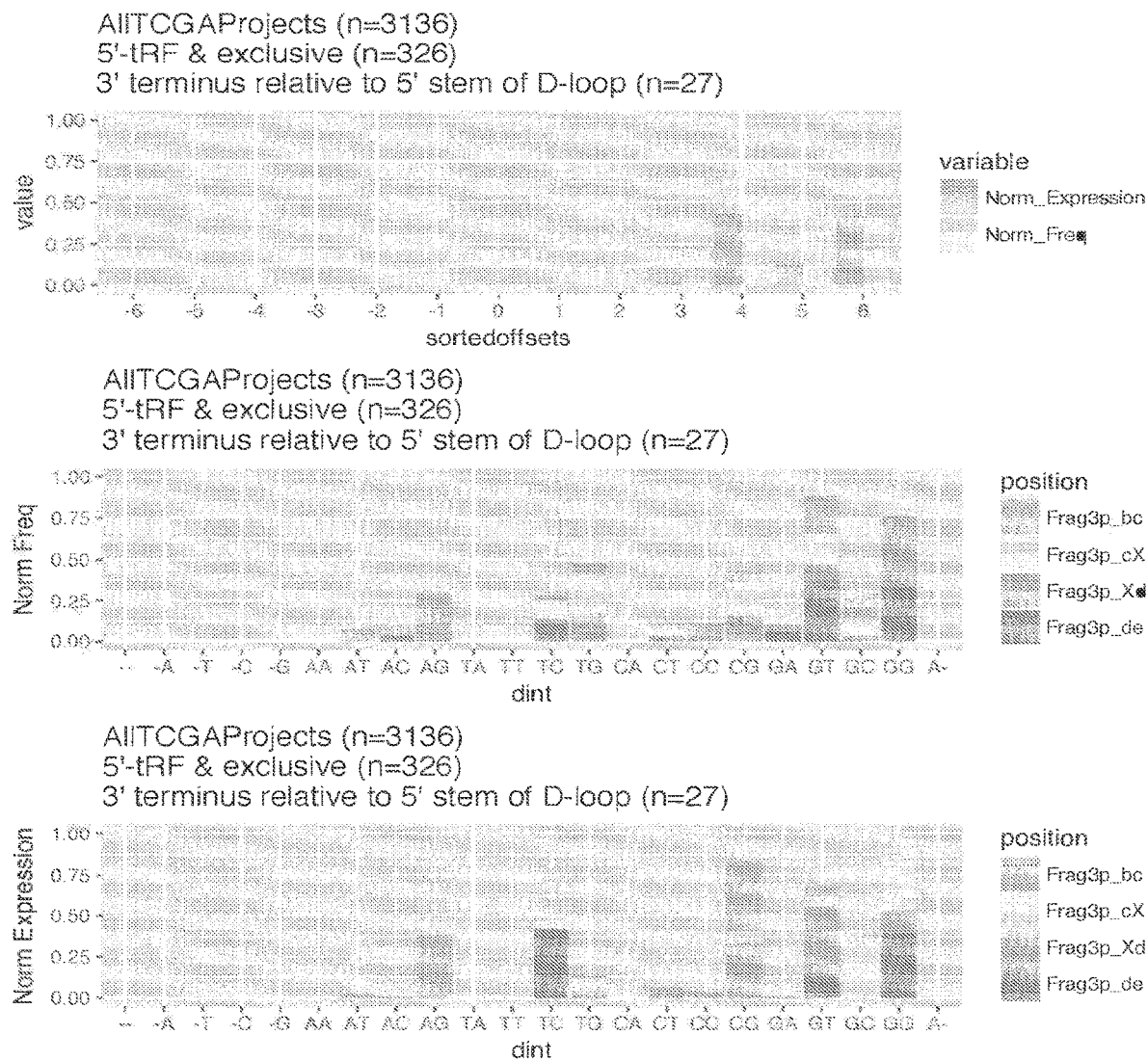
Figure 14:
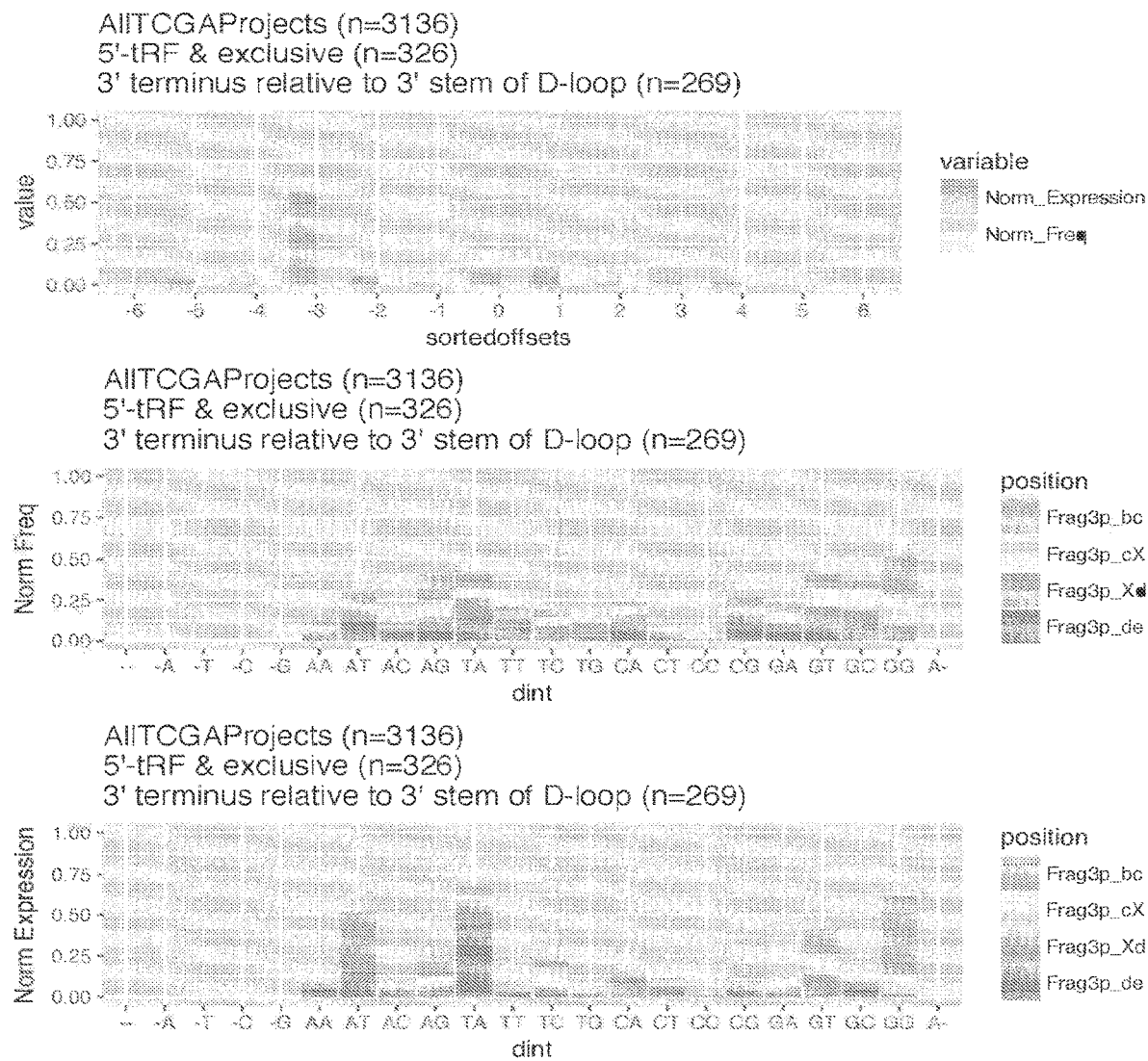
Figure 14:
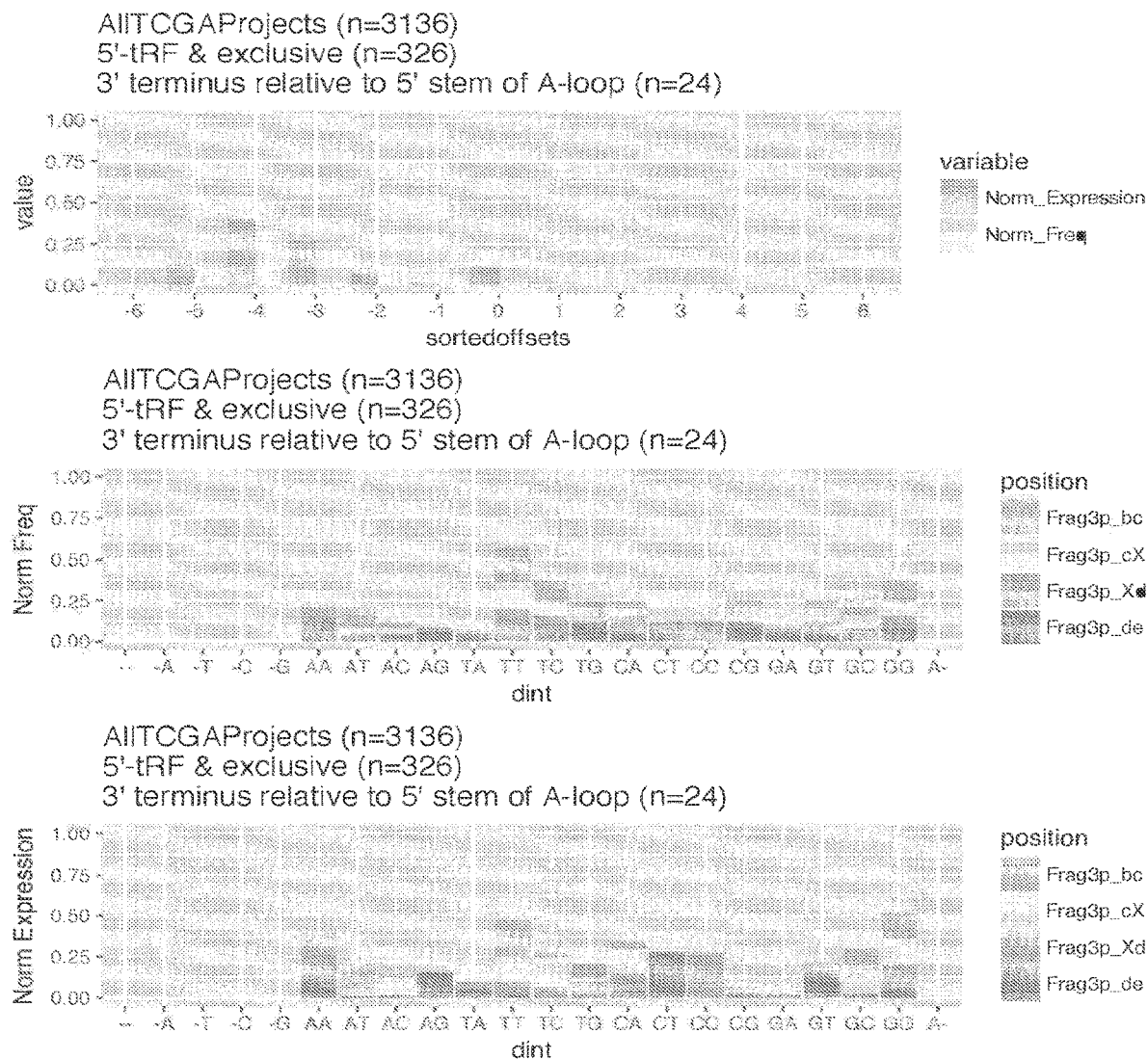
Figure 14:
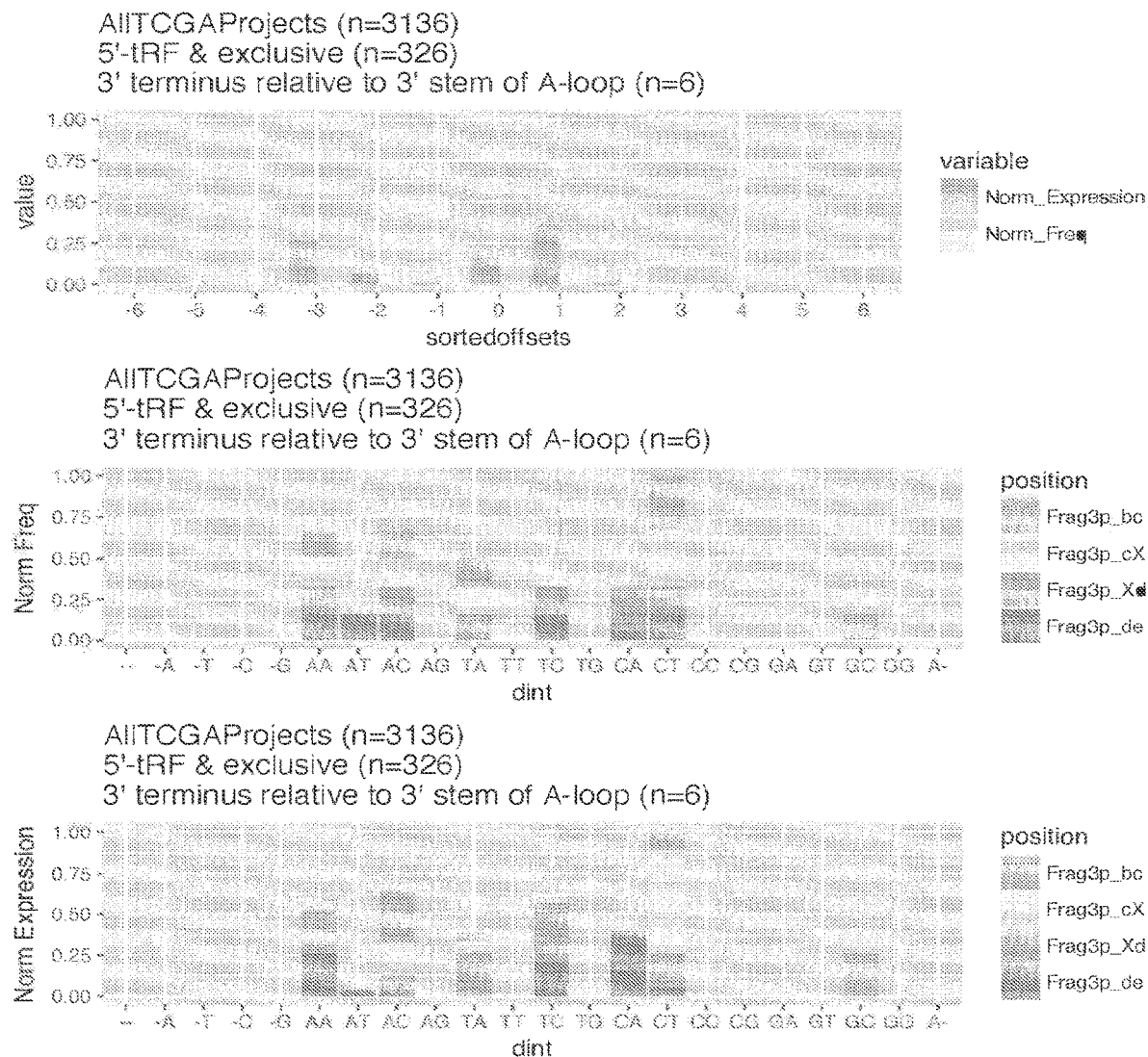
Figure 14:
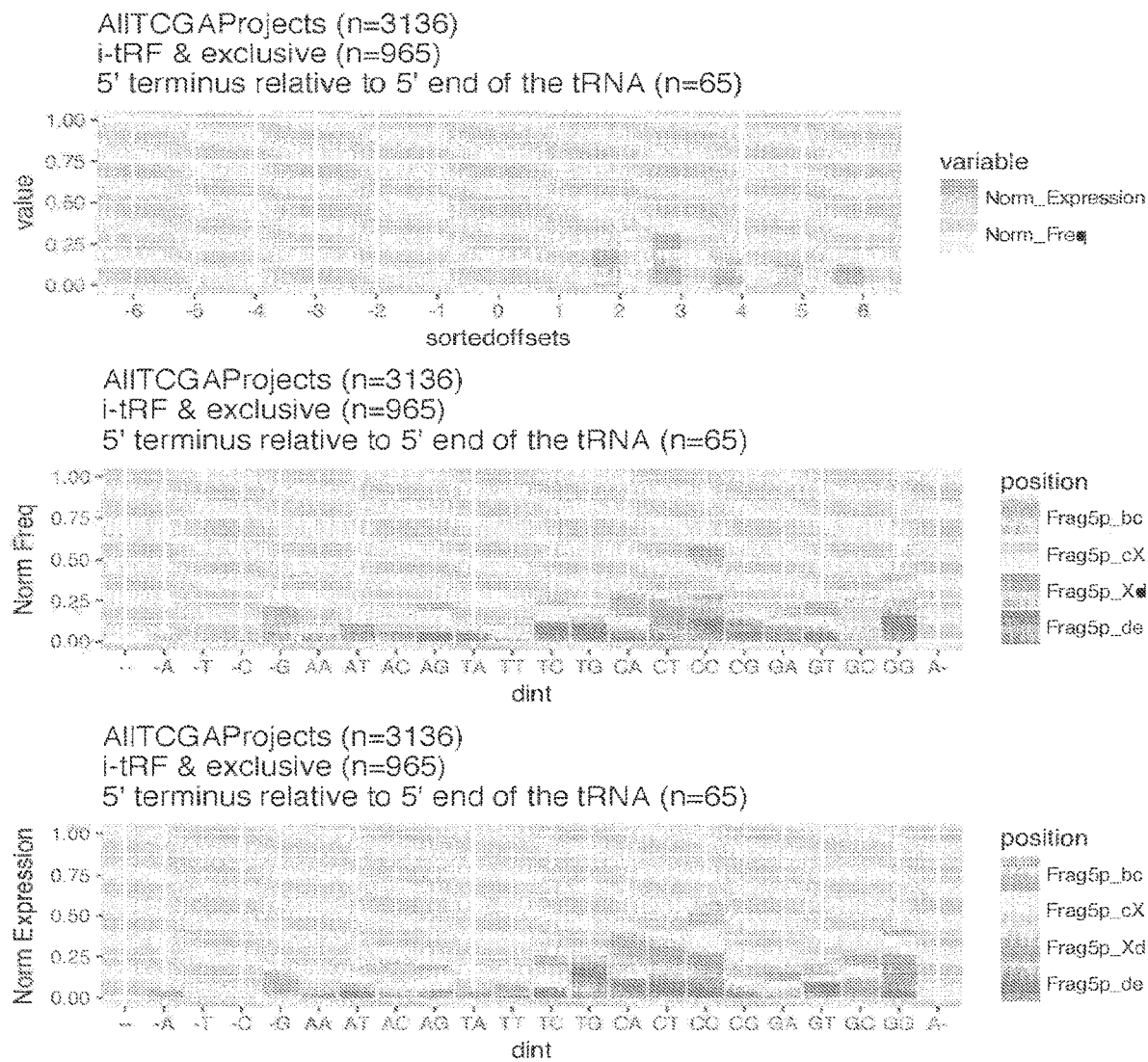
Figure 14:
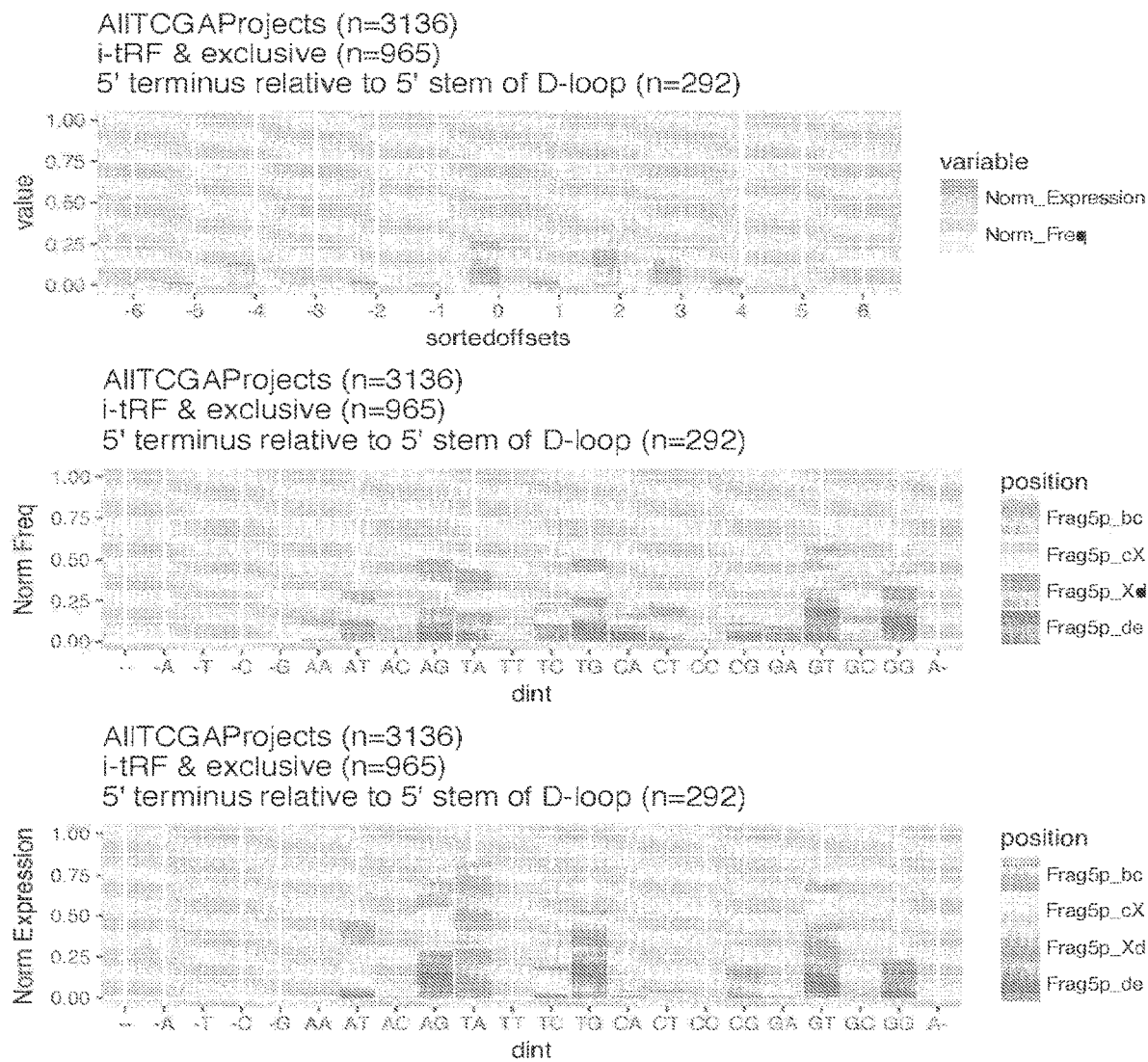
Figure 14:
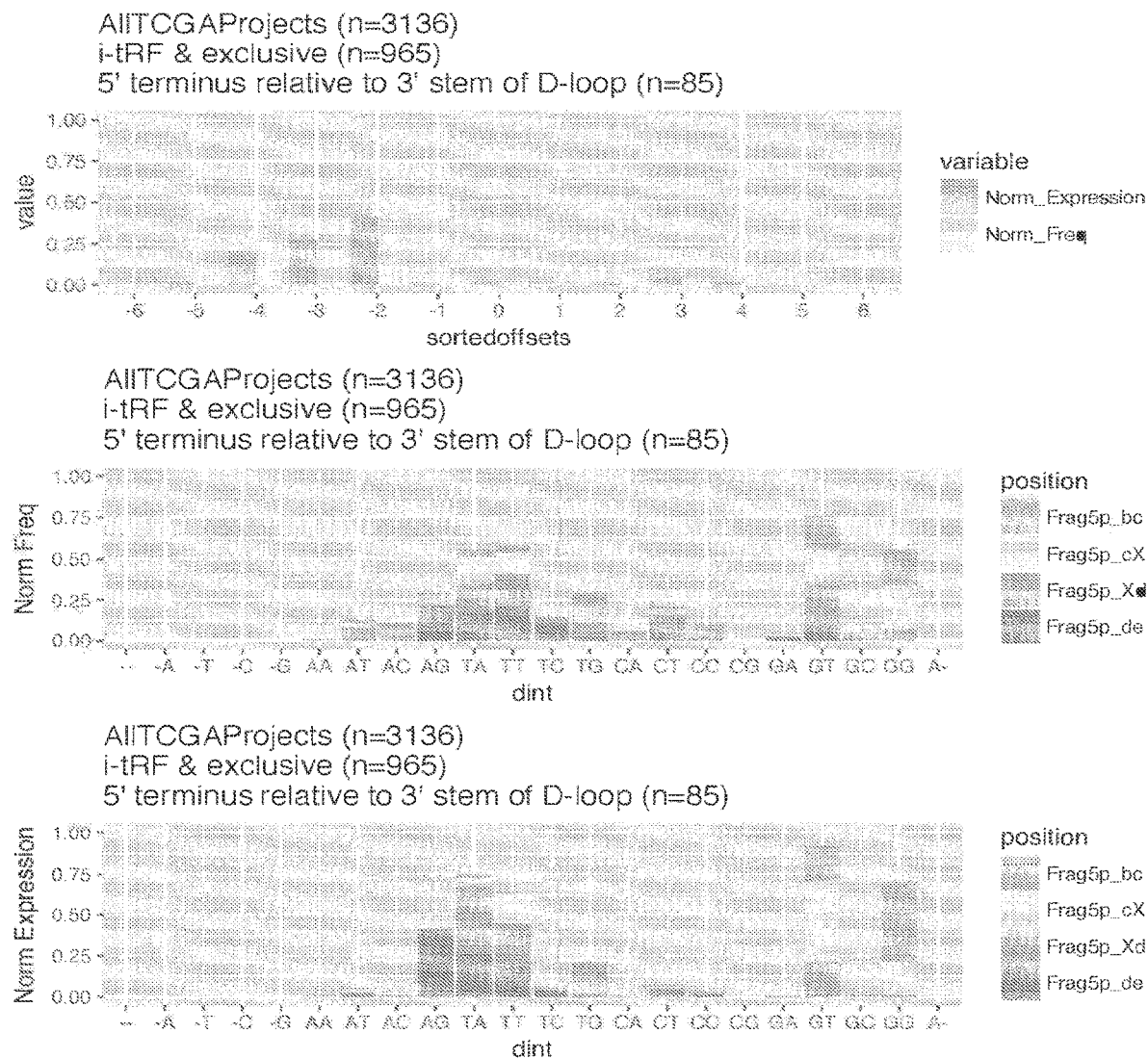
Figure 14:
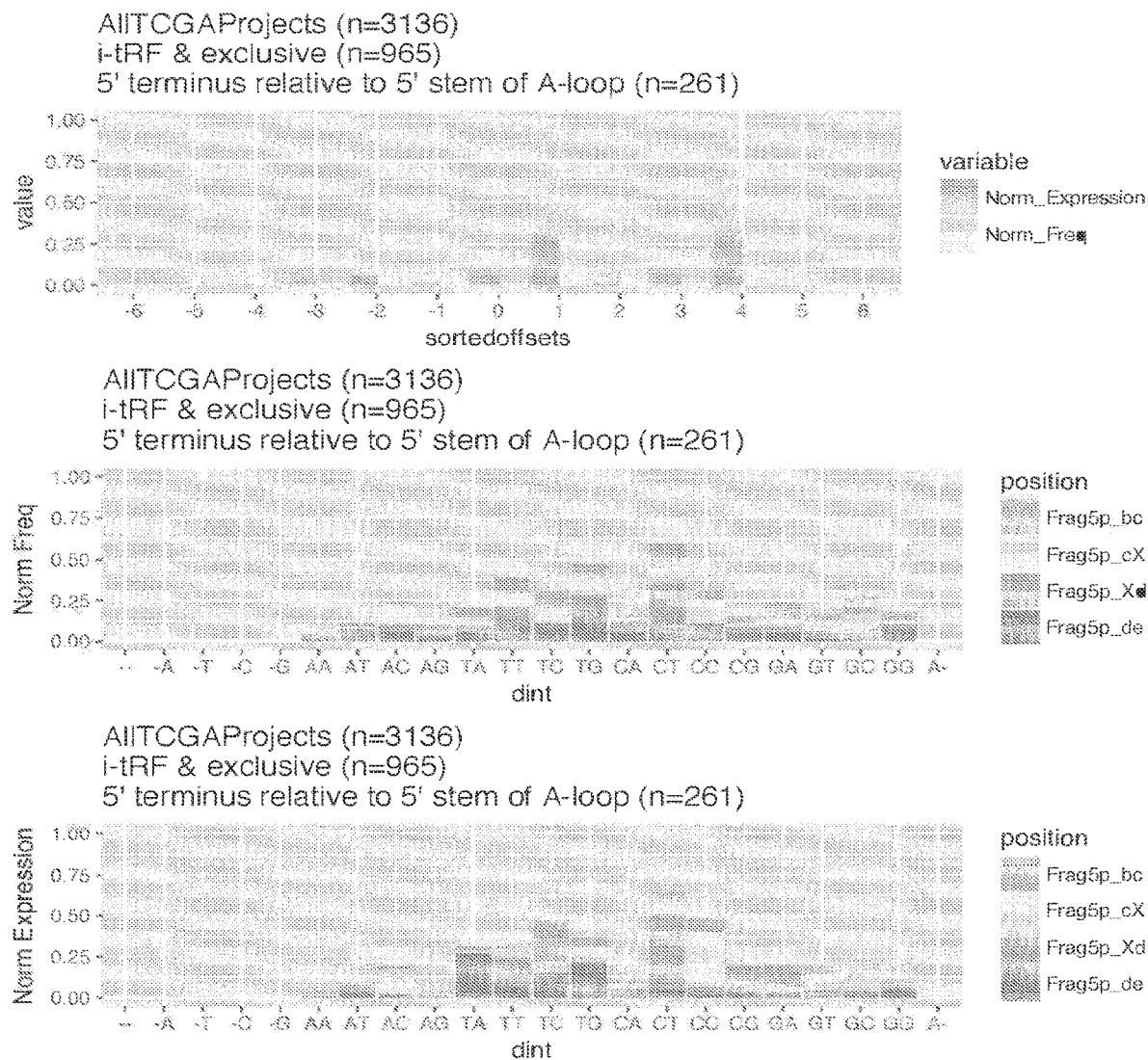
Figure 14:
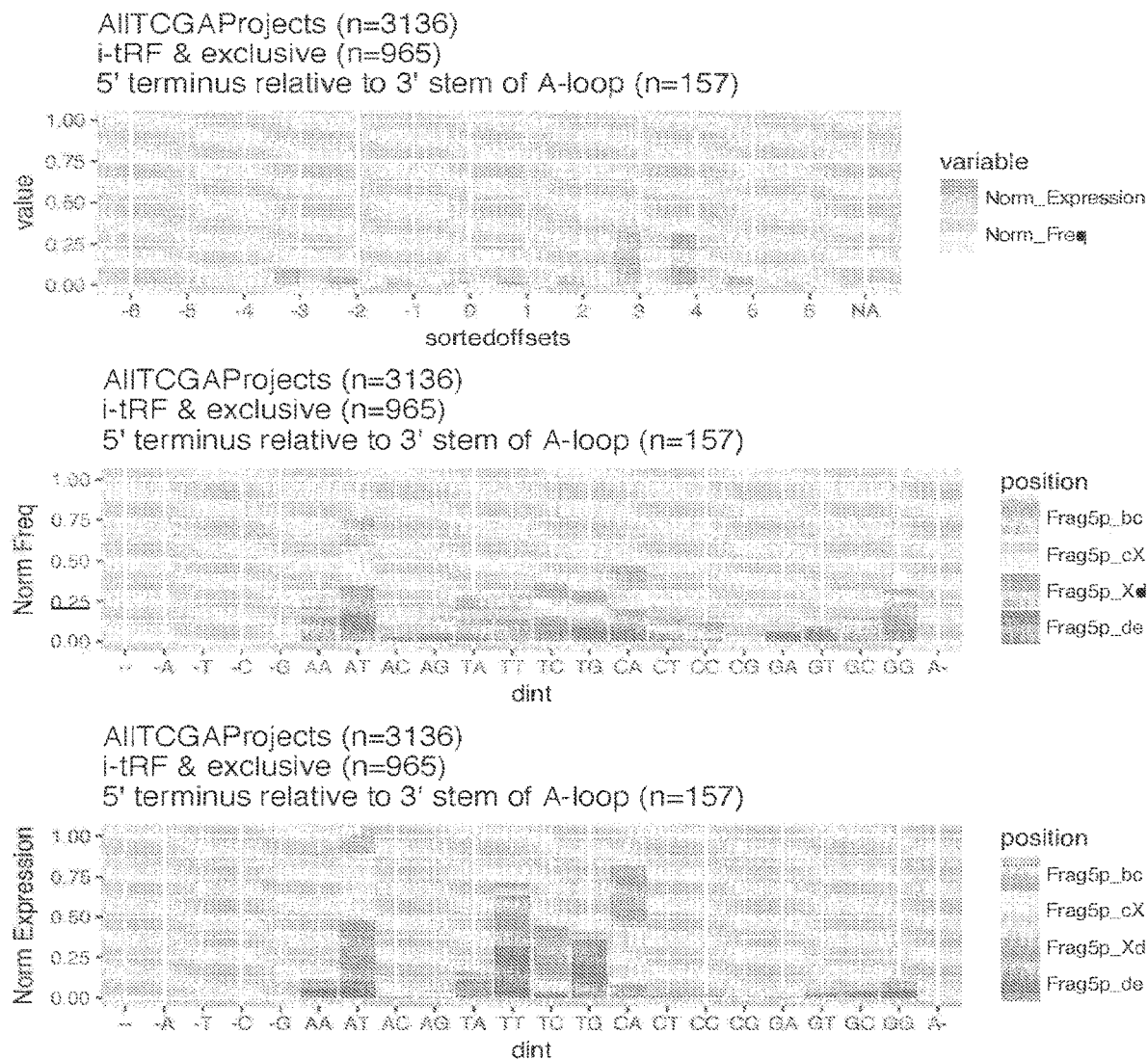
Figure 14:
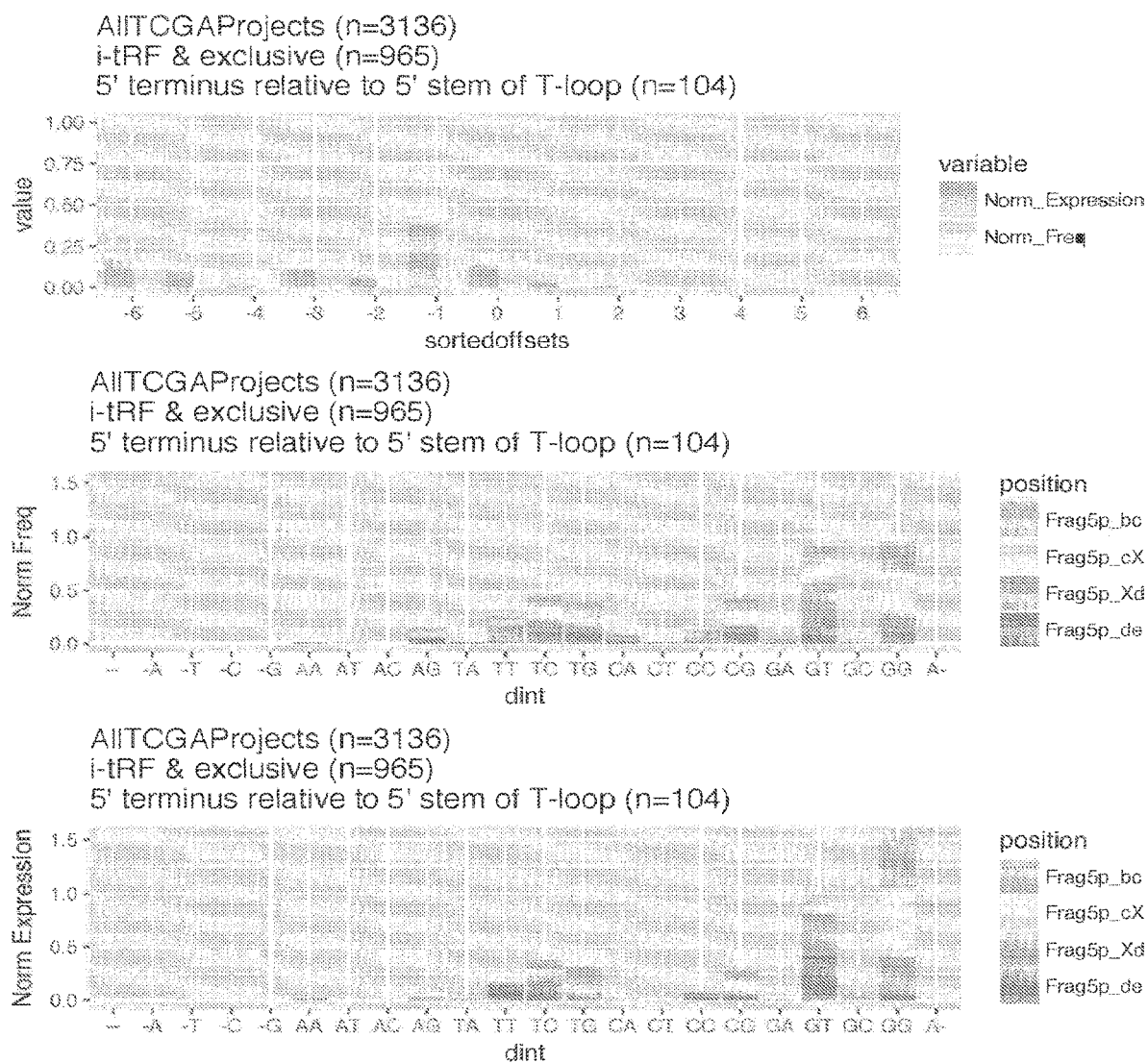
Figure 14:
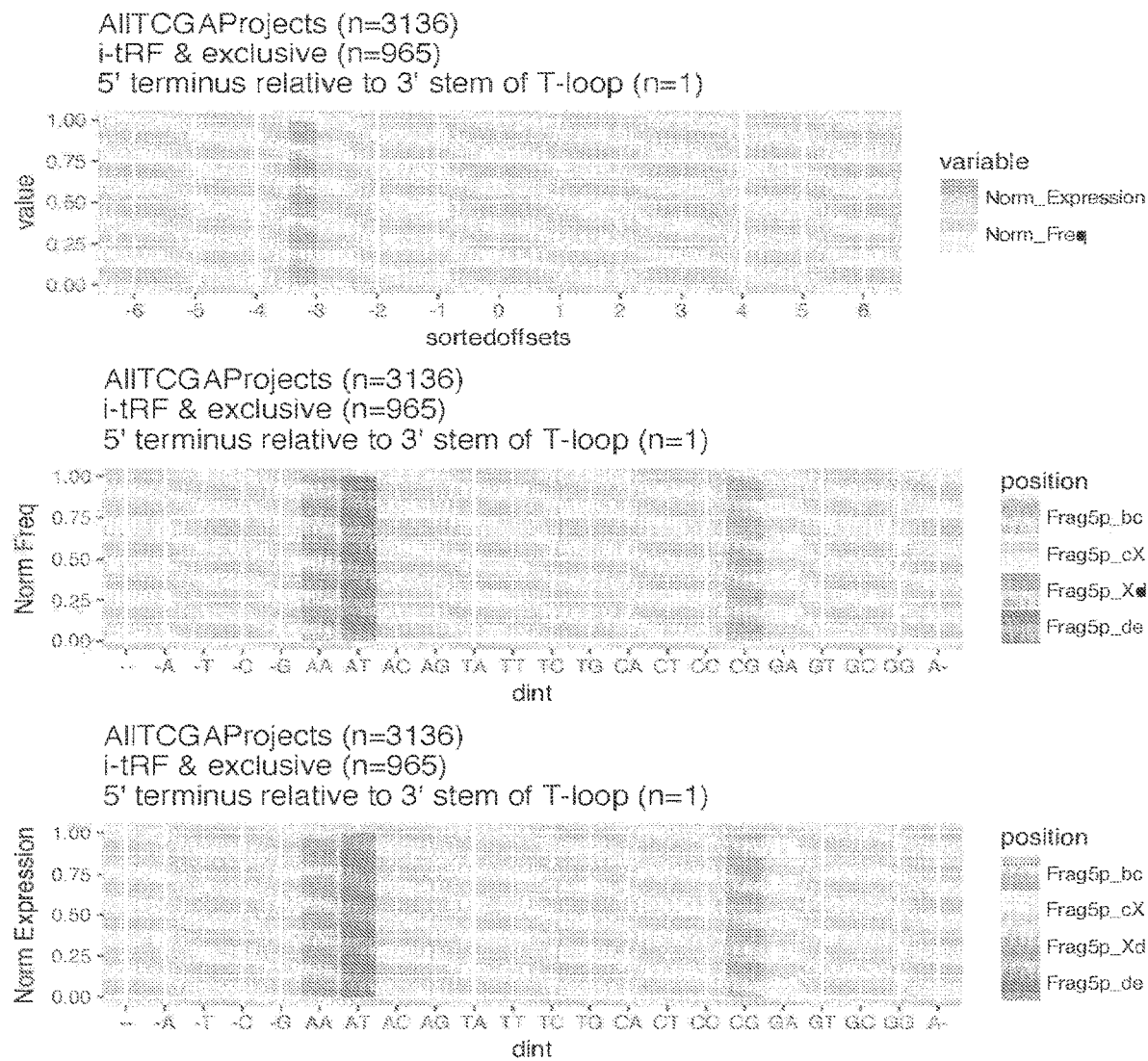
Figure 14:
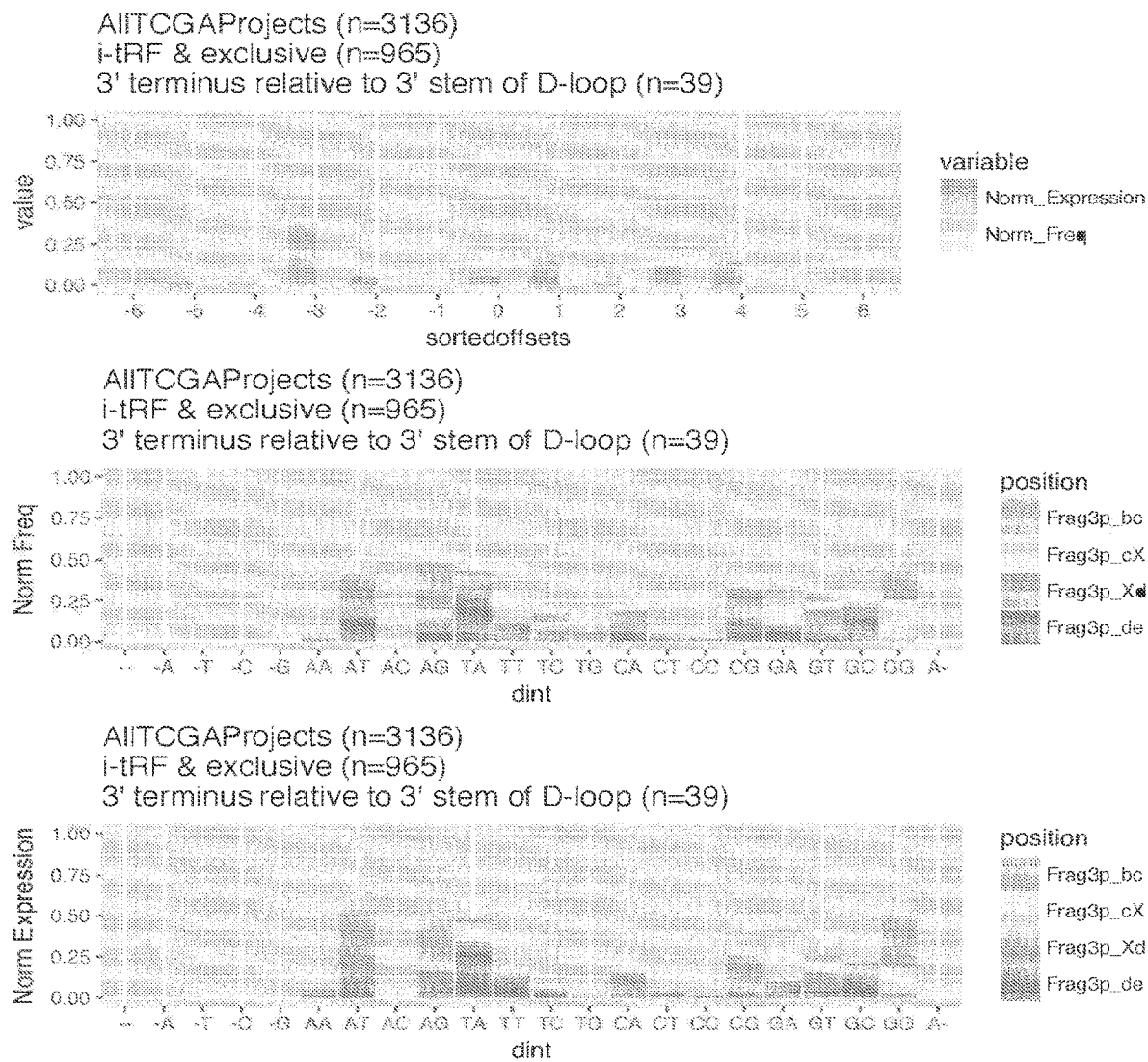
Figure 14:
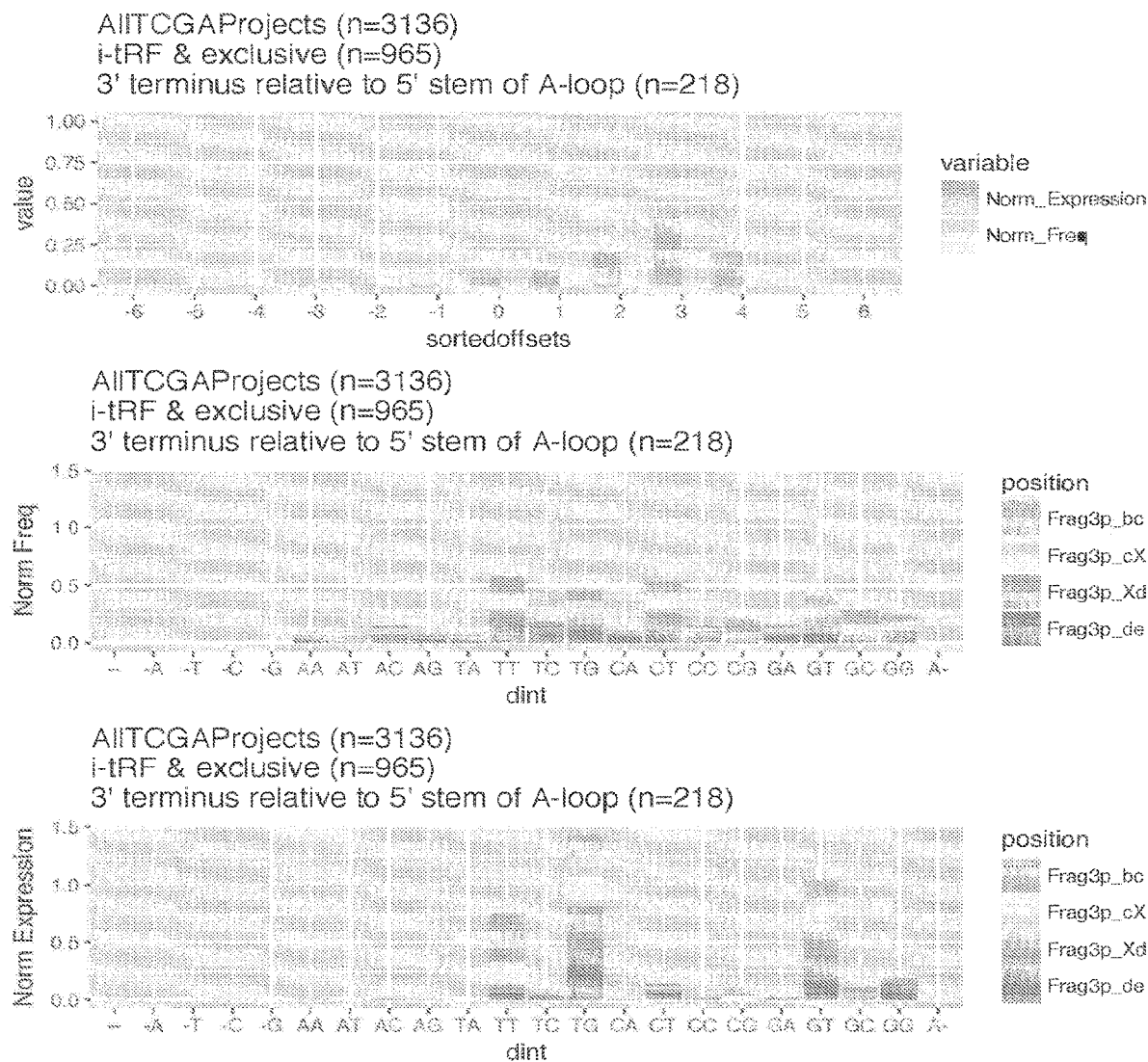
Figure 14:
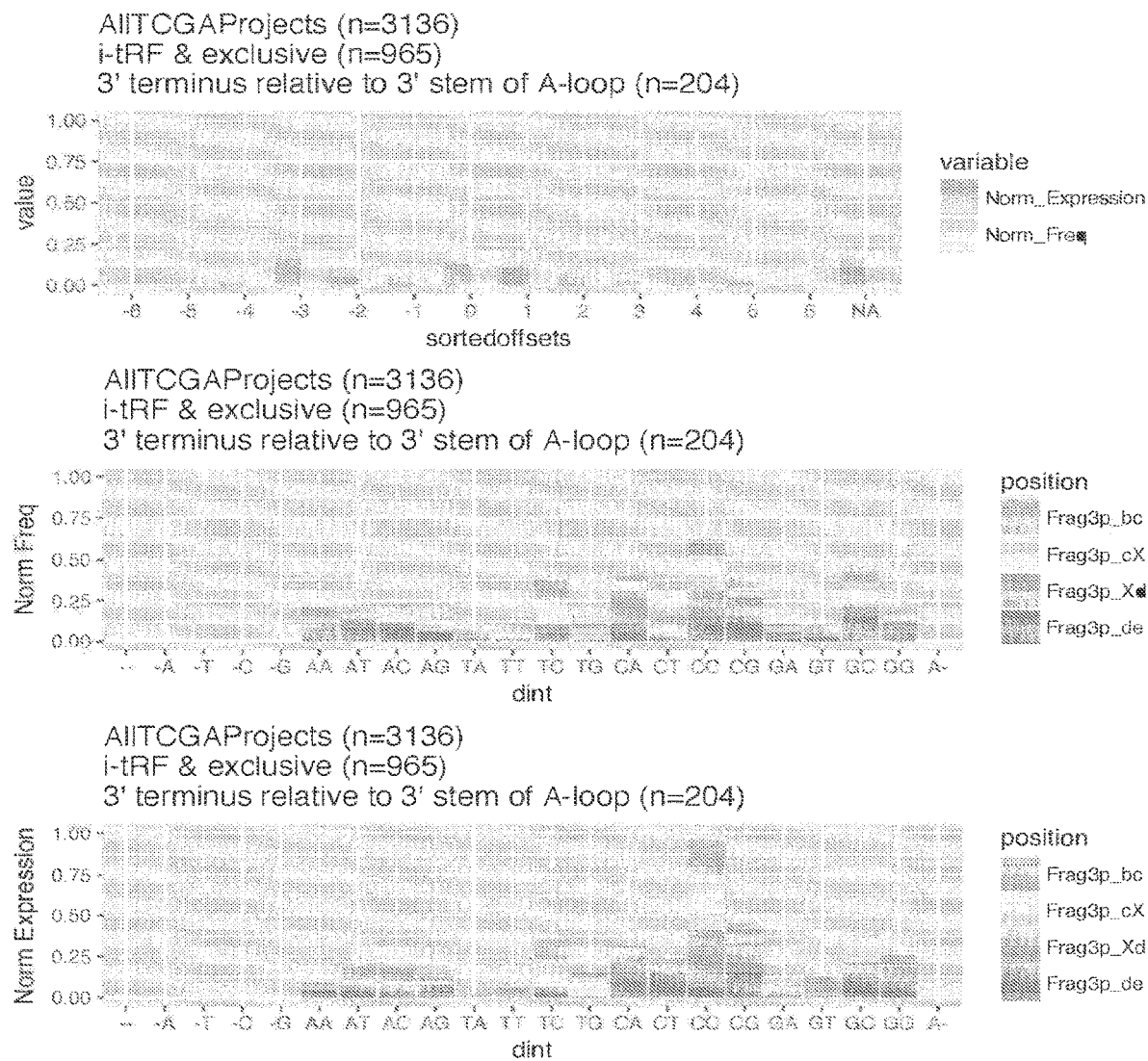
Figure 14:
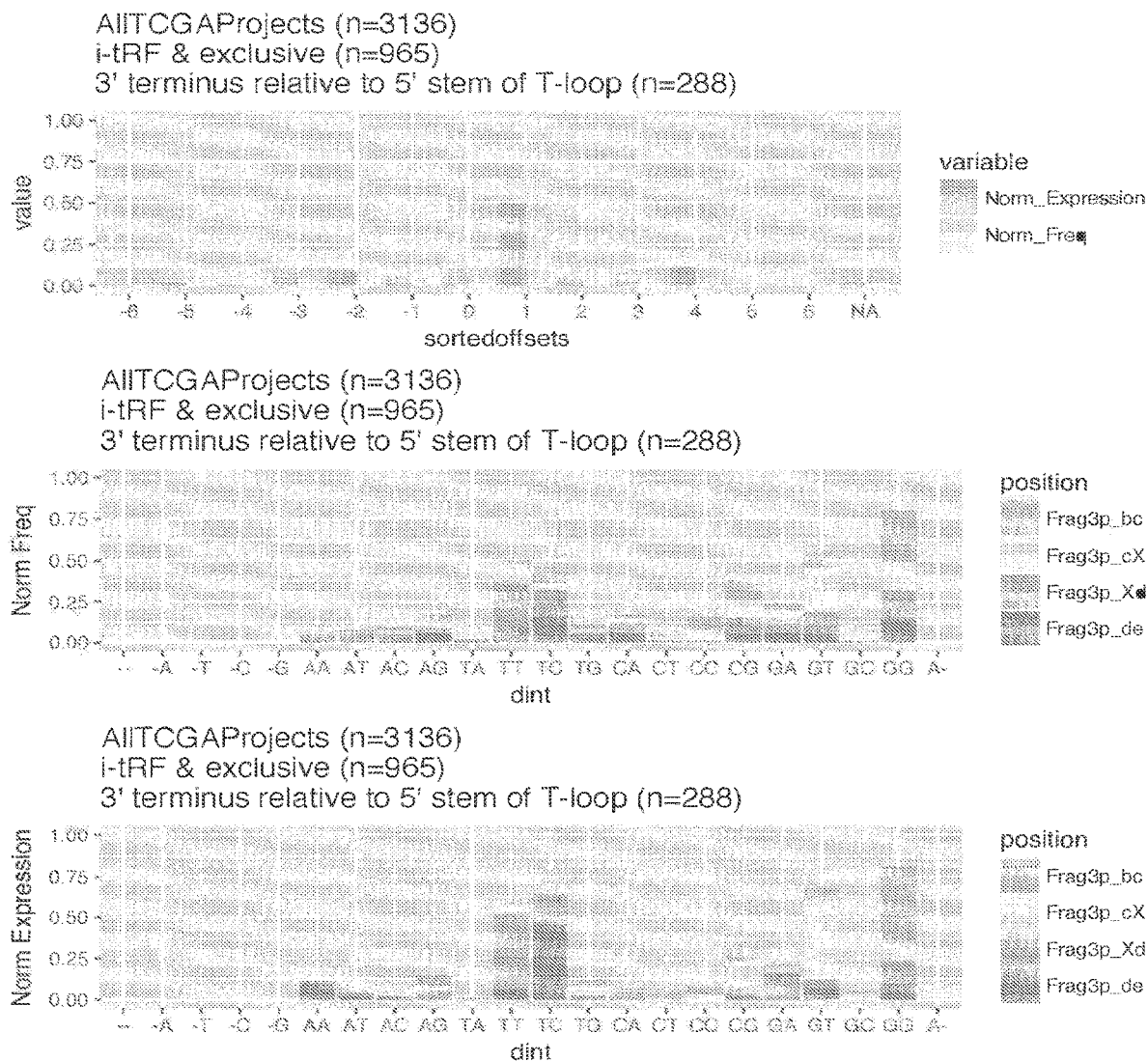
Figure 14:
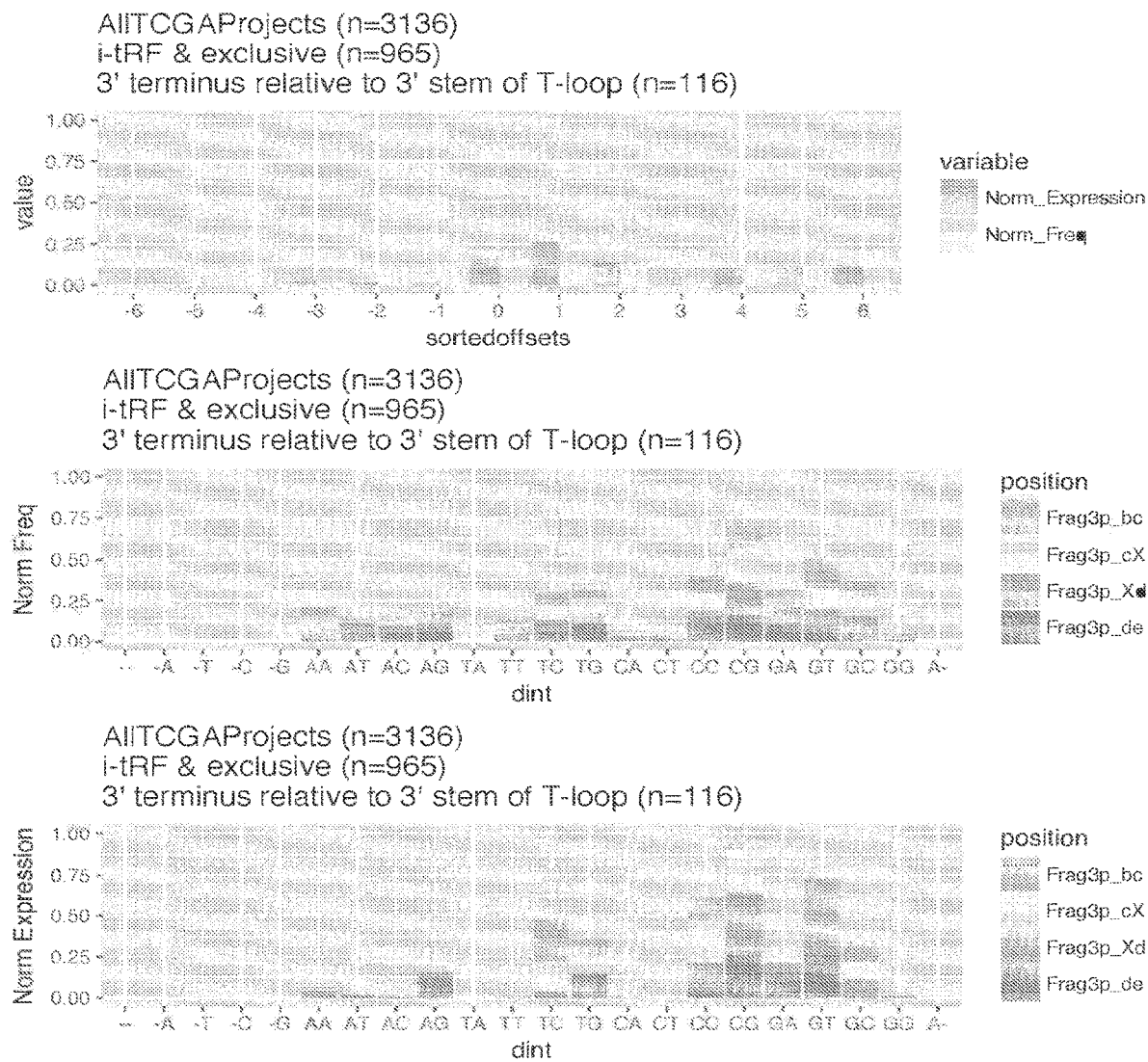
Figure 14:
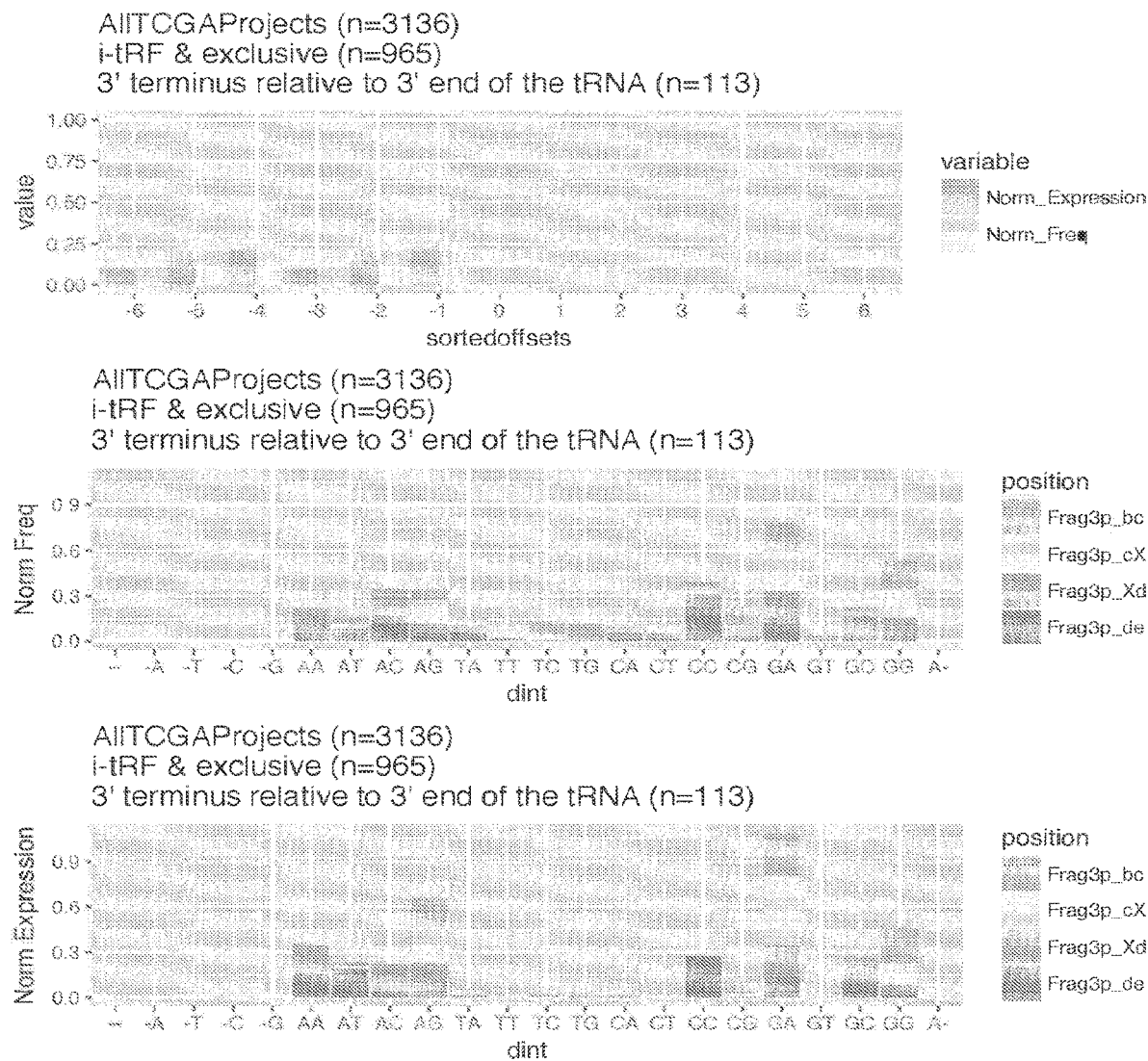
Figure 14:
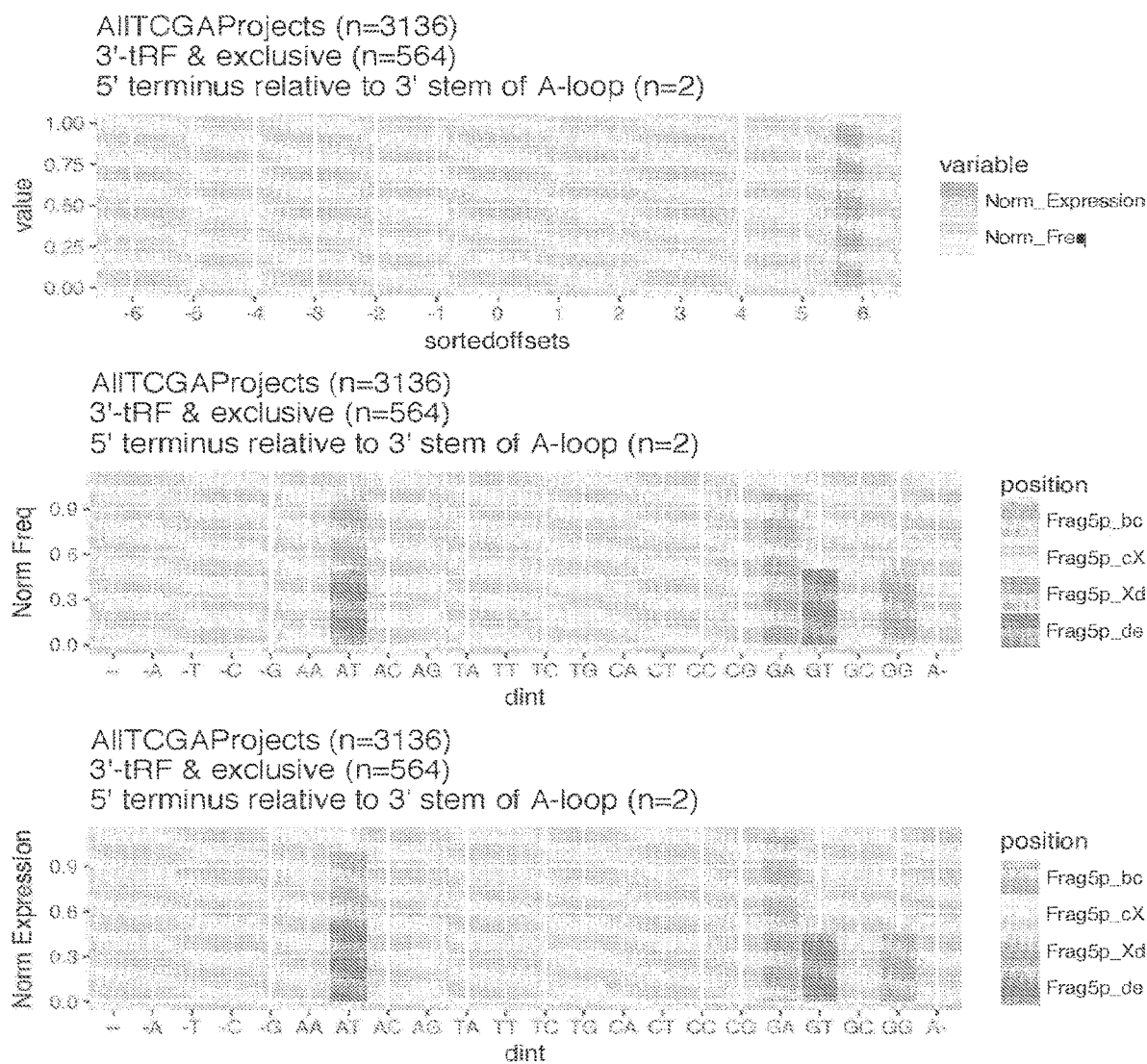
Figure 14:
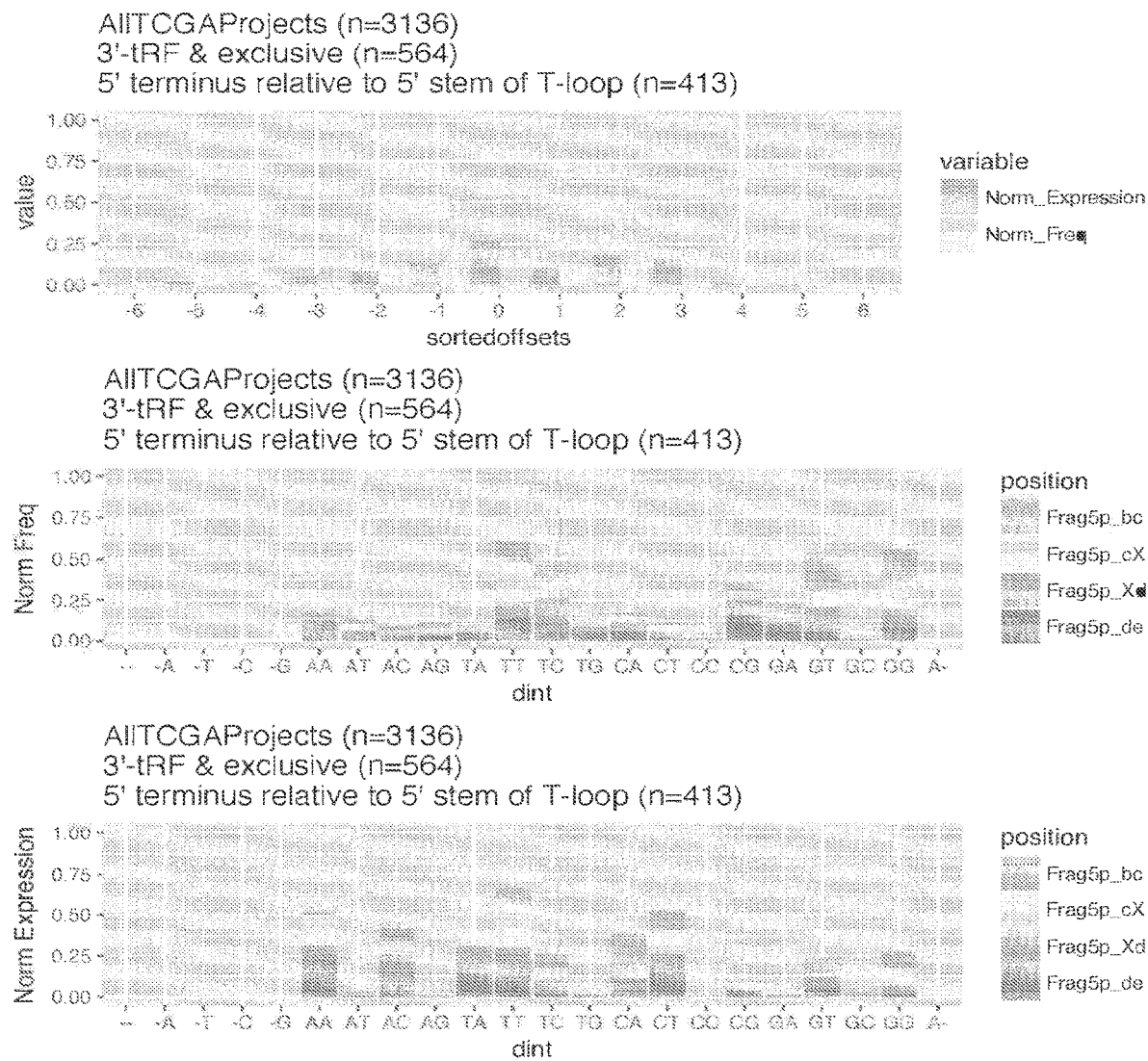
Figure 14:
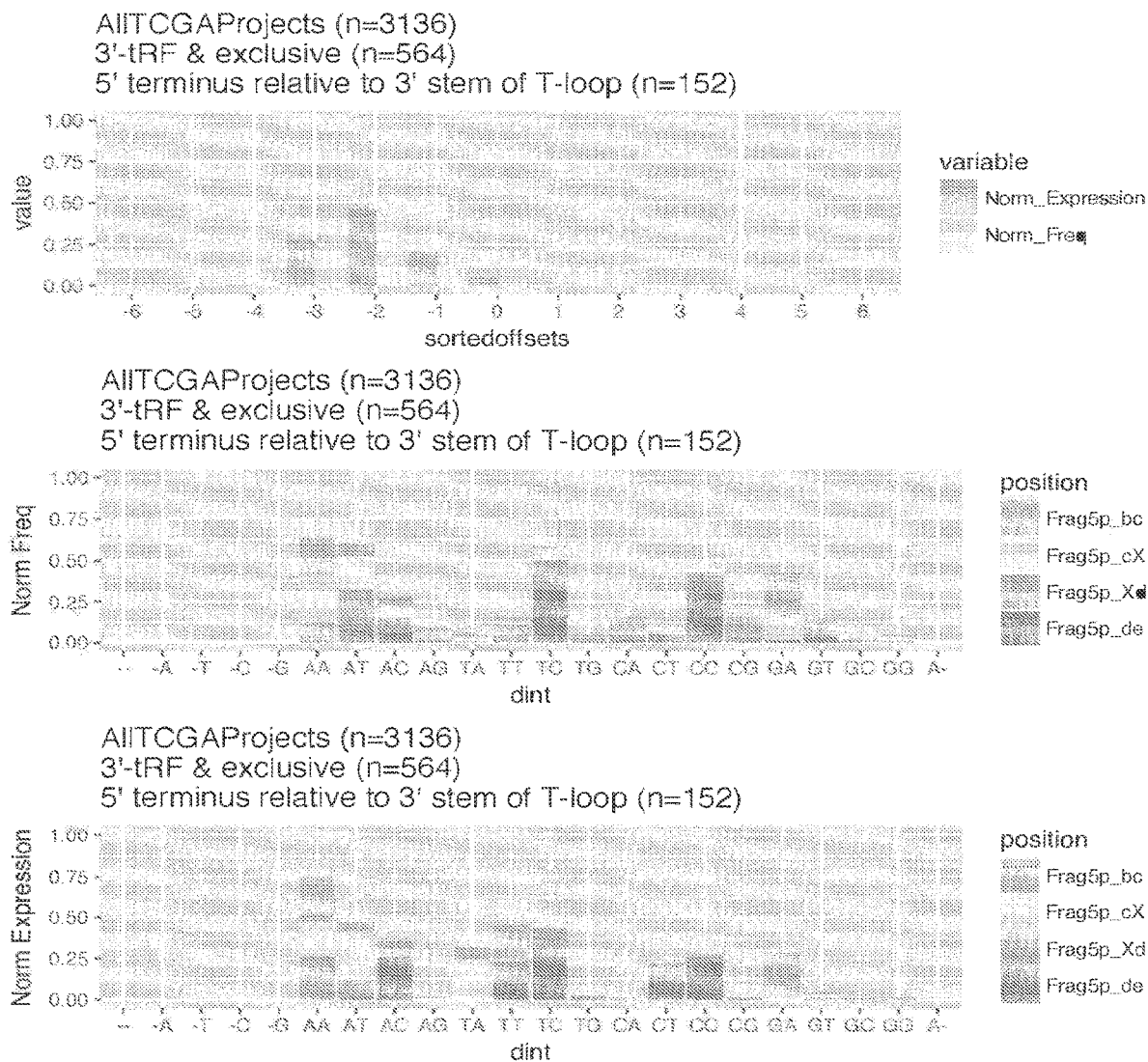
Figure 14:
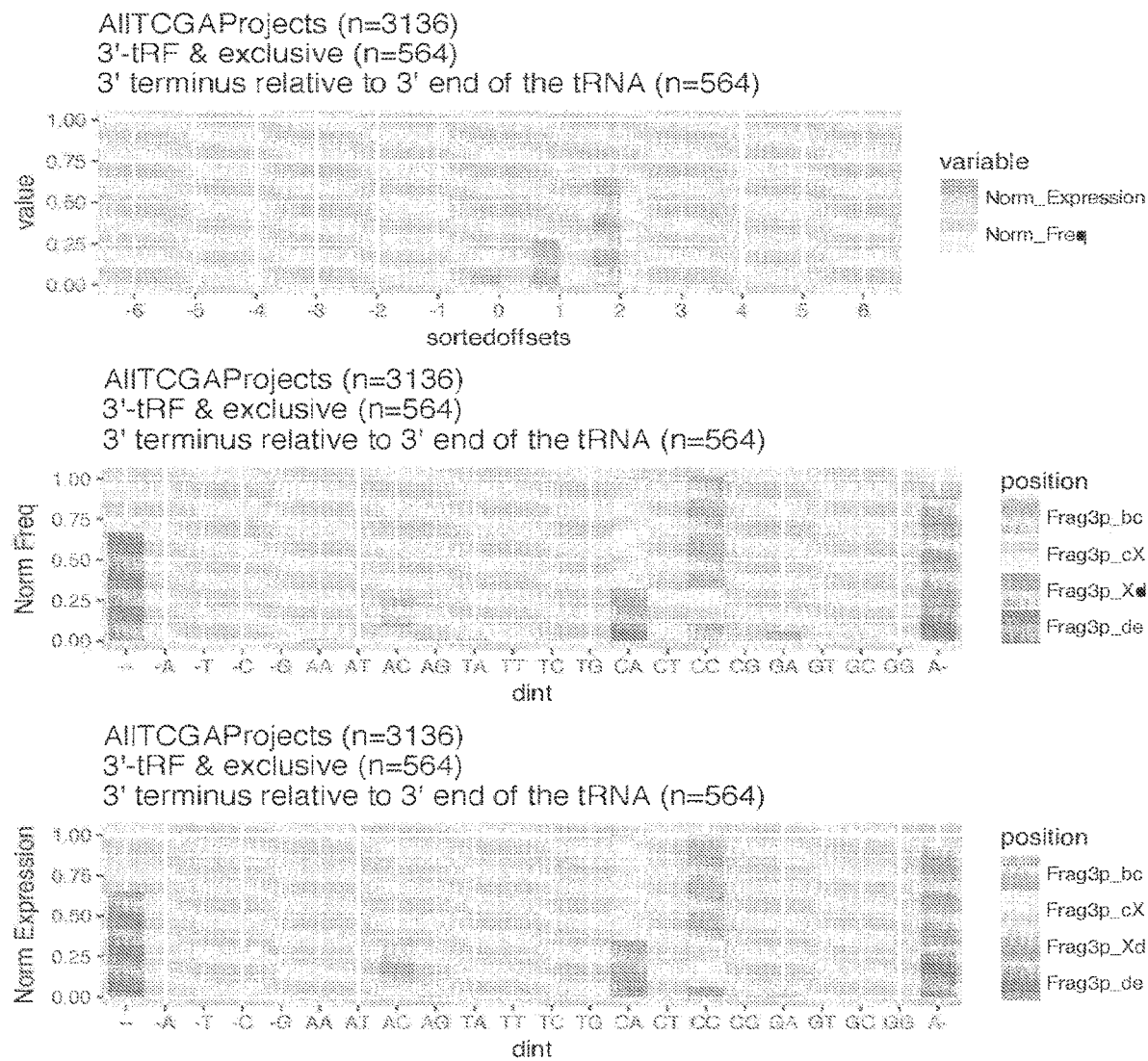

FIG. 14 lists the complete set of histograms for all of the attributes that we tracked and all tRF categories. In addition to showing the results for each of the 32 cancers, we also provided histograms that combine the findings from all 32 cancer types.

NMF Analyses

The TCGA working groups have been making great use of non-negative matrix factorization (78), or NMF, to cluster in an unsupervised manner the microRNAs (miRNAs) in the generated RNA-seq datasets. For this study, we replicated the NMF approach pioneered by the TCGA working groups leveraging tRF profiles (instead of miRNA profiles). We ran NMF (with R's NMF module, version 0.20.6) in an unsupervised manner using the top 30% most variable tRFs that passed Threshold-seq and had mean RPM>=1. Only tRFs with lengths 16-27 nt inclusive were used in these analyses. For each cancer type, the input used during clustering was a matrix comprising the RPM-normalized tRF profiles of the whitelisted datasets (see above) for the cancer type. Only the tumor datasets of each cancer type were used. For SKCM, NMF clustering was carried out separately on the primary tumor and the metastatic samples. Silhouette widths were generated from the final NMF consensus membership matrix (n=500 iterations per run). NMF79 was run using values of k ranging from 2 through 10 inclusive. For GBM, NMF clustering was not carried out because of the small number (5) of available datasets.

Correlation Analyses

For each cancer type separately, we first filtered the tRFs, miRNAs and the genes based on their abundance. We used the isomiR profiles as constructed for our previous study (66). For increased stringency in the correlation analyses among tRFs, miRNAs/isomiRs and mRNAs, we required that the median normalized abundance of each miRNA or isomiR and tRF was at least 2 RPM within the group of samples under consideration. For the mRNA profiles, we used TCGA's files of normalized results ("rsem_genes.normalized_results") and kept the most expressed genes. Specifically, we filtered out all genes whose average abundance was less than the median of the means of abundances of all mRNAs across the primary tumor samples of the group under consideration. Then, we computed all pairwise tRF-tRF Spearman correlation coefficients, as well as all tRF-mRNA and all miRNA-mRNA Spearman correlation coefficients for all expressed genes. We corrected the P-values to FDR scores, using the p.adjust function in the R base package with the method argument 'FDR.' We only kept correlation coefficients that had an FDR≤0.01 and an absolute value larger than 0.333. For the sex- and race-specific networks, we relaxed the FDR threshold to 0.05. Determination of which molecules enter the correlation analyses was done separately for each cancer type, sex (LUAD and BLCA), or race (TNBC). In all instances, we kept at most 5,000 top (for positive correlations) or at most 5,000 bottom (for negative correlations) correlations. Computations were done using python and the numpy (version 1.11.1) and scipy (version 0.18.1) packages.

Probabilities for the tRF-tRF networks were computed as the number of nodes that satisfy the respective criteria divided by the total number of nodes in each network.

Pathway analysis was run separately for the collection of genes that were negatively correlated with a) tRFs, or b) miRNAs. Specifically, DAVID (version 6.8) (80) was run with these two collections of genes and the overlap with GOTERM_BPFAT, GOTERM_MFFAT, GOTERM_CCFAT, and, KEGG PATHWAY terms was calculated and filtered at an FDR threshold of 5%. The genes that were used in the correlation analysis in each cancer served as the background gene list for the DAVID tool.

Protein Localization

Information on protein localization was downloaded from UniProt (81) and only the manually reviewed human proteome (queried on Nov. 27, 2016) was used. For each cancer type and correlation group (positive or negative), the distribution of the localization of gene products was computed as a percentage in each of the following seven cellular destinations: nucleus, cytoplasm, endoplasmic reticulum or Golgi, mitochondrion, cell membrane, secreted, and "other" organelles (e.g. vesicles, endosomes, unknown localization, etc.).

Overlap with RepeatMasker Entries

To calculate the overlap with RepeatMasker (http://www.repeatmasker.org; hg19 version 4.0.5) elements, we delineated the genomic span of a gene by forming the union of the genomic extent all its unspliced variants. We computed the frequency of the genes that contain at least one sense (respectively, antisense) instance of each family of repeat elements. In order to evaluate whether this 'observed' overlap corresponded to enrichment or depletion of repeat elements, we ran Monte-Carlo simulations to create an 'expected' distribution of overlap with RepeatMasker elements. In more detail, in each of 10,000 iterations we randomly selected from the total pool of genes included in the correlation analysis the same number of genes as the number of unique genes that were correlated with tRFs. For each cancer type, positive and negative correlations were analyzed separately (a total of 64 simulations each with 10,000 iterations). After each iteration, we calculated the overlap with RepeatMasker elements as described above and used it to create the 'expected' distribution. Based on this distribution, we calculated the z-score of the observed enrichment for each repeat family.

Disambiguation of the Genomic Origin of tRFs

To investigate whether non-exclusive tRFs as well as nuclear tRFs are enriched or depleted in our correlation analyses, we performed Monte-Carlo simulations analogously to the way we calculated overlap with repeat elements. Specifically, we performed 10,000 iterations and in each one we calculated the ratio of non-exclusive tRF and of nuclear tRF based on a randomly chosen set of tRFs equal in size to the set of tRFs participating in the tRF-mRNA correlations. This was carried out separately for each cancer type.

Multivariate Statistical Analysis and Data Visualization

Hierarchical Clustering and Principal Component Analysis, as well as network visualizations were run and plotted in R, as we previously described (4,66,72).

Disambiguation of the Genomic Origin of tRFs

Our recent publications extensively discussed the possibility of tRFs of ambiguous origin. We also described the choices that are available for working with such tRFs (9,60).

Figure 20A:
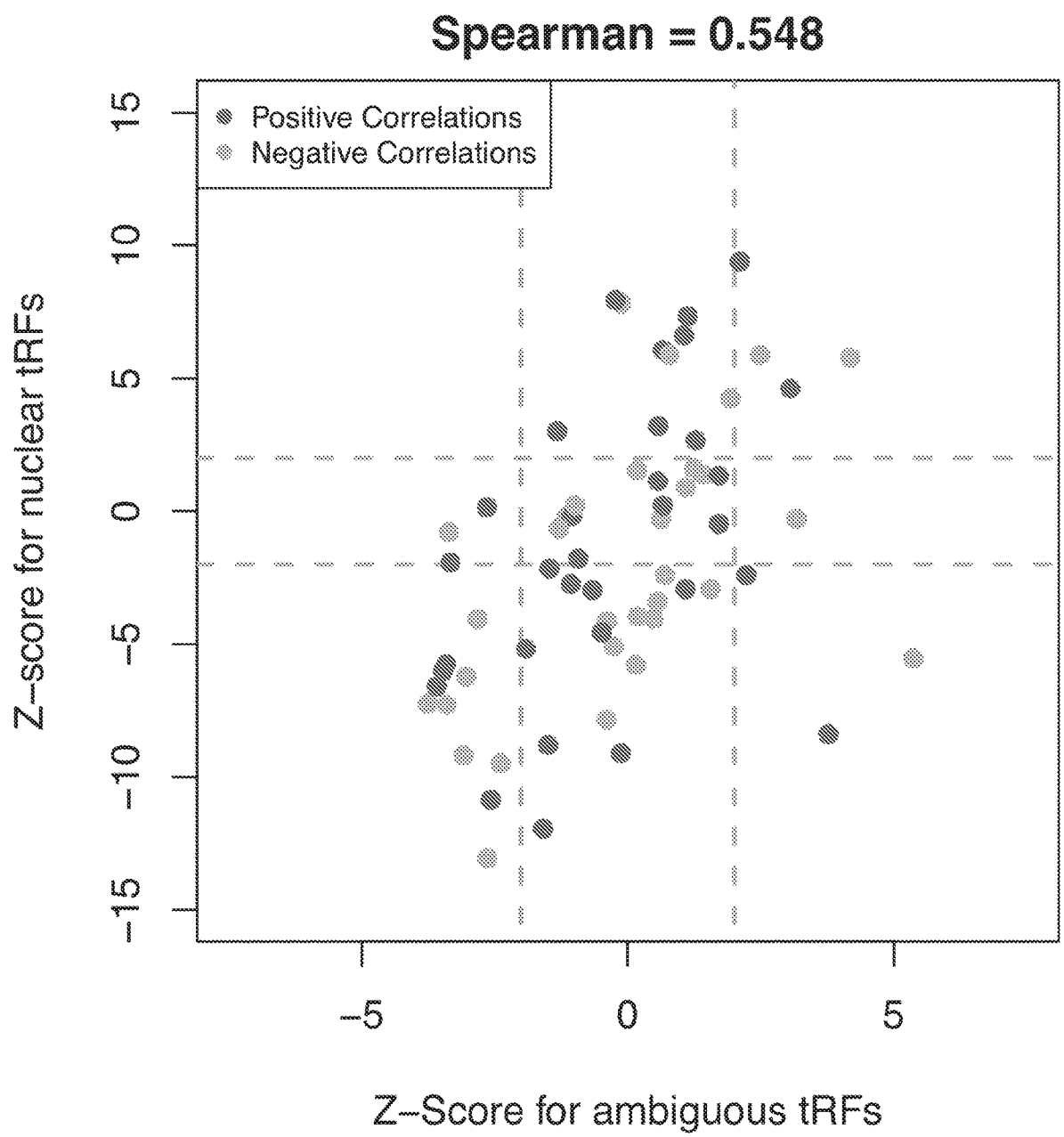
FIG. 20 Tracking the origin of non-exclusive tRFs. (A) Scatter plot of the enrichment (or depletion) of non-exclusive tRFs among nuclear tRFs that participate in correlation pairs with mRNAs. Shown on X-axis is the Z-score of the observed percentage of non-exclusive tRFs as compared to the distribution of percentages of randomly chosen sets of tRFs. Accordingly, the Y-axis is the Z-score for the enrichment (or depletion). Each dot represents a specific correlation type (i.e. negative or positive) for each of the 32 cancer types. Dashed lines mark a Z-score threshold of +2 and −2. (B) Examples of overlap of instances of non-exclusive tRFs with genes. Of all 32 cancer types, and the numerous tRFs and mRNAs that were analyzed, these are the only pairs that we found to be significantly correlated.

Looking at our analyses globally, we find that an average of 42±3% of the tRFs that entered our correlation analyses are not exclusive to tRNA space. However, the 58:42 split is not mirrored by tRFs that participate in statistically significant correlation pairs with mRNAs. In fact, in each cancer type, we find a ratio that differs from the "expected" 58:42 (FIG. 20A). For example, the majority of tRFs that are correlated with mRNAs in LIHC and TGCT are exclusive to tRNA space (z-score of ≤−3.0, for both positive and negative correlations, with reference to a randomly chosen set of tRFs) but the respective set of tRFs in LAML and LUSC is enriched in non-exclusive instances (z-score≥3.0, for both positive and negative correlations). We also note that there is a positive correlation between the number of non-exclusive tRFs and the number of nuclear tRFs in our correlation analysis (FIG. 20A).

Based on the above results, we checked whether our correlation analyses results could be driven by events where an instance of a non-exclusive tRF overlaps with one or more mRNA transcripts. In such cases, we would expect to see strong correlations between the tRF and the mRNA, across multiple cancer types. To test this hypothesis, we enumerated all genomic instances of non-exclusive tRFs outside of tRNA space. Then, we checked whether ambiguous tRFs in tRF-mRNA pairs had a sense instance inside the genomic span of the respective mRNA. We found only 23 such instances in 12 cancer types (FIG. 20B). Compared to the total number of tRF-mRNA correlation pairs, these 23 examples are too few and do not support the hypothesis that the observed tRF-mRNA correlations are the result of coupled biogenetic mechanisms. Nonetheless, it is important to note that such examinations may be necessary when working with non-exclusive tRFs.

Therefore, we have identified that correlations have revealed mRNA that would not be predicted to be useful in the first place is sometimes correlated for direct or proxy impact for specific cancers. Therefore, upon determining such elements from a cancer tissue, we can directly or by proxy (indirectly) impact the mRNA by increasing or decreasing concentrations. For example, treatment of any one of the 32 cancers can be impacted by application of therapeutics to the genes or the Sequences identified herein.

Supplemental Table Captions

Supp. Table S1|Statistics of the tRFs identified in the 10,274 TCGA datasets.

Supp. Table S2|Length distributions of tRFs listed by genomic origin (nucleus or mitochondrion), structural category, and length.

Supp. Table S3|Probabilities for tRF-tRF pairs.

Supp. Table S4|List of positive and negative correlation between tRF-tRF and tRF-mRNA pairs for the case of BRCA. A complete list for all 32 cancer types can be generated according to the methods described herein.

Supp. Table S5|DAVID analysis results for the genes whose mRNAs are anti-correlated with tRFs or miRNAs. GO terms and KEGG pathways are analyzed and the results reported separately for each of 32 cancers.

Supp. Table S6|GO terms and descriptions of the four general clusters of FIG. 5.

Lengthy table referenced here

US11715549-20230801-T00001

Please refer to the end of the specification for access instructions.

Lengthy table referenced here

US11715549-20230801-T00002

Please refer to the end of the specification for access instructions.

Lengthy table referenced here

US11715549-20230801-T00003

Please refer to the end of the specification for access instructions.

Lengthy table referenced here

US11715549-20230801-T00004

Please refer to the end of the specification for access instructions.

Lengthy table referenced here

US11715549-20230801-T00005

Please refer to the end of the specification for access instructions.

Lengthy table referenced here

US11715549-20230801-T00006

Please refer to the end of the specification for access instructions.

REFERENCES

1. Keam, S. P. & Hutvagner, G. tRNA-Derived Fragments (tRFs): Emerging New Roles for an Ancient RNA in the Regulation of Gene Expression. *Life (Basel)* 5, 1638-51 (2015).
2. Sobala, A. & Hutvagner, G. Small RNAs derived from the 5' end of tRNA can inhibit protein translation in human cells. *RNA Biol* 10, 553-63 (2013).
3. Shigematsu, M. & Kirino, Y. tRNA-Derived Short Non-coding RNA as Interacting Partners of Argonaute Proteins. *Gene Regul Syst Bio* 9, 27-33 (2015).
4. Telonis, A. G. et al. Dissecting tRNA-derived fragment complexities using personalized transcriptomes reveals novel fragment classes and unexpected dependencies. *Oncotarget* 6, 24797-822 (2015).
5. Ivanov, P., Emara, M. M., Villen, J., Gygi, S. P. & Anderson, P. Angiogenin-induced tRNA fragments inhibit translation initiation. *Mol Cell* 43, 613-23 (2011).
6. Yamasaki, S., Ivanov, P., Hu, G. F. & Anderson, P. Angiogenin cleaves tRNA and promotes stress-induced translational repression. *J Cell Biol* 185, 35-42 (2009).
7. Honda, S. et al. Sex hormone-dependent tRNA halves enhance cell proliferation in breast and prostate cancers. *Proc Natl Acad Sci USA* 112, E3816-25 (2015).
8. Magee, R., Loher, P., Telonis, A. G., Kirino, Y. & Rigoutsos, I. Comments on: "A comprehensive repertoire of tRNA-derived fragments in prostate cancer". *bioRxiv* (2016).
9. Telonis, A. G., Loher, P., Kirino, Y. & Rigoutsos, I. Consequential considerations when mapping tRNA fragments. *BMC Bioinformatics* (2016).
10. Kumar, P., Anaya, J., Mudunuri, S. B. & Dutta, A. Meta-analysis of tRNA derived RNA fragments reveals that they are evolutionarily conserved and associate with AGO proteins to recognize specific RNA targets. *BMC Biol* 12, 78 (2014).
11. Yeung, M. L. et al. Pyrosequencing of small non-coding RNAs in HIV-1 infected cells: evidence for the processing of a viral-cellular double-stranded RNA hybrid. *Nucleic Acids Res* 37, 6575-86 (2009).
12. Deng, J. et al. Respiratory Syncytial Virus Utilizes a tRNA Fragment to Suppress Antiviral Responses Through a Novel Targeting Mechanism. *Mol Ther* 23, 1622-9 (2015).
13. Selitsky, S. R. et al. Small tRNA-derived RNAs are increased and more abundant than microRNAs in chronic hepatitis B and C. *Sci Rep* 5, 7675 (2015).
14. Olvedy, M. et al. A comprehensive repertoire of tRNA-derived fragments in prostate cancer. *Oncotarget* (2016).
15. Sharma, U. et al. Biogenesis and function of tRNA fragments during sperm maturation and fertilization in mammals. *Science* 351, 391-6 (2016).
16. Gapp, K. et al. Implication of sperm RNAs in transgenerational inheritance of the effects of early trauma in mice. *Nature neuroscience* 17, 667-669 (2014).
17. Chen, Q. et al. Sperm tsRNAs contribute to intergenerational inheritance of an acquired metabolic disorder. *Science (New York, N.Y.)* 351, 397-400 (2016).

18. Gebetsberger, J., Wyss, L., Mleczko, A. M., Reuther, J. & Polacek, N. A tRNA-derived fragment competes with mRNA for ribosome binding and regulates translation during stress. *RNA Biol,* 0 (2016).
19. Anderson, P. & Ivanov, P. tRNA fragments in human health and disease. *FEBS Lett* 588, 4297-304 (2014).
20. Grewal, S. S. Why should cancer biologists care about tRNAs? tRNA synthesis, mRNA translation and the control of growth. *Biochim Biophys Acta* 1849, 898-907 (2015).
21. Magee, R., Loher, P., Londin, E. & Rigoutsos, I. Threshold-seq: a tool for determining the threshold in short RNA-seq datasets. *Bioinformatics* (2017).
22. Pliatsika, V., Loher, P., Telonis, A. G. & Rigoutsos, I. MINTbase: a framework for the interactive exploration of mitochondrial and nuclear tRNA fragments. *Bioinformatics, btw*194-9 (2016).
23. Suzuki, T. & Suzuki, T. A complete landscape of post-transcriptional modifications in mammalian mitochondrial tRNAs. *Nucleic Acids Research* 42, 7346-7357 (2014).
24. Cognat, V. et al. The nuclear and organellar tRNA-derived RNA fragment population in *Arabidopsis thaliana* is highly dynamic. *Nucleic Acids Res* (2016).
25. Gu, W., Jackman, J. E., Lohan, A. J., Gray, M. W. & Phizicky, E. M. tRNAHis maturation: an essential yeast protein catalyzes addition of a guanine nucleotide to the 5' end of tRNAHis. *Genes Dev* 17, 2889-901 (2003).
26. Heinemann, I. U., Nakamura, A., O'Donoghue, P., Eiler, D. & Soll, D. tRNAHis-guanylyltransferase establishes tRNAHis identity. *Nucleic Acids Res* 40, 333-44 (2012).
27. Jackman, J. E. & Phizicky, E. M. tRNAHis guanylyltransferase adds G-1 to the 5' end of tRNAHis by recognition of the anticodon, one of several features unexpectedly shared with tRNA synthetases. *RNA* 12, 1007-14 (2006).
28. Shigematsu, M. & Kirino, Y. 5'-Terminal nucleotide variations in human cytoplasmic tRNAHisGUG and its 5'-halves. *RNA* 23, 161-168 (2017).
29. Maute, R. L. et al. tRNA-derived microRNA modulates proliferation and the DNA damage response and is down-regulated in B cell lymphoma. *Proc Natl Acad Sci USA* 110, 1404-9 (2013).
30. Rigoutsos, I. et al. Short blocks from the noncoding parts of the human genome have instances within nearly all known genes and relate to biological processes. *Proc Natl Acad Sci USA* 103, 6605-10 (2006).
31. Tsirigos, A. & Rigoutsos, I. Human and mouse introns are linked to the same processes and functions through each genome's most frequent non-conserved motifs. *Nucleic Acids Res* 36, 3484 (2008).
32. Tsirigos, A. & Rigoutsos, I. Alu and b1 repeats have been selectively retained in the upstream and intronic regions of genes of specific functional classes. *PLoS Comput Biol* 5, e1000610 (2009).
33. Bao, W., Kojima, K. K. & Kohany, O. Repbase Update, a database of repetitive elements in eukaryotic genomes. *Mob DNA* 6, 11 (2015).
34. Rigoutsos, I. Short RNAs: how big is this iceberg? *Curr Biol* 20, R110-3 (2010).
35. Spratt, D. E. et al. Racial/Ethnic Disparities in Genomic Sequencing. *JAMA Oncology* 2, 1070-5 (2016).
36. Paggi, M. G., Vona, R., Abbruzzese, C. & Malorni, W. Gender-related disparities in non-small cell lung cancer. *Cancer Letters* 298, 1-8 (2010).
37. Dela Cruz Md PhD, C. S., Md, L. T. T. & Md, R. A. M. Lung Cancer: Epidemiology, Etiology, and Prevention. *CME* 32, 605-644 (2011).
38. Alberg, A. J., Brock, M. V., Ford, J. G., Samet, J. M. & Spivack, S. D. Epidemiology of lung cancer: Diagnosis and management of lung cancer, 3rd ed: American College of Chest Physicians evidence-based clinical practice guidelines. *Chest* 143, e1S-29S (2013).
39. Association, A. L. Lung cancer fact sheet. 4, http://www.lung.org/lung-disease/lungcancer/resources/facts-figures/lung-cancer-fact-sheet.html, Dec. 8, 2013, 1 (2014).
40. Lathan, C. S. Lung Cancer Disparities in the Era of Personalized Medicine. American *Journal of Hematology/Oncology®* (2015).
41. Meza, R., Meernik, C., Jeon, J. & Cote, M. L. Lung Cancer Incidence Trends by Gender, Race and Histology in the United States, 1973-2010. *PLoS ONE* 10, e0121323 (2015).
42. Jemal, A. et al. Global cancer statistics. *CA: a cancer journal for clinicians* 61, 69-90 (2011).
43. Dawson, S. J., Provenzano, E. & Caldas, C. Triple negative breast cancers: clinical and prognostic implications. *Eur J Cancer* 45 Suppl 1, 27-40 (2009).
44. Koboldt, D. C. et al. Comprehensive molecular portraits of human breast tumours. *Nature* 490, 61-70 (2012).
45. van't Veer, L. J. et al. Gene expression profiling predicts clinical outcome of breast cancer. *Nature* 415, 530-6 (2002).
46. Slamon, D. J. et al. Human breast cancer: correlation of relapse and survival with amplification of the HER-2/neu oncogene. *Science* 235, 177-82 (1987).
47. Paik, S. et al. A multigene assay to predict recurrence of tamoxifen-treated, node-negative breast cancer. *N Engl J Med* 351, 2817-26 (2004).
48. Perou, C. M. Molecular stratification of triple-negative breast cancers. *Oncologist* 16 Suppl 1, 61-70 (2011).
49. Carey, L. A. et al. Race, breast cancer subtypes, and survival in the Carolina Breast Cancer Study. *JAMA* 295, 2492-502 (2006).
50. Kirchner, S. & Ignatova, Z. Emerging roles of tRNA in adaptive translation, signalling dynamics and disease. *Nat Rev Genet* 16, 98-112 (2015).
51. Machnicka, M. A. et al. MODOMICS: a database of RNA modification pathways—2013 update. *Nucleic Acids Res* 41, D262-7 (2013).
52. Suzuki, T., Nagao, A. & Suzuki, T. Human Mitochondrial tRNAs: Biogenesis, Function, Structural Aspects, and Diseases. *Annual review of genetics* 45, 299-329 (2011).
53. Durdevic, Z. & Schaefer, M. tRNA modifications: Necessary for correct tRNA-derived fragments during the recovery from stress? *BioEssays* 35, 323-327 (2013).
54. Abbott, J. A., Francklyn, C. S. & Robey-Bond, S. M. Transfer RNA and human disease. *Frontiers in Genetics* 5, 158 (2014).
55. Torres, A. G., Batlle, E. & de Pouplana, L. R. Role of tRNA modifications in human diseases. *Trends in Molecular Medicine* 20, 306-314 (2014).
56. Gu, C., Begley, T. J. & Dedon, P. C. tRNA modifications regulate translation during cellular stress. *FEBS Letters* 588, 4287-4296 (2014).

57. Cozen, A. E. et al. ARM-seq: AlkB-facilitated RNA methylation sequencing reveals a complex landscape of modified tRNA fragments. *Nature Methods,* 1-8 (2015).
58. Zheng, G. et al. Efficient and quantitative high-throughput tRNA sequencing. *Nat Methods* 12, 835-7 (2015).
59. Zheng, L.-L. et al. tRF2Cancer: A web server to detect tRNA-derived small RNA fragments (tRFs) and their expression in multiple cancers. *Nucleic Acids Research* 44, W185-W193 (2016).
60. Loher, P., Telonis, A. G. & Rigoutsos, I. MINTmap: fast and exhaustive profiling of nuclear and mitochondrial tRNA fragments from short RNA-seq data. *Sci Rep* 7, 41184 (2017).
61. Telonis, A. G., Loher, P., Kirino, Y. & Rigoutsos, I. Nuclear and mitochondrial tRNA-lookalikes in the human genome. *Front Genet* 5, 344 (2014).
62. Hasler, D. et al. The Lupus Autoantigen La Prevents Mis-channeling of tRNA Fragments into the Human MicroRNA Pathway. *Molecular Cell,* 1-16 (2016).
63. Mustoe, A. M., Brooks, C. L. & Al-Hashimi, H. M. Hierarchy of RNA Functional Dynamics. *Annual review of biochemistry* 83, 441-466 (2014).
64. Goodarzi, H. et al. Endogenous tRNA-Derived Fragments Suppress Breast Cancer Progression via YBX1 Displacement. *Cell* 161, 790-802 (2015).
65. Keam, S. P., Sobala, A., Ten Have, S. & Hutvágner, G. tRNA-Derived RNA Fragments Associate with Human Multisynthetase Complex (MSC) and Modulate Ribosomal Protein Translation. *Journal of proteome research,* acs.jproteome.6b00267 (2016).
66. Telonis, A. G. et al. Knowledge about the presence or absence of miRNA isoforms (isomiRs) can successfully discriminate amongst 32 TCGA cancer types. *Nucleic Acids Res* (2017).
67. Laurent, L. et al. Dynamic changes in the human methylome during differentiation. *Genome Research* 20, 320-331 (2010).
68. Belancio, V. P., Roy-Engel, A. M. & Deininger, P. L. All y'all need to know 'bout retroelements in cancer. *Seminars in Cancer Biology* 20, 200-210 (2010).
69. Martinez, G., Choudury, S. G. & Slotkin, R. K. tRNA-derived small RNAs target transposable element transcripts. *Nucleic Acids Research,* 1-11 (2017).
70. Belancio, V. P., Roy-Engel, A. M. & Deininger, P. L. All y'all need to know 'bout retroelements in cancer. *Semin Cancer Biol* 20, 200-10 (2010).
71. Loher, P., Londin, E. R. & Rigoutsos, I. IsomiR expression profiles in human lymphoblastoid cell lines exhibit population and gender dependencies. *Oncotarget* 5, 8790-802 (2014).
72. Telonis, A. G., Loher, P., Jing, Y., Londin, E. & Rigoutsos, I. Beyond the one-locus-one-miRNA paradigm: microRNA isoforms enable deeper insights into breast cancer heterogeneity. *Nucleic Acids Res,* gkv922 (2015).
73. Fu, H. et al. Stress induces tRNA cleavage by angiogenin in mammalian cells. *FEBS Lett* 583, 437-42 (2009).
74. Thompson, D. M. & Parker, R. The RNase Rny1p cleaves tRNAs and promotes cell death during oxidative stress in *Saccharomyces cerevisiae. J Cell Biol* 185, 43-50 (2009).
75. Kawaji, H. et al. Hidden layers of human small RNAs. *BMC Genomics* 9, 157 (2008).
76. Lee, Y. S., Shibata, Y., Malhotra, A. & Dutta, A. A novel class of small RNAs: tRNA-derived RNA fragments (tRFs). *Genes Dev* 23, 2639-49 (2009).
77. Chu, A. et al. Large-scale profiling of microRNAs for The Cancer Genome Atlas. *Nucleic Acids Research,* gkv808-9 (2015).
78. Sra, S. & Dhillon, I. S. Generalized nonnegative matrix approximations with Bregman divergences. *Advances in neural information* . . . (2005).
79. Brunet, J.-P., Tamayo, P., Golub, T. R. & Mesirov, J. P. Metagenes and molecular pattern discovery using matrix factorization. *Proceedings of the National Academy of Sciences of the United States of America* 101, 4164-4169 (2004).
80. Huang, D. W., Sherman, B. T. & Lempicki, R. A. Systematic and integrative analysis of large gene lists using DAVID bioinformatics resources. *Nature protocols* 4, 44-57 (2009).
81. UniProt, C. UniProt: a hub for protein information. *Nucleic Acids Res* 43, D204-12 (2015).
82. Burge, F. and Kockelbergh, R. (2016) Closing the Gender Gap: Can We Improve Bladder Cancer Survival in Women?—A Systematic Review of Diagnosis, Treatment and Outcomes. *Urol Int,* 97, 373-379.
83. Cohn, J. A., Vekhter, B., Lyttle, C., Steinberg, G. D. and Large, M. C. (2014) Sex disparities in diagnosis of bladder cancer after initial presentation with hematuria: a nationwide claims-based investigation. *Cancer,* 120, 555-561.
84. Dobruch, J., Daneshmand, S., Fisch, M., Lotan, Y., Noon, A. P., Resnick, M. J., Shariat, S. F., Zlotta, A. R. and Boorjian, S. A. (2016) Gender and Bladder Cancer: A Collaborative Review of Etiology, Biology, and Outcomes. *Eur Urol,* 69, 300-310.
85. Fajkovic, H., Halpern, J. A., Cha, E. K., Bahadori, A., Chromecki, T. F., Karakiewicz, P. I., Breinl, E., Merseburger, A. S. and Shariat, S. F. (2011) Impact of gender on bladder cancer incidence, staging, and prognosis. *World J Urol,* 29, 457-463.
86. Zhang, Y. (2013) Understanding the gender disparity in bladder cancer risk: the impact of sex hormones and liver on bladder susceptibility to carcinogens. *J Environ Sci Health C Environ Carcinog Ecotoxicol Rev,* 31, 287-304.
87. Hollenbeck, B. K., Dunn, R. L., Ye, Z., Hollingsworth, J. M., Lee, C. T. and Birkmeyer, J. D. (2010) Racial differences in treatment and outcomes among patients with early stage bladder cancer. *Cancer,* 116, 50-56.
88. Jacobs, B. L., Montgomery, J. S., Zhang, Y., Skolarus, T. A., Weizer, A. Z. and Hollenbeck, B. K. (2012) Disparities in bladder cancer. *Urol Oncol,* 30, 81-88.
89. Lee, C. T., Dunn, R. L., Williams, C. and Underwood, W., 3rd. (2006) Racial disparity in bladder cancer: trends in tumor presentation at diagnosis. *J Urol,* 176, 927-933; discussion 933-924.
90. Siegel, R. L., Miller, K. D. and Jemal, A. (2015) Cancer statistics, 2015. *CA Cancer J Clin,* 65, 5-29.
91. Underwood, W., 3rd, Dunn, R. L., Williams, C. and Lee, C. T. (2006) Gender and geographic influence on the racial disparity in bladder cancer mortality in the US. *J Am Coll Surg,* 202, 284-290.

LENGTHY TABLES

The patent contains a lengthy table section. A copy of the table is available in electronic form from the USPTO web site (https://seqdata.uspto.gov/?pageRequest=docDetail&DocID=US11715549B2). An electronic copy of the table will also be available from the USPTO upon request and payment of the fee set forth in 37 CFR 1.19(b)(3).

What is claimed is:

1. A method of treating cancer in a patient comprising administering a gene modulating therapy, wherein at least one gene that is transcribed in an ailing tissue of the patient is correlated with an abundance of at least one cancer regulating tRF that is transcribed in the ailing tissue, wherein the ailing tissue and the tRF transcribed in the ailing tissue is selected from the group comprising:

ACC (Adrenocortical carcinoma) and the tRF is selected from the group of sequences consisting of: SEQ ID NO: 1 through SEQ ID NO: 31;

BLCA (Bladder Urothelial Carcinoma) and the tRF is selected from the group of sequences consisting of: SEQ ID NO: 32 through SEQ ID NO: 40;

BRCA (Breast invasive carcinoma) and the tRF is selected from the group of sequences consisting of: SEQ ID NO: 41 through SEQ ID NO: 58;

CESC (Cervical squamous cell carcinoma and endocervical adenocarcinoma) and the tRF is selected from the group of sequences consisting of: SEQ ID NO: 59 through SEQ ID NO: 71;

COAD (Colon adenocarcinoma) and the tRF is selected from the group of sequences consisting of: SEQ ID NO: 72 through SEQ ID NO: 77;

DLBC (Lymphoid Neoplasm Diffuse Large B-cell Lymphoma) and the tRF is selected from the group of sequences consisting of: SEQ ID NO: 78 through SEQ ID NO: 88;

ESCA (Esophageal carcinoma) and the tRF is selected from the group of sequences consisting of: SEQ ID NO: 89 through SEQ ID NO: 94;

HNSC (Head and Neck squamous cell carcinoma) and the tRF is selected from the group of sequences consisting of: SEQ ID NO: 95 through SEQ ID NO: 109;

KICH (Kidney Chromophobe) and the tRF is selected from the group of sequences consisting of: SEQ ID NO: 110 through SEQ ID NO: 120;
KIRC (Kidney renal clear cell carcinoma) and the tRF is selected from the group of sequences consisting of: SEQ ID NO: 121 through SEQ ID NO: 128;
KIRP (Kidney renal papillary cell carcinoma) and the tRF is selected from the group of sequences consisting of: SEQ ID NO: 129 through SEQ ID NO: 132;
LAML (Acute Myeloid Leukemia) and the tRF is selected from the group of sequences consisting of: SEQ ID NO: 133 through SEQ ID NO: 165;
LGG (Brain Lower Grade Glioma) and the tRF is selected from the group of sequences consisting of: SEQ ID NO: 166 through SEQ ID NO: 180;
LIHC (Liver hepatocellular carcinoma) and the tRF is selected from the group of sequences consisting of: SEQ ID NO: 181 through SEQ ID NO: 186;
LUAD (Lung adenocarcinoma) and the tRF is selected from the group of sequences consisting of: SEQ ID NO: 187 through SEQ ID NO: 194;
LUSC (Lung squamous cell carcinoma) and the tRF is selected from the group of sequences consisting of: SEQ ID NO: 195 through SEQ ID NO: 217;
MESO (Mesothelioma) and the tRF is selected from the group of sequences consisting of: SEQ ID NO: 218 through SEQ ID NO: 235;
OV (Ovarian serous cystadenocarcinoma), and the tRF is sequence SEQ ID NO: 236;
PAAD (Pancreatic adenocarcinoma) and the tRF is selected from the group of sequences consisting of: SEQ ID NO: 237 through SEQ ID NO: 242;
PCPG (Pheochromocytoma and Paraganglioma) and the tRF is selected from the group of sequences consisting of: SEQ ID NO: 243 through SEQ ID NO: 251;
PRAD (Prostate adenocarcinoma) and the tRF is selected from the group of sequences consisting of: SEQ ID NO: 252 through SEQ ID NO: 261;
READ (Rectum adenocarcinoma) and the tRF is selected from the group of sequences consisting of: SEQ ID NO: 262 through SEQ ID NO: 270;
SARC (Sarcoma) and the tRF is selected from the group of sequences consisting of: SEQ ID NO: 271 through SEQ ID NO: 275;
SKCM (Skin Cutaneous Melanoma) and the tRF is selected from the group of sequences consisting of: SEQ ID NO: 276 through SEQ ID NO: 283;
STAD (Stomach adenocarcinoma) and the tRF is selected from the group of sequences consisting of: SEQ ID NO: 284 through SEQ ID NO: 291;
TGCT (Testicular Germ Cell Tumors) and the tRF is selected from the group of sequences consisting of: SEQ ID NO: 292 through SEQ ID NO: 308;
THCA (Thyroid carcinoma) and the tRF is selected from the group of sequences consisting of: SEQ ID NO: 309 through SEQ ID NO: 324;
THYM (Thymoma) and the tRF is selected from the group of sequences consisting of: SEQ ID NO: 325 through SEQ ID NO: 331;
UCEC (Uterine Corpus Endometrial Carcinoma) and the tRF is selected from the group of sequences consisting of: SEQ ID NO: 332 through SEQ ID NO: 344; and
UVM (Uveal Melanoma) and the tRF is selected from the group of sequences consisting of: SEQ ID NO: 345 through SEQ ID NO: 372.

2. The method of claim 1 further comprising first collecting an ailing tissue sample from said patient and determining the correlation between the at least one gene and the at least one tRF.

3. The method of claim 1, wherein the ailing tissue and the tRF transcribed in the ailing tissue is selected from the group consisting of: PAAD (Pancreatic adenocarcinoma) and the tRF is selected from the group of sequences consisting of: SEQ ID NO: 237 through SEQ ID NO: 242; and COAD (Colon adenocarcinoma) and the tRF is selected from the group of sequences consisting of: SEQ ID NO: 72 through SEQ ID NO: 77.

4. The method of claim 1, wherein the tRF and the gene are positively correlated.

5. The method of claim 1, wherein the tRF and the gene are negatively correlated.

6. The method of claim 1, further comprising the step of determining the abundance of the tRF in the ailing tissue.

7. The method of claim 1, further comprising the step of determining the abundance of the gene in the ailing tissue.

8. A method of treating cancer in a patient comprising administering a gene modulating therapy, wherein at least one gene that is transcribed in an ailing tissue of the patient is correlated with an abundance of at least one cancer regulating tRF that is transcribed in the ailing tissue, wherein the ailing tissue is selected from the group comprising:
ACC (Adrenocortical carcinoma), and the gene is selected from the group consisting of: CSDC2, CSGALNACTI, RERG, PCMTD1, PLCB3, YEATS2, BIRC2, MVP, MYST3, ARL6IP5, TRANK1, TMEM45A, ACVR1, PGCP, VCL, MSRA, C10orf54, DCUN1D3, CTD-SPL2, SIK2, TMCO6, SRCAP, TMEM159, PLEKHO2, HLA-E, TAX1BP3, C11orf75, RCE1, NDRG4, MRI, MARK2, FAM21B, HLA-B, RBL2, CABC1; BLCA (Bladder Urothelial Carcinoma), and the gene is selected from the group consisting of: ACTG2, TGFBR3, PRELP, RERE, OSR1, TCEAL1, NNAT, GCOM1, MMP2, MYST4, SYNPO2, C16orf45, FYCO1, MYH11, CSRP1, MEIS2, ACTA2, CLU, LOXL1, IGFBP4, TXNIP, SLIT3, CHRDL2, MYL9; BRCA (Breast invasive carcinoma), and the gene is selected from the group consisting of: CRTC1, CALCOCO1, SLC27A1, CROCC, PGPEP1, PSD4, TBC1D17, PHF15, ARAP1, TNFRSF14, NISCH, MED16, RGS12, MYO15B, AGXT2L2, RFX1, C21orf2, NEURL4, TPCN1, HOOK2, LTBP3, SPHK2, ABTB1, ABCD4, ZBTB48, CIRBP, CYTH2, ZNF446, PHF1, RPS9, MZF1, FAM160A2, KIF13B, GLTSCR2, WDR81, SH2B1, RHOBTB2, CRY2, LTBP4, HDAC7, ZNF219, MUM1, REMS, RAPGEF3, CCDC9; CESC (Cervical squamous cell carcinoma and endocervical adenocarcinoma), and the gene is selected from the group consisting of: NBPF10, JRK, SMGS, ALDH1A2, MFAP4, ZFYVE1, CDC42BPB, ENTPD4, IGF1, ZFYVE26, APOLD1, LOC200030, KIAA0430, UBN1, VASH1, RANBP10, WDR37, MGP, MON1E, CNN1, MAT2A, PGR, KIAA0100, C14orf21, HCFC1, LRP1O, DIDO1, FBXL18, ATP6V0A1, RGS2, MLXIP, TRIM56, CTGF, KIAA0284, DES, SFRP4, PDPK1, TAOK2, SMCR8, CLN8, UNC119B, TRIM25, CYB561D1, TBC1D2B, DNAJCS, CRAMP1L, ZNF646, ZC3HAV1, KHNYN, PSKH1, RGS1; COAD (Colon adenocarcinoma), and the gene is selected from the group consisting of: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL10RA, HEG1, HIPK3, NEXN, TMEM140, AMOTL1, A2M, TIE1, AKT3, CD163, LPHN2, OSMR, CSF1R, DAAM2, IL1R1, GPC6, SLC8A1, FBN1, GNB4, GPNMB, DOCK2, KIAA1462, CSF2RB, MYOSA, S1PR1, ARHGEF6; DLBC (Lymphoid Neoplasm Diffuse Large B-cell Lymphoma), GOLGA2, DCHS1, CLDND1, CSRNP2, FRMD8, SLCO2A1, ARHGAP23, NID1, DUSP7, TBC1D20, YAP1, WDR82, TMEM43, TJP1, CARDS, ZNF213, KIAA0232, EPAS1, VPS11, PHC1, SKI, DAG1, ANKRD40, FAT1, PHF12; ESCA (Esophageal carcinoma), and the gene is selected from the group consisting of: SSCSD, PDLIM3, CELF2, TIMP3, ABCC9, CALD1, COL8A1, GREM1, THBS4, PRUNE2, TMEM47, PBXIP1, PLN, CCDC80, C7, PODN, DDR2, PPP1R12B, MRVI1, LMOD1, C7orf58, HSPB7, TAGLN, PPP1R16B, GFRA1, LOC728264, SGCD, PGMS; HNSC (Head and Neck squamous cell carcinoma), and the gene is selected from the group consisting of: GABBR1, C14orf179, METT11D1, C6orf125, ZNF692, FKBP2, FAM1 13A, LOC388789, TAZ, WASH3P, CDK5RAP3, PLBD2, SDR39U1, CPTIB, UBLS, C14orf2, LOC146880, THAP3, ANKRD13D, C12orf47, ATPSE, ATPIF1, SYF2, C8orf59, WASH7P, NPIPL3, CDK10, C1orf151, MRPS21, C19orf60, C7orf47, CENPT, GASS, KIFC2, NFIC, RPL39, UQCRB, COX6C, LUC7L, CCS, COMMD6, ZNF133, SNHG12, C11orf31, NPEPL1; KICH (Kidney Chromophobe), and the gene is selected from the group consisting of: BMPR1A, EXT1, TFAM, PDCD1 1, MTIF2, POLR3A, MAPK8, PRDX3, COQS; KIRC (Kidney renal clear cell carcinoma), and the gene is selected from the group consisting of: ARHGAP19, KIAA1671, KIAA0754, KIAA1 147, ZNF45, KLF13, MYO9A, FUT1 1, ASHIL, KIF13A, TUBGCP3, MTF1, FAM168A; KIRP (Kidney renal papillary cell carcinoma), and the gene is selected from the group consisting of: GLCCII, CDK13, POGZ, UBN2, CREBZF, NPHP3, VEZF1, CHD1, YPEL2, LRRC37B2, GPATCH8, ENC1, TTC18, C1 lorf61, RSBN1L, EFNB2, PHIP, RBAK, SPEN, RBM9, SMURF2, ZNF264, ZNF587, PTPN12, TPBG, RBM33, DMTF1, CCNT2, ARID4B, ARGLU1, CREB1, KIAA0753, BTAF1, C17orf85, RLF, MLLS, ZFC3H1, ZNF160, PRPF38B, SETDS, ARRDC4, HOOK3, RC3H1, MLL3, RNF207, MAP3K1, PLEKHH2, CCDC57, DAPK1, LUC7L3; LAML (Acute Myeloid Leukemia), and the gene is selected from the group consisting of: SUPTSH, SKIV2L, IKBKG, HGS, MIB2, MED15, STK25, ANAPC2, RHOT2, SFil, CUL9, ARHGEF1, GTPBP2, KIAA0892, MBD1, UCKL1, DHX16, ZFYVE27, APBA3, PI4KB, C19orf6, SPSB3, CAPN10, FLYWCH1, ATG4B, CDC37, LZTR1, MAN2C1, C1orf63, DVL1, EDC4, DHX34, PCNXL3, EXOC3, FUK, FBXL6, LMF2, HDAC1O, E4F1, TSC2, ZDHHC8, CPSF3L, FAM160B2, CLCN7, LRRC14, D2HGDH, ZNF335, FHOD1, SOLH, ZBTB17, POLRMT, SLC26A1, KIAA0415, SELO, SAPS2, NME3, KLHL36, SCYL1, USP19, DGKZ, CYHR1, ATG2A, VPS16, XAB2, ACTRS, ZNF76, ATP13A1, RNF31, GPN2, MUS81, FAM73B, TTC15, CXXC1, TRMT2A, WDR8, PTGES2, TEL02, RFNG, SLC39A13; LGG (Brain Lower Grade Glioma), and the gene is: EXD3; LIHC (Liver hepatocellular carcinoma), and the gene is DYRK2; LUAD (Lung adenocarcinoma), and the gene is selected from the group consisting of: CROCCLI, RHPNI, ABCA7, RGL3, PDXDC2, ENGASE, ATG16L2, CSAD, TTLL3, ARHGEF12, ANKS3, LOC100132287, SGSM2, HEXDC, LPIN3, ACCS, PLEKHMIP, ANO9, ELMOD3, KIAA0895L, APIG2, ACAP3, ECHDC2, NXFI, JMJD7-PLA2G4B, TMEM175, CCDC64B, ANKMYI; LUSC (Lung squamous cell carcinoma), and the gene is selected from the group consisting of: PKDI, CHKB-CPTIB, WDR90, MACFI, RBM6, LENG8, TAFIC, COL16A1, CAPN12, RBM39, ACINI, FNBP4, PILRB, DMPK, SFRSS, AHSA2, RBM25, PLCGI, SNRNP70, NCRNA00201, GIGYFI, SRRM2, GOLGA8B, ZGPAT, RTELI, COL27A1, MAPK8IP3, PABPCIL, HSPG2, AKAP13, LRPI, NKTR, ATAD3B, TUBGCP6, ZNF276, MICALL2, CLCN6, NSUN5P2, NEATI, LAMAS, CHD2, PPPIR12C, FAM193B, NPIP, CDKIIA, STX16, LTBP2, LOC91316, NBEAL2, FLJ45340, LRDD, CCDC88B, GOLGA8A; MESO (Mesothelioma), and the gene is selected from the group consisting of: C15orf40, SNUPN, CHTF8, CLNSIA, CSNKID, DPF2, PCIFI, DNAJC4, SECISBP2, C5orf32, RPRDIB, RPL38, NDUFA10, RPRM, BAT4, RSLIDI; OV (Ovarian serous cystadenocarcinoma), and the gene is selected from the group consisting of: KIAA0907, ULK3; PAAD (Pancreatic adenocarcinoma), and the gene is selected from the group consisting of: NUAKI, KBTBD4, HMCNI, DSTYK; PCPG (Pheochromocytoma and Paraganglioma), and the gene is selected from the group consisting of: CACNA2D1, TP53BP1, KIAA1244, MARCH8, PCDHGC4, ESYT2, DHX15, TECPRI, MAP3K2, TBCID24, PCDHI, IPOI 1, MGATS, TRAM2, ADAMI0, GNA1 1, CBX6, SNURF, RIF1, CNTN1, LMBRD2, CANDI, TRIP12, RC3H2, PAK3, TMCO3, CSNK2AIP, ASBI, AKAP2, ROCK2, NUP155, PIK3C3, KLHDC10, RAB35, GTF2I, HSPA8, FAM49A; PRAD (Prostate adenocarcinoma), and the gene is selected from the group consisting of: FEM1B, TGOLN2, SEPT9, MYOCD, LUZP1, TLNI, PIASI, RNFI 11, DCBLD2, URB1, ZBTB40, ZNF516, ATX-NIL, RHBDD1, HUWEI, VP513D, ITPRI, NNT, ERCI; READ (Rectum adenocarcinoma), and the gene is selected from the group consisting of: FZD4, CD93, DYNCII2, ENG, ELK3, KDR, FAM1OIB, PXDN, GIMAP4, F13A1, VCAMI, ARHGAP31, CD34, GNG2, LCP2, VWF, CSF1, GPR116, KIRREL, MMRN2, ETSI, ITGA4, FAM120B; SARC (Sarcoma), SH3BGRL, SORBSI, MAPK4, LYNXI, MICAL3, AKAP1, LIMS2, RNF38, LOC283174, CAND2, PLIN4, MOAP1, RNF19A, RABGAP1, C5orf4, FRY, ARHGEF1 7, SETMAR, SSH3, NUMA1, PBXI, TORIAIP1, TACC2, RAB3D, BBSI, CEP68, GPRASPI, SVIL, CRBN, CRTC3, ZFYVE21, SLMAP, RASL12, SCAPER, STAT5B, ZAK, EZHI; SKCM (Skin Cutaneous Melanoma), and the gene is selected from the group consisting of: MLL4, LMTK2, APBB3, C17orf56, LOC388796, ANO8; STAD (Stomach adenocarcinoma), and the gene is selected from the group consisting of: KCNMAI, MAST4, FHL1, ATP2B4, TENC1, C20orf194, ASB2, C10orf26, TTC28, FAM13B, ITPKB, GNAO1, FAM129A, ZBTB4, FNBPI, FLNA, CCDC69, STONI, NFASC, PAPLN, ADCY5, LPP, NEGRI, ABBBP, INPP5B, TNXB, ANGPTLI, ANK2, EPHA3, ZCCHC24, SETBPI, PRICKLE2, LTBP1, RGMA, DARC, KANK2, SYNPO; TGCT (Testicular Germ Cell Tumors), and the gene is selected from the group consisting of: ATF6, CTDSP2, MKL2, TEAD1, ZNF407, TRAPPC9, AHDC1, LANCL1, KCTD20, OXR1, SNX1, CSNK1G1, KIAA0247, LDOCIL, EPCI, GRLFI, ABHD2, RAil, ARIDIB, ITFGI, MUT, KIAA1 737, LAMA2, KIAA1 109, CCNI, DIXDCI, C6orf89, RNF144A, APPBP2, KLF12, ZFP91; THCA (Thyroid carcinoma), and the gene is selected from the group consisting of: KIAA0495, PHF21A, ZBTB5, SFRS6, NCOA5, ZNF814, IP6K2, IFT140, INTS3, ZNF559, SETD4, TGIF2, VILL, KCNC3, UBE2G2, FBXO9, IPW, DUOXA1, CACNA2D2, EFHC1, FAM189A2, GTF2IRD2P1, KIAA1683, AP4B1, SCAND2, CDRT4, UNKL, NYNRIN, ARMC5, MAPKBP1, USP40, VEGFA, OLFM2, FBF1, TCF7L1, MXD4, IKBKB, POFUT2, BOC, TCF7L2, RMST, TRO; THYM (Thymoma), and the gene is selected from the group consisting of: ZFYVE9, LOC399959, SIX1, PDGFC; UCEC (Uterine Corpus Endometrial Carcinoma), and the gene is selected from the group consisting of: RNMT, SON, MDN1, CELF1, RIPK1, YLPM1, XRN2, BPTF, RQCD1, PAFAH1B2, BOD1L, SBNO1, RNF169, PIK3R4, LRCH3, DCP1A, SF3A1, SLC9A8, TNRC6A, BRPF3; UCS (Uterine Carcinosarcoma), and the gene is RHBDF1; and UVM (Uveal Melanoma), and the gene is selected from the group consisting of: MAP1A, TCIRG1, ECM1, C14orf159, WARS, PCYOX1L.

9. The method of claim 8, wherein the ailing tissue and the gene is selected from the group consisting of: PAAD (Pancreatic adenocarcinoma), and the gene is selected from the group consisting of: NUAKI, KBTBD4, HMCNI, DSTYK; and COAD (Colon adenocarcinoma), and the gene is selected from the group consisting of: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL10RA, HEG1, HIPK3, NEXN, TMEM140, AMOTL1, A2M, TIE1, AKT3, CD163, LPHN2, OSMR, CSF1R, DAAM2, IL1R1, GPC6, SLC8A1, FBN1, GNB4, GPNMB, DOCK2, KIAA1462, CSF2RB, MYOSA, S1PR1, ARHGEF6.

10. The method of claim 8 further comprising first collecting an ailing tissue sample from said patient and determining the correlation between the at least one gene and the at least one tRF.

11. A method of treating cancer in a patient comprising: administering a gene modulating therapy, wherein at least one tumorigenic mRNA transcribed from the gene of an ailing tissue of the patient is correlated with an abundance of at least one cancer regulating tRF that is transcribed in the ailing tissue, wherein the method further comprises: (i) first collecting an ailing tissue sample from said patient and determining the correlation between the at least one mRNA and the at least one tRF; (ii) computing an average negative correlations (A) for each tRF that exceed a threshold (T) in the ailing tissue, (iii) determining whether the average negative correlations (A) for each tRF is equal to or less than a second threshold (t) in the ailing tissue, wherein the at least one tRF is selected from the tRFs that were determined to have an average negative correlation (A) equal to or less than the second threshold (t), and wherein the ailing tissue and the tRF transcribed in the ailing tissue is selected from the group comprising: ACC (Adrenocortical carcinoma) and the tRF is selected from the group of sequences consisting of: SEQ ID NO: 1 through SEQ ID NO: 31; BLCA (Bladder Urothelial Carcinoma) and the tRF is selected from the group of sequences consisting of: SEQ ID NO: 32 through SEQ ID NO: 40; BRCA (Breast invasive carcinoma) and the tRF is selected from the group of sequences consisting of: SEQ ID NO: 41 through SEQ ID NO: 58; CESC (Cervical squamous cell carcinoma and endocervical adenocarcinoma) and the tRF is selected from the group of sequences consisting of: SEQ ID NO: 59 through SEQ ID NO: 71; COAD (Colon adenocarcinoma) and the tRF is selected from the group of sequences consisting of: SEQ ID NO: 72 through SEQ ID NO: 77; DLBC (Lymphoid Neoplasm Diffuse Large B-cell Lymphoma) and the tRF is selected from the group of sequences consisting of: SEQ ID NO: 78 through SEQ ID NO: 88; ESCA (Esophageal carcinoma) and the tRF is selected from the group of sequences consisting of: SEQ ID NO: 89 through SEQ ID NO: 94; HNSC (Head and Neck squamous cell carcinoma) and the tRF is selected from the group of sequences consisting of: SEQ ID NO: 95 through SEQ ID NO: 109; KICH (Kidney Chromophobe) and the tRF is selected from the group of sequences consisting of: SEQ ID NO: 110 through SEQ ID NO: 120; KIRC (Kidney renal clear cell carcinoma) and the tRF is selected from the group of sequences consisting of: SEQ ID NO: 121 through SEQ ID NO: 128; KIRP (Kidney renal papillary cell carcinoma) and the tRF is selected from the group of sequences consisting of: SEQ ID NO: 129 through SEQ ID NO: 132; LAML (Acute Myeloid Leukemia) and the tRF is selected from the group of sequences consisting of: SEQ ID NO: 133 through SEQ ID NO: 165; LGG (Brain Lower Grade Glioma) and the tRF is selected from the group of sequences consisting of: SEQ ID NO: 166 through SEQ ID NO: 180; LIHC (Liver hepatocellular carcinoma) and the tRF is selected from the group of sequences consisting of: SEQ ID NO: 181 through SEQ ID NO: 186; LUAD (Lung adenocarcinoma) and the tRF is selected from the group of sequences consisting of: SEQ ID NO: 187 through SEQ ID NO: 194; LUSC (Lung squamous cell carcinoma) and the tRF is selected from the group of sequences consisting of: SEQ ID NO: 195 through SEQ ID NO: 217; MESO (Mesothelioma) and the tRF is selected from the group of sequences consisting of: SEQ ID NO: 218 through SEQ ID NO: 235; OV (Ovarian serous cystadenocarcinoma), and the tRF is sequence SEQ ID NO: 236; PAAD (Pancreatic adenocarcinoma) and the tRF is selected from the group of sequences consisting of: SEQ ID NO: 237 through SEQ ID NO: 242; PCPG (Pheochromocytoma and Paraganglioma) and the tRF is selected from the group of sequences consisting of: SEQ ID NO: 243 through SEQ ID NO: 251; PRAD (Prostate adenocarcinoma) and the tRF is selected from the group of sequences consisting of: SEQ ID NO: 252 through SEQ ID NO: 261; READ (Rectum adenocarcinoma) and the tRF is selected from the group of sequences consisting of: SEQ ID NO: 262 through SEQ ID NO: 270; SARC (Sarcoma) and the tRF is selected from the group of sequences consisting of: SEQ ID NO: 271 through SEQ ID NO: 275; SKCM (Skin Cutaneous Melanoma) and the tRF is selected from the group of sequences consisting of: SEQ ID NO: 276 through SEQ ID NO: 283; STAD (Stomach adenocarcinoma) and the tRF is selected from the group of sequences consisting of: SEQ ID NO: 284 through SEQ ID NO: 291; TGCT (Testicular Germ Cell Tumors) and the tRF is selected from the group of sequences consisting of: SEQ ID NO: 292 through SEQ ID NO: 308; THCA (Thyroid carcinoma) and the tRF is selected from the group of sequences consisting of: SEQ ID NO: 309 through SEQ ID NO: 324; THYM (Thymoma) and the tRF is selected from the group of sequences consisting of: SEQ ID NO: 325 through SEQ ID NO: 331; UCEC (Uterine Corpus Endometrial Carcinoma) and the tRF is selected from the group of sequences consisting of: SEQ ID NO: 332 through SEQ ID NO: 344; and UVM (Uveal Melanoma) and the tRF is selected from the group of sequences consisting of: SEQ ID NO: 345 through SEQ ID NO: 372.

12. The method of claim 11, wherein the mRNA and the tRF are positively correlated.

13. The method of claim 11, wherein the mRNA and the tRF are negatively correlated.

14. The method of claim 11 further comprising the step of determining the abundance of the mRNA in the ailing tissue.

15. The method of claim 11 further comprising the step of determining the abundance of the tRF in the ailing tissue.

16. The method of claim 11, wherein the ailing tissue and the tRF transcribed in the ailing tissue is selected from the group consisting of: PAAD (Pancreatic adenocarcinoma) and the tRF is selected from the group of sequences consisting of: SEQ ID NO: 237 through SEQ ID NO: 242; and COAD (Colon adenocarcinoma) and the tRF is selected from the group of sequences consisting of: SEQ ID NO: 72 through SEQ ID NO: 77.

17. A method of treating cancer in a patient comprising administering a gene modulating therapy, wherein at least one tumorigenic mRNA transcribed from the gene of an ailing tissue of the patient is correlated with an abundance of at least one cancer regulating tRF that is transcribed in the ailing tissue, further comprising first collecting an ailing tissue sample from said patient and determining the correlation between the at least one mRNA and the at least one tRF, wherein the ailing tissue is selected from the group comprising: ACC (Adrenocortical carcinoma), and the at least one mRNA is transcribed from a gene selected from the group consisting of: CSDC2, CSGALNACTI, RERG, PCMTD1, PLCB3, YEATS2, BIRC2, MVP, MYST3, ARL6IP5, TRANK1, TMEM45A, ACVR1, PGCP, VCL, MSRA, C10orf54, DCUN1D3, CTDSPL2, SIK2, TMCO6, SRCAP, TMEM159, PLEKHO2, HLA-E, TAX1BP3, C11orf75, RCE1, NDRG4, MRI, MARK2, FAM21B, HLA-B, RBL2, CABC1; BLCA (Bladder Urothelial Carcinoma), and the gene is selected from the group consisting of: ACTG2, TGFBR3, PRELP, RERE, OSR1, TCEAL1, NNAT, GCOM1, MMP2, MYST4, SYNPO2, C16orf45, FYCO1, MYH1 1, CSRP1, MEIS2, ACTA2, CLU, LOXL1, IGFBP4, TXNIP, SLIT3, CHRDL2, MYL9; BRCA (Breast invasive carcinoma), and the gene is selected from the group consisting of: CRTC1, CALCOCO1, SLC27A1, CROCC, PGPEP1, PSD4, TBC1D17, PHF15, ARAP1, TNFRSF14, NISCH, MED16, RGS12, MYO15B, AGXT2L2, RFX1, C21orf2, NEURL4, TPCN1, HOOK2, LTBP3, SPHK2, ABTB1, ABCD4, ZBTB48, CIRBP, CYTH2, ZNF446, PHF1, RPS9, MZF1, FAM160A2, KIF13B, GLTSCR2, WDR81, SH2B1, RHOBTB2, CRY2, LTBP4, HDAC7, ZNF219, MUM1, REMS, RAPGEF3, CCDC9; CESC (Cervical squamous cell carcinoma and endocervical adenocarcinoma), and the gene is selected from the group consisting of: NBPF10, JRK, SMGS, ALDH1A2, MFAP4, ZFYVE1, CDC42BPB, ENTPD4, IGF1, ZFYVE26, APOLD1, LOC200030, KIAA0430, UBN1, VASH1, RANBP10, WDR37, MGP, MONIE, CNN1, MAT2A, PGR, KIAA0100, C14orf21, HCFC1, LRP1O, DIDO1, FBXL18, ATP6V0A1, RGS2, MLXIP, TRIM56, CTGF, KIAA0284, DES, SFRP4, PDPK1, TAOK2, SMCR8, CLN8, UNC119B, TRIM25, CYB561D1, TBC1D2B, DNAJCS, CRAMP1L, ZNF646, ZC3HAV1, KHNYN, PSKH1, RGS1; COAD (Colon adenocarcinoma), and the gene is selected from the group consisting of: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL10RA, HEG1, HIPK3, NEXN, TMEM140, AMOTL1, A2M, TIE1, AKT3, CD163, LPHN2, OSMR, CSF1R, DAAM2, IL1R1, GPC6, SLC8A1, FBN1, GNB4, GPNMB, DOCK2, KIAA1462, CSF2RB, MYOSA, S1PR1, ARHGEF6; DLBC (Lymphoid Neoplasm Diffuse Large B-cell Lymphoma), GOLGA2, DCHS1, CLDND1, CSRNP2, FRMD8, SLCO2A1, ARHGAP23, NID1, DUSP7, TBC1D20, YAP1, WDR82, TMEM43, TJP1, CARDS, ZNF213, KIAA0232, EPAS1, VPS11, PHC1, SKI, DAG1, ANKRD40, FAT1, PHF12; ESCA (Esophageal carcinoma), and the gene is selected from the group consisting of: SSCSD, PDLIM3, CELF2, TIMP3, ABCC9, CALD1, COL8A1, GREM1, THBS4, PRUNE2, TMEM47, PBXIP1, PLN, CCDC80, C7, PODN, DDR2, PPP1R12B, MRVI1, LMOD1, C7orf58, HSPB7, TAGLN, PPP1R16B, GFRA1, LOC728264, SGCD, PGMS; HNSC (Head and Neck squamous cell carcinoma), and the gene is selected from the group consisting of: GABBR1, C14orf179, METT11D1, C6orf125, ZNF692, FKBP2, FAM1 13A, LOC388789, TAZ, WASH3P, CDK5RAP3, PLBD2, SDR39U1, CPTIB, UBLS, C14orf2, LOC146880, THAP3, ANKRD13D, C12orf47, ATPSE, ATPIF1, SYF2, C8orf59, WASH7P, NPIPL3, CDK10, C1orf151, MRPS21, C19orf60, C7orf47, CENPT, GASS, KIFC2, NFIC, RPL39, UQCRB, COX6C, LUC7L, CCS, COMMD6, ZNF133, SNHG12, C11orf31, NPEPL1; KICH (Kidney Chromophobe), and the gene is selected from the group consisting of: BMPR1A, EXT1, TFAM, PDCD1 1, MTIF2, POLR3A, MAPK8, PRDX3, COQS; KIRC (Kidney renal clear cell carcinoma), and the gene is selected from the group consisting of: ARHGAP19, KIAA1671, KIAA0754, KIAA1 147, ZNF45, KLF13, MYO9A, FUT1 1, ASHIL, KIF13A, TUBGCP3, MTF1, FAM168A; KIRP (Kidney renal papillary cell carcinoma), and the gene is selected from the group consisting of: GLCCII, CDK13, POGZ, UBN2, CREBZF, NPHP3, VEZF1, CHD1, YPEL2, LRRC37B2, GPATCH8, ENC1, TTC18, C1 1orf61, RSBN1L, EFNB2, PHIP, RBAK, SPEN, RBM9, SMURF2, ZNF264, ZNF587, PTPN12, TPBG, RBM33, DMTF1, CCNT2, ARID4B, ARGLU1, CREB1, KIAA0753, BTAF1, C17orf85, RLF, MLLS, ZFC3H1, ZNF160, PRPF38B, SETDS, ARRDC4, HOOK3, RC3H1, MLL3, RNF207, MAP3K1, PLEKHH2, CCDC57, DAPK1, LUC7L3; LAML (Acute Myeloid Leukemia), and the gene is selected from the group consisting of: SUPTSH, SKIV2L, IKBKG, HGS, MIB2, MED15, STK25, ANAPC2, RHOT2, SFil, CUL9, ARHGEF1, GTPBP2, KIAA0892, MBD1, UCKL1, DHX16, ZFYVE27, APBA3, PI4KB, C19orf6, SPSB3, CAPN10, FLYWCH1, ATG4B, CDC37, LZTR1, MAN2C1, C1orf63, DVL1, EDC4, DHX34, PCNXL3, EXOC3, FUK, FBXL6, LMF2, HDAC1O, E4F1, TSC2, ZDHHC8, CPSF3L, FAM160B2, CLCN7, LRRC14, D2HGDH, ZNF335, FHOD1, SOLH, ZBTB17, POLRMT, SLC26A1, KIAA0415, SELO, SAPS2, NME3, KLHL36, SCYL1, USP19, DGKZ, CYHR1, ATG2A, VPS16, XAB2, ACTRS, ZNF76, ATP13A1, RNF31, GPN2, MUS81, FAM73B, TTC15, CXXC1, TRMT2A, WDR8, PTGES2, TEL02, RFNG, SLC39A13; LGG (Brain Lower Grade Glioma), and the gene is: EXD3; LIHC (Liver hepatocellular carcinoma), and the gene is: DYRK2; LUAD (Lung adenocarcinoma), and the gene is selected from the group consisting of: CROCCLI, RHPNI, ABCA7, RGL3, PDXDC2, ENGASE, ATG16L2, CSAD, TTLL3, ARHGEF12, ANKS3, LOC100132287, SGSM2, HEXDC, LPIN3, ACCS, PLEKHMIP, ANO9, ELMOD3, KIAA0895L, APIG2, ACAP3, ECHDC2, NXFI, JMJD7-PLA2G4B, TMEM175, CCDC64B, ANKMYI; LUSC (Lung squamous cell carcinoma), and the gene is selected from the group consisting of: PKDI, CHKB-CPTIB, WDR90, MACFI, RBM6, LENG8, TAFIC, COL16A1, CAPN12, RBM39, ACINI, FNBP4, PILRB, DMPK, SFRSS, AHSA2, RBM25, PLCGI, SNRNP70, NCRNA00201, GIGYFI, SRRM2, GOLGA8B, ZGPAT, RTELI, COL27A1, MAPK8IP3, PABPCIL, HSPG2, AKAP13, LRPI, NKTR, ATAD3B, TUBGCP6, ZNF276, MICALL2, CLCN6, NSUN5P2, NEATI, LAMAS, CHD2, PPPIR12C, FAM193B, NPIP, CDKIIA, STX16, LTBP2, LOC91316, NBEAL2, FLJ45340, LRDD, CCDC88B, GOLGA8A; MESO (Mesothelioma), and the gene is selected from the group consisting of: C15orf40, SNUPN, CHTF8, CLNSIA, CSNKID, DPF2, PCIFI, DNAJC4, SECISBP2, C5orf32, RPRDIB, RPL38, NDUFAIO, RPRM, BAT4, RSLIDI; OV (Ovarian serous cystadenocarcinoma), and the gene is selected from the group consisting of: KIAA0907, ULK3; PAAD (Pancreatic adenocarcinoma), and the gene is selected from the group consisting of: NUAKI, KBTBD4, HMCNI, DSTYK; PCPG (Pheochromocytoma and Paraganglioma), and the gene is selected from the group consisting of: CACNA2D1, TP53BP1, KIAA1244, MARCH8, PCDHGC4, ESYT2, DHX15, TECPRI, MAP3K2, TBCID24, PCDHI, IPOI 1, MGATS, TRAM2, ADAMI0, GNA1 1, CBX6, SNURF, RIF1, CNTN1, LMBRD2, CANDI, TRIP12, RC3H2, PAK3, TMCO3, CSNK2AIP, ASBI, AKAP2, ROCK2, NUP155, PIK3C3, KLHDC10, RAB35, GTF2I, HSPA8, FAM49A; PRAD (Prostate adenocarcinoma), and the gene is selected from the group consisting of: FEM1B, TGOLN2, SEPT9, MYOCD, LUZP1, TLNI, PIASI, RNFI 11, DCBLD2, URB1, ZBTB40, ZNF516, ATXNIL, RHBDD1, HUWEI, VPS13D, ITPRI, NNT, ERCI; READ (Rectum adenocarcinoma), and the gene is selected from the group consisting of: FZD4, CD93, DYNCII2, ENG, ELK3, KDR, FAM1OIB, PXDN, GIMAP4, F13A1, VCAMI, ARHGAP31, CD34, GNG2, LCP2, VWF, CSF1, GPR116, KIRREL, MMRN2, ETSI, ITGA4, FAM120B; SARC (Sarcoma), SH3BGRL, SORBSI, MAPK4, LYNXI, MICAL3, AKAP1, LIMS2, RNF38, LOC283174, CAND2, PLIN4, MOAP1, RNF19A, RABGAP1, C5orf4, FRY, ARHGEF1 7, SETMAR, SSH3, NUMA1, PBXI, TORIAIP1, TACC2, RAB3D, BBSI, CEP68, GPRASPI, SVIL, CRBN, CRTC3, ZFYVE21, SLMAP, RASL12, SCAPER, STAT5B, ZAK, EZHI; SKCM (Skin Cutaneous Melanoma), and the gene is selected from the group consisting of: MLL4, LMTK2, APBB3, C17orf56, LOC388796, ANO8; STAD (Stomach adenocarcinoma), and the gene is selected from the group consisting of: KCNMAI, MAST4, FHL1, ATP2B4, TENC1, C20orf194, ASB2, C10orf26, TTC28, FAM13B, ITPKB, GNAO1, FAM129A, ZBTB4, FNBPI, FLNA, CCDC69, STONI, NFASC, PAPLN, ADCY5, LPP, NEGRI, ABBBP, INPP5B, TNXB, ANGPTLI, ANK2, EPHA3, ZCCHC24, SETBPI, PRICKLE2, LTBP1, RGMA, DARC, KANK2, SYNPO; TGCT (Testicular Germ Cell Tumors), and the gene is selected from the group consisting of: ATF6, CTDSP2, MKL2, TEAD1, ZNF407, TRAPPC9, AHDC1, LANCL1, KCTD20, OXR1, SNX1, CSNK1G1, KIAA0247, LDOCIL, EPCI, GRLFI, ABHD2, RAil, ARIDIB, ITFGI, MUT, KIAA1737, LAMA2, KIAA1 109, CCNI, DIXDCI, C6orf89, RNF144A, APPBP2, KLF12, ZFP91; THCA (Thyroid carcinoma), and the gene is selected from the group consisting of: KIAA0495, PHF21A, ZBTB5, SFRS6, NCOA5, ZNF814, IP6K2, IFT140, INTS3, ZNF559, SETD4, TGIF2, VILL, KCNC3, UBE2G2, FBXO9, IPW, DUOXA1, CACNA2D2, EFHC1, FAM189A2, GTF2IRD2P1, KIAA1683, AP4B1, SCAND2, CDRT4, UNKL, NYNRIN, ARMC5, MAPKBP1, USP40, VEGFA, OLFM2, FBF1, TCF7L1, MXD4, IKBKB, POFUT2, BOC, TCF7L2, RMST, TRO; THYM (Thymoma), and the gene is selected from the group consisting of: ZFYVE9, LOC399959, SIX1, PDGFC; UCEC (Uterine Corpus Endometrial Carcinoma), and the gene is selected from the group consisting of: RNMT, SON, MDN1, CELF1, RIPK1, YLPM1, XRN2, BPTF, RQCD1, PAFAH1B2, BOD1L, SBNO1, RNF169, PIK3R4, LRCH3, DCP1A, SF3A1, SLC9A8, TNRC6A, BRPF3; UCS (Uterine Carcinosarcoma), and the gene is: RHBDF1; and UVM (Uveal Melanoma), and the gene is selected from the group consisting of: MAP1A, TCIRG1, ECM1, C14orf159, WARS, PCYOX1L.

18. The method of claim 17, wherein the ailing tissue is COAD (Colon adenocarcinoma), and the gene is selected from the group consisting of: ATP8B2, SYNE1, WIPF1, AOC3, LIMS1, FZD1, CYBB, MAFB, GIMAP6, REST, STAB1, FPR3, MSRB3, FRMD6, CALCRL, MPEG1, MYLK, ELTD1, FGL2, SPARCL1, PLXDC2, LAIR1, ITGB2, NRP1, MRC1, ZEB1, SYT11, NCKAP1L, AXL, APLNR, ZEB2, EDIL3, FERMT2, PTPRM, RASSF2, PKD2, PHLDB2, TCF4, IL10RA, HEG1, HIPK3, NEXN, TMEM140, AMOTL1, A2M, TIE1, AKT3, CD163, LPHN2, OSMR, CSF1R, DAAM2, IL1R1, GPC6, SLC8A1, FBN1, GNB4, GPNMB, DOCK2, KIAA1462, CSF2RB, MYOSA, S1PR1, ARHGEF6.

19. The method of claim 17, wherein the ailing tissue is PAAD (Pancreatic adenocarcinoma), and the gene is selected from the group consisting of: NUAKI, KBTBD4, HMCNI, DSTYK.

* * * * *